US008129376B2

(12) United States Patent
Sundaresan et al.

(10) Patent No.: US 8,129,376 B2
(45) Date of Patent: Mar. 6, 2012

(54) PIPERIDINE DERIVATIVES AS INHIBITORS OF STEAROYL-COA DESATURASE

(76) Inventors: Kumar Sundaresan, Madurai (IN); P. Bala Koteswara Rao, Nagaram (IN); Bharathiraja Ainan, Trichy (IN); Hariharasubramanian Ayyamperumal, Tirunelveli (IN); Girish A R, Mysore (IN); Srinivas Tatiparthy, Hyderabad (IN); Ganesh Prabhu, Shimoga (IN); Hosahalli Subramanya, Bangalore (IN); Alexander Bischoff, Smithtown, NY (US)

( * ) Notice: Subject to any disclaimer, the term of this patent is extended or adjusted under 35 U.S.C. 154(b) by 302 days.

(21) Appl. No.: 12/408,486

(22) Filed: Mar. 20, 2009

(65) Prior Publication Data

US 2009/0239810 A1 Sep. 24, 2009

Related U.S. Application Data

(60) Provisional application No. 61/049,480, filed on May 1, 2008.

(30) Foreign Application Priority Data

Mar. 20, 2008 (IN) .............................. 575/KOL/2008

(51) Int. Cl.
*A61K 31/5375* (2006.01)
*A61K 31/445* (2006.01)
*C07D 413/02* (2006.01)
*C07D 211/00* (2006.01)

(52) U.S. Cl. ..................... 514/235.5; 544/129; 514/327; 546/194; 546/221; 546/224

(58) Field of Classification Search ............... 514/235.5, 514/327; 544/129; 546/194, 221, 224
See application file for complete search history.

(56) References Cited

U.S. PATENT DOCUMENTS

| 5,459,151 | A | 10/1995 | Lombardo |
| 5,846,514 | A | 12/1998 | Foster et al. |
| 6,334,997 | B1 | 1/2002 | Foster et al. |
| 2007/0299081 | A1 | 12/2007 | Kamboj et al. |

FOREIGN PATENT DOCUMENTS

| EP | 0433662 A2 | 6/1991 |
| WO | WO0162954 A2 | 8/2001 |
| WO | WO0226944 A2 | 4/2002 |
| WO | WO2005047253 A2 | 5/2005 |

OTHER PUBLICATIONS

Golub et al. Science (1999), vol. 286 531-537.*
Lala et al. Cancer and Metastasis Reviews (1998), 17(1), 91-106.*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
International Search Report for PCT/US2009/037835, mailed Jun. 12, 2009.
Written Opinion of the International Searching Authority for PCT/US2009/037835, mailed Jun. 12, 2009.
Dobrzyn, Agnieszka, et al., Inhibition of Stearoyl-CoA Desaturase by Cyclic Amine Derivatives, Expert Opin. Ther. Patents, 18(4):457-460, 2008.
Xin, Zhili, et al., Discovery of Piperidine-aryl Urea-based Stearoyl-CoA Desaturase 1 Inhibitors, Bioorganic & Medicinal Chemistry Letters 18, 4298-4302, 2008.
Dean, D., Editor, Recent Advances in the Synthesis and Applications of Radiolabeled Compounds for Drug Discovery and Development, vol. 6, No. 10, pp. i-i(1), 2000.
Lindqvuist, Y., et al., Crystal Structure of Δ9 Stearoyl-acyl Carrier Protein Desaturase From Castor Seed and its Relationship to Other Di-iron Proteins, The EMBO Journal, vol. 15, No. 16, pp. 4081-4092, 1996.
de Antueno, RJ, et al., Relationship Between Mouse Liver Delta 9 Desaturase Activity and Plasma Lipds, Lipids, vol. 28, No. 4, pp. 285-290, 1993.
Kabalka, GW, The Synthesis of Radiolabeled Compounds via Organometallic Intermediates, Tetrahedron, vol. 45, No. 21, pp. 6601-6621, 1989.
Jeffcoat, R., et al., Numa, S., Editor, The Regulation of Desaturation and Elongation of Fatty Acids in Mammals, Fatty Acid Metabolism and Its Regulation, pp. 84-112, 1984.
Evans, EA, Synthesis of Radiolabelled Compounds, Journal of Radioanalytical and Nuclear Chemistry, vol. 64, Nos. 1-2, pp. 9-32, 1981.

* cited by examiner

*Primary Examiner* — Rebecca Anderson
*Assistant Examiner* — Samantha Shterengarts

(57) ABSTRACT

The present invention relates to piperidine derivatives that act as inhibitors of stearoyl-CoA desaturase. The invention also relates to methods of preparing the compounds, compositions containing the compounds, and to methods of treatment using the compounds.

22 Claims, No Drawings

PIPERIDINE DERIVATIVES AS INHIBITORS OF STEAROYL-COA DESATURASE

CROSS-REFERENCE TO RELATED APPLICATIONS

This application claims priority to U.S. Provisional Patent Application 61/049,480, which was filed on May 1, 2008; and to Indian Patent Application 575/KOL/2008, which was filed on Mar. 20, 2008.

FIELD OF THE INVENTION

The present invention relates to piperidine derivatives that act as inhibitors of stearoyl-CoA desaturase. The invention also relates to methods of preparing the compounds, compositions containing the compounds, and to methods of treatment using the compounds.

BACKGROUND OF THE INVENTION

Metabolic syndrome has become one of the leading health problems in the world. As a component of metabolic syndrome, obesity also has causal roles in other components of the syndrome, including insulin resistance, dyslipidemia, and cardiovascular diseases. Effective treatments for metabolic syndrome in general and obesity in particular have been lacking. Effective therapies for the treatment of obesity, a key element of metabolic syndrome, are urgently needed.

A number of mammalian stearoyl-coenzyme A desaturase (SCD) genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (see, e.g., Jeffcoat, R. et al., Elsevier Science, Vol. 4, pp. 85-112, 1984; de Antueno, R J, *Lipids*, Vol. 28, No. 4, pp. 285-290, 1993), it has only recently been directly implicated in human disease processes.

A single SCD gene, stearoyl-coenzyme A desaturase-1 (SCD1) has been characterized in humans. SCD1 is described in, e.g., International Publication No. application, WO 01/62954. A second human SCD isoform has recently been identified, and because it bears little sequence homology to alternate mouse or rat isoforms it has been named human SCD5 or hSCD5 (see, e.g., International Publication No. WO 02/26944).

SCD-1 catalyzes conversion of saturated fatty acids, stearoyl-CoA and palmitoyl-CoA, to monounsaturated fatty acids, oleoyl-CoA and pamitoleoyl-CoA, respectively. These fatty acids are components of membrane phospholipids, triglycerides, and cholesterol esters. Changes in SCD activity ultimately change membrane fluidity, lipoprotein metabolism, and adiposity. SCD-1 inhibition can lead to decreased adiposity and thus be a potential therapy for metabolic syndrome.

Since obesity is becoming increasingly prevalent worldwide, much effort is being devoted to understanding its pathogenesis and treatment. In recent years, several candidate genes have been proposed as therapeutic targets. However, stearoyl-CoA desaturase 1 is of special significance, because it is the major gene target of leptin—a central mediator of energy homeostasis. There is evidence that SCD1 deficiency activates metabolic pathways that promote b-oxidation and decrease lipogenesis in liver and skeletal muscles. One mechanism is via increased activation of AMP-activated protein kinase. SCD1 mutation results also in global changes in expression of genes involved in lipid metabolism. SCD1 deficient mice have increased energy expenditure, reduced body adiposity, and are resistant to diet-induced obesity.

Thus, SCD1 inhibition represents a new and important target for the treatment of various disorders such as obesity and related metabolic disorders. Accordingly, there is a need in the art for derivatives that act as inhibitors of stearoyl-CoA desaturase, such as SCD1.

SUMMARY OF THE INVENTION

The present invention relates to piperidine derivatives that act as inhibitors of stearoyl-CoA desaturase. The invention also relates to methods of preparing the compounds, compositions containing the compounds, and to methods of treatment using the compounds.

DETAILED DESCRIPTION OF THE INVENTION

In some embodiments, the present invention provides compounds of the formula:

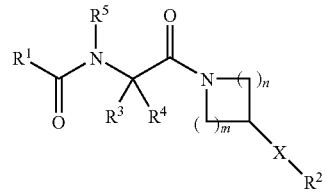

wherein
$R^1$ is aryl or heteroaryl;
$R^2$ is aryl or heteroaryl;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
m and n are, independently, 1 or 2;
X is —O—, —NR$^6$—, —S—, —S(O)— or —S(O)$_2$—
where $R^6$ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, solvates of pharmaceutically acceptable salts thereof, or enantiomer or diasteromer thereof;
with the proviso that said compound is not
4-[[(2R)-2,3-dihydro-2-methyl-6-nitroimidazo[2,1-b]oxazol-2-yl]methoxy]-N-[2-oxo-2-[4-[4-(trifluoromethoxy) phenoxy]-1-piperidinyl]ethyl]-benzamide,
N-[2-[4-[[4-amino-5-(2,6-difluorobenzoyl)-2-thiazolyl] amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

In some embodiments, the present invention provides compounds of the formula:

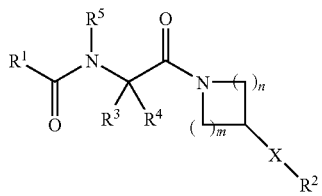

wherein
R¹ is heteroaryl;
R² is aryl or heteroaryl;
R³ and R⁴ are each independently hydrogen, halogen or alkyl; or
R³ and R⁴, together with the carbon atom to which they are attached, form a cycloalkyl group;
R⁵ is hydrogen or alkyl;
m and n are, independently, 1 or 2;
X is —O—, —NR⁶—, —S—, —S(O)— or —S(O)₂— where R⁶ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, solvates of pharmaceutically acceptable salts thereof, or enantiomer or diasteromer thereof.

In some embodiments, the present invention provides compounds of the formula:

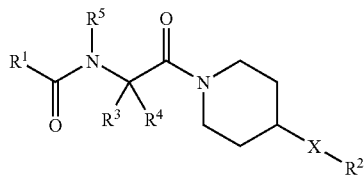

wherein
R¹ is aryl or heteroaryl;
R² is aryl or heteroaryl;
R³ and R⁴ are each independently hydrogen, halogen or alkyl; or
R³ and R⁴, together with the carbon atom to which they are attached, form a cycloalkyl group;
R⁵ is hydrogen or alkyl;
X is —O—, —NR⁶—, —S—, —S(O)— or —S(O)₂— where R⁶ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts or solvates, hydrates, or solvates of pharmaceutically acceptable salts thereof;
with the proviso that said compound is not 4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

In some embodiments, the present invention provides compounds of the formula:

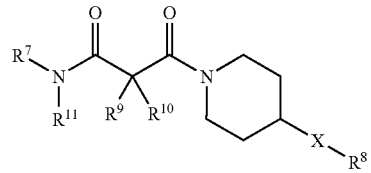

wherein
R⁷ is aryl or heteroaryl;
R⁸ is aryl or heteroaryl;
R⁹ and R¹⁰ are each independently hydrogen, halogen or alkyl; or
R⁹ and R¹⁰, together with the carbon atom to which they are attached, form a cycloalkyl group;
R¹¹ is hydrogen or alkyl;
X is —O—, —NR¹²—, —S—, —S(O)— or —S(O)₂— where R¹² is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof.

In some embodiments, the present invention includes compounds of the formula:

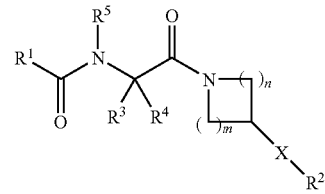

wherein
R¹ is aryl or heteroaryl;
R² is aryl or heteroaryl
R³ and R⁴ are each independently hydrogen, halogen or alkyl; or
R³ and R⁴, together with the carbon atom to which they are attached, form a cycloalkyl group;
R⁵ is hydrogen or alkyl;
m and n are, independently, 1 or 2 (in some embodiments, m is 1 or 2; and n is 1 or 2; wherein the sum of m and n is between 2 and 4, such as, for example, wherein the difference between m and n is 0 or 1);
X is —O—, —NR⁶—, —S—, —S(O)— or —S(O)₂— where R⁶ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, solvates of pharmaceutically acceptable salts thereof, or enantiomer or diasteromer thereof;
such as, with the proviso that said compound is not
4-[[(2R)-2,3-dihydro-2-methyl-6-nitroimidazo[2,1-b]ox-azol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
In some embodiments, the present invention includes compounds of the formula:

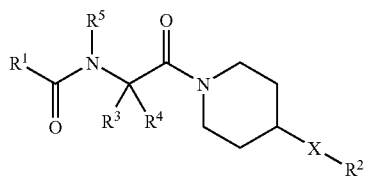

wherein
R¹ is aryl or heteroaryl;
R² is aryl or heteroaryl;
R³ and R⁴ are each independently hydrogen, halogen or alkyl; or
R³ and R⁴, together with the carbon atom to which they are attached, form a cycloalkyl group;
R⁵ is hydrogen or alkyl;
X is —O—, —NR⁶—, —S—, —S(O)— or —S(O)₂— where R⁶ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, solvates of pharmaceutically acceptable salts thereof, or enantiomer or diasteromer thereof;
such as, with the proviso that said compound is not
4-[[(2R)-2,3-dihydro-2-methyl-6-nitroimidazo[2,1-b]ox-azol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.
In some embodiments, the present invention includes compounds of the formula:

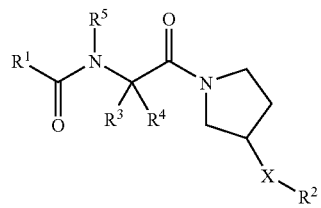

wherein
R¹ is aryl or heteroaryl;
R² is aryl or heteroaryl
R³ and R⁴ are each independently hydrogen, halogen or alkyl; or
R³ and R⁴, together with the carbon atom to which they are attached, form a cycloalkyl group;
R⁵ is hydrogen or alkyl;
X is —O—, —NR⁶—, —S—, —S(O)— or —S(O)₂— where R⁶ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, solvates of pharmaceutically acceptable salts thereof, or enantiomer or diasteromer thereof;
such as, with the proviso that said compound is not
4-[[(2R)-2,3-dihydro-2-methyl-6-nitroimidazo[2,1-b]ox-azol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

In some embodiments, the present invention includes compounds of the formula:

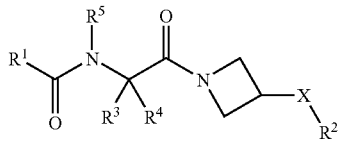

wherein

R¹ is aryl or heteroaryl;

R² is aryl or heteroaryl;

R³ and R⁴ are each independently hydrogen, halogen or alkyl; or

R³ and R⁴, together with the carbon atom to which they are attached, form a cycloalkyl group;

R⁵ is hydrogen or alkyl;

X is —O—, —NR⁶—, —S—, —S(O)— or —S(O)₂— where R⁶ is hydrogen or alkyl;

wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

and pharmaceutically acceptable salts, solvates, hydrates, solvates of pharmaceutically acceptable salts thereof, or enantiomer or diasteromer thereof;

such as, with the proviso that said compound is not

4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide, N-[2-[4-[[4-amino-5-(2,6-difluorobenzoyl)-2-thiazolyl]amino]-1-piperidinyl]-2-oxoethyl]-M-methyl-benzamide, 4-amino-N-[2-[4-[[4-amino-5-(2,6-difluorobenzoyl)-2-thiazolyl]amino]-1-piperidinyl]-2-oxoethyl]-benzamide, or a pharmaceutically acceptable salt thereof.

In another aspect, the present invention includes compounds of the formula:

(II)

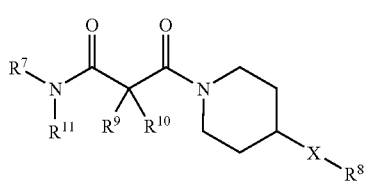

wherein

R⁷ is aryl or heteroaryl;

R⁸ is aryl or heteroaryl;

R⁹ and R¹⁰ are each independently hydrogen, halogen or alkyl; or

R⁹ and R¹⁰, together with the carbon atom to which they are attached, form a cycloalkyl group;

R¹¹ is hydrogen or alkyl;

X is —O—, —NR¹²—, —S—, —S(O)— or —S(O)₂— where R¹² is hydrogen or alkyl;

In some embodiments, R¹ is aryl (e.g., phenyl) or heteroaryl (e.g., pyridinyl, oxazolyl, imidazolyl), R² is aryl (e.g., phenyl), R³, R⁴ and R⁵ are each hydrogen, and X is —O—, —S—, or —NR⁶— where R⁶ is hydrogen or alkyl (e.g., methyl).

In some embodiments, R¹ is optionally substituted aryl (e.g., phenyl) or heteroaryl (e.g., pyridinyl, isoxazolyl, pyrazolyl). For example, R¹ is aryl (e.g., phenyl) or heteroaryl (e.g., pyridinyl, isoxazolyl, pyrazolyl) optionally substituted by one or more aryl (e.g., phenyl, substituted phenyl (e.g., -hydroxyphenyl)), or arylamino (i.e., —NH-aryl, e.g., —NHC₆H₅). For example, R¹ may be biphenyl (e.g., 4-biphenyl), (phenyl)isoxazolyl (e.g., 5-phenyl-isoxazol-3-yl), (phenylamino)phenyl (e.g., 4-phenylaminophenyl), (phenyl)pyrazolyl (e.g., 5-phenyl-1H-pyrazol-3-yl), (hydroxyphenyl)pyrazolyl (e.g., 5-(3-hydroxyphenyl)-1H-pyrazol-3-yl, 5-(4-hydroxyphenyl)-1H-pyrazol-3-yl), (phenyl)pyridinyl (e.g., 5-phenyl-pyridin-2-yl), (hydroxyphenyl)methylpyrazolyl (e.g., 5-(2-hydroxyphenyl)-1-methyl-1H-pyrazol-3-yl), (hydroxyphenyl)isoxazolyl (e.g., 5-(2-hydroxyphenyl)-isoxazol-3-yl, 5-(4-hydroxyphenyl)-isoxazol-3-yl), (phenylamino)pyridinyl (e.g., 6-phenylamino-pyridin-3-yl, 5-phenylamino-pyridin-2-yl). In some embodiments, R1 is aryl that is substituted by one or more aryl groups. In some embodiments, R1 is heteroaryl and is substituted by one or more aryl or heteroaryl groups. In some embodiments, R1 is pyrazole, triazole, or isoxazole.

In some embodiments, R² is optionally substituted aryl (e.g., phenyl). For example, R² is aryl (e.g., phenyl) optionally substituted by one or more halogen (e.g., F, Cl, Br), alkyl (e.g., methyl, t-butyl) nitro, amino or halogenated alkyl (e.g., CF₃). For example, R² is trifluoromethylphenyl (e.g., 2-trifluoromethylphenyl), bromophenyl (e.g., 2-bromophenyl), chlorophenyl (e.g., 2-chlorophenyl), trifluoromethylphenyl (e.g., 2-trifluoromethylphenyl), (chloro)fluorophenyl (e.g., 2-chloro-5-fluorophenyl), nitrophenyl (e.g., 2-nitrophenyl), aminophenyl (e.g., 2-aminophenyl), methylphenyl (e.g., 2-methylphenyl), dimethylphenyl (e.g., 2,3-dimethylphenyl, 2,4-dimethylphenyl, 2,5-dimethylphenyl), t-butylphenyl (e.g., 2-t-butylphenyl) or difluorophenyl (e.g., 2,5-difluorophenyl).

In some embodiments, X is —O—, —S—, or —NR⁶— where R⁶ is hydrogen or alkyl (e.g., methyl). For example, X is —O—, —S—, —NH— or —N(CH₃)—

In some embodiments, R³ and R⁴ are each independently hydrogen, halogen (e.g., F, Cl, Br) or alkyl (e.g., methyl). In other embodiments, R³ and R⁴ are hydrogen or alkyl (e.g., methyl).

In some embodiments, R³ and R⁴ are hydrogen or halogen (e.g., F). In one embodiment, R³ and R⁴ are hydrogen. In further embodiments, R³ and R⁴, together with the carbon atom to which they are attached, form a cycloalkyl group, such as a C₃-C₆ cycloalkyl (e.g., cyclopropyl, cyclobutyl, cyclopentyl, cyclohexyl), e.g., R³ and R⁴, together with the carbon atom to which they are attached, form a cyclopropyl ring.

In some embodiments, R⁵ is hydrogen or methyl. For example R⁵ is hydrogen.

In some embodiments, R⁷ is aryl (e.g., phenyl, biphenyl) or heteroaryl (e.g., pyridinyl, thiazolyl, thiadiazolyl), R⁸ is aryl (e.g., phenyl), X is —O—, —S—, or —NH—, R¹¹ is hydrogen, and R⁹ and R¹⁰ are hydrogen or together with the carbon atom to which they are attached R⁹ and R¹⁰ form a C₃-C₆ ring (e.g., cyclopropyl).

In some embodiments, $R^7$ is optionally substituted aryl (e.g., phenyl) or heteroaryl (e.g., pyridinyl, thiazolyl, thiadiazolyl). For example, $R^7$ is aryl (e.g., phenyl) or heteroaryl (e.g., pyridinyl, isoxazolyl, pyrazolyl) optionally substituted by one or more aryl (e.g., phenyl), or heteroaryl (e.g., oxadiazolyl).

For example, $R^7$ may be biphenyl (e.g., 4-biphenyl), (phenyl)pyridinyl (e.g., 6-phenyl-pyridin-3-yl, 5-phenyl-pyridin-2-yl), (phenyl)thiadiazolyl (e.g., 3-phenyl-[1,2,4]thiadiazol-5-yl), (oxadiazolyl)phenyl (e.g., 4-[1,2,4]oxadiazol-3-yl-phenyl) or (phenyl)thiazolyl (e.g., 5-phenyl-thiazol-2-yl).

In some embodiments, $R^8$ is optionally substituted aryl (e.g., phenyl). For example, $R^8$ is aryl (e.g., phenyl) optionally substituted by one or more halogen (e.g., F, Cl, Br), alkyl (e.g., methyl, t-butyl) nitro, amino or halogenated alkyl (e.g., $CF_3$). For example, $R^8$ is trifluoromethylphenyl (e.g., 2-trifluoromethylphenyl), bromophenyl (e.g., 2-bromophenyl), chlorophenyl (e.g., 2-chlorophenyl), (chloro)fluorophenyl (e.g., 2-chloro-5-fluorophenyl), nitrophenyl (e.g., 2-nitrophenyl), aminophenyl (e.g., 2-aminophenyl), methylphenyl (e.g., 2-methylphenyl), dimethylphenyl (e.g., 2,3-dimethylphenyl, 2,4-dimethylphenyl, 2,5-dimethylphenyl), t-butylphenyl (e.g., 2-t-butylphenyl) or difluorophenyl (e.g., 2,5-difluorophenyl).

In certain embodiments, X is —O—, —S—, or —$NR^{12}$— where $R^{12}$ is hydrogen or alkyl (e.g., methyl). For example, X is —O—, —S— or —NH—.

In certain embodiments, $R^9$ and $R^{10}$ are each independently hydrogen, halogen (e.g., F, Cl, Br) or alkyl (e.g., methyl). In other embodiments, $R^9$ and $R^{10}$ are hydrogen or alkyl (e.g., methyl). In other embodiments, $R^9$ and $R^{10}$ are hydrogen or halogen (e.g., F). In one embodiment, $R^9$ and $R^{10}$ are hydrogen. In further embodiments, $R^9$ and $R^{10}$, together with the carbon atom to which they are attached, form a cycloalkyl group, such as a $C_3$-$C_6$ cycloalkyl (e.g., cyclopropyl, cyclobutyl, cyclopentyl, cyclohexyl), e.g., $R^9$ and $R^{10}$, together with the carbon atom to which they are attached, form a cyclopropyl ring.

In some embodiments, $R^{11}$ is hydrogen or methyl. For example $R^{11}$ is hydrogen.

In some embodiments, $R^{12}$ is hydrogen or methyl. For example $R^{12}$ is hydrogen.

In certain embodiments, the compound is selected from:
i) 1-Cyclopentyl-1H-[1,2,3]triazole-4-carboxylic acid {2-[4-(5-chloro-pyridin-3-yloxy)-piperidin-1-yl]-2-oxo-ethyl}-amide;
ii) 1-Pyridin-3-yl-1H-[1,2,3]triazole-4-carboxylic acid {2-[4-(5-cyano-2-methyl-phenoxy)-piperidin-1-yl]-2-oxo-ethyl}-amide;
iii) 1-Morpholin-4-yl-1H-[1,2,3]triazole-4-carboxylic acid {2-oxo-2-[4-(3-trifluoromethyl-phenoxy)-piperidin-1-yl]-ethyl}-amide;
iv) 1-Morpholin-4-yl-1H-[1,2,3]triazole-4-carboxylic acid {2-[4-(2-chloro-5-fluoro-phenoxy)-piperidin-1-yl]-2-oxo-ethyl}-amide;
v) 1-Pyridin-3-yl-1H-[1,2,3]triazole-4-carboxylic acid {2-[3-(2,5-difluoro-phenoxy)-pyrrolidin-1-yl]-2-oxo-ethyl}-amide;
vi) 1-Phenyl-1H-imidazole-4-carboxylic acid {2-[4-(2,5-difluoro-phenoxy)-piperidin-1-yl]-2-oxo-ethyl}-amide; and
vii) 1-Phenyl-1H-imidazole-4-carboxylic acid {2-[4-(2-chloro-phenoxy)-piperidin-1-yl]-2-oxo-ethyl}-amide,
and pharmaceutically acceptable salts thereof, pharmaceutically acceptable solvates thereof, and solvates of pharmaceutically acceptable salts thereof.

In certain embodiments, the compound is selected from:
1. Biphenyl-4-carboxylic acid {2-oxo-2-[4-(2-trifluoromethyl-phenoxy)-piperidin-1-yl]-ethyl}-amide
2. Biphenyl-4-carboxylic acid {2-[4-(2-bromo-phenoxy)-piperidin-1-yl]-2-oxo-ethyl}-amide
3. Biphenyl-4-carboxylic acid {2-[4-(2-bromo-phenylamino)-piperidin-1-yl]-2-oxo-ethyl}-amide
4. Biphenyl-4-carboxylic acid {2-[4-(2-chloro-phenylamino)-piperidin-1-yl]-2-oxo-ethyl}-amide
5. Biphenyl-4-carboxylic acid {2-oxo-2-[4-(2-trifluoromethyl-phenylamino)-piperidin-1-yl]-ethyl}-amide
6. Biphenyl-4-carboxylic acid (2-{4-[methyl-(2-trifluoromethyl-phenyl)-amino]-piperidin-1-yl}-2-oxo-ethyl)-amide
7. Biphenyl-4-carboxylic acid (2-{4-[(2-chloro-phenyl)-methyl-amino]-piperidin-1-yl}-2-oxo-ethyl)-amide
8. Biphenyl-4-carboxylic acid (2-{4-[(2-bromo-phenyl)-methyl-amino]-piperidin-1-yl}-2-oxo-ethyl)-amide
9. 5-Phenyl-isoxazole-3-carboxylic acid {2-[4-(2-bromo-phenoxy)-piperidin-1-yl]-2-oxo-ethyl}-amide
10. 5-Phenyl-isoxazole-3-carboxylic acid {2-[4-(2-bromo-phenylamino)-piperidin-1-yl]-2-oxo-ethyl}-amide
11. 5-Phenyl-isoxazole-3-carboxylic acid {2-[4-(2-chloro-phenylamino)-piperidin-1-yl]-2-oxo-ethyl}-amide
12. 5-Phenyl-isoxazole-3-carboxylic acid (2-{4-[(2-bromo-phenyl)-methyl-amino]-piperidin-1-yl}-2-oxo-ethyl)-amide
13. 5-Phenyl-isoxazole-3-carboxylic acid {2-oxo-2-[4-(2-trifluoromethyl-phenylamino)-piperidin-1-yl]-ethyl}-amide
14. 5-Phenyl-isoxazole-3-carboxylic acid (2-{4-[methyl-(2-trifluoromethyl-phenyl)-amino]-piperidin-1-yl}-2-oxo-ethyl)-amide
15. N-{2-Oxo-2-[4-(2-trifluoromethyl-phenylamino)-piperidin-1-yl]-ethyl}-4-phenylamino-benzamide
16. N-{2-[4-(2-Chloro-phenylamino)-piperidin-1-yl]-2-oxo-ethyl}-4-phenylamino-benzamide
17. N-{2-[4-(2-Bromo-phenylamino)-piperidin-1-yl]-2-oxo-ethyl}-4-phenylamino-benzamide
18. N-(2-{4-[Methyl-(2-trifluoromethyl-phenyl)-amino]-piperidin-1-yl}-2-oxo-ethyl)-4-phenylamino-benzamide
19. N-{2-[4-(2-Bromo-phenoxy)-piperidin-1-yl]-2-oxo-ethyl}-4-phenylamino-benzamide
20. 5-Phenyl-1H-pyrazole-3-carboxylic acid {2-[4-(2-bromo-phenylamino)-piperidin-1-yl]-2-oxo-ethyl}-amide
21. 5-Phenyl-1H-pyrazole-3-carboxylic acid {2-[4-(2-chloro-phenylamino)-piperidin-1-yl]-2-oxo-ethyl}-amide
22. 5-Phenyl-1H-pyrazole-3-carboxylic acid {2-[4-(2-bromo-phenoxy)-piperidin-1-yl]-2-oxo-ethyl}-amide
23. 5-Phenyl-1H-pyrazole-3-carboxylic acid {2-[4-(2-chloro-phenylamino)-piperidin-1-yl]-2-oxo-ethyl}-amide
24. 5-Phenyl-1H-pyrazole-3-carboxylic acid {2-[4-(2-chloro-5-fluoro-phenoxy)-piperidin-1-yl]-2-oxo-ethyl}-amide
25. 5-Phenyl-1H-pyrazole-3-carboxylic acid {2-oxo-2-[4-(2-trifluoromethyl-phenylsulfanyl)-piperidin-1-yl]-ethyl}-amide
26. 5-Phenyl-1H-pyrazole-3-carboxylic acid {2-[4-(2-chlorophenylsulfanyl)-piperidin-1-yl]-2-oxo-ethyl}-amide
27. 5-Phenyl-1H-pyrazole-3-carboxylic acid {2-[4-(2-nitrophenoxy)-piperidin-1-yl]-2-oxo-ethyl}-amide
28. 5-Phenyl-1H-pyrazole-3-carboxylic acid {2-[4-(2-amino-phenoxy)-piperidin-1-yl]-2-oxo-ethyl}-amide
29. 5-Phenyl-1H-pyrazole-3-carboxylic acid {2-[4-(2,3-dimethyl-phenylamino)-piperidin-1-yl]-2-oxo-ethyl}-amide
30. 5-Phenyl-1H-pyrazole-3-carboxylic acid {2-[4-(2,4-dimethyl-phenylamino)-piperidin 1-yl]-2-oxo-ethyl}-amide, and pharmaceutically acceptable salts thereof, pharmaceutically acceptable solvates thereof, and solvates of pharmaceutically acceptable salts thereof.

In certain embodiments, the compound is selected from:

31. 5-Phenyl-1H-pyrazole-3-carboxylic acid {2-[4-(2,5-dimethyl-phenylamino)-piperidin-1-yl]-2-oxo-ethyl}-amide
32. 5-Phenyl-1H-pyrazole-3-carboxylic acid {2-[4-(2-tert-butyl-phenylamino)-piperidin-1-yl]-2-oxo-ethyl}-amide
33. 5-Phenyl-1H-pyrazole-3-carboxylic acid {2-[4-(2,5-difluoro-phenoxy)-piperidin-1-yl]-2-oxo-ethyl}-amide
34. 5-Phenyl-1H-pyrazole-3-carboxylic acid {2-[4-(2-bromo-phenylsulfanyl)-piperidin-1-yl]-2-oxo-ethyl}-amide
35. 5-Phenyl-1H-pyrazole-3-carboxylic acid [2-oxo-2-(4-o-tolylamino-piperidin-1-yl)-ethyl]-amide
36. 5-(3-Hydroxy-phenyl)-1H-pyrazole-3-carboxylic acid {2-[4-(2-chloro-phenylamino)-piperidin-1-yl]-2-oxo-ethyl}-amide
37. 5-Phenyl-pyridine-2-carboxylic acid {2-oxo-2-[4-(2-chloro-phenoxy)-piperidin-1-yl]-ethyl}-amide
38. 5-Phenyl-pyridine-2-carboxylic acid {2-[4-(2-chloro-5-fluoro-phenoxy)-piperidin-1-yl]-2-oxo-ethyl}-amide
39. 5-(4-Hydroxy-phenyl)-1H-pyrazole-3-carboxylic acid {2-[4-(2-chloro-phenylamino)-piperidin-1-yl]-2-oxo-ethyl}-amide
40. 5-(2-Hydroxy-phenyl)-1-methyl-1H-pyrazole-3-carboxylic acid {2-[4-(2-chloro-phenylamino)-piperidin-1-yl]-2-oxo-ethyl}-amide
41. Synthesis of 5-(2-Hydroxy-phenyl)-isoxazole-3-carboxylic acid {2-[4-(2-chloro-phenoxy)-piperidin-1-yl]-2-oxo-ethyl}-amide
42. 5-(2-Hydroxy-phenyl)-isoxazole-3-carboxylic acid {2-[4-(2-chloro-phenylamino)-piperidin-1-yl]-2-oxo-ethyl}-amide
43. 5-(2-Hydroxy-phenyl)-1H-pyrazole-3-carboxylic acid {2-[4-(2-chloro-phenylamino)-piperidin-1-yl]-2-oxo-ethyl}-amide
44. 5-(2-Hydroxy-phenyl)-1H-pyrazole-3-carboxylic acid {2-[4-(2-chloro-phenoxy)-piperidin-1-yl]-2-oxo-ethyl}-amide
45. N-{2-[4-(2-Chloro-phenoxy)-piperidin-1-yl]-2-oxo-ethyl}-6-phenylamino-nicotinamide
46. N-{2-[4-(2-Chloro-phenylamino)-piperidin-1-yl]-2-oxo-ethyl}-6-phenylamino-nicotinamide
47. 5-Phenylamino-pyridine-2-carboxylic acid {2-[4-(2-chloro-phenylamino)-piperidin-1-yl]-2-oxo-ethyl}-amide
48. 5-Phenylamino-pyridine-2-carboxylic acid {2-[4-(2-chloro-phenylamino)-piperidin-1-yl]-2-oxo-ethyl}-amide
49. 5-Phenyl-1H-pyrazole-3-carboxylic acid {2-[4-(5-bromo-2-methoxy-phenylamino)-piperidin-1-yl]-2-oxo-ethyl}-amide
50. 5-Phenyl-1H-pyrazole-3-carboxylic acid {2-oxo-2-[4-(3-trifluoromethyl-phenoxy)-piperidin-1-yl]-ethyl}-amide
51. 5-Phenyl-1H-pyrazole-3-carboxylic acid {2-[4-(2-cyano-phenoxy)-piperidin-1-yl]-2-oxo-ethyl}-amide
52. 5-(2-Fluoro-phenyl)-1H-pyrazole-3-carboxylic acid {2-[4-(2-chloro-phenylamino)-piperidin-1-yl]-2-oxo-ethyl}-amide
53. 5-Phenyl-1H-pyrazole-3-carboxylic acid {2-[4-(2,4-difluoro-phenylamino)-piperidin-1-yl]-2-oxo-ethyl}-amide
54. 5-Phenyl-1H-pyrazole-3-carboxylic acid {2-[4-(5-fluoro-2-trifluoromethyl-phenylamino)-piperidin-1-yl]-2-oxo-ethyl}-amide
55. 5-Phenyl-1H-pyrazole-3-carboxylic acid {2-[4-(4-fluoro-2-trifluoromethyl-phenylamino)-piperidin-1-yl]-2-oxo-ethyl}-amide
56. 5-Phenyl-1H-pyrazole-3-carboxylic acid {2-[4-(2-acetyl-phenoxy)-piperidin-1-yl]-2-oxo-ethyl}-amide
57. 5-Phenyl-1H-pyrazole-3-carboxylic acid {2-[4-(5-cyano-2-methyl-phenylamino)-piperidin-1-yl]-2-oxo-ethyl}-amide
58. 5-Phenyl-1H-pyrazole-3-carboxylic acid {2-oxo-2-[4-(2-trifluoromethyl-benzenesulfinyl)-piperidin-1-yl]-ethyl}-amide
59. 5-Phenyl-1H-pyrazole-3-carboxylic acid {2-oxo-2-[4-(pyridin-4-yloxy)-piperidin-1-yl]-ethyl}-amide
60. 5-Phenyl-1H-pyrazole-3-carboxylic acid {2-[4-(5-chloro-pyridin-3-yloxy)-piperidin-1-yl]-2-oxo-ethyl}-amide, and pharmaceutically acceptable salts thereof, pharmaceutically acceptable solvates thereof,
and solvates of pharmaceutically acceptable salts thereof.

In certain embodiments, the compound is selected from:

61. 5-Phenyl-1H-pyrazole-3-carboxylic acid {2-[4-(2-hydroxy-phenoxy)-piperidin-1-yl]-2-oxo-ethyl}-amide
62. 5-Phenyl-1H-pyrazole-3-carboxylic acid {2-oxo-2-[4-(2-trifluoromethyl-benzenesulfonyl)-piperidin-1-yl]-ethyl}-amide
63. 5-Phenyl-1H-pyrazole-3-carboxylic acid {2-[4-(6-chloro-pyridin-2-yloxy)-piperidin-1-yl]-2-oxo-ethyl}-amide
64. 4-Methyl-3-(1-{2-[(5-phenyl-1H-pyrazole-3-carbonyl)-amino]-acetyl}-piperidin-4-yloxy)-benzoic acid methyl ester
65. 5-Phenyl-1H-pyrazole-3-carboxylic acid {2-[4-(2-fluoro-5-trifluoromethyl-phenoxy)-piperidin-1-yl]-2-oxo-ethyl}-amide
66. 5-(2-Fluoro-phenyl)-1H-pyrazole-3-carboxylic acid {2-[4-(2-chloro-phenoxy)-piperidin-1-yl]-2-oxo-ethyl}-amide
67. 5-(2-Fluoro-phenyl)-1H-pyrazole-3-carboxylic acid {2-oxo-2-[4-(3-trifluoromethyl-phenoxy)-piperidin-1-yl]-ethyl}-amide
68. 5-(4-Trifluoromethyl-phenyl)-1H-pyrazole-3-carboxylic acid {2-[4-(2-chloro-phenoxy)-piperidin-1-yl]-2-oxo-ethyl}-amide
69. 5-(3-Fluoro-phenyl)-1H-pyrazole-3-carboxylic acid {2-oxo-2-[4-(3-trifluoromethyl-phenoxy)-piperidin-1-yl]-ethyl}-amide
70. 5-(3-Fluoro-phenyl)-1H-pyrazole-3-carboxylic acid {2-[4-(2-chloro-phenoxy)-piperidin-1-yl]-2-oxo-ethyl}-amide
71. 5-(2-Trifluoromethyl-phenyl)-1H-pyrazole-3-carboxylic acid {2-oxo-2-[4-(3-trifluoromethyl-phenoxy)-piperidin-1-yl]-ethyl}-amide
72. 5-(4-Hydroxy-phenyl)-1H-pyrazole-3-carboxylic acid {2-oxo-2-[4-(3-trifluoromethyl-phenoxy)-piperidin-1-yl]-ethyl}-amide
73. 5-(3-Hydroxy-phenyl)-1H-pyrazole-3-carboxylic acid {2-oxo-2-[4-(3-trifluoromethyl-phenoxy)-piperidin-1-yl]-ethyl}-amide
74. 5-(4-Fluoro-phenyl)-1H-pyrazole-3-carboxylic acid {2-oxo-2-[4-(3-trifluoromethyl-phenoxy)-piperidin-1-yl]-ethyl}-amide
75. 5-(4-Fluoro-phenyl)-1H-pyrazole-3-carboxylic acid {2-[4-(2-chloro-pyridin-3-yloxy)-piperidin-1-yl]-2-oxo-ethyl}-amide
76. 5-(4-Fluoro-phenyl)-1H-pyrazole-3-carboxylic acid {2-[4-(5-chloro-pyridin-3-yloxy)-piperidin-1-yl]-2-oxo-ethyl}-amide
77. 5-Phenyl-1H-pyrazole-3-carboxylic acid {2-[4-(3-chloro-phenoxy)-piperidin-1-yl]-2-oxo-ethyl}-amide 78. 3-(1-{2-[(5-Phenyl-1H-pyrazole-3-carbonyl)-amino]-acetyl}-piperidin-4-yloxy)-benzoic acid
79. 5-(3-Fluoro-phenyl)-1H-pyrazole-3-carboxylic acid {2-[4-(5-chloro-pyridin-3-yloxy)-piperidin-1-yl]-2-oxo-ethyl}-amide
80. 5-Phenyl-1H-pyrazole-3-carboxylic acid [2-oxo-2-(4-m-tolyloxy-piperidin-1-yl)-ethyl]-amide
81. 5-Phenyl-1H-pyrazole-3-carboxylic acid {2-[4-(2-methyl-pyridin-3-yloxy)-piperidin-1-yl]-2-oxo-ethyl}-amide
82. 5-Pyridin-2-yl-1H-pyrazole-3-carboxylic acid {2-[4-(2-chloro-phenoxy)-piperidin-1-yl]-2-oxo-ethyl}-amide
83. 3-(5-{2-Oxo-2-[4-(3-trifluoromethyl-phenoxy)-piperidin-1-yl]-ethylcarbamoyl}-1H-pyrazol-3-yl)-benzoic acid
84. 5-Pyridin-3-yl-1H-pyrazole-3-carboxylic acid {2-oxo-2-[4-(3-trifluoromethyl-phenoxy)-piperidin-1-yl]-ethyl}-amide
85. 5-Pyridin-3-yl-1H-pyrazole-3-carboxylic acid {2-[4-(2-chloro-phenoxy)-piperidin-1-yl]-2-oxo-ethyl}-amide
86. 5-Phenyl-1H-pyrazole-3-carboxylic acid {2-[4-(4-methyl-pyridin-3-yloxy)-piperidin-1-yl]-2-oxo-ethyl}-amide
87. 5-Phenyl-1H-pyrazole-3-carboxylic acid {2-oxo-2-[4-(5-trifluoromethyl-pyridin-3-yloxy)-piperidin-1-yl]-ethyl}-amide
88. 5-(5-Chloro-thiophen-2-yl)-1H-pyrazole-3-carboxylic acid {2-oxo-2-[4-(3-trifluoromethyl-phenoxy)-piperidin-1-yl]-ethyl}-amide
89. 5-(5-Chloro-thiophen-2-yl)-1H-pyrazole-3-carboxylic acid {2-[4-(2,5-difluoro-phenoxy)-piperidin-1-yl]-2-oxo-ethyl}-amide
90. 5-(2-Hydroxy-phenyl)-1H-pyrazole-3-carboxylic acid {2-oxo-2-[4-(3-trifluoromethyl-phenoxy)-piperidin-1-yl]-ethyl}-amide, and pharmaceutically acceptable salts thereof, pharmaceutically acceptable solvates thereof, and solvates of pharmaceutically acceptable salts thereof.

In certain embodiments, the compound is selected from:
91. 5-Phenyl-1H-pyrazole-3-carboxylic acid {2-[4-(2-methanesulfonyl-phenoxy)-piperidin-1-yl]-2-oxo-ethyl}-amide
92. 5-(2-Fluoro-phenyl)-isoxazole-3-carboxylic acid {2-[4-(2-chloro-phenylamino)-piperidin-1-yl]-2-oxo-ethyl}-amide
93. 5-Phenyl-isoxazole-3-carboxylic acid {2-oxo-2-[4-(3-trifluoromethyl-phenoxy)-piperidin-1-yl]-ethyl}-amide
94. 5-(2-Fluoro-phenyl)-isoxazole-3-carboxylic acid {2-oxo-2-[4-(3-trifluoromethyl-phenoxy)-piperidin-1-yl]-ethyl}-amide
95. 5-(2-Hydroxy-phenyl)-isoxazole-3-carboxylic acid {2-oxo-2-[4-(3-trifluoromethyl-phenoxy)-piperidin-1-yl]-ethyl}-amide
96. 5-(3-Hydroxy-phenyl)-isoxazole-3-carboxylic acid {2-oxo-2-[4-(3-trifluoromethyl-phenoxy)-piperidin-1-yl]-ethyl}-amide
97. 5-(4-Hydroxy-phenyl)-isoxazole-3-carboxylic acid {2-oxo-2-[4-(3-trifluoromethyl-phenoxy)-piperidin-1-yl]-ethyl}-amide
98. 5-(3-Fluoro-phenyl)-isoxazole-3-carboxylic acid {2-oxo-2-[4-(3-trifluoromethyl-phenoxy)-piperidin-1-yl]-ethyl}-amide
99. 5-(4-Fluoro-phenyl)-isoxazole-3-carboxylic acid {2-oxo-2-[4-(3-trifluoromethyl-phenoxy)-piperidin-1-yl]-ethyl}-amide
100. 5-(4-Fluoro-phenyl)-isoxazole-3-carboxylic acid {2-[4-(5-chloro-pyridin-3-yloxy)-piperidin-1-yl]-2-oxo-ethyl}-amide
101. 5-(4-Fluoro-phenyl)-isoxazole-3-carboxylic acid {2-[4-(2-chloro-pyridin-3-yloxy)-piperidin-1-yl]-2-oxo-ethyl}-amide
102. 5-(3-Fluoro-phenyl)-isoxazole-3-carboxylic acid {2-[4-(5-chloro-pyridin-3-yloxy)-piperidin-1-yl]-2-oxo-ethyl}-amide
103. 1-Phenyl-1H-pyrazole-4-carboxylic acid {2-[4-(2-chloro-phenoxy)-piperidin-1-yl]-2-oxo-ethyl}-amide
104. 2-[(Biphenyl-4-ylmethyl)-amino]-1-[4-(2-chloro-phenoxy)-piperidin-1-yl]-ethanone
105. N-{2-[4-(2-Chloro-phenoxy)-piperidin-1-yl]-2-oxo-ethyl}-4-[1,3,4]oxadiazol-2-yl-benzamide
106. 4-Phenyl-pyrazole-1-carboxylic acid {2-[4-(2-chloro-phenoxy)-piperidin-1-yl]-2-oxo-ethyl}-amide
107. 1-Phenyl-1H-[1,2,3]triazole-4-carboxylic acid {2-[4-(2-chloro-phenoxy)-piperidin-1-yl]-2-oxo-ethyl}-amide
108. 1-Phenyl-1H-[1,2,3]triazole-4-carboxylic acid {2-[4-(2-chloro-phenoxy)-piperidin-1-yl]-2-oxo-ethyl}-amide
109. 1-(3-Fluoro-phenyl)-1H-[1,2,3]triazole-4-carboxylic acid {2-oxo-2-[4-(3-trifluoromethyl-phenoxy)-piperidin-1-yl]-ethyl}-amide
110. 1-(3-Fluoro-phenyl)-1H-[1,2,3]triazole-4-carboxylic acid {2-[4-(2-chloro-5-fluoro-phenoxy)-piperidin-1-yl]-2-oxo-ethyl}-amide
111. 1-m-Tolyl-1H-[1,2,3]triazole-4-carboxylic acid {2-oxo-2-[4-(3-trifluoromethyl-phenoxy)-piperidin-1-yl]-ethyl}-amide
112. 1-m-Tolyl-1H-[1,2,3]triazole-4-carboxylic acid {2-[4-(2-chloro-5-fluoro-phenoxy)-piperidin-1-yl]-2-oxo-ethyl}-amide
113. 1-(2-Cyano-phenyl)-1H-[1,2,3]triazole-4-carboxylic acid {2-oxo-2-[4-(3-trifluoromethyl-phenoxy)-piperidin-1-yl]-ethyl}-amide
114. 1-(2-Cyano-phenyl)-1H-[1,2,3]triazole-4-carboxylic acid {2-oxo-2-[4-(3-trifluoromethyl-phenoxy)-piperidin-1-yl]-ethyl}-amide
115. 1-o-Tolyl-1H-[1,2,3]triazole-4-carboxylic acid {2-oxo-2-[4-(3-trifluoromethyl-phenoxy)-piperidin-1-yl]-ethyl}-amide
116. 1-Pyridin-3-yl-1H-[1,2,3]triazole-4-carboxylic acid {2-[4-(2-chloro-phenoxy)-piperidin-1-yl]-2-oxo-ethyl}-amide
117. 1-Cyclopentyl-1H-[1,2,3]triazole-4-carboxylic acid {2-[4-(5-chloro-pyridin-3-yloxy)-piperidin-1-yl]-2-oxo-ethyl}-amide
118. 1-(5-Fluoro-pyridin-3-yl)-1H-[1,2,3]triazole-4-carboxylic acid {2-[4-(2-chloro-phenoxy)-piperidin-1-yl]-2-oxo-ethyl}-amide
119. N-{2-[4-(2-Chloro-phenoxy)-piperidin-1-yl]-2-oxo-ethyl}-4-(5-methyl-[1,3,4]oxadiazol-2-yl)-benzamide
120. 3'-Dimethylamino-biphenyl-4-carboxylic acid {2-[4-(2-chloro-phenoxy)-piperidin-1-yl]-2-oxo-ethyl}-amide, and pharmaceutically acceptable salts thereof, pharmaceutically acceptable solvates thereof, and solvates of pharmaceutically acceptable salts thereof.

In certain embodiments, the compound is selected from:
121. N-{2-Oxo-2-[4-(3-trifluoromethyl-phenoxy)-piperidin-1-yl]-ethyl}-4-(pyrrolidine-1-carbonyl)-benzamide
122. 9H-Carbazole-3-carboxylic acid {2-oxo-2-[4-(3-trifluoromethyl-phenoxy)-piperidin-1-yl]-ethyl}-amide
123. 1-Phenyl-1H-imidazole-4-carboxylic acid {2-oxo-2-[4-(3-trifluoromethyl-phenoxy)-piperidin-1-yl]-ethyl}-amide
124. 1-Phenyl-1H-imidazole-4-carboxylic acid {2-[4-(2-chloro-5-fluoro-phenoxy)-piperidin-1-yl]-2-oxo-ethyl}-amide 125. 5-Phenyl-1H-pyrazole-3-carboxylic acid {2-[4-(2-formyl-phenoxy)-piperidin-1-yl]-2-oxo-ethyl}-amide
126. 2-(1-{2-[(5-Phenyl-1H-pyrazole-3-carbonyl)-amino]-acetyl}-piperidin-4-yloxy)-benzoic acid
127. 5-Phenyl-1H-pyrazole-3-carboxylic acid {2-[4-(2-hydroxymethyl-phenoxy)-piperidin-1-yl]-2-oxo-ethyl}-amide
128. 5-Phenyl-1H-pyrazole-3-carboxylic acid {2-oxo-2-[4-(3,4,5-trifluoro-phenoxy)-piperidin-1-yl]-ethyl}-amide
129. 5-Phenyl-1H-pyrazole-3-carboxylic acid (2-{4-[2-(hydroxyimino-methyl)-phenoxy]-piperidin-1-yl}-2-oxo-ethyl)-amide
130. 5-Phenyl-1H-pyrazole-3-carboxylic acid {2-oxo-2-[4-(2-trifluoromethyl-phenoxy)-piperidin-1-yl]-ethyl}-amide
131. 5-Phenyl-1H-pyrazole-3-carboxylic acid {2-[4-(3-cyano-phenoxy)-piperidin-1-yl]-2-oxo-ethyl}-amide
132. 5-Phenyl-1H-pyrazole-3-carboxylic acid (2-{4-[2-(methoxyimino-methyl)-phenoxy]-piperidin-1-yl}-2-oxo-ethyl)-amide
133. 5-Phenyl-1H-pyrazole-3-carboxylic acid {2-[4-(2-methylcarbamoyl-phenoxy)-piperidin-1-yl]-2-oxo-ethyl}-amide
134. 5-Phenyl-1H-pyrazole-3-carboxylic acid {2-[4-(2-carbamoyl-phenoxy)-piperidin-1-yl]-2-oxo-ethyl}-amide
135. 5-(2-Trifluoromethyl-phenyl)-1H-pyrazole-3-carboxylic acid {2-[4-(2-chloro-phenylamino)-piperidin-1-yl]-2-oxo-ethyl}-amide
136. 5-Phenyl-1H-pyrazole-3-carboxylic acid {2-[4-(3-cyano-phenylamino)-piperidin-1-yl]-2-oxo-ethyl}-amide
137. 5-Phenyl-1H-pyrazole-3-carboxylic acid {2-[4-(adamantan-2-ylamino)-piperidin-1-yl]-2-oxo-ethyl}-amide
138. 5-(2-Methoxy-phenyl)-1H-pyrazole-3-carboxylic acid {2-[4-(2-chloro-phenylamino)-piperidin-1-yl]-2-oxo-ethyl}-amide
139. 1-Pyrrolidin-3-yl-1H-[1,2,3]triazole-4-carboxylic acid {2-oxo-2-[4-(3-trifluoromethyl-phenoxy)-piperidin-1-yl]-ethyl}-amide
140. 1-(1-Methyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide
141. 1-(3,5-Difluoro-phenyl)-1H-[1,2,3]triazole-4-carboxylic acid {2-[4-(2-chloro-phenoxy)-piperidin-1-yl]-2-oxo-ethyl}-amide
142. 1-(3,5-Difluoro-phenyl)-1H-[1,2,3]triazole-4-carboxylic acid {2-[4-(5-chloro-pyridin-3-yloxy)-piperidin-1-yl]-2-oxo-ethyl}-amide
143. 1-Piperidin-4-yl-1H-[1,2,3]triazole-4-carboxylic acid {2-oxo-2-[4-(3-trifluoromethyl-phenoxy)-piperidin-1-yl]-ethyl}-amide hydrochloride
144. 1-(1-Methyl-piperidin-4-yl)-1H-[1,2,3]triazole-4-carboxylic acid {2-oxo-2-[4-(3-trifluoromethyl-phenoxy)-piperidin-1-yl]-ethyl}-amide
145. 1-Pyridin-3-yl-1H-[1,2,3]triazole-4-carboxylic acid {2-[4-(2,5-difluoro-phenoxy)-piperidin-1-yl]-2-oxo-ethyl}-amide
146. 1-Pyridin-3-yl-1H-[1,2,3]triazole-4-carboxylic acid {2-[4-(5-cyano-2-methyl-phenoxy)-piperidin-1-yl]-2-oxo-ethyl}-amide
147. 5-Phenyl-1H-pyrazole-3-carboxylic acid {2-oxo-2-[3-(3-trifluoromethyl-phenoxy)-pyrrolidin-1-yl]-ethyl}-amide
148. 4-(2-Oxo-pyrrolidin-1-yl)-N-{2-oxo-2-[4-(3-trifluoromethyl-phenoxy)-piperidin-1-yl]-ethyl}-benzamide
149. 1-Cyclopropyl-1H-[1,2,3]triazole-4-carboxylic acid {2-oxo-2-[4-(3-trifluoromethyl-phenoxy)-piperidin-1-yl]-ethyl}-amide
150. 1-Morpholin-4-yl-1H-[1,2,3]triazole-4-carboxylic acid {2-oxo-2-[4-(3-trifluoromethyl-phenoxy)-piperidin-1-yl]-ethyl}-amide, and pharmaceutically acceptable salts thereof, pharmaceutically acceptable solvates thereof, and solvates of pharmaceutically acceptable salts thereof.

In certain embodiments, the compound is selected from:
151. 1-Phenyl-1H-[1,2,3]triazole-4-carboxylic acid {2-[4-(3-cyano-phenoxy)-piperidin-1-yl]-2-oxo-ethyl}-amide
152. 1-Pyridin-3-yl-1H-[1,2,3]triazole-4-carboxylic acid {2-[3-(2,5-difluoro-phenoxy)-pyrrolidin-1-yl]-2-oxo-ethyl}-amide
153. 5-Phenyl-1H-pyrazole-3-carboxylic acid {2-oxo-2-[3-(3-trifluoromethyl-phenoxy)-azetidin-1-yl]-ethyl}-amide
154. 5-Pyridin-3-yl-1H-pyrazole-3-carboxylic acid {2-oxo-2-[3-(3-trifluoromethyl-phenoxy)-azetidin-1-yl]-ethyl}-amide
155. 5-Phenyl-1H-pyrazole-3-carboxylic acid {2-[3-(2,5-difluoro-phenoxy)-pyrrolidin-1-yl]-2-oxo-ethyl}-amide
156. 1-Phenyl-1H-imidazole-4-carboxylic acid {2-[4-(2,5-difluoro-phenoxy)-piperidin-1-yl]-2-oxo-ethyl}-amide
157. 1-Phenyl-1H-imidazole-4-carboxylic acid {2-[4-(2-chloro-phenoxy)-piperidin-1-yl]-2-oxo-ethyl}-amide
158. 1-Phenyl-1H-imidazole-4-carboxylic acid {2-[4-(5-cyano-2-methyl-phenoxy)-piperidin-1-yl]-2-oxo-ethyl}-amide
159. 1-Phenyl-1H-imidazole-4-carboxylic acid {2-[3-(3-fluoro-5-trifluoromethyl-phenoxy)-azetidin-1-yl]-2-oxo-ethyl}-amide
160. 1-Phenyl-1H-imidazole-4-carboxylic acid {2-[4-(3-fluoro-5-trifluoromethyl-phenoxy)-piperidin-1-yl]-2-oxo-ethyl}-amide
161. 1-Phenyl-1H-imidazole-4-carboxylic acid {2-[4-(4-fluoro-3-trifluoromethyl-phenoxy)-piperidin-1-yl]-2-oxo-ethyl}-amide
162. 1-Phenyl-1H-imidazole-4-carboxylic acid {2-[3-(2-chloro-phenoxy)-azetidin-1-yl]-2-oxo-ethyl}-amide
163. 1-Phenyl-1H-imidazole-4-carboxylic acid {2-[3-(5-cyano-2-methyl-phenoxy)-azetidin-1-yl]-2-oxo-ethyl}-amide
164. 1-Phenyl-1H-imidazole-4-carboxylic acid {2-[3-(2-chloro-phenoxy)-pyrrolidin-1-yl]-2-oxo-ethyl}-amide
165. 5-Phenyl-isoxazole-3-carboxylic acid {2-[3-(2,5-difluoro-phenoxy)-pyrrolidin-1-yl]-2-oxo-ethyl}-amide
166. 2-Phenyl-4H-thieno[3,2-b]pyrrole-5-carboxylic acid {2-[4-(2-chloro-5-fluoro-phenoxy)-piperidin-1-yl]-2-oxo-ethyl}-amide
167. 6-Pyrazol-1-yl-imidazo[1,2-a]pyridine-2-carboxylic acid {2-[4-(2-chloro-phenoxy)-piperidin-1-yl]-2-oxo-ethyl}-amide
168. 1-Pyridin-3-yl-1H-[1,2,3]triazole-4-carboxylic acid {2-[4-(3-cyano-phenoxy)-piperidin-1-yl]-2-oxo-ethyl}-amide
169. 1-Pyridin-3-yl-1H-[1,2,3]triazole-4-carboxylic acid {2-[3-(3-fluoro-5-trifluoromethyl-phenoxy)-azetidin-1-yl]-2-oxo-ethyl}-amide
170. 1-Pyridin-3-yl-1H-[1,2,3]triazole-4-carboxylic acid {2-[4-(3-fluoro-5-trifluoromethyl-phenoxy)-piperidin-1-yl]-2-oxo-ethyl}-amide
171. 1-Pyridin-3-yl-1H-[1,2,3]triazole-4-carboxylic acid {2-[3-(2-chloro-phenoxy)-pyrrolidin-1-yl]-2-oxo-ethyl}-amide
172. 1-Pyridin-3-yl-1H-[1,2,3]triazole-4-carboxylic acid {2-[4-(4-fluoro-3-trifluoromethyl-phenoxy)-piperidin-1-yl]-2-oxo-ethyl}-amide 173. 1-Pyridin-3-yl-1H-[1,2,3]triazole-4-carboxylic acid {2-[3-(2-chloro-phenoxy)-azetidin-1-yl]-2-oxo-ethyl}-amide
174. 1-Pyridin-3-yl-1H-[1,2,3]triazole-4-carboxylic acid {2-[3-(5-cyano-2-methyl-phenoxy)-azetidin-1-yl]-2-oxo-ethyl}-amide
175. 1-Pyridin-3-yl-1H-[1,2,3]triazole-4-carboxylic acid {2-oxo-2-[4-(2-trifluoromethyl-phenoxy)-piperidin-1-yl]-ethyl}-amide
176. 5-Phenyl-1H-pyrazole-3-carboxylic acid {2-[3-(3-fluoro-5-trifluoromethyl-phenoxy)-azetidin-1-yl]-2-oxo-ethyl}-amide
177. 5-Phenyl-1H-pyrazole-3-carboxylic acid {2-[4-(3-fluoro-5-trifluoromethyl-phenoxy)-piperidin-1-yl]-2-oxo-ethyl}-amide
178. 5-Phenyl-1H-pyrazole-3-carboxylic acid {2-[4-(4-fluoro-3-trifluoromethyl-phenoxy)-piperidin-1-yl]-2-oxo-ethyl}-amide
179. 5-Phenyl-1H-pyrazole-3-carboxylic acid {2-[3-(2-chloro-phenoxy)-azetidin-1-yl]-2-oxo-ethyl}-amide
180. 5-Phenyl-1H-pyrazole-3-carboxylic acid {2-[3-(5-cyano-2-methyl-phenoxy)-azetidin-1-yl]-2-oxo-ethyl}-amide,
and pharmaceutically acceptable salts thereof, pharmaceutically acceptable solvates thereof, and solvates of pharmaceutically acceptable salts thereof.

In certain embodiments, the compound is selected from:
181. N-Biphenyl-4-yl-3-[4-(2-bromo-phenoxy)-piperidin-1-yl]-3-oxo-propionamide
182. N-Biphenyl-4-yl-3-[4-(2-chloro-5-fluoro-phenoxy)-piperidin-1-yl]-3-oxo-propionamide
183. N-Biphenyl-4-yl-3-[4-(2-bromo-phenylamino)-piperidin-1-yl]-3-oxo-propionamide
184. N-Biphenyl-4-yl-3-[4-(2-bromo-phenylsulfanyl)-piperidin-1-yl]-3-oxo-propionamide
185. N-Biphenyl-4-yl-3-oxo-3-(4-o-tolylamino-piperidin-1-yl)-propionamide
186. N-Biphenyl-4-yl-3-[4-(2-nitro-phenoxy)-piperidin-1-yl]-3-oxo-propionamide
187. 3-[4-(2-Amino-phenoxy)-piperidin-1-yl]-N-biphenyl-4-yl-3-oxo-propionamide
188. N-Biphenyl-4-yl-3-[4-(2,3-dimethyl-phenylamino)-piperidin-1-yl]-3-oxo-propionamide
189. N-Biphenyl-4-yl-3-[4-(2,4-dimethyl-phenylamino)-piperidin-1-yl]-3-oxo-propionamide
190. N-Biphenyl-4-yl-3-[4-(2,5-dimethyl-phenylamino)-piperidin-1-yl]-3-oxo-propionamide
191. N-Biphenyl-4-yl-3-[4-(2-tert-butyl-phenylamino)-piperidin-1-yl]-3-oxo-propionamide
192. N-Biphenyl-4-yl-3-[4-(2,5-difluoro-phenoxy)-piperidin-1-yl]-3-oxo-propionamide
193. Synthesis of 3-[4-(2-Chloro-5-fluoro-phenoxy)-piperidin-1-yl]-3-oxo-N-(6-phenyl-pyridin-3-yl)-propionamide
194. 3-[4-(2-Chloro-5-fluoro-phenoxy)-piperidin-1-yl]-3-oxo-N-(5-phenyl-pyridin-2-yl)-propionamide
195. 3-[4-(2-Chloro-phenoxy)-piperidin-1-yl]-3-oxo-N-(6-phenyl-pyridin-3-yl)-propionamide
196. 3-[4-(2-Chloro-phenylamino)-piperidin-1-yl]-3-oxo-N-(6-phenyl-pyridin-3-yl)-propionamide
197. 3-[4-(2-Bromo-phenylamino)-piperidin-1-yl]-3-oxo-N-(6-phenyl-pyridin-3-yl)-propionamide
198. 3-Oxo-N-(6-phenyl-pyridin-3-yl)-3-[4-(2-trifluoromethyl-phenylamino)-piperidin-1-yl]-propionamide
199. 3-[4-(2-Chloro-phenylsulfanyl)-piperidin-1-yl]-3-oxo-N-(6-phenyl-pyridin-3-yl)-propionamide
200. 3-[4-(2-Bromo-phenylsulfanyl)-piperidin-1-yl]-3-oxo-N-(6-phenyl-pyridin-3-yl)-propionamide
201. 3-Oxo-N-(6-phenyl-pyridin-3-yl)-3-[4-(2-trifluoromethyl-phenylsulfanyl)-piperidin-1-yl]-propionamide
202. 3-Oxo-N-(6-phenyl-pyridin-3-yl)-3-[4-(2-trifluoromethyl-phenoxy)-piperidin 1-yl]-propionamide
203. 3-Oxo-N-(6-phenyl-pyridin-3-yl)-3-(4-o-tolylamino-piperidin-1-yl)-propionamide
204. 3-[4-(2-Chloro-phenoxy)-piperidin-1-yl]-3-oxo-N-(3-phenyl-[1,2,4]thiadiazol-5-yl)-propionamide
205. 3-[4-(2-Chloro-phenoxy)-piperidin-1-yl]-N-(4-[1,2,4]oxadiazol-3-yl-phenyl)-3-oxo-propionamide
206. 3-[4-(2-Chloro-phenoxy)-piperidin-1-yl]-3-oxo-N-(5-phenyl-thiazol-2-yl)-propionamide
207. 3-[4-(2-Chloro-phenylamino)-piperidin-1-yl]-3-oxo-N-(5-phenyl-thiazol-2-yl)-propionamide
208. 1-[4-(2-Chloro-phenoxy)-piperidine-1-carbonyl]-cyclopropane carboxylic acid biphenyl-4-ylamide
209. N-Biphenyl-4-yl-3-oxo-3-[4-(3,4,5-trifluoro-phenoxy)-piperidin-1-yl]-propionamide
210. N-Biphenyl-4-yl-3-[4-(3-cyano-phenoxy)-piperidin-1-yl]-3-oxo-propionamide,
and pharmaceutically acceptable salts thereof, pharmaceutically acceptable solvates thereof, and solvates of pharmaceutically acceptable salts thereof.

wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one or more halogens, such as, but not limited to, —$CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —$NH_2$.

The term "alkylamino" means —NH(alkyl), wherein alkyl is as described above.

The term "dialkylamino" means —N(alkyl)$_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —N(aryl)$_2$, wherein aryl is as described above.

The term "amido" means —$CONH_2$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocycle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocycloalkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion.

Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of the present invention can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of the invention can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN: 0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN: 0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, aDIPEAtes, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of the present invention can exist in different solvate forms. Solvates of the compounds of the invention may also form when solvent molecules are incorporated into the crystalline lattice structure of the compound molecule during the crystallization process.

The present invention also includes prodrugs of compounds of the present invention. The term prodrug is intended to represent covalently bonded carriers, which are capable of releasing the active ingredient of the present invention when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the present invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like. Prodrugs of compounds discussed herein are also within the scope of this invention.

The present invention also provides processes for preparing the compounds discussed herein through methods described in the following General Scheme:

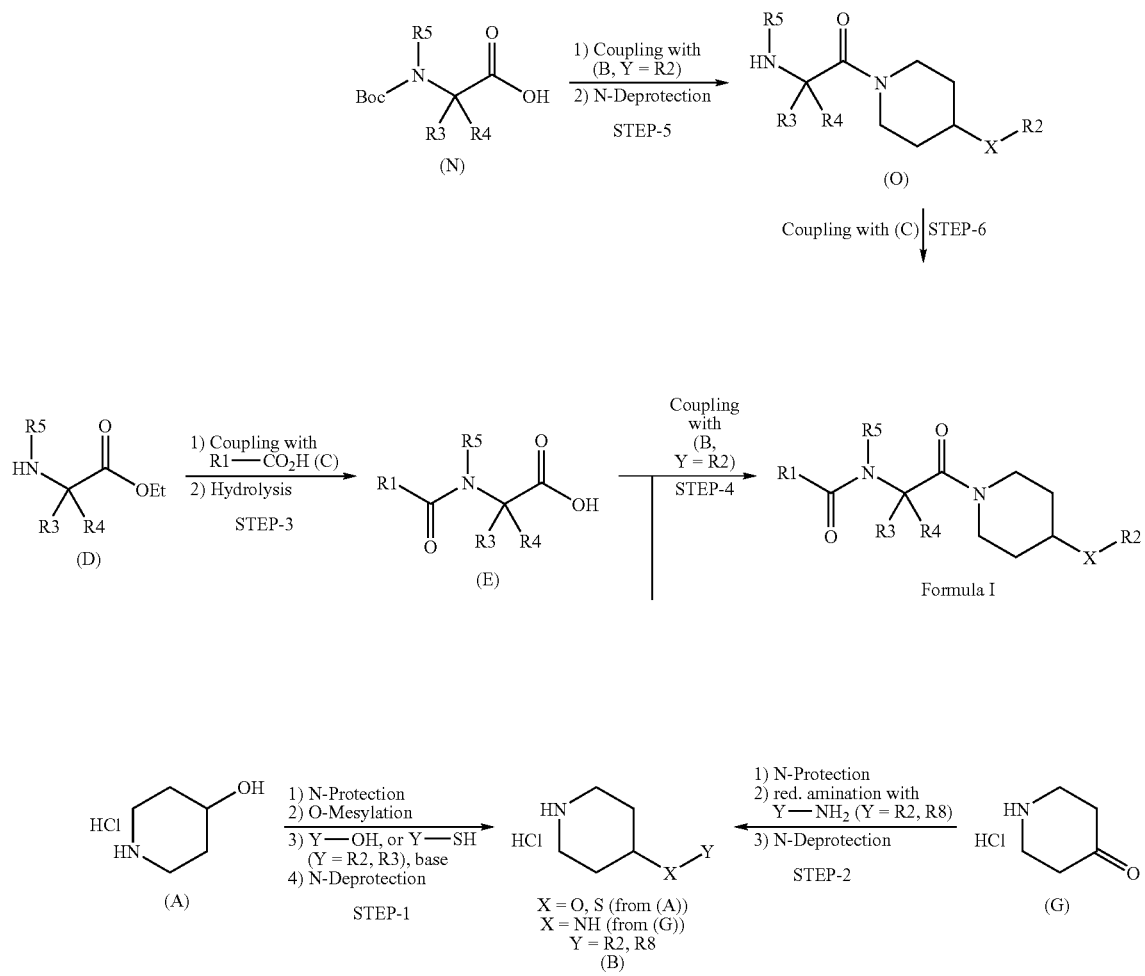

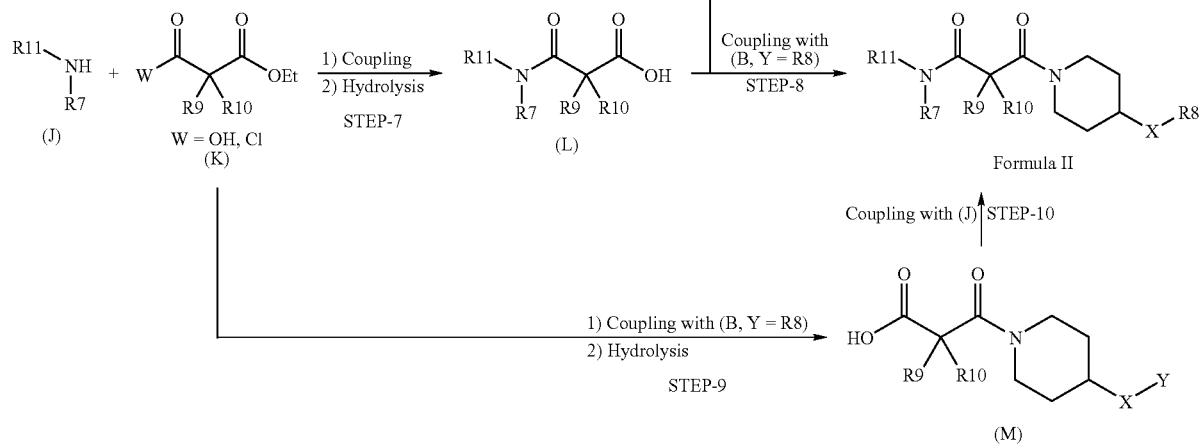

The starting materials for the above reaction scheme are commercially available or can be prepared according to methods known to one skilled in the art or by methods disclosed herein.

Compound (A) may be N-protected with a Boc or Cbz group via standard protection procedures and then activated as a mesylate or tosylate using procedures known in the art. The activated intermediate may then be reacted with an appropriately substituted ArOH or ArSH nucleophile or, alternatively, the alcohol intermediate can be reacted directly with a nucleophile under Mitsunobu conditions. Deprotection in a standard manner affords the desired amine compound (B) wherein X is O or S.

Compound (G), which is commercially available (for example, from Aldrich, St Louis, Miss.) may be protected with a Boc or Cbz group via standard protecting conditions known to the one skilled in the art and then treated with an appropriately substituted aryl amine under reductive amination conditions to generate compound (B).

Carboxylic acid (C) may be reacted with an appropriately substituted amine (D) in the presence of a standard peptide coupling reagent (such as EDCI) to give the desired amide product, which undergoes standard hydrolysis procedure known to the one skilled in the art to generate the carboxylic acid (E). Coupling between compounds (B) and (E) under standard amide bond formation conditions known to the one skilled in the art affords a compound of the present invention.

Compound (N), a glycine derivative, may be reacted with compound (B) under standard amide bond formation conditions known to the one skilled in the art to afford compound (O). Following standard hydrolysis of the N-protection group, compound (O) may be reacted with compound (C) under standard amide bond formation conditions known to the one skilled in the art affords a compound of the present invention.

Compound (J) may be reacted with an appropriately substituted malonic acid mono-ethyl ester (K) (when W=OH) in the presence of a standard peptide coupling reagents known to one skilled in the art, or alternatively compound (J) may be reacted with (K) as an acid chloride (when W=Cl) to give the desired amide product, which undergoes standard hydrolysis by procedures known to the one skilled in the art to generate the carboxylic acid (L). The coupling between compounds (L) and (B) under standard amide bond formation conditions known to the one skilled in the art affords a compound of the present invention.

Compound (B) may be reacted with an appropriately substituted malonic acid mono-ethyl ester (K) (when W=OH) in the presence of a standard peptide coupling reagents known to one skilled in the art, or alternatively compound (B) may be reacted with (K) as an acid chloride (when W=Cl) to give the desired amide product, which undergoes standard hydrolysis procedure known to the one skilled in the art to generate the carboxylic acid (M). The coupling between compounds (M) and (B) under standard amide bond formation conditions known to the one skilled in the art affords the compound of the present invention.

The compounds of the invention can be administered alone or as an active ingredient of a formulation. Thus, the present invention also includes pharmaceutical compositions of compounds of the present invention, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds of the present invention can be administered by inhalation in the form of a powder (e.g., micronized) or in the form of atomized solutions or suspensions. The aerosol formulation can be placed into a pressurized acceptable propellant.

The compounds of the present invention may be useful as inhibitors of stearoyl-CoA desaturase (SCD) enzymes, for example, as inhibitors of SCD-1 enzyme. Therefore, the compounds are useful in the treatment of conditions mediated by stearoyl-CoA desaturase (SCD) enzymes, e.g., SCD-1 enzyme.

According to another embodiment, the present invention relates to a method of treating a disease or condition mediated by stearoyl-CoA desaturase (e.g., SCD-1) by administering to a patient in need thereof a therapeutically effective amount of a compound of the present invention.

An SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including, but not limited to stroke, ischemic stroke and transient ischemic attack (TIA)), peripheral vascular disease, and ischemic retinopathy. In an embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In an embodiment, the compounds of the present invention are useful in the treatment of diabetes mellitus and obesity. In another embodiment, the compounds of the present invention are useful in the treatment of obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoaguability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes, but is not limited to, a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including, but not limited to, eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hyper virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Rymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

In one embodiment, the compounds of the inventions are useful in the treatment of elevated levels of lipids, cardiovascular diseases, diabetes, obesity, and metabolic syndrome.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of the present invention that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of the present invention may be used in combination with other drugs or therapies that are used in the treatment/prevention/suppression or amelioration of the diseases or conditions for which compounds discussed herein are useful.

Such other drug(s) may be administered, by a route and in an amount commonly used therefor, contemporaneously or sequentially with a compound of the present invention. When a compound of the present invention is used contemporaneously with one or more other drugs, a pharmaceutical unit dosage form containing such other drugs in addition to the compound of formula I may be employed. Accordingly, the pharmaceutical compositions of the present invention include those that also contain one or more other active ingredients, in addition to a compound of the present invention.

The present invention also provides processes for preparing the compounds of the present invention through methods described in the following General Scheme:

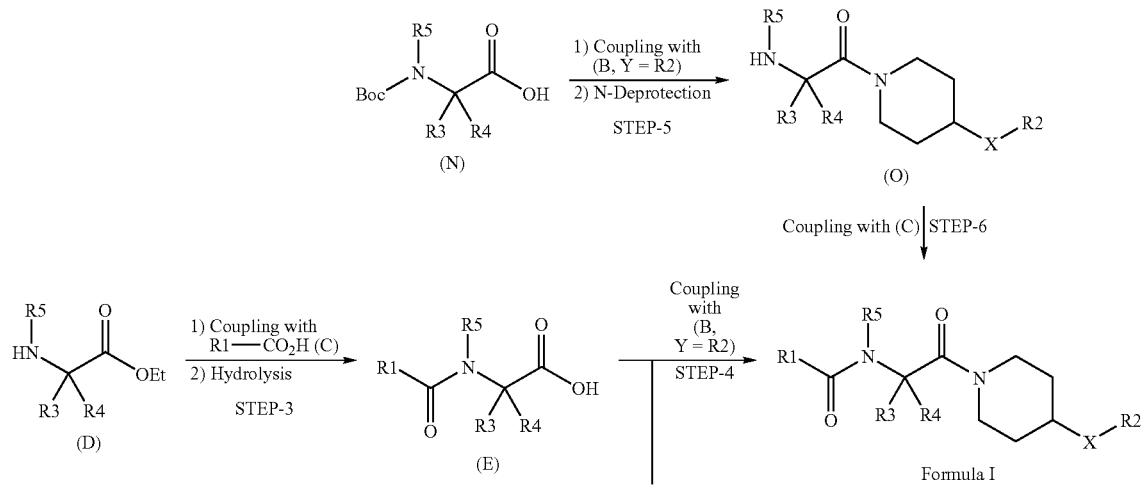

-continued

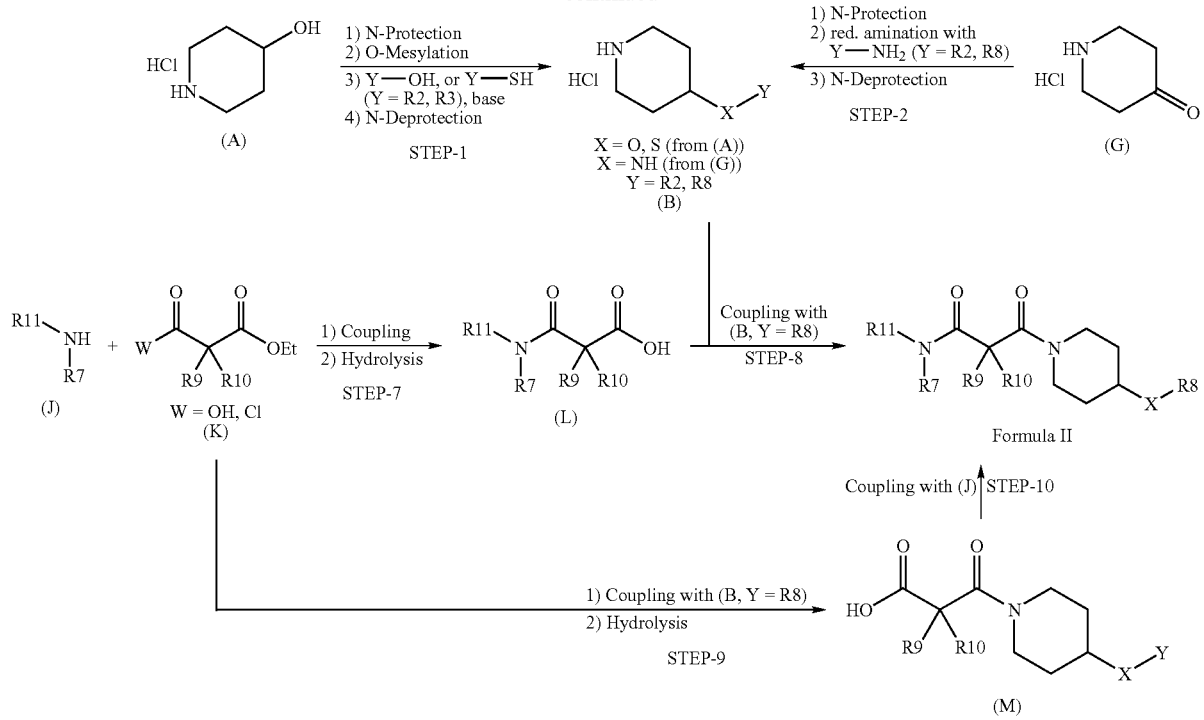

The starting materials for the above reaction Scheme are commercially available or can be prepared according to methods known to one skilled in the art or by methods disclosed herein.

Compound (A) may be N-protected with a Boc or Cbz group via standard protection procedures and then activated as a mesylate or tosylate using procedures known in the art. The activated intermediate may then be reacted with an appropriately substituted ArOH or ArSH nucleophile or, alternatively, the alcohol intermediate can be reacted directly with a nucleophile under Mitsunobu conditions. Deprotection in a standard manner affords the desired amine compound (B) wherein X is O or S.

Compound (G), which is commercially available (for example, from Aldrich, St Louis, Miss.) may be protected with a Boc or Cbz group via standard protecting conditions known to the one skilled in the art and then treated with an appropriately substituted aryl amine under reductive amination conditions to generate compound (B).

Carboxylic acid (C) may be reacted with an appropriately substituted amine (D) in the presence of a standard peptide coupling reagent (such as EDCI) to give the desired amide product, which undergoes standard hydrolysis procedure known to the one skilled in the art to generate the carboxylic acid (E). Coupling between compounds (B) and (E) under standard amide bond formation conditions known to the one skilled in the art affords a compound of the present invention.

Compound (N), a glycine derivative, may be reacted with compound (B) under standard amide bond formation conditions known to the one skilled in the art to afford compound (O). Following standard hydrolysis of the N-protection group, compound (O) may be reacted with compound (C) under standard amide bond formation conditions known to the one skilled in the art affords a compound of the present invention.

Compound (J) may be reacted with an appropriately substituted malonic acid mono-ethyl ester (K) (when W=OH) in the presence of a standard peptide coupling reagents known to one skilled in the art, or alternatively compound (J) may be reacted with (K) as an acid chloride (when W=Cl) to give the desired amide product, which undergoes standard hydrolysis by procedures known to the one skilled in the art to generate the carboxylic acid (L). The coupling between compounds (L) and (B) under standard amide bond formation conditions known to the one skilled in the art affords a compound of the present invention.

Compound (B) may be reacted with an appropriately substituted malonic acid mono-ethyl ester (K) (when W=OH) in the presence of a standard peptide coupling reagents known to one skilled in the art, or alternatively compound (B) may be reacted with (K) as an acid chloride (when W=Cl) to give the desired amide product, which undergoes standard hydrolysis procedure known to the one skilled in the art to generate the carboxylic acid (M). The coupling between compounds (M) and (B) under standard amide bond formation conditions known to the one skilled in the art affords the compound of the present invention.

EXAMPLES

The present invention will now be further described by way of the following non-limiting examples. In applying the disclosure of these examples, it should be kept clearly in mind that other and different embodiments of the methods and synthetic schemes disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The following abbreviations are used herein: Ac (acetyl), BINAP (2,2'-bis(diphenylphosphino)-1,1'-binaphthyl), Bn (benzyl), DCM (dichloromethane), DMF (dimethylformamide), DIPEA/DIEA (N,N-diisopropyl ethyl amine), EDCI (1-ethyl-3-[3-dimethylaminopropyl]carbodiimide hydrochloride), Et (ethyl), HOBT (1-hydroxybenzotriazole), Me (methyl), TFA (trifluoroacetic acid), THF (tetrahydrofuran), EtOAc (ethyl acetate), MeOH (methanol), Pd(OAc)$_2$ (palladium acetate), K$_2$CO$_3$ (potassium carbonate), HCOONH$_4$ (ammonium formate), Pd/C (palladium on carbon), Boc (tert-butoxycarbonyl), Na$_2$SO$_4$ (sodium sulfate), NaHCO$_3$ (sodium bicarbonate) HCl (hydrochloric acid), HBr (hydrogen bromide), NaCl (sodium chloride), brine (saturated aqueous sodium chloride solution), CHCl$_3$ (chloroform), Cs$_2$CO$_3$ (caesium carbonate, cesium carbonate), NaClO$_2$ (sodium chlorite), NH$_3$SO$_3$ [NH$_2$.SO$_3$H] (sulphamic acid), NaOH (sodium hydroxide), Cbz (benzyloxy carbonyl), DMAP (4-(dimethylamino)pyridine), celite (diatomaceous earth), TLC (thin layer chromatography), NMR (nuclear magnetic resonance), DMSO-d$_6$ (deuterated dimethyl sulfoxide), CDCl$_3$ (deuterated chloroform), LC-MS (LC-MS liquid chromatography-mass spectrometry), HPLC (high pressure liquid chromatography or high performance liquid chromatography), Intermediate 1

Synthesis of 4-Oxo-piperidine-1-carboxylic acid tert-butyl ester

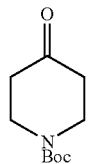

To a stirred solution of sodium carbonate (4.76 g, 0.0567 mole) in water (5.4 mL), was added 4-piperidone hydrochloride monohydrate (7.27 g, 0.0473 mole) in water (24 mL) followed by dropwise addition of di-tert-butyl dicarbonate (10.5 g, 0.048 mole) over a period of 30 minutes. The reaction mixture was warmed to 35° C. for 1 hour then heated to 50° C. for 2.5 hours. The reaction mixture was cooled to 10° C. The solid precipitate so obtained was filtered, washed with water and dried to afford 8.6 g (81%) of 4-oxo-piperidine-1-carboxylic acid tert-butyl ester. $^1$H NMR (DMSO-d$_6$): δ 3.6 (t, 4H), 2.4 (t, 4H), 1.4 (s, 9H).

Intermediate 2

Synthesis of (2-Bromo-phenyl)-piperidin-4-yl-amine dihydrochloride

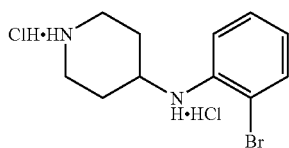

To a stirred solution of 4-oxo-piperidine-1-carboxylic acid tert-butyl ester (0.5 g, 0.0025 mole) in dry 1,2-dichloroethane (5 mL) under an atmosphere of nitrogen was added 2-bromoaniline (0.474 g, 0.00276 mole), acetic acid (0.18 g, 0.00301 mole) and sodium triacetoxyborohydride (0.638 g, 0.00301 mole). Stirring was continued at ambient temperature for 14 hours. The reaction mixture was quenched in cold aqueous 1N NaOH solution and the product extracted with ether. The organic layer was washed with brine solution, dried over sodium sulfate and concentrated under reduced pressure to afford the crude product as transparent viscous liquid. Purification by column chromatography using silica gel 60-120 mesh (2% ethyl acetate in hexane) afforded 0.320 g (35%) of desired 4-(2-bromo-phenylamino)-piperidine-1-carboxylic acid tert-butyl ester. $^1$H NMR (DMSO-d$_6$): δ 7.44-7.38 (m, 1H), 7.2-7.12 (m, 1H), 6.84-6.78 (m, 1H), 6.58-6.48 (m, 1H), 4.65 (d, 1H), 3.9 (m, 2H), 3.5 (m, 1H), 3.0-2.8 (m, 2H), 2.0-1.8 (m, 2H), 1.4 (s, 9H). To a cooled solution (0° C.) of 4-(2-bromo-phenylamino)-piperidine-1-carboxylic acid tert-butyl ester (0.31 g, 0.00087 mole) in dioxane (0.5 mL) was added dioxane.HCl (2.5 mL). The mixture was stirred at the same temperature for 10 minutes, then gradually brought to ambient temperature with continued stirring for a further 15 minutes. The reaction mixture was evaporated under reduced pressure to afford a residue which was washed with dry ether to afford 0.106 g (42%) of 2-bromo-phenyl)-piperidin-4-yl-amine dihydrochloride.

Intermediate 3

Synthesis of Piperidin-4-yl-(2-trifluoromethyl-phenyl)-amine dihydrochloride

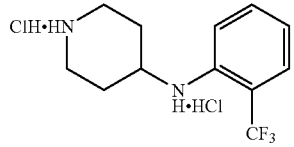

To a stirred solution of 4-oxo-piperidine-1-carboxylic acid tert-butyl ester (0.20 g, 0.0001 mole) in dry 1,2-dichloroethane (7 mL) under an atmosphere of nitrogen for 10 minutes, was added 2-trifluoromethylaniline (0.161 g, 0.0001 mole), acetic acid (0.06 g, 0.0001 mole) and sodium triacetoxyborohydride (1.05 g, 0.0005 mole). The stirring was continued at ambient temperature for 14 hours. The reaction mixture was then quenched in cold aqueous 1N NaOH solution and the product extracted with ether. The ether layer was washed with brine solution, dried over sodium sulfate and concentrated under reduced pressure to get the crude product as transparent viscous liquid. Purification by column chromatography using silica gel 60-120 mesh (2% ethyl acetate in hexane) afforded 0.106 g (31%) of 4-(2-trifluoromethyl-phenylamino)-piperidine-1-carboxylic acid tert-butyl ester. $^1$H NMR (DMSO-d$_6$): δ 7.4 (t, 2H), 7.0 (d, 1H), 6.7 (t, 1H), 3.9 (m, 2H), 2.9 (m, 2H), 1.9 (m, 2H), 1.4 (s, 9H). To a solution of 4-(2-trifluoromethyl-phenylamino)-piperidine-1-carboxylic acid tert-butyl ester (0.106 g, 0.000307 mole) in dioxane (0.5 mL) which was cooled to 0° C., was added, dioxane.HCl (2.5 mL) and the mixture was stirred at the same temperature for 10 minutes. The reaction mixture was gradually brought to ambient temperature and stirring was continued for 15 minutes. The reaction mixture was evaporated under reduced pressure and the resulting residue was washed with dry ether to afford 0.04 g (41%) of piperidin-4-yl-(2-trifluoromethyl-phenyl)-amine dihydrochloride. ¹H NMR (DMSO-d₆): δ 7.41 (t, 2H), 7.0 (d, 2H), 6.75 (t, 1H), 4.8 (d, 1H), 3.7 (bs, 1H), 3.3 (bs, 1H), 3.0 (m, 2H), 2.1 (m, 2H), 1.7 (m, 2H).

Intermediate 4

Synthesis of Piperidin-4-yl-o-tolyl-amine dihydrochloride

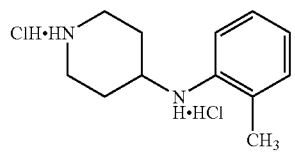

To a stirred solution of 4-oxo-piperidine-1-carboxylic acid tert-butyl ester (1 g, 0.00502 mole) in dry 1,2-dichloroethane (10 mL) under an atmosphere of nitrogen was added o-toluidine (0.699 g, 0.00652 mole), acetic acid (0.301 g, 0.005 mole) and sodium triacetoxyborohydride (1.596 g, 0.00753 mole) portionwise. The resulting mixture was stirred at ambient temperature for 16 hours. The mixture was then basified with sodium bicarbonate solution and the product extracted with dichloromethane. The organic layer was washed with brine solution, dried over sodium sulfate and concentrated under reduced pressure to afford a viscous liquid which was purified by column chromatography using neutral aluminium oxide (0.5% ethyl acetate in hexane) to afford 1.2 g (82%) of 4-O-tolylamino-piperidine-1-carboxylic acid tert-butyl ester. LCMS: 291.2 (M+1)⁺,%, ¹H NMR (CDCl₃): δ 7.1 (dd, 2H), 6.6 (t, 2H), 4.0 (d, 2H), 3.5-3.2 (m, 2H), 3.0-2.8 (t, 2H), 2.1 (m, 4H), 1.45 (s, 9H). A solution of 4-O-tolylamino-piperidine-1-carboxylic acid tert-butyl ester (1.2 g, 0.00413 mole) in ethyl acetate.HCl (10 mL) was stirred at ambient temperature for 2 hours. The reaction mixture was then concentrated under reduced pressure and the resulting residue was washed with ether to afford 0.9 g (96%) of piperidin-4-yl-o-tolyl-amine dihydrochloride. LCMS: 191.15 (M+1)⁺, 98%

¹H NMR (DMSO-D⁶): δ 9.5 (d, 1H), 9.0 (d, 1H), 7.3 (m, 4H), 3.7 (m, 1H), 3.3 (d, 2H), 2.9 (q, 2H), 2.4 (s, 3H), 2.1 (m, 4H).

Intermediate 5

Synthesis of (2-Chloro-phenyl)-piperidin-4-yl-amine dihydrochloride

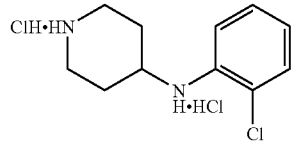

To a stirred solution of 4-oxo-piperidine-1-carboxylic acid tert-butyl ester (0.5 g, 0.0025 mole) in dry 1,2-dichloroethane (5 mL) (under an atmosphere of nitrogen for 10 minutes) was added, 2-chloroaniline (0.352 g, 0.0027 mole), acetic acid (0.125 g, 0.00209 mole) and sodium triacetoxyborohydride (0.442 g, 0.00209 mole). The resulting mixture was stirred at ambient temperature for 16 hours. The reaction mixture was quenched in cold aqueous 1N NaOH solution and the product was extracted with dichloromethane. The organic layer was washed with brine solution, dried over sodium sulfate and concentrated under reduced pressure. The resulting residue was stirred with hexane. The hexane was then decanted and the residue was dried to afford 0.615 g (79%) of 4-(2-chloro-phenylamino)-piperidine-1-carboxylic acid tert-butyl ester as a solid. ¹H NMR (DMSO-d₆): δ 7.6 (dd, 1H), 7.1 (t, 1H), 6.8 (d, 1H), 6.54 (t, 1H), 4.8 (d, 1H), 3.9 (d, 3H), 3.5 (m, 1H), 2.9 (bs, 2H), 1.8 (d, 2H), 1.4 (s, 9H), 1.3 (d, 1H). To a stirred, cooled (0° C.) solution of 4-(2-chloro-phenylamino)-piperidine-1-carboxylic acid tert-butyl ester (0.150 g, 0.00048 mole) in dioxane (0.5 mL) was added dioxane.HCl (1.5 mL). The stirring was continued at the same temperature for 10 minutes, then the mixture was gradually brought to ambient temperature with continued stirring for a further 15 minutes. The reaction mixture was evaporated under reduced pressure and the resulting residue was washed with dry ether and dried to afford 0.118 g (99%) of (2-chloro-phenyl)-piperidin-4-yl-amine dihydrochloride.

Intermediate 6

Synthesis of (2,3-Dimethyl-phenyl)-piperidin-4-yl-amine dihydrochloride

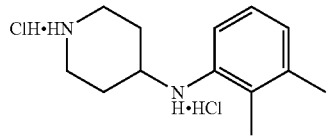

To a stirred solution of 4-oxo-piperidine-1-carboxylic acid tert-butyl ester (1 g, 0.00502 mole) in dry 1,2-dichloroethane (10 mL) (under an atmosphere of nitrogen for 10 minutes) was added 2,3-dimethylaniline (0.73 g, 0.00602 mole), acetic acid (0.301 g, 0.005 mole) and sodium triacetoxyborohydride (1.596 g, 0.00753 mole) portionwise with stirring. The stirring was continued at ambient temperature for a further 16 hours. The reaction mixture was basified with sodium bicarbonate solution and the product extracted with dichloromethane. The dichloromethane layer was washed with brine solution, dried over sodium sulfate and concentrated under reduced pressure to as afford a transparent viscous liquid which was purified by column chromatography using neutral aluminium oxide (1% ethyl acetate in hexane) to afford 1.5 g (98%) of 4-(2,3-dimethyl-phenylamino)-piperidine-1-carboxylic acid tert-butyl ester. ¹H NMR (CDCl₃): δ 7.0 (t, 1H), 6.6 (m, 2H), 4.1 (m, 2H), 3.5 (m, 1H), 3.0-2.9 (t, 2H), 2.3 (s, 3H), 2.1 (m, 2H), 2.0 (s, 3H), 1.5 (s, 9H), 1.4 (m, 2H). A solution of 4-(2,3-dimethyl-phenylamino)-piperidine-1-carboxylic acid tert-butyl ester (1.45 g, 0.00476 mole) in ethyl acetate.HCl (15 mL) was stirred at ambient temperature for 2 hours. The reaction mixture was concentrated under reduced pressure and the resulting residue was washed with ether and dried to afford 1.1 g (83) of (2,3-dimethyl-phenyl)-piperidin-4-yl-amine dihydrochloride. LCMS: 205.16 (M+1)⁺, 95.98%, ¹H NMR (DMSO-d₆): δ 9.4 (d, 1H), 9.0 (d, 1H), 7.3 (m, 3H), 3.7 (m, 2H), 3.3 (d, 2H), 3.1 (bs, 1H), 2.9 (m, 2H), 2.3 (d, 6H), 2.1 (m, 4H).

Intermediate 7

Synthesis of (2,4-Dimethyl-phenyl)-piperidin-4-yl-amine dihydrochloride

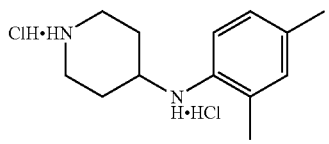

To a stirred solution of 4-oxo-piperidine-1-carboxylic acid tert-butyl ester (1 g, 0.00502 mole) in dry 1,2-dichloroethane (10 mL) (under an atmosphere of nitrogen for 10 minutes) was added 2,4-dimethylaniline (0.73 g, 0.00602 mole), followed by acetic acid (0.301 g, 0.005 mole) and sodium triacetoxyborohydride (1.596 g, 0.00753 mole) portionwise. The resulting mixture was stirred at ambient temperature for a further 16 hours. The reaction mixture was basified with sodium bicarbonate solution and the product was extracted with dichloromethane. The organic layer was washed with brine solution, dried over sodium sulfate and concentrated under reduced pressure. The resulting transparent viscous liquid was purified by column chromatography using neutral aluminium oxide (1% ethyl acetate in hexane) to 1.5 g (82%) of 4-(2,4-dimethyl-phenylamino)-piperidine-1-carboxylic acid tert-butyl ester. $^1$H NMR (CDCl$_3$): δ 6.9 (d, 2H), 6.6 (d, 1H), 4.1 (bs, 2H), 3.4 (m, 1H), 3.2 (bs, 1H), 2.9 (t, 2H), 2.2 (s, 3H), 2.1 (s, 3H), 2.1 (s, 3H), 2.0 (s, 2H), 1.5 (s, 9H), 1.4-1.2 (m, 2H). A solution of 4-(2,4-dimethyl-phenylamino)-piperidine-1-carboxylic acid tert-butyl ester (1.26 g, 0.00413 mole) in ethyl acetate.HCl (10 mL) was stirred at ambient temperature for 2 hours. The reaction mixture was concentrated under reduced pressure and the resulting residue was washed with ether and dried to afford 1.12 g (97%) of (2,4-dimethyl-phenyl)-piperidin-4-yl-amine dihydrochloride. LCMS: 205.16 (M+1)$^+$, 95.9%. $^1$H NMR (DMSO-d$_6$): δ 9.2 (d, 1H), 8.2 (d, 1H), 7.2 (m, 3H), 3.7 (m, 3H), 3.3 (d, 3H), 3.0 (q, 2H), 2.3 (m, 5H), 2.1 (d, 2H), 1.9 (d, 2H).

Intermediate 8

Synthesis of (2,5-Dimethyl-phenyl)-piperidin-4-yl-amine dihydrochloride

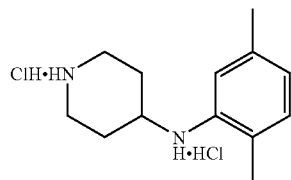

A solution of 4-oxo-piperidine-1-carboxylic acid tert-butyl ester (1 g, 0.00502 mole) in dry 1,2-dichloroethane (10 mL) was stirred under an atmosphere of nitrogen for 10 minutes. 2,5-dimethylaniline (0.73 g, 0.00602 mole), acetic acid (0.301 g, 0.005 mole) and sodium triacetoxyborohydride (1.596 g, 0.00753 mole) were then added portionwise and stirring was continued at ambient temperature for 16 hours. The reaction mixture was basified with sodium bicarbonate solution and the product was extracted with dichloromethane. The dichloromethane layer was washed with brine solution, dried over sodium sulfate and concentrated under reduced pressure. The resulting transparent viscous liquid was purified by column chromatography using neutral aluminium oxide (1% ethyl acetate in hexane) to afford 1.5 g (82%) of 4-(2,5-dimethyl-phenylamino)-piperidine-1-carboxylic acid tert-butyl ester. $^1$H NMR (CDCl$_3$): δ 7.0 (t, 1H), 6.6 (d, 2H), 4.2 (dd, 2H), 3.5 (m, 1H), 2.9 (t, 2H), 2.3 (t, 3H), 2.15 (s, 3H), 2.05 (s, 3H), 1.5 (s, 9H), 1.3 (t, 2H). A solution of 4-(2,5-dimethyl-phenylamino)-piperidine-1-carboxylic acid tert-butyl ester (1.5 g, 0.00492 mole) in ethyl acetate.HCl (7 mL) was stirred at ambient temperature for 2 hours. The reaction mixture was concentrated under reduced pressure and the residue was washed with ether and dried to afford 1.1 g (80%) of (2,5-dimethyl-phenyl)-piperidin-4-yl-amine dihydrochloride. LCMS: 205.16 (M+1)$^+$, 92.74%, $^1$H NMR (DMSO-d$_6$): δ 9.4 (d, 1H), 9.0 (d, 1H), 7.2 (d, 2H), 7.1 (s, 1H), 3.7 (m, $^1$H), 3.6 (s, 1H), 3.4 (d, 2H), 3.2 (bs, 1H), 2.9 (m, 2H), 2.4 (s, 3H), 2.3 (s, 3H), 2.1 (m, 4H).

Intermediate 9

Synthesis of (2-tert-Butyl-phenyl)-piperidin-4-yl-amine dihydrochloride

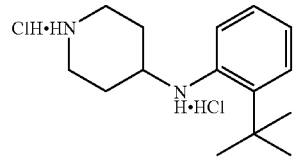

A solution of 4-oxo-piperidine-1-carboxylic acid tert-butyl ester (1 g, 0.00502 mole) in dry 1,2-dichloroethane (10 mL) was stirred under an atmosphere of nitrogen for 10 minutes. 2-Tert-butylaniline (0.974 g, 0.00652 mole), acetic acid (0.301 g, 0.005 mole) and sodium triacetoxyborohydride (1.596 g, 0.00753 mole) were then added portionwise and stirring was continued at ambient temperature for 16 hours. The reaction mixture was basified with sodium bicarbonate solution and the product was extracted with dichloromethane. The dichloromethane layer was washed with brine solution, dried over sodium sulfate and concentrated under reduced pressure. The resulting transparent viscous liquid was purified by column chromatography using neutral aluminium oxide (1-2% ethyl acetate in hexane) to afford 1.4 g (83%) of 4-(2-tert-butyl-phenylamino)-piperidine-1-carboxylic acid tert-butyl ester. $^1$H NMR (CDCl$_3$): δ 7.25 (m, 1H), 7.15 (t, 1H), 6.8-6.6 (m, 2H), 4.0 (dd, 2H), 3.9-3.8 (dd, 2H), 3.6 (bs, 1H), 3.1 (t, 2H), 2.2-2.2 (dd, 2H), 1.5-1.4 (d, 18H). A solution of 4-(2-tert-butyl-phenylamino)-piperidine-1-carboxylic acid tert-butyl ester (1.35 g, 0.00406 mole) in ethyl acetate. HCl (10 mL) was stirred at ambient temperature for 2 hours. The reaction mixture was concentrated under reduced pressure and the resulting residue was washed with ether and dried to afford 0.9 g (72%) of (2-tert-butyl-phenyl)-piperidin-4-yl-amine dihydrochloride. LCMS: 233.19 (M+1)$^+$, 86.32%, $^1$H NMR (DMSO-d$_6$): δ 9.1 (d, 2H), 7.2 (d, 1H), 7.1

(s, 3H), 6.8 (d, 1H), 6.6 (t, 1H), 3.7 (m, 1H), 3.4 (m, 3H), 3.0 (q, 3H), 2.6 (t, 1H), 2.2 (d, 2H), 1.7 (m, 2H), 1.4 (s, 9H).

Intermediate 10

Synthesis of (2-Bromo-phenyl)-methyl-piperidin-4-yl-amine

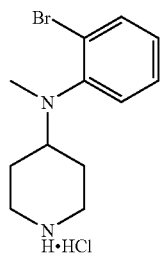

To a solution of 4-(2-bromophenylamino)-piperidine-1-carboxylic acid tert-butyl ester (2.0 g, 0.00562 mole), in DMF (10 mL) was added NaH (60% w/w dispersion in oil) (0.9 g, 0.02251 mole) and the resulting mixture was stirred at ambient temperature for 10 minutes under an atmosphere of nitrogen. Methyl iodide (3.19 g, 0.0225 mole) was then added and stirring was continued for 30 minutes at ambient temperature. The reaction mixture was quenched with aqueous $NH_4Cl$ solution and the product was extracted with ether. The ether layer with washed with aqueous $NaHCO_3$ solution followed by brine solution. The ether layer collected was dried over sodium sulfate and concentrated under reduced pressure. The resulting residue was washed with ether and dried to afford 0.893 g (45%) of 4-[(2-bromo-phenyl)-methyl-amino]-piperidine-1-carboxylic acid tert-butyl ester. $^1$H NMR ($CDCl_3$): δ 7.6-7.54 (m, 1H), 7.28-7.2 (m, 1H), 7.14-7.08 (m, 1H), 6.96-6.88 (m, 1H), 4.2-4.0 (m, 2H), 3.3-3.2 (m, 1H), 2.8-2.7 (m, 2H), 2.7 (s, 3H), 1.7-1.6 (m, 2H), 1.6 (m, 1H), 1.45 (s, 9H). A solution of 4-[(2-bromo-phenyl)-methyl-amino]-piperidine-1-carboxylic acid tert-butyl ester (0.89 g, 0.0024 mole) in dioxane.HCl was stirred for 30 minutes. The reaction was concentrated under reduced pressure to afford 0.704 g (95%) of (2-bromo-phenyl)-methyl-piperidin-4-yl-amine. $^1$H NMR (DMSO-$d_6$): δ 9.0 (bd, 3H), 7.6 (m, 1H), 7.4 (m, 2H), 7.0 (m, 1H), 3.2 (m, 3H), 2.9 (m, 2H), 2.6 (s, 3H), 1.9 (m, 3H).

Intermediate 11

Synthesis of (2-Chloro-phenyl)-methyl-piperidin-4-yl-amine hydrochloride

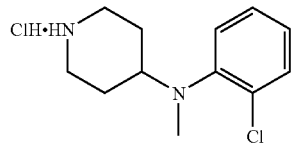

To a solution of 4-(2-chloro-phenylamino)-piperidine-1-carboxylic acid tert-butyl ester (0.166 g, 0.00053 mole), in DMF (10 mL) was added, NaH (60% w/w dispersion in oil) (0.0512 g, 0.0021 mole) and the resulting mixture was stirred at ambient temperature for 10 minutes under an atmosphere of nitrogen. Methyl iodide (0.303 g, 0.0021 mole) was then added, and the stirring was continued for 30 minutes at ambient temperature. The reaction mixture was heated to 45° C. for 30 minutes. The reaction mixture was then quenched with aqueous 10% $NH_4Cl$ solution and the product was extracted with ethyl acetate. The ethyl acetate layer was washed with aqueous $NaHCO_3$ solution followed by brine solution. The organic layer was collected, dried over sodium sulfate and concentrated under reduced pressure to afford 0.08 g (46%) of 4-[(2-chloro-phenyl)-methyl-amino]-piperidine-1-carboxylic acid tert-butyl ester. $^1$H NMR ($CDCl_3$): δ 7.6-7.54 (m, 1H), 7.28-7.2 (m, 1H), 7.14-7.08 (m, 1H), 6.96-6.88 (m, 1H), 4.2-4.0 (m, 2H), 3.3-3.2 (m, 1H), 2.8-2.7 (m, 2H), 2.7 (s, 3H), 1.7-1.6 (m, 2H), 1.6 (m, 1H), 1.45 (s, 9H). A solution of 4-(2-chloro-phenylamino)-piperidine-1-carboxylic acid tert-butyl ester (0.078 g, 0.00024 mole) in dioxane.HCl (1 mL) was stirred for 30 minutes. The reaction mixture was then concentrated under reduced pressure to afford 0.072 g (99%) of (2-chloro-phenyl)-methyl-piperidin-4-yl-amine hydrochloride which was used in the next step without further purification.

Intermediate 12

Synthesis of Methyl-piperidin-4-yl-(2-trifluoromethyl-phenyl)-amine hydrochloride

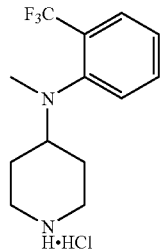

To a solution of 4-(2-trifluoromethyl-phenylamino)-piperidine-1-carboxylic acid tert-butyl ester (0.5 g, 0.00053 mole), in DMF (5 mL) was added, NaH (60% w/w dispersion in oil) (0.0696 g, 0.0029 mole) and the resulting mixture was stirred at ambient temperature for 10 minutes under an atmosphere of nitrogen. Methyl iodide (0.617 g, 0.00435 mole) was then added, and stirring was continued for 30 minutes at ambient temperature. The reaction mixture was quenched with aqueous 10% $NH_4Cl$ solution and the product was extracted with ether. The organic layer was washed with aqueous $NaHCO_3$ solution followed by brine solution. The ether layer was then collected, dried over sodium sulfate and concentrated under reduced pressure to afford 0.5 g of 4-[methyl-(2-trifluoromethyl-phenyl)-amino]-piperidine-1-carboxylic acid tert-butyl ester that which was used in the next step without further purification. 4-[Methyl-(2-trifluoromethyl-phenyl)-amino]-piperidine-1-carboxylic acid tert-butyl ester obtained (0.5 g) was stirred in dioxane.HCl (5 mL) for 30 minutes. The reaction mixture was concentrated under reduced pressure to afford 0.36 g (88%) of methyl-piperidin- 4-yl-(2-trifluoromethyl-phenyl)-amine hydrochloride which was used in the next step without further purification.

Intermediate 13

Synthesis of 4-Methanesulfonyloxy-piperidine-1-carboxylic acid tert-butyl ester

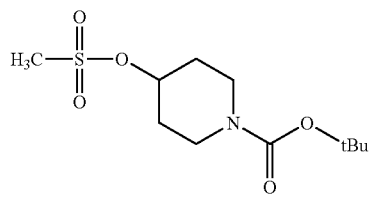

To a stirred solution of 4-hydroxy-piperidine hydrochloride monohydrate (10 g, 0.0988 mole) in THF (80 mL) was added triethylamine (11.98 g, 16.48 mL 0.1186 mole) and the resulting mixture was cooled to 10° C. Di-tert-butyl dicarbonate (23.68 g, 0.1086 mole) was added dropwise and stirring was continued at ambient temperature overnight. The reaction mixture was concentrated under reduced pressure and the resulting residue was acidified with concentrated HCl and extracted with ethyl acetate. The ethyl acetate layer was collected, dried over sodium sulfate and concentrated under reduced pressure to afford 19.47 g (98%) of 4-hydroxy-piperidine-1-carboxylic acid tert-butyl ester. $^1$H NMR (DMSO-$d_6$): δ 4.7 (d, 1H), 3.7-3.5 (m, 3H), 3.0-2.8 (t, 2H), 1.7-1.6 (m, 2H), 1.4 (s, 9H), 1.3-1.2 (m, 2H). To a stirred solution of 4-hydroxy-piperidine-1-carboxylic acid tert-butyl ester (10 g, 0.0497 mole) in THF (100 mL), was added triethylamine (6.026 g, 8.29 mL, 0.0596 mole) and the resulting mixture was cooled to 0-5° C. Methane sulfonyl chloride (6.76 g, 0.1086 mole) was then added dropwise over a period of 30 minutes and the mixture was maintained at 0-5° C. for 2 hrs. The reaction mixture was then diluted with cold water and the product extracted with ethyl acetate. The ethyl acetate layer was washed with 1N aqueous HCl solution, followed by saturated aqueous sodium bicarbonate solution and brine solution. The organic layer was collected, dried over sodium sulfate and concentrated under reduced pressure to afford 13.59 g (98%) of 4-methanesulfonyloxy-piperidine-1-carboxylic acid tert-butyl ester. $^1$H NMR (CDCl$_3$): δ 5.0-4.9 (m, 1H), 3.8-3.6 (m, 2H), 3.4-3.2 (m, 2H), 3.0 (s, 3H), 2.04-1.9 (m, 2H), 1.9-1.74 (m, 2H), 1.5-1.42 (s, 9H).

Intermediate 14

Synthesis of 4-(2-Trifluoromethyl-phenoxy)-piperidine trifluoracetate

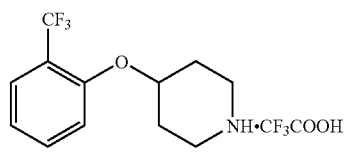

To a stirred solution of 2-trifluoromethyl-phenol (1 g, 0.00617 mole) in DMF (10 mL) was added cesium carbonate (4.01 g, 0.0123 mole), followed by 4-methanesulfonyloxy-piperidine-1-carboxylic acid tert-butyl ester (1.72 g, 0.00616 mole). The reaction mixture was heated at 60° C. overnight. The mixture was then diluted with water and the product was extracted with ethyl acetate. The ethyl acetate layer was washed with brine solution, dried over sodium sulfate, and concentrated under reduced pressure. The resulting residue was purified by column chromatography using silica gel 60-120 mesh (0.1% ethyl acetate in hexane) to afford 0.72 g (34%) of 4-(2-trifluoromethyl-phenoxy)-piperidine-1-carboxylic acid tert-butyl ester. LCMS: 346.16 (M+1)$^+$, 94.42%. A solution of 4-(2-trifluoromethyl-phenoxy)-piperidine-1-carboxylic acid tert-butyl ester (0.72 g, 0.00208 mole) in dichloromethane was stirred at 0-5° C. To the cold solution was added TFA (1 mL) dropwise and stirring was continued at 10° C. for 2 hours. The reaction mixture was concentrated under reduced pressure and the resulting residue was washed with ether and dried to afford 0.22 g (99%) of 4-(2-trifluoromethyl-phenoxy)-piperidine trifluoracetate. LCMS: 360.1 (M+1)$^+$, 99.3%, $^1$H NMR (CDCl$_3$): δ 8.9-8.5 (bd, 2H), 7.62-7.6 (d, 1H), 7.56-7.46 (t, 1H), 7.1-7.02 (t, 1H), 7.0-6.94 (d, 1H), 5.0-4.8 (m, 1H), 3.5-3.3 (s, 4H), 2.3-2.2 (s, 4H).

Intermediate 15

Synthesis of 4-(2-Chloro-phenoxy)-piperidine hydrochloride

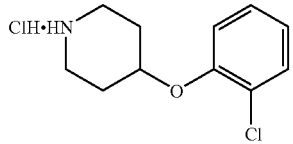

To a stirred solution of 2-chlorophenol (20 g, 0.155 mole) in DMF (200 mL), was added cesium carbonate (101 g, 0.311 mole), followed by 4-methanesulfonyloxy-piperidine-1-carboxylic acid tert-butyl ester (43.45 g, 0.155 mole). The reaction mixture was heated at 65° C. for 7 hours. The mixture was then filtered and concentrated under reduced. The resulting residue was diluted with ice cold water and the solid obtained was filtered and washed with water. The solid was dissolved in ether, washed with 2.5N aqueous NaOH solution, dried over sodium sulfate and concentrated under reduced pressure to afford 24.24 g (50%) of 4-(2-chloro-phenoxy)-piperidine-1-carboxylic acid tert-butyl ester. LCMS: 312.13 (M+1)$^+$, 98.35%. A solution of 4-(2-chloro-phenoxy)-piperidine-1-carboxylic acid tert-butyl ester (24.2 g, 0.0776 mole) in dioxane.HCl (30 mL), was stirred at ambient temperature for 2 hours. The reaction mixture was then concentrated under reduced pressure and the resulting residue was washed with hexane twice to afford 19.13 g (99.6%) of 4-(2-chloro-phenoxy)-piperidine hydrochloride. LCMS: 248.05 (M+1)$^+$, 92.79%. $^1$H NMR (DMSO-$d_6$): δ 9.3-8.9 (bs, 2H), 7.5-7.42

(d, 1H), 7.38-7.24 (m, 2H), 7.04-6.94 (t, 2H), 4.8-4.7 (m, 1H), 3.3-3.0 (bd, 4H), 2.2-2.05 (bs, 2H), 2.0-1.8 (bs, 2H).

Intermediate 16

Synthesis of 4-(2-Bromo-phenoxy)-piperidine trifluoroacetate

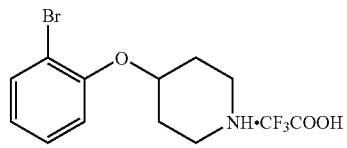

To a stirred solution of 2-bromophenol (0.5 g, 0.00289 mole) in DMF (4 mL) was added potassium carbonate (0.478 g, 0.003468 mole), followed by 4-methanesulfonyloxy-piperidine-1-carboxylic acid tert-butyl ester (0.888 g, 0.00318 mole). The reaction mixture was heated at 80° C. for 6 hours. The mixture was then diluted with water and the product was extracted with ethyl acetate. The ethyl acetate layer was washed with brine solution, dried over sodium sulfate, and concentrated under reduced pressure. The resulting residue was purified by column chromatography using silica gel 60-120 mesh (2% ethyl acetate in hexane) to afford 0.64 g (68%) of 4-(2-bromo-phenoxy)-piperidine-1-carboxylic acid tert-butyl ester. LCMS: 356.08 (M+1)$^+$, 99.56%. A solution of 4-(2-bromo-phenoxy)-piperidine-1-carboxylic acid tert-butyl ester (0.64 g, 0.0018 mole) in dichloromethane (6.4 mL) was stirred at 0-5° C. To the cold solution was added TFA (3.2 mL) dropwise and stirring was continued at ambient temperature for 3 hours. The reaction mixture was concentrated under reduced pressure and the resulting residue was washed with hexane to afford 0.64 g (96%) of 4-(2-bromo-phenoxy)-piperidine trifluoroacetate. LCMS: 370.02 (M+1)$^+$, 91.37%. $^1$H NMR (CDCl$_3$-D$_2$O): δ 7.6-7.54 (d, 1H), 7.32-7.26 (d, 1H), 6.94-6.86 (d, 2H), 4.8-4.7 (bs, 1H), 3.5-3.4 (m, 2H), 3.3-3.2 (m, 2H), 2.2-2.1 (s, 4H).

Intermediate 17

Synthesis of 4-(2,5-Difluoro-phenoxy)-piperidine hydrochloride

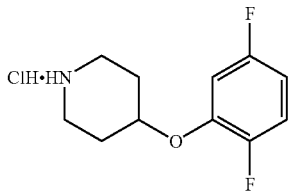

To a stirred solution of 2,5-difluorophenol (1.0 g, 0.0076 mole) in DMF (20 mL) was added cesium carbonate (12.4 g, 0.038 mole) followed by 4-methanesulfonyloxy-piperidine-1-carboxylic acid tert-butyl ester (2.1 g, 0.076 mole). The reaction mixture was heated at 80° C. overnight. The reaction mixture was then diluted with water and the product extracted with ethyl acetate. The ethyl acetate layer was washed with brine solution, dried over sodium sulfate, and concentrated. The resulting residue was purified by column chromatography using silica gel 60-120 mesh (10% ethyl acetate in hexane) to afford 1.5 g (63.0%) of 4-(2,5-Difluoro-phenoxy)-piperidine-1-carboxylic acid tert-butyl ester. LCMS: 356.08 (M+1)$^+$, 85%. $^1$H NMR (CDCl$_3$): δ 7.0 (m, 1H), 6.6 (m, 1H), 6.5 (m, 1H), 4.5 (m, 1H), 3.7 (m, 2H), 3.4 (m, 4H), 2 (m, 2H), 1.9 (m, 2H). 1.5 (s, 9H). A solution of 4-(2,5-difluoro-phenoxy)-piperidine-1-carboxylic acid tert-butyl ester (1.5 g, 0.0047 mole) in dioxane.HCl (2 mL) was stirred at ambient temperature for 1 hour. Ether was then added, and the resulting precipitate was isolated by filtration and dried to afford 0.65 g (65%) of 4-(2,5-difluoro-phenoxy)-piperidine hydrochloride. LCMS: 214.1 (M+1)$^+$, 100%. $^1$H NMR (CDCl$_3$): δ 9.2 (bs, 2H), 7.4 (m, 2H), 6.9 (m, 1H), 4.8 (m, 1H), 3.2 (m, 2), 3.0 (m, 2H), 2.2 (m, 2H), 1.9 (m, 2H).

Intermediate 18

Synthesis of 4-(2-Chloro-5-fluoro-phenoxy)-piperidine hydrochloride

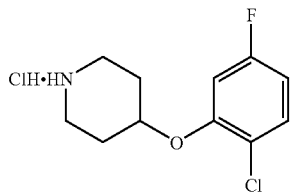

To a stirred solution of 2-chloro-5-fluorophenol (6 g, 0.0413 mole) in DMF (20 mL) was added cesium carbonate (26.89 g, 0.00827 mole) followed by 4-methanesulfonyloxy-piperidine-1-carboxylic acid tert-butyl ester (11.54 g, 0.04137 mole). The reaction mixture was heated at 80° C. for overnight. The mixture was then diluted with water and the product was extracted with ethyl acetate. The ethyl acetate layer was washed with brine solution, dried over sodium sulfate, and concentrated under reduced pressure. The resulting residue was purified by column chromatography using silica gel 230-400 mesh (2% ethyl acetate in hexane) to afford 8.9 g (65%) of 4-(2-chloro-5-fluoro-phenoxy)-piperidine-1-carboxylic acid tert-butyl ester. LCMS: 330.12 (M+1)$^+$, 100%. A solution of 4-(2-chloro-5-fluoro-phenoxy)-piperidine-1-carboxylic acid tert-butyl ester (8.9 g, 0.027 mole) in ethyl acetate.HCl (10 mL) was stirred at ambient temperature for 2 hours. The reaction mixture was then concentrated under reduced pressure and the resulting residue was washed with ether to afford 6.54 g (92%) of. LCMS: 230.07 (M+1)$^+$, 100%, $^1$H NMR (DMSO-d$_6$): δ 9.6-9.1 (bs, 2H), 7.55-7.45 (t, 1H), 7.35-7.2 (d, 1H), 6.9-6.8 (t, 1H), 4.9-4.7 (s, 1H), 3.26-3.0 (s, 4H), 2.2-2.06 (s, 2H), 2.0-1.8 (s, 2H).

Intermediate 19

Synthesis of 4-(2-Nitro-phenoxy)-piperidine hydrochloride

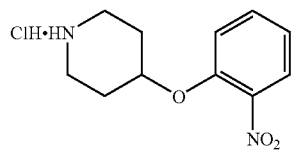

To a stirred solution of 2-nitrophenol (1.5 g, 0.0101 mole) in DMF (15 mL) was added cesium carbonate (16.4 g, 0.0505 mole) followed by 4-methanesulfonyloxy-piperidine-1-carboxylic acid tert-butyl ester (3.0 g, 0.0101 mole). The reaction mixture was heated at 80° C. overnight. The mixture was then diluted with water and the product was extracted with ethyl acetate. The ethyl acetate layer was washed with brine solution, dried over sodium sulfate, and concentrated under reduced pressure. The resulting residue was purified by column chromatography using silica gel 60-120 mesh (20% ethyl acetate in hexane) to afford 1.5 g (47%) of 4-(2-nitrophenoxy)-piperidine-1-carboxylic acid tert-butyl ester. LCMS: 323.15 (M+1)$^+$, 98%, $^1$H NMR (CDCl$_3$): δ 7.8 (m, 1H), 7.6 (m, 1H), 7.0 (m, 2H), 4.7 (m, 1H), 3.6 (m, 4H), 1.9 (m, 4H), 1.5 (s, 9H). A solution of 4-(2-nitro-phenoxy)-piperidine-1-carboxylic acid tert-butyl ester (1.5 g, 0.00465 mole) in dioxane.HCl (10 mL) was stirred at ambient temperature for 1 hour. Ether was then added the resulting precipitate was isolated by filtration and dried to afford 1 g (99%) of 4-(2-nitro-phenoxy)-piperidine hydrochloride. LCMS: 223.1 (M+1)$^+$, 55%, $^1$H NMR (DMSO-d$_6$): δ 9.0 (bs, 2H), 7.9 (m, 1H), 7.8 (m, 1H), 7.4 (m, 1H), 7.0 (m, 1H), 5.0 (m, 1H), 3.2 (m, 4H), 2.2 (m, 2H), 2.0 (m, 2H).

Intermediate 20

Synthesis of 4-(2-Bromo-phenylsulfanyl)-piperidine hydrochloride

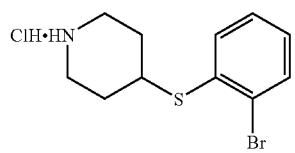

To a stirred solution of 2-bromobenzenethiol (1.0 g, 0.00529 mole) in DMF (10 mL) was added cesium carbonate (2.063 g, 0.0063 mole) followed by 4-methanesulfonyloxy-piperidine-1-carboxylic acid tert-butyl ester (1.478 g, 0.00529 mole). The reaction mixture was heated at 80° C. overnight. The mixture was then diluted with water and the product was extracted with ethyl acetate. The ethyl acetate layer was washed brine solution, dried over sodium sulfate and concentrated under reduced pressure. The resulting residue was washed with hexane to afford 1.93 g (98%) of 4-(2-bromo-phenylsulfanyl)-piperidine-1-carboxylic acid tert-butyl ester. LCMS: 372.06 (M+1)$^+$, 92.78%. A solution of 4-(2-bromo-phenylsulfanyl)-piperidine-1-carboxylic acid tert-butyl ester (1.93 g, 0.0052 mole) in dioxane.HCl (3 mL), was stirred at ambient temperature for 30 minutes. The reaction mixture was then concentrated under reduced pressure and the resulting residue was washed with hexane twice to afford 1.38 g (99%) of 4-(2-bromo-phenylsulfanyl)-piperidine hydrochloride. $^1$H NMR (DMSO-d$_6$): δ 9.1-8.9 (bs, 1H), 7.7-7.64 (d, 1H), 7.56-7.52 (d, 1H), 7.46-7.36 (t, 1H), 7.24-7.16 (t, 1H), 3.7-3.6 (m, 1H), 3.34-3.2 (bd, 3H), 3.1-2.94 (q, 2H), 2.16-2.04 (d, 2H), 1.84-1.66 (q, 2H).

Intermediate 21

Synthesis of 4-(2-Trifluoromethyl-phenylsulfanyl)-piperidine hydrochloride

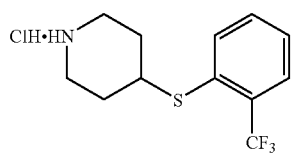

To a stirred solution of 2-trifluoromethylbenzenethiol (0.637 g, 0.00358 mole) in DMF (5 mL) was added cesium carbonate (1.396 g, 0.00429 mole) followed by 4-methanesulfonyloxy-piperidine-1-carboxylic acid tert-butyl ester (1.0 g, 0.00358 mole). The reaction mixture was heated at 80° C. overnight. The mixture was then diluted with water and the product was extracted with ethyl acetate. The ethyl acetate layer was washed brine solution, dried over sodium sulfate, filtered and concentrated. The resulting residue was washed with hexane to afford 0.81 g (99%) of 4-(2-trifluoromethyl-phenylsulfanyl)-piperidine-1-carboxylic acid tert-butyl ester. LCMS: 362.13 (M+1)$^+$, 99%. A solution of 4-(2-trifluoromethyl-phenylsulfanyl)-piperidine-1-carboxylic acid tert-butyl ester (0.81 g, 0.00224 mole) in dioxane.HCl (2 mL) was stirred at ambient temperature for 30 minutes. The reaction mixture was then concentrated under reduced pressure and the resulting residue was washed with hexane twice to afford 0.604 g (90%) of 4-(2-trifluoromethyl-phenylsulfanyl)-piperidine hydrochloride which was used in the next step without further purification. LCMS: 262.08 (M+1)$^+$, 95.07%.

Intermediate 22

Synthesis of 4-(2-Chloro-phenylsulfanyl)-piperidine hydrochloride

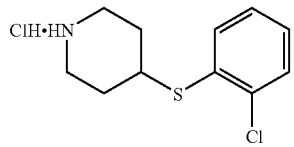

To a stirred solution of 2-chlorobenzenethiol (2.5 g, 0.017 mole) in DMF (20 mL) was added cesium carbonate (6.77 g, 0.0208 mole), followed by 4-methanesulfonyloxy-piperidine-1-carboxylic acid tert-butyl ester (4.8 g, 0.0173 mole). The reaction mixture was heated at 80° C. overnight. The mixture was then diluted with cold water and the product was extracted with ethyl acetate. The ethyl acetate layer was washed with brine solution, dried over sodium sulfate and concentrated under reduced pressure to afford 4.64 g (82%) of 4-(2-chloro-phenylsulfanyl)-piperidine-1-carboxylic acid tert-butyl ester. LCMS: 328.11 (M+1)$^+$, 95.12%. A solution of 4-(2-chloro-phenylsulfanyl)-piperidine-1-carboxylic acid tert-butyl ester (4 g, 0.0122 mole) in dioxane.HCl (7 mL) was stirred at ambient temperature for 30 minutes. The reaction mixture was then concentrated under reduced pressure and the resulting residue was washed with hexane twice to afford 3.75 g (99%) of 4-(2-chloro-phenylsulfanyl)-piperidine hydrochloride. LCMS: 228.05 (M+1)$^+$, 92.02%.

Intermediate 23

Synthesis of [(Biphenyl-4-carbonyl)-amino]-acetic acid

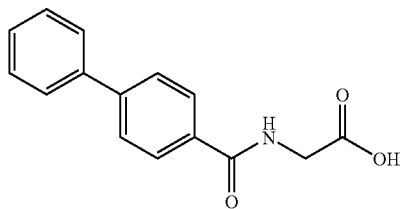

To a stirred solution of biphenyl-4-carboxylic acid (10 g, 0.05044 mole) in DMF (50 mL), was added DIPEA (22.82 g, 0.176 mol), HOBt (7.496 g, 0.0554 mol) and EDCI.HCl (17.4 g, 0.09 mol) at ambient temperature. After 2 minutes glycine ethyl ester hydrochloride (8.45 g, 0.06 mol) was added and the resulting mixture was stirred overnight. The reaction mixture was diluted with cold water and the resulting precipitate was isolated by filtration and dried to afford 14.26 g (99.8%) of [(biphenyl-4-carbonyl)-amino]-acetic acid ethyl ester. $^1$H NMR (DMSO-d$_6$): δ9.0 (t, 1H), 8.0-7.9 (d, 2H), 7.84-7.7 (dd, 4H), 7.5 (t, 2H), 7.46-7.36 (m, 1H), 4.2-4.1 (q, 2H), 4.0 (d, 2H), 1.25 (t, 3H). To a stirred solution of [(biphenyl-4-carbonyl)-amino]-acetic acid ethyl ester (14.26 g, 0.05 mol) in a mixture of THF (60 mL), methanol (60 mL) and H$_2$O (30 mL) was added LiOH.H$_2$O (12.68 g, 0.3023 mol) and the resulting mixture was stirred at ambient temperature for 1 hour. The volatiles were then evaporated and the residue was acidified with 10% aqueous HCl solution. The resulting precipitate was isolated by filtration washed with water followed by hexane and dried to afford 12.8 g (99%) of [(biphenyl-4-carbonyl)-amino]-acetic acid. $^1$H NMR (DMSO-d$_6$): δ 8.0-7.85 (m, 3H), 7.8-7.7 (m, 4H), 7.55-7.45 (t, 2H), 7.45-7.35 (t, 1H), 3.5 (d, 2H).

Example 1

Synthesis of Biphenyl-4-carboxylic acid {2-oxo-2-[4-(2-trifluoromethyl-phenoxy)-piperidin-1-yl]-ethyl}-amide

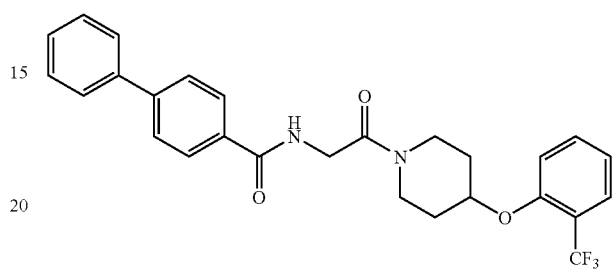

To a stirred solution of [(biphenyl-4-carbonyl)-amino]-acetic acid (0.09128 g, 0.00036 mol) in DMF (2 mL) was added DIPEA (0.126 g, 0.00098 mol), HOBt (0.05266 g, 0.0003901 mol) and EDCI.HCl (0.07457 g, 0.00039 mol) at ambient temperature. After 2 minutes 4-(2-trifluoromethyl-phenoxy)-piperidine trifluoroactetate (0.11 g, 0.00033 mol) was added and the resulting mixture was stirred at the same temperature overnight. The reaction mixture was diluted with cold water and the resulting precipitate was isolated by filtration and dried to afford 0.072 g (46%) of biphenyl-4-carboxylic acid {2-oxo-2-[4-(2-trifluoromethyl-phenoxy)-piperidin-1-yl]-ethyl}-amide. LCMS: 483.18 (M+1)$^+$, 95.73%, $^1$H NMR (CDCl$_3$): δ 7.9 (d, 2H), 7.64-7.54 (m, 4H), 7.46-7.3 (m, 4H), 7.02-6.9 (q, 2H), 4.75 (s, 1H), 4.4-4.2 (dd, 2H), 4.2-4.0 (m, 2H), 3.65-3.35 (m, 4H), 2.05-1.8 (m, 4H).

Example 2

Synthesis of Biphenyl-4-carboxylic acid {2-[4-(2-bromo-phenoxy)-piperidin-1-yl]-2-oxo-ethyl}-amide

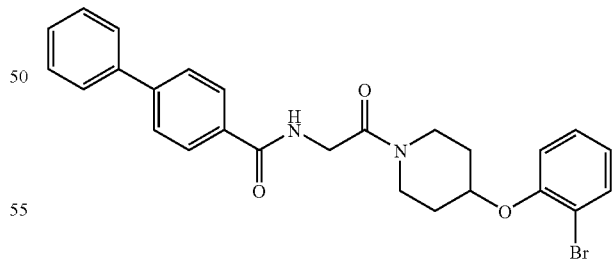

To a stirred solution of [(biphenyl-4-carbonyl)-amino]-acetic acid (0.08278 g, 0.00032 mol) in DMF (2 mL) was added, DIPEA (0.104 g, 0.00081 mol), HOBt (0.0437 g, 0.00032 mol) and EDCI.HCl (0.0619 g, 0.00032 mol) at ambient temperature. After 2 minutes 4-(2-bromo-phenoxy)-piperidine trifluoroacetate (0.1 g, 0.00027 mol) was added and the resulting mixture was stirred at the same temperature overnight. The reaction mixture was diluted with cold water and the product was extracted with ethyl acetate. The ethyl acetate layer was washed with saturated brine solution, dried over sodium sulfate and concentrated under reduced pressure. The resulting residue was purified by preparative HPLC [(column-Zorbax XDB $C_{18}$-21.2×150 mm, mobile phase-0.1% TFA in water (A)/acetonitrile (B), gradient: (Time): (% B)-0:50; 2:50; 5:80)]) to afford 0.033 g (22%) of biphenyl-4-carboxylic acid {2-[4-(2-bromo-phenoxy)-piperidin-1-yl]-2-oxo-ethyl}-amide. LCMS: 493.1 (M+1)$^+$, 98.35%, $^1$H NMR (DMSO-$d_6$): δ 8.65 (t, 1H), 8.0 (d, 2H), 7.8 (m, 4H), 7.6 (dd, 1H), 7.52 (t, 2H), 7.4 (m, 2H), 7.24 (m, 1H), 6.95 (m, 1H), 4.8 (m, 1H), 4.3 (m, 2H), 3.7 (m, 2H), 3.55 (m, 2H), 1.9 (m, 2H), 1.7 (m, 2H).

Example 3

Synthesis of Biphenyl-4-carboxylic acid {2-[4-(2-bromo-phenylamino)-piperidin-1-yl]-2-oxo-ethyl}-amide

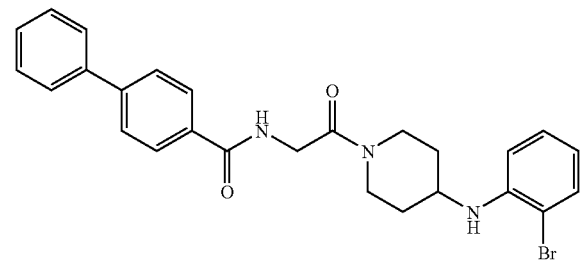

To a stirred solution of [(biphenyl-4-carbonyl)-amino]-acetic acid (0.075 g, 0.00029 mol) in DMF (2 mL), was added DIPEA (0.1139 g, 0.00088 mol) HOBt (0.0398 g, 0.00029 mol) and EDCI.HCl (0.06758 g, 0.00035 mol) at ambient temperature. After 2 minutes (2-bromo-phenyl)-piperidin-4-yl-amine dihydrochloride (0.09639 g, 0.00029 mol) was added and the resulting mixture was stirred at the same temperature for overnight. The reaction mixture was diluted with cold water and the resulting precipitate was isolated by filtration, washed with hexane followed by ether and dried to afford 0.067 g (46%) of biphenyl-4-carboxylic acid {2-[4-(2-bromo-phenylamino)-piperidin-1-yl]-2-oxo-ethyl}-amide. LCMS: 492.0 (M+1)$^+$, 90.08%, $^1$H NMR (DMSO-$d_6$): δ 8.62 (t, 1H), 7.94 (d, 2H), 7.79 (m, 4H), 7.5 (t, 2H), 7.4 (t, 2H), 7.2 (t, 1H), 6.84 (d, 1H), 6.57 (d, 1H), 4.6 (d, 1H), 4.3 (d, 1H), 4.2 (d, 2H), 3.9 (d, 1H), 3.6 (d, 1H), 2.7 (t, 1H), 1.9 (bs, 2H), 1.5-1.2 (m, 3H).

Example 4

Synthesis of Biphenyl-4-carboxylic acid {2-[4-(2-chloro-phenylamino)-piperidin-1-yl]-2-oxo-ethyl}-amide

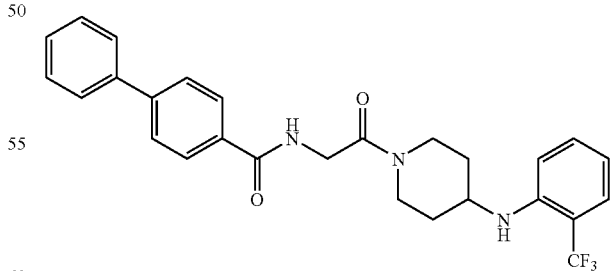

To a stirred solution of [(biphenyl-4-carbonyl)-amino]-acetic acid (0.134 g, 0.00053 mol) in DMF (2 mL) was added DIPEA (0.185 g, 0.00143 mol), HOBt (0.0646 g, 0.00048 mol) and EDCI.HCl (0.1098 g, 0.00057 mol) at ambient temperature. After 2 minutes (2-chloro-phenyl)-piperidin-4-yl-amine dihydrochloride (0.118 g, 0.00048 mol) was added and the resulting mixture was stirred at the same temperature overnight. The reaction mixture was then diluted with cold water and the resulting precipitate was isolated by filtration. Purification by preparative TLC using 30% ethyl acetate in hexane as eluent afforded 0.105 g (45%) of biphenyl-4-carboxylic acid {2-[4-(2-chloro-phenylamino)-piperidin-1-yl]-2-oxo-ethyl}-amide. LCMS: 448 (M+1)$^+$, 97.78%, $^1$H NMR (CDCl$_3$): δ 7.94 (d, 2H), 7.74-7.6 (m, 4H), 7.5-7.38 (m, 2H), 7.2-7.1 (m, 1H), 6.75-6.6 (m, 2H), 4.5 (m, 1H), 4.3 (d, 2H), 4.25 (d, 1H), 3.9 (m, 1H), 3.6 (m, 1H), 3.3 (m, 2H), 3.1 (m, 1H), 2.2 (bt, 2H), 1.5 (m, 2H).

Example 5

Synthesis of Biphenyl-4-carboxylic acid {2-oxo-2-[4-(2-trifluoromethyl-phenylamino)-piperidin-1-yl]-ethyl}-amide To a stirred solution of [(biphenyl-4-carbonyl)-amino]-acetic acid (0.03219 g, 0.00012 mol) in DMF (1 mL), was added, DIPEA (0.065 g, 0.0005 mol), HOBt (0.017 g, 0.00012 mol) and EDCI.HCl (0.2689 g, 0.00013 mol) at ambient temperature. After 2 minutes piperidin-4-yl-(2-trifluoromethyl-phenyl)-amine dihydrochloride (0.04 g, 0.00012 mol) was and the resulting mixture was stirred at the same temperature overnight. The reaction mixture was diluted with cold water, and the resulting precipitate was isolated by filtration. The solid was recrystallized from a mixture of ethyl acetate and hexane to afford 0.042 g (61%) of biphenyl-4-carboxylic acid {2-oxo-2-[4-(2-trifluoromethyl-phenylamino)-piperidin-1-yl]-ethyl}-amide. LCMS: 482.1 (M+1)+, 97.99%, $^1$H NMR (DMSO-$d_6$): δ 8.6 (t, 1H), 8.0 (m, 2H), 7.78-7.5 (m, 4H), 7.6-7.4 (m, 5H), 7.0 (d, 1H), 6.7 (t, 1H), 4.7 (d, 1H), 4.3 (m, 1H), 4.2 (d, 2H), 4.0-3.7 (m, 2H), 3.2 (m, 2H), 2.8 (m, 2H), 2.0 (m, 3H), 1.6-1.2 (m, 4H).

Example 6

Synthesis of Biphenyl-4-carboxylic acid (2-{4-[methyl-(2-trifluoromethyl-phenyl)-amino]-piperidin-1-yl}-2-oxo-ethyl)-amide

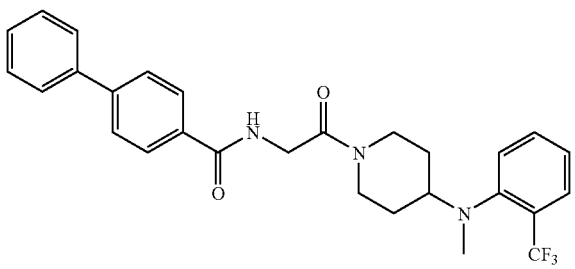

To a stirred solution of [(biphenyl-4-carbonyl)-amino]-acetic acid (0.075 g, 0.00029 mol) in DMF (3 mL), was added DIPEA (0.1519 g, 0.00117 mol), HOBt (0.03981 g, 0.00029 mol) and EDCI.HCl (0.06758 g, 0.00035 mol) at ambient temperature. After 2 minutes methyl-piperidin-4-yl-(2-trifluoromethyl-phenyl)-amine hydrochloride (0.06959 g, 0.00026 mol) was added and the resulting mixture was stirred at the same temperature overnight. The reaction mixture was diluted with cold water and the product was extracted with ethyl acetate. The ethyl acetate layer was washed aqueous sodium bicarbonate solution followed by brine solution, dried over sodium sulfate and concentrated under reduced pressure. The resulting residue was purified by preparative HPLC to afford 0.023 g (16%) of biphenyl-4-carboxylic acid (2-{4-[methyl-(2-trifluoromethyl-phenyl)-amino]-piperidin-1-yl}-2-oxo-ethyl)-amide. LCMS: 496.2 (M+1)+, 98.28%, $^1$H NMR (DMSO-$d_6$): δ 8.6 (t, 1H), 7.56-7.3 (m, 4H), 7.8-7.6 (m, 7H), 7.98 (d, 2H), 4.4 (bs, 1H), 4.15 (d, 2H), 3.9 (bs, 1H), 3.2-2.9 (m, 2H), 1.7 (bs, 2H), 1.5-1.2 (m, 2H).

Example 7

Synthesis of Biphenyl-4-carboxylic acid (2-{4-[(2-chloro-phenyl)-methyl-amino]-piperidin-1-yl}-2-oxo-ethyl)-amide

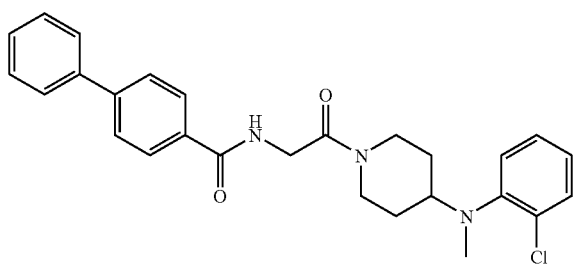

To a stirred solution of [(biphenyl-4-carbonyl)-amino]-acetic acid (0.0659 g, 0.00025 mol) in DMF (1 mL), was added DIPEA (0.0911 g, 0.0007 mol), HOBt (0.0318 g, 0.00023 mol) and EDCI.HCl (0.054 g, 0.00028 mol) at ambient temperature. After 2 minutes (2-chloro-phenyl)-methyl-piperidin-4-yl-amine hydrochloride (0.07 g, 0.00023 mol) was added and the resulting mixture was stirred at the same temperature overnight. The reaction mixture was diluted with cold water and the product was extracted with ethyl acetate. The ethyl acetate layer was washed with aqueous sodium bicarbonate solution followed by brine solution, dried over sodium sulfate and concentrated under reduced pressure. The resulting residue obtained was purified by column chromatography using basic aluminium oxide (10-30% ethyl acetate in hexane) to afford 0.028 g (23%) of biphenyl-4-carboxylic acid (2-{4-[(2-chloro-phenyl)-methyl-amino]-piperidin-1-yl}-2-oxo-ethyl)-amide. LCMS: 462.1 (M+1)+, 96.19%, $^1$H NMR (DMSO-$d_6$): δ 8.6 (t, 1H), 7.95 (d, 2H), 7.75 (m, 3H), 7.5 (t, 2H), 7.42 (m, 2H), 7.3-7.2 (m, 2H), 7.05 (m, 1H), 4.4 (d, 1H), 4.2 (m, 2H), 3.95 (d, 1H), 3.05 (t, 1H), 2.65 (s, 3H), 1.6 (bs, 3H), 1.6-1.4 (m, 1H).

Example 8

Synthesis of Biphenyl-4-carboxylic acid (2-{4-[(2-bromo-phenyl)-methyl-amino]-piperidin-1-yl}-2-oxo-ethyl)-amide

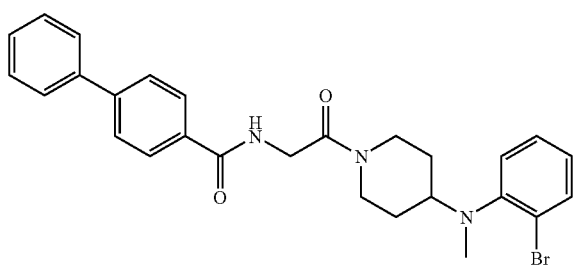

To a stirred solution of [(biphenyl-4-carbonyl)-amino]-acetic acid (0.1 g, 0.00039 mol) in DMF (2 mL), was added DIPEA (0.2025 g, 0.00156 mol), HOBt (0.053 g, 0.00039 mol) and EDCI.HCl (0.0901 g, 0.00047 mol) at ambient temperature. After 2 minutes (2-bromo-phenyl)-methyl-piperidin-4-yl-amine hydrochloride (0.119 g, 0.00039 mol) was added and the resulting mixture was stirred at the same temperature overnight. The reaction mixture was diluted with cold water, and the resulting precipitate was isolated by filtration. Purification by preparative TLC using 30% ethyl acetate in hexane afforded 0.072 g (36%) of biphenyl-4-carboxylic acid (2-{4-[(2-bromo-phenyl)-methyl-amino]-piperidin-1-yl}-2-oxo-ethyl)-amide. LCMS: 506.1 (M+1)$^+$, 97.07%, $^1$H NMR (DMSO-d$_6$): δ 8.6 (t, 1H), 8.0 (d, 2H), 7.8 (d, 2H), 7.75 (m, 4H), 7.6-7.25 (m, 6H), 7.0 (t, 1H), 4.4 (m, 1H), 4.2 (m, 1H), 3.9 (m, 1H), 3.05 (m, 1H), 2.7 (m, 1H), 2.6 (s, 3H), 1.8-1.5 (m, 4H).

Intermediate 24

Synthesis of 2,4-Dioxo-4-phenyl-butyric acid ethyl ester

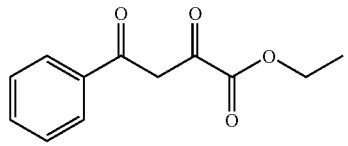

A stirred solution of acetophenone (5 g, 0.0416 mole), diethyl oxalate (7.23 g, 0.0416 mole) in DMF (40 mL) was cooled to 0° C. for 10 minutes. NaH (60% w/w dispersion in oil) (2.0 g, 0.083 mole) was then added, and the resulting mixture was stirred at the same temperature for 30 minutes, then stirred at ambient temperature for 1 hour. The mixture was then heated at 50° C. for 30 minutes. The reaction mixture was quenched with iced water, acidified with aqueous 2.4N HCl solution and the resulting precipitate was isolated by filtration and dried to afford 3.8 g (42%) of 2,4-dioxo-4-phenyl-butyric acid ethyl ester. LCMS: 221.07 (M+1)$^+$, 85.2%.

Intermediate 25

Synthesis of 5-Phenyl-isoxazole-3-carboxylic acid

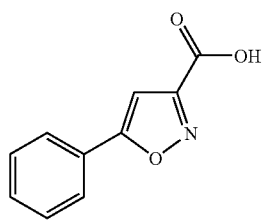

To a stirred solution of 2,4-dioxo-4-phenyl-butyric acid ethyl ester (3.86 g, 0.01754 mole) in methanol (78 mL) was added hydroxylamine hydrochloride (3.657 g, 0.0526 mole) at ambient temperature. The resulting mixture was then heated to reflux overnight. Volatiles were then removed by evaporation and the resulting residue was diluted with water and the product extracted with chloroform. The chloroform layer was collected and washed with brine solution, dried over sodium sulfate and concentrated under reduced pressure. The resulting residue was purified by column chromatography using silica gel 60-120 mesh (4% ethyl acetate in hexane) to afford 2.8 g (79%) of 5-phenyl-isoxazole-3-carboxylic acid methyl ester. LCMS: 204.06 (M+1)$^+$, 97.58%. To a stirred solution of 5-phenyl-isoxazole-3-carboxylic acid methyl ester (2.8 g, 0.01379 mol) in a mixture of THF (10 mL), methanol (10 mL) and H$_2$O (10 mL) was added LiOH.H$_2$O (0.87 g, 0.02073 mol) and the resulting mixture was stirred at ambient temperature for 2.5 hours. Volatiles were then evaporated and the resulting residue was diluted with water, acidified with concentrated HCl and extracted with ethyl acetate. The ethyl acetate layer was collected and washed with brine solution, dried over sodium sulfate and concentrated under reduced pressure to afford 2.2 g (85%) of 5-phenyl-isoxazole-3-carboxylic acid. LCMS: 190.04 (M+1)$^+$, 96.4%.

Intermediate 26

Synthesis of [(5-Phenyl-isoxazole-3-carbonyl)-amino]-acetic acid

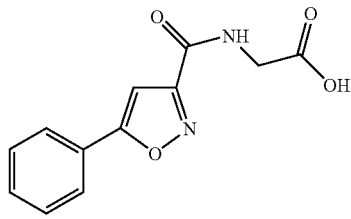

To a stirred solution of 5-phenyl-isoxazole-3-carboxylic acid (1 g, 0.00529 mol) in DMF (5 mL) was added DIPEA (2.73 g, 0.0211 mol), HOBt (0.89 g, 0.006078 mol) and EDCl.HCl (1.266 g, 0.00661 mol) at ambient temperature. After 2 minutes glycine ethyl ester hydrochloride (0.811 g, 0.00581 mol) was added and the resulting mixture was stirred at ambient temperature overnight. The reaction mixture was diluted with cold water and the resulting precipitate was isolated by filtration and dried to afford 0.744 g (56%) of 5-phenyl-isoxazole-3-carbonyl)-amino]-acetic acid ethyl ester. LCMS: 275.1 (M+1)$^+$, 94%. To a stirred solution of [(5-phenyl-isoxazole-3-carbonyl)-amino]-acetic acid ethyl ester (0.74 g, 0.00270 mol) in a mixture of THF (5 mL), methanol (5 mL) and H$_2$O (5 mL) was added LiOH.H$_2$O (0.34 g, 0.00809 mol) and the resulting mixture was stirred at ambient temperature for 1 hour. Volatiles were then evaporated and the resulting residue was diluted with water and acidified with concentrated HCl. The resulting precipitate was isolated by filtration and dried to afford 0.57 g (76%) of

[(5-phenyl-isoxazole-3-carbonyl)-amino]-acetic acid. LCMS: 247.06 (M+1)+, 98.18%.

Example 9

Synthesis of 5-Phenyl-isoxazole-3-carboxylic acid {2-[4-(2-bromo-phenoxy)-piperidin-1-yl]-2-oxo-ethyl}-amide

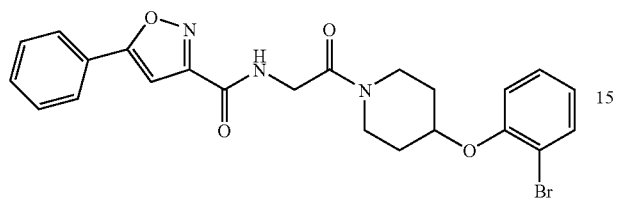

To a stirred solution of [(5-phenyl-isoxazole-3-carbonyl)-amino]-acetic acid (72.5 mg, 0.00026 mol) in DMF (1.5 mL) was added DIPEA (0.166 g, 0.00128 mol), HOBt (43.3 mg, 0.00032 mol) and EDCI.HCl (61.5 mg, 0.00032 mol) at ambient temperature. After 2 minutes 4-(2bromo-phenoxy)-piperidine trifluoroacetate (0.1 g, 0.00027 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure. The resulting residue was purified by column chromatography using silica gel, 60-120 mesh (40% ethyl acetate in hexane) to afford 0.044 g (35%) of 5-phenyl-isoxazole-3-carboxylic acid {2-[4-(2-bromo-phenoxy)-piperidin-1-yl]-2-oxo-ethyl}-amide. LCMS: 484.08 (M+1)+, 77.84%, $^1$H NMR (DMSO-d$_6$): δ 8.63 (t, 1H), 7.98 (m, 2H), 7.6 (m, 4H), 7.4 (m, 2H), 7.2 (m, 1H), 6.9 (t, 1H), 4.8 (s, 1H), 4.3 (m, 2H), 3.5 (m, 4H), 1.5 (m, 4H).

Example 10

Synthesis of 5-Phenyl-isoxazole-3-carboxylic acid {2-[4-(2-bromo-phenylamino)-piperidin-1-yl]-2-oxo-ethyl}-amide

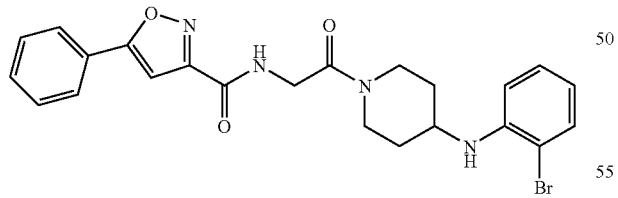

To a stirred solution of [(5-phenyl-isoxazole-3-carbonyl)-amino]-acetic acid (0.075 g, 0.00027 mol) in DMF (2 mL), was added DIPEA (171.5 mg, 0.00133 mol), HOBt (44.8 mg, 0.00033 mol) and EDCI.HCl (0.064 g, 0.00033 mol) at ambient temperature. After 2 minutes (2-bromo-phenyl)-piperidin-4-yl-amine dihydrochloride (0.078 g, 0.00026 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure. The resulting residue was purified by column chromatography using basic aluminium oxide (35% ethyl acetate in hexane) to afford 0.028 g (22%) of 5-phenyl-isoxazole-3-carboxylic acid {2-[4-(2-bromo-phenylamino)-piperidin-1-yl]-2-oxo-ethyl}-amide. LCMS: 483.1 (M+1)+, 97.4%, $^1$H NMR (DMSO-d$_6$): δ 8.6 (t, 1H), 7.85 (m, 2H), 7.6 (m, 3H), 7.4 (m, 2H), 7.2 (t, 1H), 6.85 (d, 1H), 6.55 (t, 1H), 4.7 (d, 1H), 4.3 (d, 1H), 4.2 (d, 2H), 3.9 (d, 1H), 3.6 (m, 1H), 3.2 (m, 1H), 2.8 (m, 1H), 2.0 (t, 2H), 1.4 (m, 2H).

Example 11

Synthesis of 5-Phenyl-isoxazole-3-carboxylic acid {2-[4-(2-chloro-phenylamino)-piperidin-1-yl]-2-oxo-ethyl}-amide

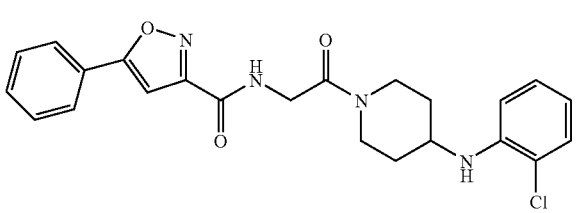

To a stirred solution of [(5-phenyl-isoxazole-3-carbonyl)-amino]-acetic acid (0.075 g, 0.00027 mol) in DMF (2 mL) was added DIPEA (0.171 g, 0.00132 mol), HOBt (0.0448 g, 0.00033 mol) and EDCI.HCl (0.064 g, 0.00033 mol) at ambient temperature. After 2 minutes piperidin-4-yl-(2-chloro-phenyl)-amine dihydrochloride (0.066 g, 0.00027 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure. The resulting residue was purified by column chromatography using basic aluminium oxide (25% ethyl acetate in hexane) to afford 0.066 g (57%) of 5-phenyl-isoxazole-3-carboxylic acid {2-[4-(2-chloro-phenylamino)-piperidin-1-yl]-2-oxo-ethyl}-amide. LCMS: 439.15 (M+1)+, 97.26%, $^1$H NMR (DMSO-d$_6$): δ 8.62 (t, 1H), 7.95 (m, 2H), 7.55 (m, 3H), 7.4 (s, 1H), 7.25 (dd, 1H), 7.2 (m, 2H), 6.85 (d, 1H), 6.6 (t, 1H), 4.9 (d, 1H), 4.4 (d, 1H), 4.2 (d, 2H), 3.9 (d, 1H), 3.7 (m, 1H), 3.2 (m, 1H), 2.8 (m, 2H), 1.95 (t, 2H), 1.4 (m, 2H).

Example 12

Synthesis of 5-Phenyl-isoxazole-3-carboxylic acid (2-{4-[(2-bromo-phenyl)-methyl-amino]-piperidin-1-yl}-2-oxo-ethyl)-amide

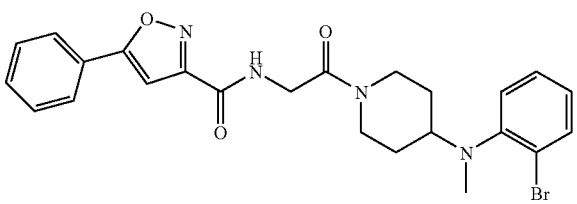

To a stirred solution of [(5-phenyl-isoxazole-3-carbonyl)-amino]-acetic acid (62.9 mg, 0.00025 mol) in DMF (2 mL) was added DIPEA (0.159 g, 0.00123 mol), HOBt (41.4 mg, 0.00031 mol) and EDCI.HCl (58.8 mg, 0.0003° mol) at ambient temperature. After 2 minutes (2-bromo-phenyl)-methyl-piperidin-4-yl-amine hydrochloride (0.068 g, 0.00025 mol) was added and the resulting mixture was stirred overnight. The reaction mixture was then diluted with cold water and the resulting precipitate was isolated by filtration. Purification by column chromatography using basic aluminium oxide (50-100% ethyl acetate in hexane) afforded 0.039 g (35%) of 5-phenyl-isoxazole-3-carboxylic acid (2-{4-[(2-bromo-phenyl)-methyl-amino]-piperidin-1-yl}-2-oxo-ethyl)-amide. LCMS: 497.11 (M+1)$^+$, 97.87%, $^1$H NMR (DMSO-d$_6$): δ 8.58 (t, 1H), 7.93 (m, 2H), 7.52 (m, 4H), 7.4 (s, 1H), 7.15 (m, 2H), 6.9 (m, 1H), 4.3 (d, 1H), 4.15 (t, 2H), 3.8 (d, 1H), 3.0 (m, 1H), 2.65 (m, 1H), 2.55 (s, 3H), 1.75 (m, 3H), 1.5 (m, 2H).

Example 13

Synthesis of 5-Phenyl-isoxazole-3-carboxylic acid {2-oxo-2-[4-(2-trifluoromethyl-phenylamino)-piperidin-1-yl]-ethyl}-amide

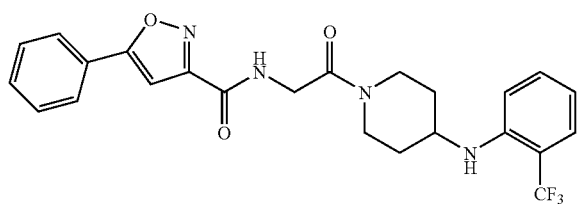

To a stirred solution of [(5-phenyl-isoxazole-3-carbonyl)-amino]-acetic acid (0.0685 g, 0.00024 mol) in DMF (2 mL) was added DIPEA (0.173 g, 0.00134 mol), HOBt (0.045 g, 0.00034 mol) and EDCI.HCl (0.064 g, 0.00034 mol) at ambient temperature. After 2 minutes piperidin-4-yl-(2-trifluoromethyl-phenyl)-amine dihydrochloride (0.068 g, 0.00024 mol) was added and the resulting mixture was stirred overnight. The reaction mixture was then diluted with cold water and the product was extracted with ethyl acetate. The ethyl acetate layer was collected and washed with brine solution, dried over sodium sulfate and concentrated. The resulting residue was purified by column chromatography using neutral aluminium oxide (35% ethyl acetate in hexane) to afford 0.0684 g (60%) of 5-phenyl-isoxazole-3-carboxylic acid {2-oxo-2-[4-(2-trifluoromethyl-phenylamino)-piperidin-1-yl]-ethyl}-amide. LCMS: 473.17 (M+1)$^+$, 97.41%, $^1$H NMR (DMSO-d$_6$): δ 8.62 (t, 1H), 7.94 (m, 2H), 7.52 (m, 3H), 7.38 (m, 3H), 6.98 (d, 1H), 6.7 (t, 1H), 4.7 (d, 1H), 4.3 (d, 1H), 4.2 (d, 2H), 3.9 (d, 1H), 3.7 (m, 1H), 3.2 (m, 1H), 2.8 (m, 1H), 2.0 (m, 2H), 1.4 (m, 2H).

Example 14

Synthesis of 5-Phenyl-isoxazole-3-carboxylic acid (2-{4-[methyl-(2-trifluoromethyl-phenyl)-amino]-piperidin-1-yl}-2-oxo-ethyl)-amide

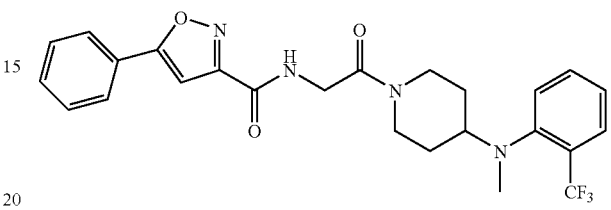

To a stirred solution of [(5-phenyl-isoxazole-3-carbonyl)-amino]-acetic acid (0.0576 g, 0.00021 mol) in DMF (1 mL), was added DIPEA (0.1317 g, 0.0010 mol), HOBt (0.035 g, 0.00025 mol) and EDCI.HCl (0.049 g, 0.00025 mol) at ambient temperature. After 2 minutes methyl-piperidin-4-yl-(2-trifluoromethyl-phenyl)-amine hydrochloride (0.06 g, 0.00021 mol) was added and the resulting mixture was stirred overnight. The reaction mixture was then diluted with cold water and the product extracted with ethyl acetate. The ethyl acetate layer was collected and washed with brine solution, dried over sodium sulfate and concentrated under reduced pressure. The resulting residue was purified by preparative HPLC [(column-Zorbax SB C$_{18}$-21.2×150 mm, mobile phase-0.1% TFA in water (A)/acetonitrile (B), gradient: (Time): (% B)-0:30; 2:50; 8:80)]) to afford 0.015 g (15%) of 5-phenyl-isoxazole-3-carboxylic acid (2-{4-[methyl-(2-trifluoromethyl-phenyl)-amino]-piperidin-1-yl}-2-oxo-ethyl)-amide. LCMS: 487.19 (M+1)$^+$, 98.16%, $^1$H NMR (DMSO-d$_6$): δ 8.58 (t, 1H), 7.94 (m, 2H), 7.7 (m, 2H), 7.56 (m, 3H), 7.34 (m, 2H), 4.3 (m, 1H), 4.15 (d, 2H), 3.8 (d, 1H), 3.0 (m, 2H), 2.6 (s, 3H), 1.7 (m, 2H), 1.4 (m, 1H), 1.3 (m, 2H).

Intermediate 27

Synthesis of 4-Phenylamino-benzoic acid

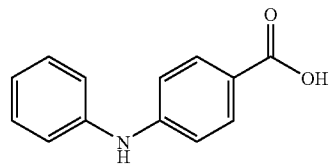

A mixture of BINAP (1.6 g, 0.00257 mole), palladium acetate (0.23 g, 0.001 mole) and toluene (30 mL) was degassed with argon for 15 minutes. This mixture was then added to a mixture of aniline (5.0 g, 0.0536 mole), 4-bromobenzoic acid (12.9 g, 0.0644 mole) and cesium carbonate (52.47 g, 0.161 mole) in toluene (30 mL) (previously degassed with argon for 15 minutes). The resulting mixture was heated at reflux for 22 hours. The reaction mixture was then concentrated under reduced pressure. The resulting residue was acidified with 10% HCl and the product was extracted with ethyl acetate. The ethyl acetate layer was washed with brine solution, dried over sodium sulfate and concentrated under reduced pressure. The residue was purified by column chromatography using silica gel 60-120 mesh (15% ethyl acetate in hexane) to afford 9.55 g (83%) of 4-phenylamino-benzoic acid.

Intermediate 28

Synthesis of (4-Phenylamino-benzoylamino)-acetic acid

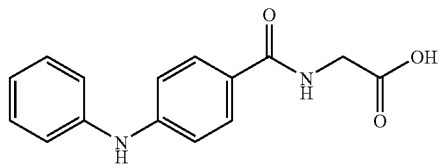

To a stirred solution of 4-phenylamino-benzoic acid (3.0 g, 0.01401 mol) in DMF (10 mL), was added DIPEA (5.4 g, 0.04205 mol), HOBt (2.27 g, 0.01682 mol) and EDCI.HCl (6.69 g, 0.03504 mol) at ambient temperature. After 2 minutes amino-acetic acid ethyl ester hydrochloride (2.33 g, 0.01682 mol) was added and the resulting mixture was stirred overnight. The reaction mixture was then diluted with cold water and the resulting precipitate was isolated by filtration, washed with water followed by hexane and dried to afford 4 g (95%) of (4-phenylamino-benzoylamino)-acetic acid ethyl ester. To a stirred solution (4-phenylamino-benzoylamino)-acetic acid ethyl ester (4 g, 0.01337 mol) in a mixture of THF (15 mL), methanol (15 mL) and H$_2$O (8 mL) was added LiOH.H$_2$O (2.24 g, 0.0535 mol). The resulting mixture was stirred at ambient temperature for 3 hours and then concentrated. The residue was diluted with water and acidified with 10% aqueous citric acid solution. The resulting precipitate was isolated by filtration and dried to afford 3.3 g (91%) of (4-phenylamino-benzoylamino)-acetic acid.

Example 15

Synthesis of N-{2-Oxo-2-[4-(2-trifluoromethyl-phenylamino)-piperidin-1-yl]-ethyl}-4-phenylamino-benzamide

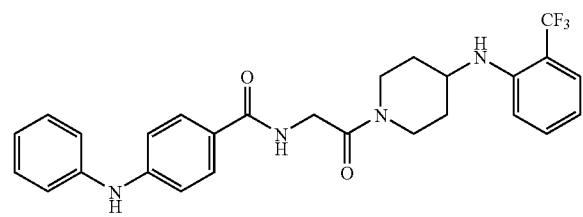

To a stirred solution of (4-phenylamino-benzoylamino)-acetic acid (0.058 g, 0.00021 mol) in DMF (5 mL) was added DIPEA (0.069 g, 0.00054 mol), HOBt (0.028 g, 0.0002142 mol) and EDCI.HCl (0.085 g, 0.00045 mol) at ambient temperature. After 2 minutes piperidin-4-yl-(2-trifluoromethyl-phenyl)-amine dihydrochloride (0.050 g, 0.00019 mol) was added and the resulting mixture was stirred overnight. The reaction mixture was then diluted with cold water and the product was extracted with ethyl acetate. The ethyl acetate layer was collected, washed with brine solution, dried over sodium sulfate and concentrated under reduced. The resulting residue was purified by column chromatography using silica gel 60-120 mesh (60% ethyl acetate in hexane) to afford 0.06 g (68%) of N-{2-oxo-2-[4-(2-trifluoromethyl-phenylamino)-piperidin-1-yl]-ethyl}-4-phenylamino-benzamide. LCMS: 497.21 (M+1)$^+$, 95.3%, $^1$H NMR (DMSO-d$_6$): δ 8.6 (s, 1H), 8.2 (t, 1H), 7.8 (d, 2H), 7.4 (m, 4H), 7.2 (d, 2H), 7.1 (m, 3H), 6.9 (t, 1H), 6.7 (t, 1H), 4.7 (d, 1H), 4.3 (d, 1H), 4.1 (s, 2H), 3.9 (d, 1H), 3.7 (s, 1H), 2.8 (t, 1H), 2.0 (t, 2H), 1.5 (m, 2H).

Example 16

Synthesis of N-{2-[4-(2-Chloro-phenylamino)-piperidin-1-yl]-2-oxo-ethyl}-4-phenylamino-benzamide

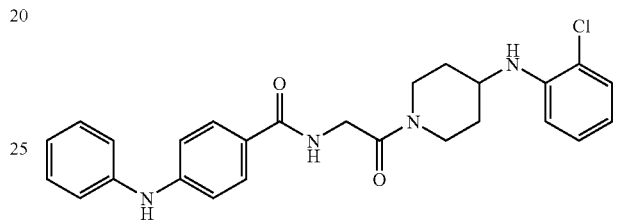

To a stirred solution of (4-phenylamino-benzoylamino)-acetic acid (0.083 g, 0.00031 mol) in DMF (5 mL) was added DIPEA (0.099 g, 0.00077 mol), HOBt (0.041 g, 0.000307 mol) and EDCI.HCl (0.073 g, 0.00038 mol) at ambient temperature. After 2 minutes (2-chloro-phenyl)-piperidin-4-yl-amine dihydrochloride (0.063 g, 0.00026 mol) was added and the resulting mixture was stirred overnight. The reaction mixture was then diluted with cold water and the product was extracted with ethyl acetate. The ethyl acetate layer was washed with brine solution, dried over sodium sulfate and concentrated. The residue was purified by column chromatography using silica gel 60-120 mesh (60% ethyl acetate in hexane) to afford 0.04 g (33%) of N-{2-[4-(2-chloro-phenylamino)-piperidin-1-yl]-2-oxo-ethyl}-4-phenylamino-benzamide. LCMS: 463.17 (M+1)$^+$, 95.82%, $^1$H NMR (DMSO-d$_6$): δ 8.6 (s, 1H), 8.2 (t, 1H), 7.8 (d, 2H), 7.5 (q, 3H), 7.2 (t, 3H), 7.1 (d, 2H), 6.9 (q, 2H), 6.6 (t, 1H), 4.9 (d, 1H), 4.3 (d, 1H), 4.1 (d, 2H), 3.9 (d, 1H), 3.6 (m, 1H), 3.2 (m, 1H), 2.8 (m, 2H), 2.0 (t, 3H).

Example 17

Synthesis of N-{2-[4-(2-Bromo-phenylamino)-piperidin-1-yl]-2-oxo-ethyl}-4-phenylamino-benzamide

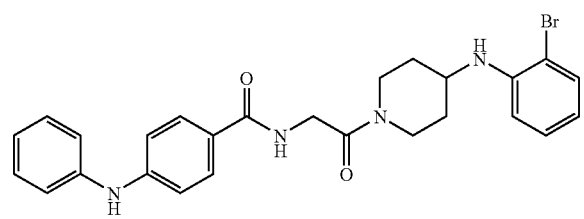

To a stirred solution of (4-phenylamino-benzoylamino)-acetic acid (0.074 g, 0.00027 mol) in DMF (5 mL) was added DIPEA (0.088 g, 0.0006827 mol), HOBt (0.036 g, 0.00027 mol) and EDCI.HCl (0.065 g, 0.00034 mol) at ambient temperature. After 2 minutes (2-bromo-phenyl)-piperidin-4-yl-amine dihydrochloride (0.066 g, 0.00023 mol) and the resulting mixture was stirred overnight. The reaction mixture was then diluted with cold water and the product was extracted with ethyl acetate. The ethyl acetate layer was washed with brine solution, dried over sodium sulfate and concentrated under reduced pressure. The resulting residue was purified by column chromatography using silica gel 60-120 mesh (60% ethyl acetate in hexane) to afford 0.036 g (31%) of N-{2-[4-(2-bromo-phenylamino)-piperidin-1-yl]-2-oxo-ethyl}-4-phenylamino-benzamide. LCMS: 507.13 (M+1)$^+$, 96.75%, $^1$H NMR (DMSO-d$_6$): δ 8.6 (s, 1H), 8.2 (t, 1H), 7.8 (d, 2H), 7.4 (dd, 1H), 7.3 (t, 2H), 7.2 (m, 3H), 7.1 (d, 2H), 6.9 (t, 1H), 6.8 (d, 1H), 6.6 (t, 1H), 4.6 (d, 1H), 4.3 (d, 1H), 4.1 (d, 2H), 3.9 (d, 1H), 3.6 (s, 1H), 3.2 (m, 3H), 2.8 (m, 2H), 2.0 (m, 3H).

Example 18

Synthesis of N-(2-{4-[Methyl-(2-trifluoromethyl-phenyl)-amino]-piperidin-1-yl}-2-oxo-ethyl)-4-phenylamino-benzamide

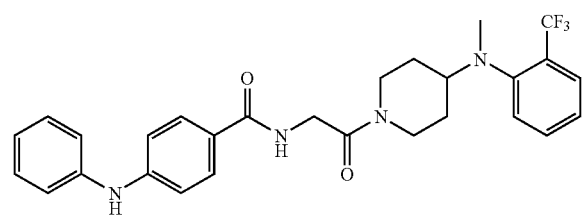

To a stirred solution of (4-phenylamino-benzoylamino)-acetic acid (0.051 g, 0.00019 mol) in DMF (5 mL) was added DIPEA (0.061 g, 0.00048 mol), HOBt (0.025 g, 0.00019 mol) and EDCI.HCl (0.076 g, 0.00040 mol) at ambient temperature. After 2 minutes methyl-piperidin-4-yl-(2-trifluoromethyl-phenyl)-amine hydrochloride (0.047 g, 0.00016 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure. The residue was purified by preparative HPLC [(column-Zorbax SB C$_{18}$-21.2×150 mm, mobile phase-0.1% TFA in water (A)/Acetonitrile (B), gradient: (Time): (% B)-0:30; 2:50; 8:80)]) to afford 0.031 g (38%) of N-(2-{4-[methyl-(2-trifluoromethyl-phenyl)-amino]-piperidin-1-yl}-2-oxo-ethyl)-4-phenylamino-benzamide. LCMS: 511.22 (M+1)$^+$, 99.08%, $^1$H NMR (DMSO-d$_6$): δ 8.6 (s, 1H), 8.2 (t, 1H), 7.8 (d, 2H), 7.7 (m, 3H), 7.4 (m, 3H), 7.2 (d, 2H), 7.1 (d, 2H), 6.9 (t, 1H), 4.4 (d, 1H), 4.1 (d, 2H), 3.9 (d, 1H), 3.1 (m, 3H), 2.6 (s, 4H), 1.8 (d, 2H), 1.4 (m, 1H).

Example 19

Synthesis of N-{2-[4-(2-Bromo-phenoxy)-piperidin-1-yl]-2-oxo-ethyl}-4-phenylamino-benzamide

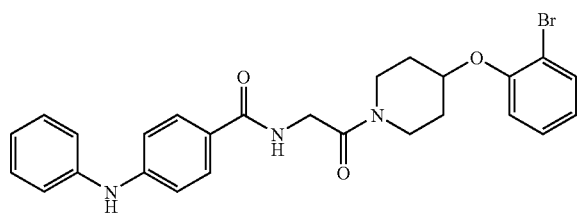

To a stirred solution of (4-phenylamino-benzoylamino)-acetic acid (0.087 g, 0.00032 mol) in DMF (5 mL) was added DIPEA (0.104 g, 0.00081 mol), HOBt (0.043 g, 0.00032 mol) and EDCI.HCl (0.061 g, 0.00032 mol) at ambient temperature. After 2 minutes 4-(2-bromo-phenoxy)-piperidine trifluoroacetate (0.1 g, 0.00027 mol) and the resulting mixture was stirred overnight. The reaction mixture was then diluted with cold water and the product was extracted with ethyl acetate. The organic layer was washed with brine solution and dried over sodium sulfate. The organic layer was collected and concentrated under reduced pressure to afford 0.045 g (32%) of N-{2-[4-(2-bromo-phenoxy)-piperidin-1-yl]-2-oxo-ethyl}-4-phenylamino-benzamide. LCMS: 508.12 (M+1)$^+$, 96.85%, $^1$H NMR (DMSO-d$_6$): δ 8.6 (s, 1H), 8.3 (t, 1H), 7.8 (d, 2H), 7.6 (dd, 1H), 7.3 (m, 4H), 7.2 (d, 2H), 7.1 (d, 2H), 6.9 (q, 2H), 4.8 (m, 1H), 4.2 (t, 2H), 3.7 (m, 2H), 3.5 (m, 2H), 2.0 (m, 2H), 1.7 (m, 2H).

Intermediate 29

Synthesis of 5-Phenyl-1H-pyrazole-3-carboxylic acid

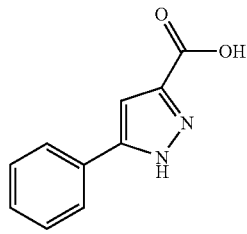

A solution of 2,4-dioxo-4-phenyl-butyric acid ethyl ester (1.68 g, 0.0076 mole), acetic acid (10 mL) and hydrazine hydrate (0.42 g, 0.0083 mole) was heated to reflux for 5 hours. The reaction mixture was then poured into iced water, basified with saturated aqueous NaHCO$_3$ solution and the product was extracted with ethyl acetate. The ethyl acetate layer was collected and washed with brine solution, dried over sodium sulfate and concentrated under reduced pressure. The resulting residue was purified by column chromatography using basic aluminium oxide (50% ethyl acetate in hexane) to afford 1.442 g (88%) of 5-phenyl-1H-pyrazole-3-carboxylic acid ethyl ester. LCMS: 217.09 (M+1)$^+$, 97.92%. To a stirred solution of 5-phenyl-1H-pyrazole-3-carboxylic acid ethyl ester (1.4 g, 0.00667 mol) in a mixture of THF (30 mL), methanol (15 mL) and H$_2$O (10 mL) was added LiOH.H$_2$O (0.839 g, 0.0199 mol) at ambient temperature. The resulting mixture was stirred at 45° C. overnight. Volatiles were evaporated and the residue was diluted with water, acidified with concentrated HCl solution and the product was extracted with ethyl acetate. The ethyl acetate layer was collected, dried over sodium sulfate and concentrated under reduced pressure to afford 1.26 g (86%) of 5-phenyl-1H-pyrazole-3-carboxylic acid. LCMS: 189.06 (M+1)$^+$, 97.7%.

Intermediate 30

Synthesis of [(5-Phenyl-1H-pyrazole-3-carbonyl)-amino]-acetic acid

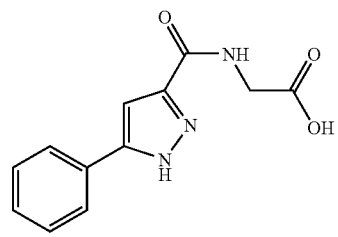

To a stirred solution of 5-phenyl-1H-pyrazole-3-carboxylic acid (1.25 g, 0.00665 mol) in DMF (3 mL) was added DIPEA (4.296 g 0.03324 mol), HOBt (1.123 g, 0.00831 mol) and EDCI.HCl (1.593 g, 0.00831 mol) at ambient temperature. After 2 minutes glycine acid ethyl ester hydrochloride (0.928 g, 0.00665 mol) was and the resulting mixture was stirred overnight. The reaction mixture was then diluted with cold water and the product was extracted with ethyl acetate. The ethyl acetate layer was collected and washed with brine solution, dried over sodium sulfate and concentrated under reduced pressure to afford 0.76 g (42% of [(5-phenyl-1H-pyrazole-3-carbonyl)-amino]-acetic acid ethyl ester. LCMS: 274.11 (M+1)$^+$, 96.7%. To a stirred solution of [(5-phenyl-1H-pyrazole-3-carbonyl)-amino]-acetic acid ethyl ester (0.615 g, 0.0025 mol) in a mixture of THF (10 mL), methanol (5 mL) and H$_2$O (5 mL) was added LiOH.H$_2$O (0.283 g, 0.00675 mol) at ambient temperature. The reaction mixture was stirred at the same temperature for 2 hours. Volatiles were evaporated and the residue was diluted with water, acidified with 10% HCl solution. The resulting precipitate was isolated by filtration, washed water followed by hexane and to afford 0.238 g (38%) of [(5-phenyl-1H-pyrazole-3-carbonyl)-amino]-acetic acid. LCMS: 246.08 (M+1)$^+$, 95.60%

Example 20

Synthesis of 5-Phenyl-1H-pyrazole-3-carboxylic acid {2-[4-(2-bromo-phenylamino)-piperidin-1-yl]-2-oxo-ethyl}-amide

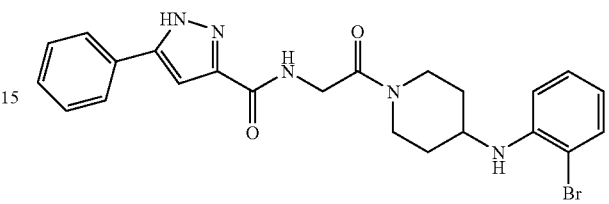

To a stirred solution of [(5-phenyl-1H-pyrazole-3-carbonyl)-amino]-acetic acid (0.038 g, 0.00013 mol) in DMF (2 mL), was added DIPEA (0.0872 g, 0.00067 mol), HOBt (0.023 g, 0.00017 mol) and EDCI.HCl (0.0325 g, 0.0001686 mol) at ambient temperature. After 2 minutes (2-bromo-phenyl)-piperidin-4-yl-amine dihydrochloride (0.0393 g, 0.00013 mol) was added and the resulting mixture was stirred overnight. The reaction mixture was then diluted with cold water. The resulting precipitate was isolated by filtration and dried to afford 0.0375 g (58%) of 5-phenyl-1H-pyrazole-3-carboxylic acid {2-[4-(2-bromo-phenylamino)-piperidin-1-yl]-2-oxo-ethyl}-amide. LCMS: 482.11 (M+1)$^+$, 91.09%, $^1$H NMR (DMSO-d$_6$): δ 13.7 (s, 1H), 8.0 (s, 1H), 7.8 (d, 2H), 7.38 (m, 4H), 7.16 (t, 1H), 7.06 (s, 1H), 6.84 (d, 1H), 6.5 (t, 1H), 4.6 (d, 1H), 4.3 (d, 1H), 4.1 (d, 2H), 3.9 (m, 1H), 3.6 (m, 1H), 3.2 (m, 1H), 2.8 (m, 1H), 1.9 (m, 2H), 1.4 (m, 2H).

Example 21

Synthesis of 5-Phenyl-1H-pyrazole-3-carboxylic acid {2-[4-(2-chloro-phenylamino)-piperidin-1-yl]-2-oxo-ethyl}-amide

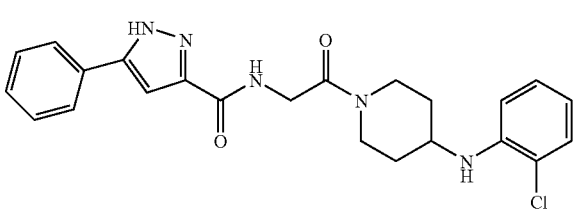

To a stirred solution of [(5-phenyl-1H-pyrazole-3-carbonyl)-amino]-acetic acid (0.038 g, 0.00013 mol) in DMF (2 mL) was added DIPEA (0.0872 g, 0.00067 mol), HOBt (0.023 g, 0.00017 mol) and EDCI.HCl (0.0325 g, 0.00017 mol) at ambient temperature. After 2 minutes (2-chloro-phenyl)-piperidin-4-yl-amine dihydrochloride (0.0334 g, 0.00013 mol) was added and the resulting mixture was stirred overnight. The reaction mixture was then diluted with cold water. The resulting precipitate was isolated by filtration and dried to afford 0.0382 g (65%) of 5-phenyl-1H-pyrazole-3-carboxylic acid {2-[4-(2-chloro-phenylamino)-piperidin-1-yl]-2-oxo-ethyl}-amide. LCMS: 438.16 (M+1)$^+$, 98.29%, $^1$H NMR (DMSO-d$_6$): δ 13.8 (s, 1H), 8.1 (s, 1H), 7.78 (d, 2H), 7.44 (m, 2H), 7.38 (m, 1H), 7.26 (d, 2H), 7.1 (m, 2H), 6.84 (d, 1H), 6.6 (t, 1H), 4.9 (d, 1H), 4.3 (d, 1H), 4.2 (d, 2H), 3.8 (d, 1H), 3.6 (m, 1H), 3.2 (m, 1H), 2.8 (m, 1H), 1.9 (t, 2H), 1.3 (m, 2H).

Example 22

Synthesis of 5-Phenyl-1H-pyrazole-3-carboxylic acid {2-[4-(2-bromo-phenoxy)-piperidin-1-yl]-2-oxo-ethyl}-amide

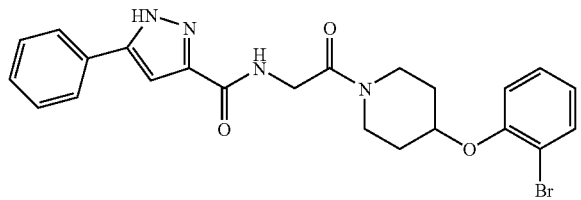

To a stirred solution of [(5-phenyl-1H-pyrazole-3-carbonyl)-amino]-acetic acid (0.038 g, 0.000135 mol) in DMF (2 mL) was added DIPEA (0.0872 g, 0.00068 mol), HOBt (0.023 g, 0.00017 mol) and EDCI.HCl (0.0325 g, 0.00017 mol) at ambient temperature. After 2 minutes 4-(2-bromophenoxy)-piperidine trifluoroacetate (0.05 g, 0.0001349 mol) was added and the resulting mixture was stirred overnight. The reaction mixture was then diluted with cold water. The resulting precipitate was isolated by filtration and dried to afford 0.044 g (68%) of 5-phenyl-1H-pyrazole-3-carboxylic acid {2-[4-(2-bromo-phenoxy)-piperidin-1-yl]-2-oxo-ethyl}-amide. LCMS: 483.1 (M+1)$^+$, 99.71%, $^1$H NMR (DMSO-d$_6$): δ 13.7 (s, 1H), 8.02 (s, 1H), 7.79 (d, 1H), 7.6 (m, 1H), 7.42 (m, 2H), 7.3 (m, 2H), 7.26 (d, 1H), 7.0 (s, 1H), 6.9 (t, 1H), 4.8 (m, 1H), 4.2 (d, 2H), 3.4 (m, 4H), 1.7 (m, 2H), 1.6 (m, 2H).

Example 23

Synthesis of 5-Phenyl-1H-pyrazole-3-carboxylic acid {2-[4-(2-chloro-phenoxy)-piperidin-1-yl]-2-oxo-ethyl}-amide

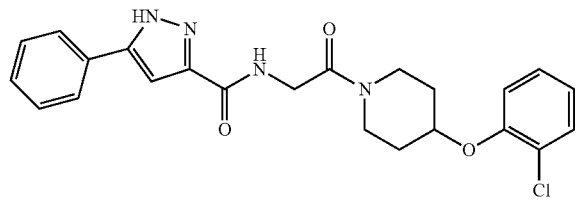

To a stirred solution of [(5-phenyl-1H-pyrazole-3-carbonyl)-amino]-acetic acid (0.038 g, 0.00013 mol) in DMF (2 mL) was added DIPEA (0.0872 g, 0.00067 mol), HOBt (0.023 g, 0.00017 mol) and EDCI.HCl (0.0325 g, 0.00017 mol) at ambient temperature. After 2 minutes 4-(2-chlorophenoxy)-piperidine hydrochloride (0.03347 g, 0.00013 mol) was added and the resulting mixture was stirred overnight. The reaction mixture was then diluted with cold water. The resulting precipitate was isolated by filtration and dried to afford 0.0517 g (87%) of 5-phenyl-1H-pyrazole-3-carboxylic acid {2-[4-(2-chloro-phenoxy)-piperidin-1-yl]-2-oxo-ethyl}-amide. LCMS: 439.15 (M+1)$^+$, 98.84%, $^1$H NMR (DMSO-d$_6$): δ 13.7 (s, 1H), 8.1 (s, 1H), 7.8 (d, 2H), 7.42 (m, 3H), 7.32 (m, 1H), 7.24 (m, 2H), 7.1 (s, 1H), 7.0 (t, 1H), 4.7 (m, 1H), 4.1 (d, 2H), 3.7 (m, 2H), 3.4 (m, 2H), 1.9 (m, 2H), 1.6 (m, 2H).

Example 24

Synthesis of 5-Phenyl-1H-pyrazole-3-carboxylic acid {2-[4-(2-chloro-5-fluoro-phenoxy)-piperidin-1-yl]-2-oxo-ethyl}-amide

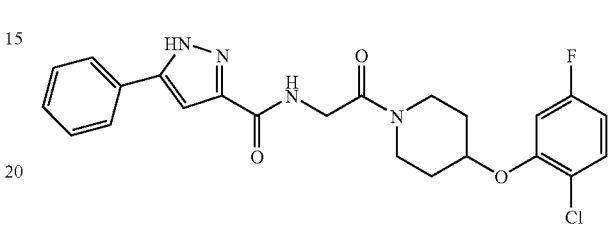

To a stirred solution of [(5-phenyl-1H-pyrazole-3-carbonyl)-amino]-acetic acid (0.038 g, 0.00013 mol) in DMF (2 mL) was added DIPEA (0.0872 g, 0.00067 mol), HOBt (0.023 g, 0.00017 mol) and EDCI.HCl (0.0325 g, 0.00017 mol) at ambient temperature. After 2 minutes 4-(2-chloro-5-fluoro-phenoxy)-piperidine hydrochloride (0.036 g, 0.0001349 mol) was added and the resulting mixture was stirred overnight. The reaction mixture was then diluted with cold water. The resulting precipitate was isolated by filtration and dried to afford 0.056 g (91%) of 5-phenyl-1H-pyrazole-3-carboxylic acid {2-[4-(2-chloro-5-fluoro-phenoxy)-piperidin-1-yl]-2-oxo-ethyl}-amide. LCMS: 457.14 (M+1)$^+$, 98.34%, $^1$H NMR (DMSO-d$_6$): δ 13.7 (s, 1H), 8.0 (s, 1H), 7.8 (d, 2H), 7.44 (m, 2H), 7.38 (m, 1H), 7.24 (m, 1H), 7.1 (s, 1H), 6.8 (m, 1H), 4.8 (m, 1H), 4.2 (d, 2H), 3.6 (m, 2H), 3.4 (m, 2H), 1.9 (m, 2H), 1.7 (m, 2H).

Example 25

Synthesis of 5-Phenyl-1H-pyrazole-3-carboxylic acid {2-oxo-2-[4-(2-trifluoromethyl-phenylsulfanyl)-piperidin-1-yl]-ethyl}-amide

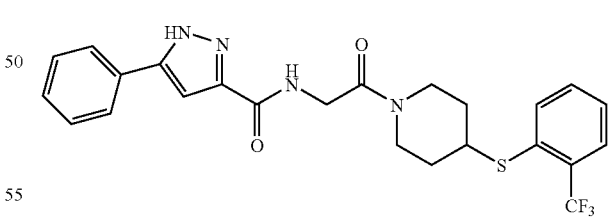

To a stirred solution of [(5-Phenyl-1H-pyrazole-3-carbonyl)-amino]-acetic acid (0.05 g, 0.00018 mol) in DMF (1 mL) was added DIPEA (0.0689 g, 0.00053 mol), HOBt (0.028 g, 0.00021 mol) and EDCI.HCl (0.0407 g, 0.00021 mol) at ambient temperature. After 2 minutes 4-(2-trifluoromethyl-phenylsulfanyl)-piperidine hydrochloride (0.063 g, 0.00021 mol) was added and the resulting mixture was stirred overnight. The reaction mixture was then diluted with cold water. The resulting precipitate was isolated by filtration and dried to afford 0.068 g (78%) of 5-phenyl-1H-pyrazole-3-carboxylic acid {2-oxo-2-[4-(2-trifluoromethyl-phenylsulfanyl)-piperidin-1-yl]-ethyl}-amide. LCMS: 489.15 (M+1)+, 94.5%, $^1$H NMR (DMSO-d$_6$): δ 13.8 (s, 1H), 8.0 (s, 1H), 7.8 (m, 4H), 7.65 (t, 1H), 7.5-7.3 (m, 4H), 7.1 (s, 1H), 4.3-4.05 (m, 3H), 3.9-3.6 (m, 2H), 3.2 (m, 1H), 2.9 (m, 1H), 1.9 (m, 2H), 1.6 (m, 1H), 1.4 (m, 1H).

Example 26

Synthesis of 5-Phenyl-1H-pyrazole-3-carboxylic acid {2-[4-(2-chloro-phenylsulfanyl)-piperidin-1-yl]-2-oxo-ethyl}-amide

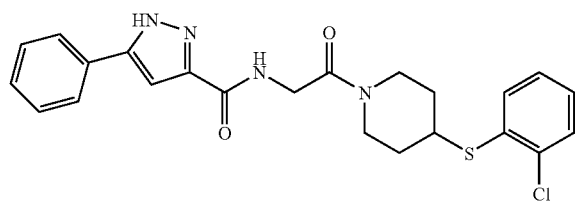

To a stirred solution of [(5-phenyl-1H-pyrazole-3-carbonyl)-amino]-acetic acid (0.04 g, 0.00014 mol) in DMF (1 mL) was added DIPEA (0.05517 g, 0.00043 mol), HOBt (0.023 g, 0.00017 mol) and EDCI.HCl (0.0326 g, 0.00017 mol) at ambient temperature. After 2 minutes 4-(2-chloro-phenylsulfanyl)-piperidine hydrochloride (0.0449 g, 0.00017 mol) was added and the resulting mixture was stirred overnight. The reaction mixture was then diluted with cold water. The resulting precipitate was isolated by filtration and dried to afford 0.054 g (84%) of 5-phenyl-1H-pyrazole-3-carboxylic acid {2-[4-(2-chlorophenylsulfanyl)-piperidin-1-yl]-2-oxo-ethyl}-amide. LCMS: 455.12 (M+1)+, 83.96%, $^1$H NMR (DMSO-d$_6$): δ 13.65 (s, 1H), 8.1 (s, 1H), 7.8 (d, 2H), 7.5 (m, 4H), 7.38 (t, 2H), 7.24 (t, 2H), 7.15 (s, 1H), 4.2 (m, 3H), 3.85 (m, 1H), 3.65 (m, 1H), 3.25 (m, 1H), 3.0 (m, 1H), 2.0 (m, 2H), 1.56 (m, 1H), 1.4 (m, 1H).

Example 27

Synthesis of 5-Phenyl-1H-pyrazole-3-carboxylic acid {2-[4-(2-nitro-phenoxy)-piperidin-1-yl]-2-oxo-ethyl}-amide

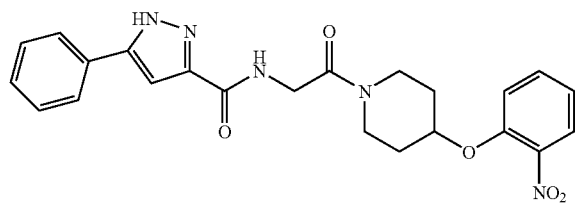

To a stirred solution of [(5-phenyl-1H-pyrazole-3-carbonyl)-amino]-acetic acid (0.15 g, 0.0006 mol) in DMF (3 mL) was added DIPEA (0.27 g, 0.0021 mol), HOBt (0.12 g, 0.0009 mol) and EDCI.HCl (0.17 g, 0.0009 mol) at ambient temperature. After 2 minutes 4-(2-nitro-phenoxy)-piperidine hydrochloride (0.19 g, 0.00073 mol) was added and the resulting mixture was stirred overnight. The reaction mixture was then diluted with cold water. The product was extracted with ethyl acetate, and the organic layer was washed with brine solution, dried over sodium sulfate and concentrated under reduced pressure. The resulting residue was purified by column chromatography using neutral aluminium oxide (5% methanol in chloroform) to afford 0.1 g (44%) of 5-phenyl-1H-pyrazole-3-carboxylic acid {2-[4-(2-nitro-phenoxy)-piperidin-1-yl]-2-oxo-ethyl}-amide. LCMS: 450.17 (M+1)+, 96.5%, $^1$H NMR (DMSO-d$_6$): δ 8.1 (bs, 1H), 7.9 (m, 3H), 7.6 (m, 1H), 7.5 (m, 4H), 7.1 (m, 2H), 5.0 (m, 1H), 4.2 (m, 2H), 3.8 (m, 8H), 2.0 (m, 2H).

Example 28

Synthesis of 5-Phenyl-1H-pyrazole-3-carboxylic acid {2-[4-(2-amino-phenoxy)-piperidin-1-yl]-2-oxo-ethyl}-amide

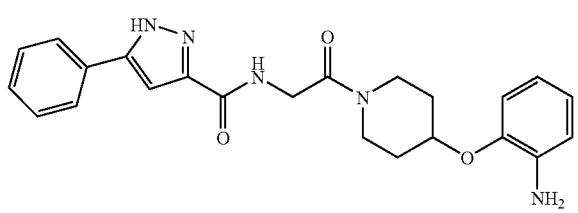

To a stirred solution of 5-phenyl-1H-pyrazole-3-carboxylic acid {2-[4-(2-nitro-phenoxy)-piperidin-1-yl]-2-oxo-ethyl}-amide (0.07 g, 0.00016 mole) in a mixture of methanol (5 mL) and THF (5 mL) was added 10% Pd/C (0.01 g). The resulting mixture was stirred under an atmosphere of hydrogen for 30 minutes. The mixture was then filtered through celite, and the celite was washed with methanol. The combined organic layers were concentrated under reduced pressure. The resulting residue was re-crystallized from a hexane/chloroform mixture to afford 0.025 g (39%) of 5-phenyl-1H-pyrazole-3-carboxylic acid {2-[4-(2-amino-phenoxy)-piperidin-1-yl]-2-oxo-ethyl}-amide. LCMS: 420.2 (M+1)+, 96.9%, $^1$H NMR (DMSO-d$_6$): δ 8.1 (bs, 1H), 7.8 (d, 2H), 7.5-7.3 (m, 3H), 7.1 (m, 1H), 6.85 (d, 1H), 6.7 (m, 2H), 6.5 (m, 1H), 4.7 (s, 2H), 4.6 (s, 1H), 4.2 (s, 2H), 3.9 (m, 2H), 2.0 (m, 2H), 1.8 (m, 2H), 1.4 (m, 2H).

Example 29

Synthesis of 5-Phenyl-1H-pyrazole-3-carboxylic acid {2-[4-(2,3-dimethyl-phenylamino)-piperidin-1-yl]-2-oxo-ethyl}-amide

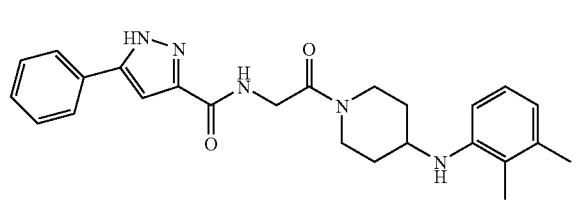

To a stirred solution of [(5-phenyl-1H-pyrazole-3-carbonyl)-amino]-acetic acid (0.097 g, 0.00036 mol) in DMF (1 mL) was added DIPEA (0.233 g, 0.00180 mol), HOBt (0.053 g, 0.00036 mol) and EDCI.HCl (0.138 g, 0.00072 mol) at ambient temperature. After 2 minutes (2,3-dimethyl-phenyl)-piperidin-4-yl-amine dihydrochloride (0.1 g, 0.00036 mol) was added and the resulting mixture was stirred overnight.

The reaction mixture was then diluted with cold water. The resulting precipitate was isolated by filtration and dried to afford 0.12 g (77%) of 5-phenyl-1H-pyrazole-3-carboxylic acid {2-[4-(2,3-dimethyl-phenylamino)-piperidin-1-yl]-2-oxo-ethyl}-amide. LCMS: 432.23 (M+1)$^+$, 95.88%, $^1$H NMR (DMSO-d$_6$): δ 13.7 (s, 1H), 8.1 (s, 1H), 7.8 (t, 2H), 7.6 (m, 3H), 7.1 (s, 1H), 6.9 (t, 1H), 6.5 (d, 1H), 6.4 (d, 1H), 4.4 (m, 2H), 4.2 (s, 2H), 3.9 (d, 1H), 3.5 (s, 1H), 3.2 (m, 1H), 2.8 (m, 1H), 2.2 (s, 3H), 2.0 (s, 5H), 1.4 (m, 2H).

Example 30

Synthesis of 5-Phenyl-1H-pyrazole-3-carboxylic acid {2-[4-(2,4-dimethyl-phenylamino)-piperidin-1-yl]-2-oxo-ethyl}-amide

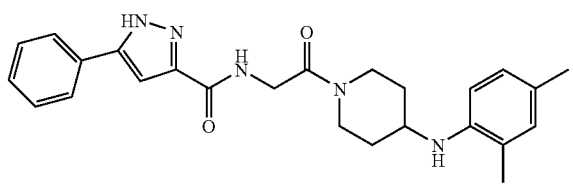

To a stirred solution of [(5-phenyl-1H-pyrazole-3-carbonyl)-amino]-acetic acid (0.097 g, 0.00040 mol) in DMF (1 mL) was added DIPEA (0.233 g, 0.00180 mol), HOBt (0.053 g, 0.00040 mol) and EDCI.HCl (0.138 g, 0.0007214 mol) at ambient temperature. After 2 minutes (2,4-dimethyl-phenyl)-piperidin-4-yl-amine dihydrochloride (0.1 g, 0.00036 mol) was added and the resulting mixture was stirred overnight. The reaction mixture was then diluted with cold water. The resulting precipitate was isolated by filtration and dried to afford 0.12 g (77%) of 5-phenyl-1H-pyrazole-3-carboxylic acid {2-[4-(2,4-dimethyl-phenylamino)-piperidin-1-yl]-2-oxo-ethyl}-amide. LCMS: 432.23 (M+1)$^+$, 97.64%, $^1$H NMR (DMSO-d$_6$): δ 8.1 (s, 1H), 7.8 (d, 2H), 7.5 (t, 2H), 7.4 (d, 1H), 7.1 (s, 1H), 6.6 (d, 1H), 4.3 (m, 2H), 4.1 (t, 2H), 3.9 (d, 1H), 3.5 (bs, 1H), 3.2 (t, 1H), 2.8 (t, 1H), 2.2 (s, 3H), 2.1 (s, 3H), 1.9 (t, 2H), 1.5 (m, 1H), 1.3 (m, 1H).

Example 31

Synthesis of 5-Phenyl-1H-pyrazole-3-carboxylic acid {2-[4-(2,5-dimethyl-phenylamino)-piperidin-1-yl]-2-oxo-ethyl}-amide

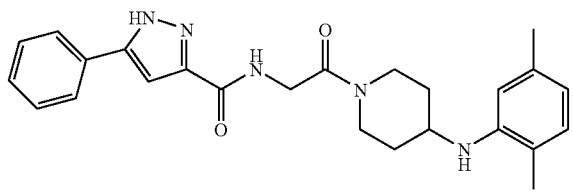

To a stirred solution of [(5-phenyl-1H-pyrazole-3-carbonyl)-amino]-acetic acid (0.097 g, 0.00040 mol) in DMF (1 mL) was added DIPEA (0.233 g, 0.00180 mol), HOBt (0.053 g, 0.00040 mol) and EDCI.HCl (0.138 g, 0.00072 mol) at ambient temperature. After 2 minutes (2,5-dimethyl-phenyl)-piperidin-4-yl-amine dihydrochloride (0.1 g, 0.00036 mol) was added and the resulting mixture was stirred overnight. The reaction mixture was then diluted with cold water. The resulting precipitate was isolated by filtration and dried to afford 0.12 g (77%) of 5-phenyl-1H-pyrazole-3-carboxylic acid {2-[4-(2,5-dimethyl-phenylamino)-piperidin-1-yl]-2-oxo-ethyl}-amide. LCMS: 432.23 (M+1)$^+$, 96.91%, $^1$H NMR (DMSO-d$_6$): δ 8.1 (s, 1H), 7.8 (d, 2H), 7.5 (t, 2H), 7.4 (t, 1H), 7.1 (s, 1H), 6.8 (d, 1H), 6.5 (s, 1H), 6.3 (d, 1H), 4.4 (d, 2H), 4.2 (bs, 2H), 3.9 (d, 1H), 3.6 (bs, 1H), 3.2 (t, 1H), 2.8 (t, 1H), 2.2 (s, 3H), 2.0 (s, 3H), 1.9 (d, 1H), 1.5 (d, 1H), 1.3 (d, 1H).

Example 32

Synthesis of 5-Phenyl-1H-pyrazole-3-carboxylic acid {2-[4-(2-tert-butyl-phenylamino)-piperidin-1-yl]-2-oxo-ethyl}-amide

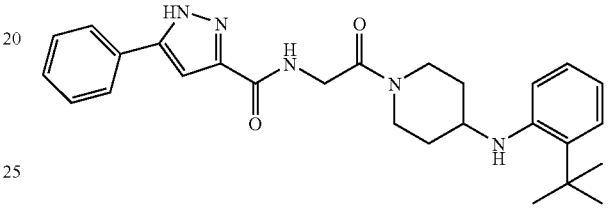

To a stirred solution of [(5-phenyl-1H-pyrazole-3-carbonyl)-amino]-acetic acid (0.088 g, 0.00036 mol) in DMF (2 mL) was added DIPEA (0.211 g, 0.0016 mol), HOBt (0.048 g, 0.00036 mol) and EDCI.HCl (0.125 g, 0.000655 mol) at ambient temperature. After 2 minutes (2-tert-butyl-phenyl)-piperidin-4-yl-amine dihydrochloride (0.1 g, 0.00033 mol) was added and the resulting mixture was stirred overnight. The reaction mixture was then diluted with cold water. The resulting precipitate was isolated by filtration and dried to afford 0.07 g (49%) of 5-phenyl-1H-pyrazole-3-carboxylic acid {2-[4-(2-tert-butyl-phenylamino)-piperidin-1-yl]-2-oxo-ethyl}-amide. LCMS: 460.26 (M+1)$^+$, 89.75%, $^1$H NMR (DMSO-d$_6$): δ 13.8 (s, 1H), 8.1 (s, 1H), 7.8 (d, 2H), 7.6-7.4 (m, 3H), 7.2-7.0 (m, 3H), 6.8 (d, 1H), 6.6 (t, 1H), 4.3 (d, 1H), 4.2 (d, 2H), 3.9 (m, 2H), 3.7 (s, 1H), 3.2 (t, 1H), 2.8 (t, 1H), 2.0 (t, 3H), 1.4 (s, 9H), 1.0 (bs, 1H).

Example 33

Synthesis of 5-Phenyl-1H-pyrazole-3-carboxylic acid {2-[4-(2,5-difluoro-phenoxy)-piperidin-1-yl]-2-oxo-ethyl}-amide

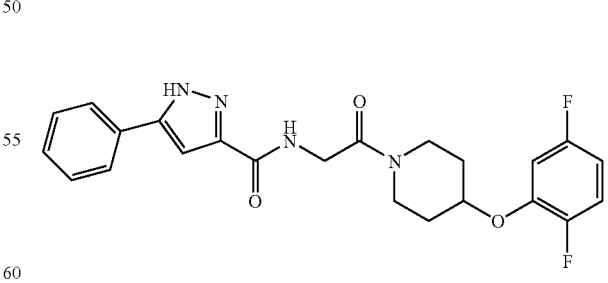

To a stirred solution of [(5-phenyl-1H-pyrazole-3-carbonyl)-amino]-acetic acid (0.075 g, 0.0003 mol) in DMF (2 mL) was added DIPEA (0.135 g, 0.0012 mol), HOBt (0.061 g, 0.00045 mol) and EDCI.HCl (0.086 g, 0.00045 mol) at ambient temperature. After 2 minutes, 4-(2,5-difluoro-phenoxy)-piperidine hydrochloride (0.076 g, 0.0003 mol) was added and the resulting mixture was stirred overnight. The reaction mixture was then diluted with cold water and the product was extracted with ethyl acetate. The ethyl acetate layer was collected and washed with brine solution, dried over sodium sulfate and concentrated. The resulting residue was purified by column chromatography using neutral aluminum oxide (5% methanol in chloroform) to afford 0.065 g (49%) of 5-phenyl-1H-pyrazole-3-carboxylic acid {2-[4-(2,5-difluoro-phenoxy)-piperidin-1-yl]-2-oxo-ethyl}-amide. LCMS: 441.17 (M+1)$^+$, 91.07%, $^1$H NMR (DMSO-d$_6$): δ 13.8 (bs, 1H), 8.0 (bs, 1H), 7.8 (m, 2H), 7.4 (m, 5H), 7.2 (m, 1H), 6.8 (m, 1H), 4.6 (m, 1H), 4.2 (m, 2H), 3.9 (m, 1H), 3.8 (m, 1H), 2.0 (m, 2H), 1.6 (m, 2H).

Example 34

Synthesis of 5-Phenyl-1H-pyrazole-3-carboxylic acid {2-[4-(2-bromo-phenylsulfanyl)-piperidin-1-yl]-2-oxo-ethyl}-amide

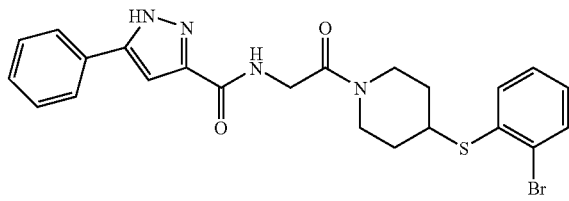

To a stirred solution of [(5-phenyl-1H-pyrazole-3-carbonyl)-amino]-acetic acid (0.15 g, 0.000533 mol) in DMF (3 mL) was added DIPEA (0.206 g, 0.00160 mol), HOBt (0.0864 g, 0.00064 mol) and EDCI.HCl (0.122 g, 0.00064 mol) at ambient temperature. After 2 minutes 4-(2-bromo-phenylsulfanyl)-piperidine hydrochloride (0.197 g, 0.00064 mol) was added and the resulting mixture was stirred overnight. The reaction mixture was then diluted with cold water. The resulting precipitate was isolated by filtration and dried. Purification by column chromatography using silica gel 60-120 mesh (40% ethyl acetate in hexane) afforded 0.097 g (36%) of 5-phenyl-1H-pyrazole-3-carboxylic acid {2-[4-(2-bromo-phenylsulfanyl)-piperidin-1-yl]-2-oxo-ethyl}-amide. LCMS: 499.07 (M+1)$^+$, 95.7%, $^1$H NMR (DMSO-d$_6$): δ 13.8 (d, 1H), 8.1 (t, 1H), 7.8 (d, 2H), 7.6 (dd, 1H), 7.58-7.3 (m, 6H), 7.22-7.06 (m, 2H), 4.3-4.1 (m, 3H), 3.9-3.6 (m, 2H), 3.0 (m, 1H), 2.0 (m, 2H), 1.7-1.4 (m, 3H).

Example 35

Synthesis of 5-Phenyl-1H-pyrazole-3-carboxylic acid [2-oxo-2-(4-O— tolylamino-piperidin-1-yl)-ethyl]-amide

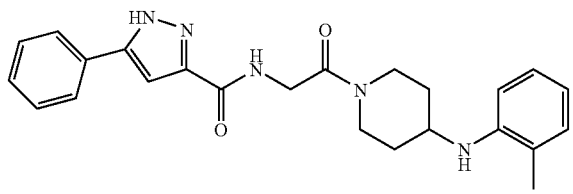

To a stirred solution of [(5-phenyl-1H-pyrazole-3-carbonyl)-amino]-acetic acid (0.102 g, 0.00042 mol) in DMF (1 mL) was added DIPEA (0.245 g, 0.00190 mol), HOBt (0.056 g, 0.000418 mol) and EDCI.HCl (0.145 g, 0.00076 mol) at ambient temperature. After 2 minutes piperidin-4-yl-o-tolylamine dihydrochloride (0.1 g, 0.00038 mol) was added and the resulting mixture was stirred for 16 hours. The reaction mixture was then diluted with cold water. The resulting precipitate was isolated by filtration and dried to afford 0.15 g (94% of 5-phenyl-1H-pyrazole-3-carboxylic acid [2-oxo-2-(4-o-tolylamino-piperidin-1-yl)-ethyl]-amide.
LCMS: 418.22 (M+1)$^+$, 92.96%, $^1$H NMR (CDCl$_3$): δ 8.8 (bs, 1H), 7.7 (d, 2H), 7.4 (m, 3H), 7.1 (t, 3H), 6.7 (q, 2H), 4.6-4.3 (m, 4H), 4.1 (d, 1H), 3.6 (s, 1H), 3.4 (t, 2H), 3.0 (t, 1H), 2.2 (d, 2H), 2.1 (s, 3H), 1.5 (q, 4H).

Intermediate 31

Synthesis of 5-(3-Benzyloxy-phenyl)-1H-pyrazole-3-carboxylic acid

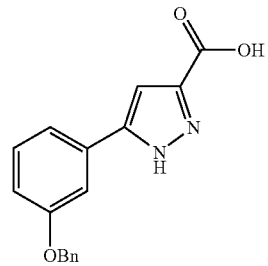

To a solution of 1-(3-hydroxy-phenyl)-ethanone (5 g, 0.03672 mole) in DMF (75 mL) was added NaH (60% w/w dispersion in oil) (1.66 g, 0.0416 mole) and the resulting mixture was stirred at ambient temperature for 15 minutes. Benzyl bromide (7.23 g, 0.0422 mole) was then added and stirring was continued for 4 hours at ambient temperature. The reaction mixture was then quenched with cold aqueous NH$_4$Cl solution. The product was extracted with ethyl acetate and the ethyl acetate layer was washed with water followed by brine solution, dried over sodium sulfate and concentrated under reduced pressure to afford 8.5 g (100%) of 1-(3-benzyloxy-phenyl)-ethanone. A mixture of THF (150 mL) and NaH (60% w/w dispersion in oil) (4.4 g, 0.11 mole) was cooled to 0° C. with stirring for 10 minutes. Diethyl oxalate (10.73 g, 0.0734 mole) was then added and the resulting mixture was heated to reflux for 10 minutes. The mixture was then cooled to ambient temperature and 1-(3-benzyloxy-phenyl)-ethanone (8.3 g, 0.0367 mole) in THF (50 mL) was added dropwise over a period of 45 minutes. The resulting mixture was then heated to 50° C. for 30 minutes. The reaction mixture was quenched with cold aqueous NH$_4$Cl solution and the product was extracted with ethyl acetate. The ethyl acetate layer was collected and washed with water followed by brine solution, dried over sodium sulfate and concentrated under reduced pressure. The resulting residue was purified by column chromatography using silica gel 60-120 mesh (4% ethyl acetate in hexane) to afford 10.9 g (92%) of 4-(3-benzyloxy-phenyl)-2,4-dioxo-butyric acid ethyl ester. LCMS: 327.12 (M+1)$^+$, 86%. A solution of 4-(3-benzyloxy-phenyl)-2,4-dioxo-butyric acid ethyl ester (5 g, 0.0153 mole), acetic acid (25 mL) and hydrazine hydrate (0.8426 g, 0.01685 mole) was heated to reflux for 3 hours. The reaction mixture was then poured into iced water, basified with saturated aqueous NaHCO₃ solution and the product was extracted with ethyl acetate. The ethyl acetate layer was collected, washed with brine solution, dried over sodium sulfate and concentrated under reduced pressure to afford 4.876 g (99%) of 5-(3-benzyloxy-phenyl)-1H-pyrazole-3-carboxylic acid ethyl ester. LCMS: 323.13 (M+1)⁺, 99%. To a stirred solution 5-(3-benzyloxy-phenyl)-1H-pyrazole-3-carboxylic acid ethyl ester (4 g, 0.0124 mol) in a mixture of THF (20 mL), methanol (10 mL) and H₂O (10 mL) was added LiOH.H₂O (1.56 g, 0.0372 mol) at ambient temperature. The resulting mixture was then stirred for 6 hours. Volatiles were removed by evaporation and the resulting residue was diluted with water and acidified with 10% HCl. The resulting precipitate was isolated by filtration and dried to afford 3.78 g (92%) of 5-(3-benzyloxy-phenyl)-1H-pyrazole-3-carboxylic acid. LCMS: 295.1 (M+1)⁺, 97.1%.

Intermediate 32

Synthesis of {[5-(3-Benzyloxy-phenyl)-1H-pyrazole-3-carbonyl]-amino}-acetic acid

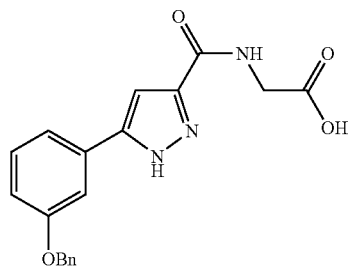

To a stirred solution of 5-(3-hydroxy-phenyl)-1H-pyrazole-3-carboxylic acid (1 g, 0.00340 mol) in DMF (5 mL) was added DIPEA (1.976 g, 0.01529 mol), HOBt (0.574 g, 0.00425 mol) and EDCI.HCl (0.814 g, 0.00425 mol) at ambient temperature. After 5 minutes glycine ethyl ester hydrochloride (0.498 g, 0.00357 mol) was added and the resulting mixture was stirred overnight. The reaction mixture was then diluted with cold water. The resulting precipitate was isolated by filtration and dried. The crude product was recrystallized from ethyl acetate to afford 0.54 g (36%) of {[5-(3-benzyloxy-phenyl)-1H-pyrazole-3-carbonyl]-amino}-acetic acid ethyl ester. LCMS: 380.15 (M+1)⁺, 92.05%. To a stirred solution of {[5-(3-benzyloxy-phenyl)-1H-pyrazole-3-carbonyl]-amino}-acetic acid ethyl ester (0.54 g, 0.00136 mmol) in a mixture of THF (50 mL), methanol (25 mL) and H₂O (25 mL) was added LiOH.H₂O (0.18 g, 0.0042 mol) at ambient temperature. The resulting mixture was stirred at ambient temperature overnight. Volatiles were removed by evaporation and the resulting residue was diluted with water, acidified with concentrated HCl solution. The resulting precipitate was isolated by filtration and dried afford 0.44 g (92%) of {[5-(3-benzyloxy-phenyl)-1H-pyrazole-3-carbonyl]-amino}-acetic acid. LCMS: 352.12 (M+1)⁺, 97.85%, Intermediate 33

Synthesis of 5-(3-Benzyloxy-phenyl)-1H-pyrazole-3-carboxylic acid {2-[4-(2-chloro-phenylamino)-piperidin-1-yl]-2-oxo-ethyl}-amide

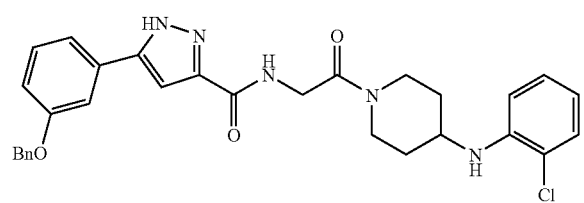

To a stirred solution of {[5-(3-benzyloxy-phenyl)-1H-pyrazole-3-carbonyl]-amino}-acetic acid (0.15 g, 0.00039 mol) in DMF (2 mL) was added DIPEA (0.224 g, 0.00174 mol) HOBt (0.065 g, 0.000482 mol) and EDCI.HCl (0.0925 g, 0.00048 mol) at ambient temperature. After 5 minutes (2-chloro-phenyl)-piperidin-4-yl-amine dihydrochloride (0.1 g, 0.00041 mol) was added and the resulting mixture was stirred overnight. The reaction mixture was then diluted with cold water. The resulting precipitate was isolated by filtration. Purification by column chromatography using basic aluminium oxide (60% ethyl acetate in hexane) afforded 0.19 g (91%) of 5-(3-benzyloxy-phenyl)-1H-pyrazole-3-carboxylic acid {2-[4-(2-chloro-phenylamino)-piperidin-1-yl]-2-oxo-ethyl}-amide. LCMS: 544.2 (M+1)⁺, 96.18%.

Example 36

Synthesis of 5-(3-Hydroxy-phenyl)-1H-pyrazole-3-carboxylic acid {2-[4-(2-chloro-phenylamino)-piperidin-1-yl]-2-oxo-ethyl}-amide

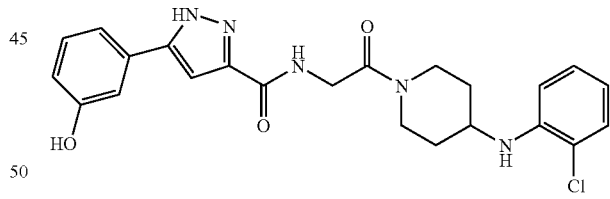

A solution of 5-(3-benzyloxy-phenyl)-1H-pyrazole-3-carboxylic acid {2-[4-(2-chloro-phenylamino)-piperidin-1-yl]-2-oxo-ethyl}-amide (0.19 g, 0.00035 mole) in dichloromethane was cooled to −70° C. 1 mL of a 1.6M solution of BBr₃ in dichloromethane was then added dropwise with vigorous stirring. The reaction mixture was slowly brought to ambient temperature and stirring was continued at the same temperature for 1 hour. The reaction mixture was then cooled to −70° C. and ice cold water was added dropwise with stirring and while the mixture was slowly brought to ambient temperature. The product was extracted with dichloromethane and the organic layers were dried over sodium sulfate. The organic layer was collected and concentrated under reduced pressure. The resulting residue was recrystallized from ethyl acetate to afford 0.071 g (45%) of 5-(3- hydroxy-phenyl)-1H-pyrazole-3-carboxylic acid {2-[4-(2-chloro-phenylamino)-piperidin-1-yl]-2-oxo-ethyl}-amide. LCMS: 454.16 (M+1)+, 94.25%, $^1$H NMR (DMSO-$d_6$): δ 13.6 (s, 1H), 9.6 (s, 1H), 8.1 (s, 1H), 7.0 (m, 5H), 6.84 (d, 1H), 6.76 (d, 1H), 6.6 (m, 1H), 4.8 (s, 1H), 4.3 (d, 1H), 4.1 (d, 2H), 3.8 (d, 1H), 3.7 (s, 1H), 3.2 (m, 1H), 2.8 (m, 1H), 1.95 (m, 2H), 1.3 (m, 2H).

Intermediate 34

Synthesis of 5-Phenyl-pyridine-2-carboxylic acid

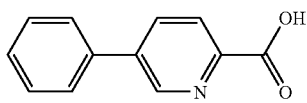

A mixture of toluene (20 mL) and water (5 mL) was degassed with argon for 5 minutes. Sodium carbonate (1.53 g, 0.01444 mole) was then added and the mixture was degassed with argon for a further 5 minutes. Phenyl boronic acid (1.126 g, 0.00866 mole) and 5-chloro-pyridine-2-carbonitrile (1 g, 0.00722 mole) were added and the resulting mixture was degassed with argon for a further 5 minutes. tetrakis(triphenylphosphine)palladium(0) (1.67 g, 0.00144 mole) was added and the resulting mixture was degassed with argon for a further 5 minutes. The reaction mixture was then heated to reflux for 3 hours. The reaction mixture was diluted with ethyl acetate. The ethyl acetate layer was washed with water followed by brine solution, dried over sodium sulfate and concentrated under reduced pressure. The resulting residue was purified by column chromatography using silica gel 60-120 mesh (4% ethyl acetate in hexane) to afford 0.9 g (69%) of 5-phenyl-pyridine-2-carbonitrile. LCMS: 181.07 (M+1)+, 28.90%, $^1$H NMR (DMSO-$d_6$): δ 9.1 (s, 1H), 8.4-8.3 (m, 1H), 8.2-8.1 (m, 1H), 7.9-7.78 (m, 2H), 7.6-7.4 (m, 3H). To a stirred solution of 5-phenyl-pyridine-2-carbonitrile (0.9 g, 0.005 mol) in a mixture of ethanol (10 mL) and water (5 mL) was added NaOH (1 g, 0.025 mol) and the resulting mixture was stirring overnight. The reaction mixture was then concentrated under reduced pressure. The residue was dissolved in water, washed with ether and the aqueous layer was acidified with citric acid. The acidified aqueous solution was extracted with ethyl acetate. The ethyl acetate layer was washed with brine solution, dried over sodium sulfate and concentrated under reduced pressure to afford 0.75 g (75%) of 5-phenyl-pyridine-2-carboxylic acid. LCMS: 200.06 (M+1)+, 97.53%, $^1$H NMR (DMSO-$d_6$): δ 13 (bs, 1H), 9.1-9.0 (d, 1H), 8.3-8.2 (dd, 1H), 8.2-8.1 (d, 1H), 7.8 (d, 1H), 7.6-7.4 (m, 3H).

Intermediate 35

Synthesis of [(5-Phenyl-pyridine-2-carbonyl)-amino]-acetic acid

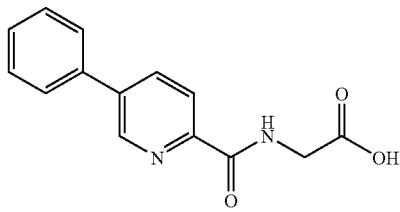

To a stirred solution of 5-phenyl-pyridine-2-carboxylic acid (0.3 g, 0.00151 mol) in DMF (5 mL) was added DIPEA (0.580 g, 0.00452 mol), HOBt (0.243 g, 0.00180 7 mol) and EDCI.HCl (0.346 g, 0.001807 mol) at ambient temperature. After 2 minutes glycine ethyl ester hydrochloride (0.252 g, 0.00181 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure to afford 0.32 g (75%) of [(5-phenyl-pyridine-2-carbonyl)-amino]-acetic acid ethyl ester. To a stirred solution of [(5-phenyl-pyridine-2-carbonyl)-amino]-acetic acid ethyl ester (0.32 g, 0.00113 mol) in a mixture of THF (3.2 mL), methanol (2 mL) and H$_2$O (1 mL) was added LiOH.H$_2$O (0.142 g, 0.00338 mol) and the resulting mixture was stirred at ambient temperature overnight. Volatiles were removed by evaporation and the resulting residue was diluted with water and acidified with 10% HCl. The product was extracted with ethyl acetate, which was dried over sodium sulfate and concentrated under reduced pressure to afford 0.24 g (83%) of [(5-phenyl-pyridine-2-carbonyl)-amino]-acetic acid.

Example 37

Synthesis of 5-Phenyl-pyridine-2-carboxylic acid {2-oxo-2-[4-(2-chloro-phenoxy)-piperidin-1-yl]-ethyl}-amide

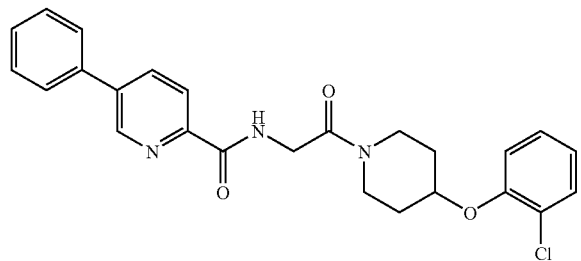

To a stirred solution of [(5-phenyl-pyridine-2-carbonyl)-amino]-acetic acid (0.07 g, 0.00027 mol) in DMF (1.5 mL) was added DIPEA (0.105 g, 0.00082 mol), HOBt (0.044 g, 0.00033 mol) and EDCI.HCl (0.062 g, 0.00033 mol) at ambient temperature. After 2 minutes 4-(2-chlorophenoxy)piperidine hydrochloride (0.081 g, 0.000327 mol) was added and the resulting mixture was stirred overnight. The reaction mixture was then diluted with cold water and the product was extracted with ethyl acetate. The ethyl acetate layer was washed with brine solution, dried over sodium sulfate and concentrated under reduced pressure to afford 0.0545 g (44%) of 5-phenyl-pyridine-2-carboxylic acid {2-oxo-2-[4-(2-chloro-phenoxy)-piperidin-1-yl]-ethyl}-amide. LCMS: 484.18 (M+1)$^+$, 95.40%, $^1$H NMR (DMSO-d$_6$): δ 9.0 (d, 1H), 8.8 (t, 1H), 8.3 (dd, 1H), 8.1 (d, 1H), 7.8 (d, 1H), 7.6-7.4 (m, 2H), 7.3-7.2 (m, 2H), 7.0-6.9 (m, 1H), 4.8-4.7 (m, 1H), 4.3 (d, 1H), 3.8-3.6 (m, 2H), 3.5 (m, 2H), 2.0-1.9 (m, 2H), 1.8-1.6 (m, 2H).

Example 38

Synthesis of 5-Phenyl-pyridine-2-carboxylic acid {2-[4-(2-chloro-5-fluoro-phenoxy)-piperidin-1-yl]-2-oxo-ethyl}-amide

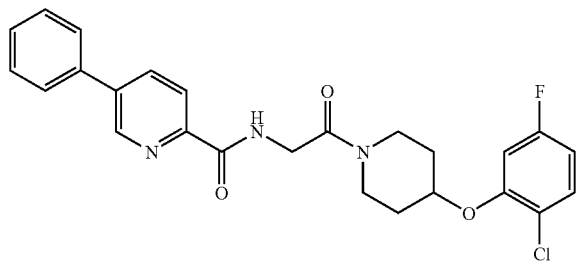

To a stirred solution of [(5-phenyl-pyridine-2-carbonyl)-amino]-acetic acid (0.07 g, 0.00027 mol) in DMF (1.5 mL) was added DIPEA (0.105 g, 0.000819 mol), HOBt (0.044 g, 0.00033 mol) and EDCI.HCl (0.062 g, 0.00033 mol) at ambient temperature. After 2 minutes 4-(2-chloro-5-fluoro-phenoxy)-piperidine hydrochloride (0.087 g, 0.00033 mol) was and the resulting mixture was stirred overnight. The reaction mixture was then diluted with cold water and the product was extracted with ethyl acetate. The ethyl acetate layer was washed with brine solution, dried over sodium sulfate and concentrated under reduced pressure afford 0.069 g (54%) of 5-phenyl-pyridine-2-carboxylic acid {2-[4-(2-chloro-5-fluoro-phenoxy)-piperidin-1-yl]-2-oxo-ethyl}-amide. LCMS: 468.14 (M+1)$^+$, 82.99%, $^1$H NMR (DMSO-d$_6$): δ 9.0 (d, 1H), 8.8 (t, 1H), 8.3 (dd, 1H), 8.1 (d, 1H), 7.8 (d, 2H), 7.6-7.4 (m, 4H), 7.2 (dd, 1H), 6.9-6.8 (m, 1H), 4.9-4.8 (m, 1H), 4.3 (d, 2H), 3.8-3.6 (m, 2H), 3.5 (m, 2H), 2.1-1.9 (m, 2H), 1.8-1.5 (m, 2H).

Intermediate 36

Synthesis of 5-(4-Benzyloxy-phenyl)-1H-pyrazole-3-carboxylic acid ethyl ester

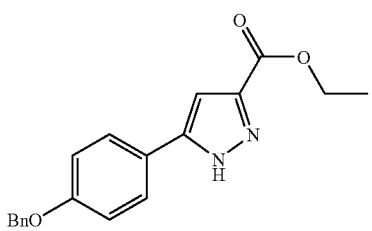

To a solution of 1-(4-hydroxy-phenyl)-ethanone (10 g, 0.0735 mole) in DMF (50 mL) was added K$_2$CO$_3$ (20.2 g, 0.147 mole) at ambient temperature. Benzyl bromide (13.83 g, 0.0808 mole) was then added and the resulting mixture was stirred at ambient temperature for 5 hours. The reaction mixture was then quenched with iced water. The resulting precipitate was isolated by filtration and dried to afford 16.2 g (98%) of 1-(4-benzyloxy-phenyl)-ethanone. LCMS: 227.1 (M+1)$^+$, 98.38%. A mixture of THF (130 mL) and NaH (60% w/w dispersion in oil) (5.28 g, 0.132 mole) was cooled to 0° C. with stirring for 5 minutes. Diethyl oxalate (12.87 g, 0.0886 mole) was added and the mixture was heated to reflux for 15 minutes. after cooling to ambient temperature 1-(4-benzyloxy-phenyl)-ethanone (10 g, 0.0442 mole) in THF (50 mL) was added dropwise over a period of 45 minutes. The resulting mixture was heated to 70° C. for 1 hour. The reaction mixture was then quenched with cold aqueous NH$_4$Cl solution. The resulting precipitate was isolated by filtration and dried to afford 21.2 g of 4-(4-benzyloxy-phenyl)-2,4-dioxo-butyric acid ethyl ester. LCMS: 327.12 (M+1)$^+$, 36.5%. A solution of 4-(4-benzyloxy-phenyl)-2,4-dioxo-butyric acid ethyl ester (10 g, 0.03064 mole), acetic acid (20 mL) and hydrazine hydrate (1.685 g, 0.0337 mole) was heated to reflux for 8 hours. The reaction mixture was then poured into iced water and basified with saturated aqueous NaHCO$_3$ solution. The product was extracted with ethyl acetate. The ethyl acetate layer was washed with brine solution, dried over sodium sulfate and concentrated under reduced pressure to afford 6.3 g (64%) of 5-(4-benzyloxy-phenyl)-1H-pyrazole-3-carboxylic acid ethyl ester. LCMS: 323.13 (M+1)$^+$, 95.10%.

Intermediate 37

Synthesis of 5-(4-Hydroxy-phenyl)-1H-pyrazole-3-carboxylic acid

To a stirred solution of 5-(4-benzyloxy-phenyl)-1H-pyrazole-3-carboxylic acid ethyl ester (5.8 g, 0.018 mole) in a mixture of methanol (50 mL) and THF (180 mL) was added 10% Pd/C (2 g) and the resulting mixture was stirred under an atmosphere of hydrogen for 5 hours. The reaction mixture was then filtered through celite, and the celite was washed with methanol. The filtrate was collected and concentrated under reduced pressure afford 4.05 g (97%) of 5-(4-Benzyloxy-phenyl)-1H-pyrazole-3-carboxylic acid ethyl ester. LCMS: 233.08 (M+1)$^+$, 97%. To a stirred solution of 5-(4-hydroxy-phenyl)-1H-pyrazole-3-carboxylic acid ethyl ester (4 g, 0.01724 mol) in a mixture of 1,4-dioxane (88 mL) and H$_2$O (88 mL) was added NaOH (1.57 g, 0.03793 mol) and the resulting mixture was stirred at ambient temperature overnight. The reaction mixture was then acidified with concentrated HCl solution. The mixture was concentrated and the resulting precipitate was isolated by filtration and dried to afford 3.1 g (76%) of 5-(4-hydroxy-phenyl)-1H-pyrazole-3-carboxylic acid. LCMS: 205.05 (M+1)+, 91.6%.

Intermediate 38

Synthesis of 2-Amino-1-[4-(2-chloro-phenylamino)-piperidin-1-yl]-ethanone hydrochloride

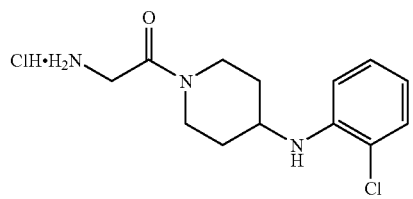

To a stirred mixture of glycine (30 g, 0.3996 mole) in 1N aqueous NaOH (39.96 g, 0.999 mole) was added tert-butanol (270 mL). The mixture was cooled to 0° C. and di-tert-butyl dicarbonate (96.42 g, 0.4395 mole) was added dropwise. The mixture was stirred at ambient temperature for 5 hours. The reaction mixture was then concentrated under reduced pressure and the resulting residue was acidified with citric acid. The product was extracted with ethyl acetate. the organic layer was washed with brine solution, dried over sodium sulfate and concentrated under reduced pressure to afford 49 g (70%) of tert-butoxycarbonylamino-acetic acid. $^1$H NMR (DMSO-$d_6$): δ 12.8-12.0 (bs, 1H), 7.1 (t, 1H), 3.6 (d, 2H), 1.4 (s 9H). To a stirred solution of tert-butoxycarbonylamino-acetic acid (0.2 g, 0.00114 mol) in DMF (5 mL) was added DIPEA (0.59 g, 0.00457 mol), HOBt (0.193 g, 0.001427 mol) and EDCI.HCl (0.274 g, 0.00143 mol) at ambient temperature. After 5 minutes (2-chloro-phenyl)-piperidin-4-yl-amine dihydrochloride (0.283 g, 0.00114 mol) was added and the resulting mixture was stirred overnight. The reaction mixture was then diluted with cold water. The resulting precipitate was isolated by filtration and purified by column chromatography using basic aluminium oxide (60% ethyl acetate in hexane) to afford 0.41 g (98%) of {2-[4-(2-chloro-phenylamino)-piperidin-1-yl]-2-oxo-ethyl}-carbamic acid tert-butyl ester. LCMS: 368.18 (M+1)+, 93.53%. A solution of {2-[4-(2-chloro-phenylamino)-piperidin-1-yl]-2-oxo-ethyl}-carbamic acid tert-butyl ester (0.41 g, 0.00111 mole) in methanol (10 mL) was added dioxane.HCl (5 mL) and the resulting mixture was stirred at ambient temperature for 10 minutes. The mixture was then concentrated under reduced and the resulting residue was washed with ether to afford 0.34 g (98%) of 2-amino-1-[4-(2-chloro-phenylamino)-piperidin-1-yl]-ethanone hydrochloride. LCMS: 268.11 (M+1)+, 84.63%.

Example 39

Synthesis of 5-(4-Hydroxy-phenyl)-1H-pyrazole-3-carboxylic acid {2-[4-(2-chloro-phenylamino)-piperidin-1-yl]-2-oxo-ethyl}-amide

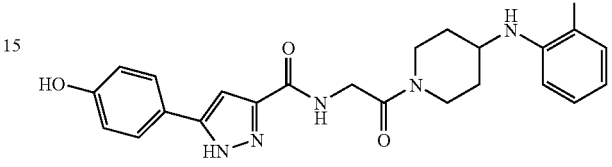

To a stirred solution of 5-(4-hydroxy-phenyl)-1H-pyrazole-3-carboxylic acid (0.1 g, 0.00049 mol) in DMF (5 mL) was added DIPEA (0.253 g, 0.00196 mol), HOBt (0.0827 g, 0.00061 mol) and EDCI.HCl (0.117 g, 0.00061 mol) at ambient temperature. After 5 minutes 2-amino-1-[4-(2-chloro-phenylamino)-piperidin-1-yl]-ethanone dihydrochloride (0.164 g, 0.00054 mol) was added and the resulting mixture was stirred overnight. The reaction mixture was then diluted with cold water. The resulting precipitate was isolated by filtration and recrystallized from ethyl acetate to afford 0.092 g (41%) of 5-(4-hydroxy-phenyl)-1H-pyrazole-3-carboxylic acid {2-[4-(2-chloro-phenylamino)-piperidin-1-yl]-2-oxo-ethyl}-amide. LCMS: 426.16 (M+1)+, 91.47%, $^1$H NMR (DMSO-$d_6$): δ 13.5 (s, 1H), 9.7 (s, 1H), 8.0 (s, 1H), 7.58 (d, 2H), 7.1 (m, 2H), 6.8 (m, 4H), 6.56 (m, 1H), 4.9 (d, 1H), 4.3 (d, 1H), 4.1 (d, 2H), 3.8 (m, 11H), 3.6 (m, 11H), 3.1 (m, 1H), 2.7 (m, 1H), 1.9 (m, 2H), 1.3 (m, 2H)

Intermediate 39

Synthesis of 5-(2-Benzyloxy-phenyl)-1H-pyrazole-3-carboxylic acid ethyl ester

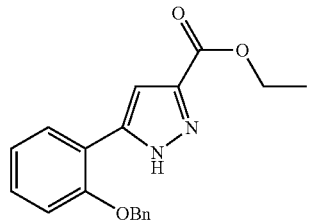

To a solution of 1-(2-hydroxy-phenyl)-ethanone (5 g, 0.03672 mole) in DMF (75 mL) was added NaH (60% w/w dispersion in oil) (1.66 g, 0.0416 mole) and the resulting mixture was stirred at ambient temperature for 15 minutes. Benzyl bromide (7.23 g, 0.0422 mole) was then added and the mixture as stirred for an additional 4 hours. The reaction mixture was then quenched with cold aqueous NH$_4$Cl solution and the product was extracted with ethyl acetate. The ethyl acetate layer was washed with water, brine solution, dried over sodium sulfate and concentrated under reduced pressure to afford 8.4 g (100%) of 1-(2-benzyloxy-phenyl)- ethanone. LCMS: 227.1 (M+1)$^+$, 84.14%. To a mixture of THF (200 mL) and NaH (60% w/w dispersion in oil) (4.4 g, 0.11 mole) cooled to 0° C. was added diethyl oxalate (10.73 g, 0.07345 mole). The resulting mixture was heated to reflux for 15 minutes. After cooing to ambient temperature, 1-(2-benzyloxy-phenyl)-ethanone (8.3 g, 0.0376 mole) was added dropwise over a period of 45 minutes. The resulting mixture was heated to 55° C. for 30 minutes. The reaction mixture was then quenched with cold aqueous NH$_4$Cl solution and the product was extracted with ethyl acetate. The ethyl acetate layer was washed with water, brine solution, dried over sodium sulfate and concentrated under reduced pressure. The resulting residue was purified by column chromatography using silica gel 60-120 mesh (4% ethyl acetate in hexane) to afford 8.7 g (71%) of 4-(2-benzyloxy-phenyl)-2,4-dioxo-butyric acid ethyl ester. LCMS: 327.12 (M+1)$^+$, 78.6%. A solution of 4-(2-benzyloxy-phenyl)-2,4-dioxo-butyric acid ethyl ester (3.75 g, 0.01149 mole), acetic acid (20 mL) and hydrazine hydrate (0.632 g, 0.01264 mole) was heated to reflux for 3 hours. The reaction mixture was then poured into iced water basified with saturated aqueous NaHCO$_3$ solution and the product was extracted with ethyl acetate. The ethyl acetate layer was washed with brine solution, dried over sodium sulfate and concentrated under reduced pressure to afford 3.703 g (100%) of 5-(2-benzyloxy-phenyl)-1H-pyrazole-3-carboxylic acid ethyl ester. LCMS: 323.13 (M+1)$^+$, 97.14%.

Intermediate 40

Synthesis of 5-(2-Hydroxy-phenyl)-1-methyl-1H-pyrazole-3-carboxylic acid

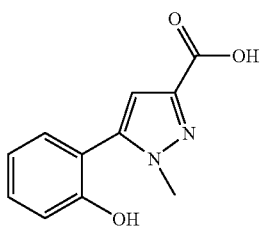

To a solution of 5-(2-benzyloxy-phenyl)-1H-pyrazole-3-carboxylic acid ethyl ester (0.25 g, 0.00078 mole) in DMF (5 mL) was added K$_2$CO$_3$ (0.225 g, 0.00163 mole) followed by methyl iodide (0.116 g, 0.00081 mole) and at the resulting mixture was stirred at ambient temperature for 1 hour. The mixture was then quenched with iced water and the resulting precipitate was isolated by filtration. The solid was recrystallized from ethyl acetate to afford 0.251 g (96%) of 5-(2-benzyloxy-phenyl)-1-methyl-1H-pyrazole-3-carboxylic acid ethyl ester. LCMS: 337.15 (M+1)$^+$, 90.13%. To a stirred solution of 5-(2-benzyloxy-phenyl)-1-methyl-1H-pyrazole-3-carboxylic acid ethyl ester (0.251 g, 0.00075 mole) in methanol (40 mL) was added 10% Pd/C (0.05 g) and the resulting mixture was stirred under an atmosphere of hydrogen for 1 hour. The mixture was then filtered through celite and the celite was washed with methanol. The combined filtrate was concentrated under reduced pressure to afford 0.169 g (92%) of 5-(2-hydroxy-phenyl)-1-methyl-1H-pyrazole-3-carboxylic acid ethyl ester. LCMS: 247.1 (M+1)$^+$, 99%. To a stirred solution of 5-(2-hydroxy-phenyl)-1-methyl-1H-pyrazole-3-carboxylic acid ethyl ester (0.169 g, 0.00069 mol) in a mixture of THF (10 mL), methanol (5 mL) and H$_2$O (5 mL), was added LiOH.H$_2$O (0.087 g, 0.00206 mol) at ambient temperature and the resulting mixture was stirred overnight. The reaction mixture was then diluted with cold water and acidified with 10% HCl. The product was extracted with ethyl acetate. The organic layer was dried over sodium sulfate and concentrated under reduced pressure to afford 0.13 g (87%) of 5-(2-hydroxy-phenyl)-1-methyl-1H-pyrazole-3-carboxylic acid. LCMS: 219.07 (M+1)$^+$, 81.5%

Example 40

Synthesis of 5-(2-Hydroxy-phenyl)-1-methyl-11H-pyrazole-3-carboxylic acid {2-[4-(2-chloro-phenylamino)-piperidin-1-yl]-2-oxo-ethyl}-amide

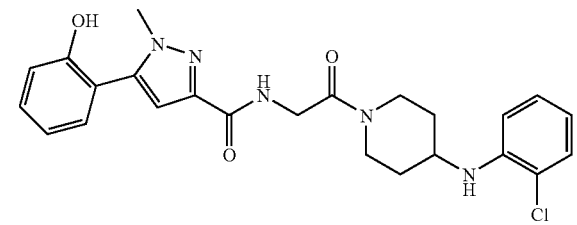

To a stirred solution of 5-(2-hydroxy-phenyl)-1-methyl-1H-pyrazole-3-carboxylic acid (0.13 g, 0.0006 mol) in DMF (2 mL) was added DIPEA (0.308 g, 0.00234 mol), HOBt (0.101 g, 0.00075 mol) and EDCI.HCl (0.143 g, 0.00075 mol) at ambient temperature. After 5 minutes 2-amino-1-[4-(2-chloro-phenylamino)-piperidin-1-yl]-ethanone hydrochloride (0.181 g, 0.00060 mol) was added and the resulting mixture was stirred overnight. The reaction mixture was then diluted with cold water. The resulting precipitate was isolated by filtration and recrystallized from ethyl acetate to afford 0.113 g (41%) of 5-(2-hydroxy-phenyl)-1-methyl-1H-pyrazole-3-carboxylic acid {2-[4-(2-chloro-phenylamino)-piperidin-1-yl]-2-oxo-ethyl}-amide. LCMS: 468.18 (M+1)$^+$, 96.98%. $^1$H NMR (DMSO-d$_6$): δ 10.2 (s, 1H), 8.7 (t, 1H), 7.7 (d, 1H), 7.4 (s, 1H), 7.1 (m, 3H), 6.8 (m, 3H), 6.6 (m, 1H), 4.9 (m, 1H), 4.3 (d, 1H), 4.1 (m, 4H), 3.9 (m, 1H), 3.6 (m, 1H), 3.1 (m, 1H), 2.7 (m, 1H), 1.9 (m, 2H), 1.4 (m, 2H).

Intermediate 41

Synthesis of 5-(2-Benzyloxy-phenyl)-isoxazole-3-carboxylic acid

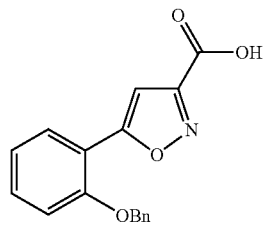

To a stirred solution of 4-(2-benzyloxy-phenyl)-2,4-dioxo-butyric acid ethyl ester (3.75 g, 0.01149 mole) in acetic acid (20 mL) was added hydroxylamine hydrochloride (0.878 g, 0.0126 mole) and the resulting mixture was heated to reflux for 3 hours. Volatiles were removed and the resulting residue was diluted with water, basified with sodium bicarbonate solution and extracted with ethyl acetate, washed the ethyl acetate with brine solution, dried over sodium sulfate and concentrated under reduced pressure to afford 3.42 g (92%) of 5-(2-benzyloxy-phenyl)-isoxazole-3-carboxylic acid ethyl ester. LCMS: 324.12 (M+1)⁺, 78.58%. To a stirred solution of 5-(2-benzyloxy-phenyl)-isoxazole-3-carboxylic acid ethyl ester (1.75 g, 0.00542 mol) in a mixture of THF (30 mL), methanol (15 mL) and H₂O (15 mL) was added NaOH (0.651 g, 0.01628 mol) and the resulting mixture was stirred for 2 hours. The reaction mixture was then diluted with cold water. Volatiles were removed by evaporation and the residue was diluted with water acidified with concentrated HCl. The resulting precipitate was isolated by filtration and dried to afford 1.57 g (98%) of 5-(2-benzyloxy-phenyl)-isoxazole-3-carboxylic acid. LCMS: 296.08 (M+1)⁺, 84.73%

Intermediate 42

Synthesis of {[5-(2-Benzyloxy-phenyl)-isoxazole-3-carbonyl]-amino}-acetic acid

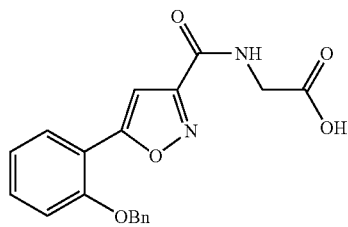

To a stirred solution of 5-(2-benzyloxy-phenyl)-isoxazole-3-carboxylic acid (0.7 g, 0.00237 mol) in DMF (4 mL) was added DIPEA (1.226 g, 0.00948 mol), HOBt (0.4 g, 0.0029 mol) and EDCI.HCl (0.57 g, 0.0029 mol) at ambient temperature. After 5 minutes glycine ethyl ester hydrochloride (0.347 g, 0.0024 8 mol) was added and the resulting mixture was stirred overnight. The reaction mixture was then diluted with cold water and the resulting precipitate was isolated by filtration. Purification by column chromatography using silica gel 60-120 mesh (65% ethyl acetate in hexane) afforded 0.66 g (73%) of {[5-(2-benzyloxy-phenyl)-isoxazole-3-carbonyl]-amino}-acetic acid ethyl ester. To a stirred solution of {[5-(2-benzyloxy-phenyl)-isoxazole-3-carbonyl]-amino}-acetic acid ethyl ester (0.65 g, 0.00171 mol) in a mixture of THF (10 mL), methanol (5 mL) and H₂O (5 mL) was added LiOH.H₂O (0.215 g, 0.00512 mol) at ambient temperature. The resulting mixture was stirred overnight. Volatiles were removed by evaporation and the residue was diluted with water acidified with concentrated HCl. The resulting precipitate was isolated by filtration and dried to afford 0.56 g of {[5-(2-benzyloxy-phenyl)-isoxazole-3-carbonyl]-amino}-acetic acid. LCMS: 353.11 (M+1)⁺, 60.4%.

Intermediate 43

Synthesis of 5-(2-Benzyloxy-phenyl)-isoxazole-3-carboxylic acid {2-[4-(2-chloro-phenoxy)-piperidin-1-yl]-2-oxo-ethyl}-amide

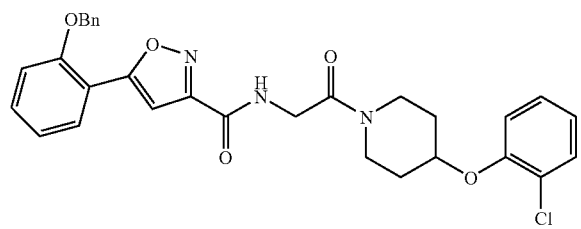

To a stirred solution of {[5-(2-benzyloxy-phenyl)-isoxazole-3-carbonyl]-amino}-acetic acid (0.15 g, 0.00039 mol) in DMF (2 mL) was added DIPEA (0.224 g, 0.00174 mol), HOBt (0.065 g, 0.000482 mol) and EDCI.HCl (0.0925 g, 0.00048 mol) at ambient temperature. After 5 minutes 4-(2-chloro-phenoxy)-piperidine hydrochloride (0.1 g, 0.00041 mol) was added and the resulting mixture was stirred overnight. The reaction mixture was then diluted with cold water and the resulting precipitate was isolated by filtration. Purification by column chromatography using silica gel 230-400 mesh (70% ethyl acetate in hexane) afforded 0.153 g (73%) of 5-(2-benzyloxy-phenyl)-isoxazole-3-carboxylic acid {2-[4-(2-chloro-phenoxy)-piperidin-1-yl]-2-oxo-ethyl}-amide. LCMS: 546.17 (M+1)⁺, 97.6%.

Example 41

Synthesis of 5-(2-Hydroxy-phenyl)-isoxazole-3-carboxylic acid {2-[4-(2-chloro-phenoxy)-piperidin-1-yl]-2-oxo-ethyl}-amide

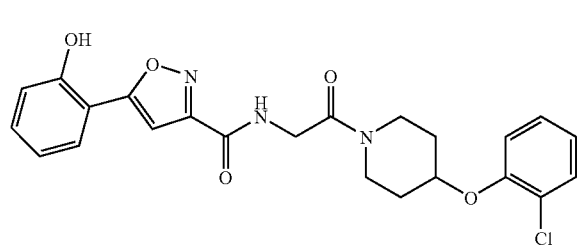

To a stirred solution of 5-(2-benzyloxy-phenyl)-isoxazole-3-carboxylic acid {2-[4-(2-chloro-phenoxy)-piperidin-1-yl]-2-oxo-ethyl}-amide (0.153 g, 0.00028 mole) in methanol (50 mL) was added 10% Pd/C (0.03 g) and the resulting mixture was stirred under an atmosphere of hydrogen for 3 hours. The mixture was then filtered through celite, the celite was washed with methanol and the organic layers were concentrated under reduced pressure. The resulting residue was purified by preparative HPLC to afford 0.055 g (43%) of 5-(2-hydroxy-phenyl)-isoxazole-3-carboxylic acid {2-[4-(2-chloro-phenoxy)-piperidin-1-yl]-2-oxo-ethyl}-amide. LCMS: 456.12 (M+1)⁺, 98.75%. ¹H NMR (DMSO-d₆): δ

10.8 (s, 1H), 8.7 (t, 1H), 7.8 (d, 1H), 7.4 (d, 1H), 7.24 (m, 3H), 7.12 (s, 1H), 7.04 (d, 1H), 6.92 (t, 2H), 4.7 (m, 1H), 4.2 (d, 2H), 3.7 (m, 2H), 3.4 (m, 2H), 1.9 (m, 2H), 1.6 (m, 2H).

Intermediate 44

Synthesis of 5-(2-Benzyloxy-phenyl)-isoxazole-3-carboxylic acid {2-[4-(2-chloro-phenylamino)-piperidin-1-yl]-2-oxo-ethyl}-amide

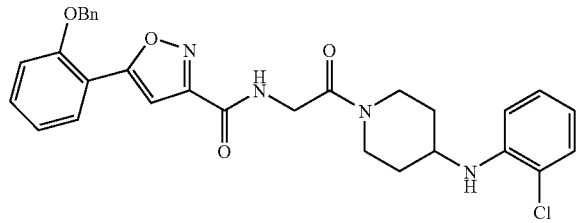

To a stirred solution of {[5-(2-benzyloxy-phenyl)-isoxazole-3-carbonyl]-amino}-acetic acid (0.15 g, 0.00039 mol) in DMF (2 mL) was added DIPEA (0.224 g, 0.00174 mol), HOBt (0.065 g, 0.000482 mol) and EDCI.HCl (0.0925 g, 0.00048 mol) at ambient temperature. After 5 minutes 4-(2-chloro-phenylamino)-piperidine dihydrochloride (0.1 g, 0.00041 mol) was added and the resulting mixture was stirred overnight. The reaction mixture was then diluted with cold water and the resulting precipitate was isolated by filtration. Purification by column chromatography using basic alumina (50% ethyl acetate in hexane) afforded 0.142 g (78%) of 5-(2-benzyloxy-phenyl)-isoxazole-3-carboxylic acid {2-[4-(2-chloro-phenylamino)-piperidin-1-yl]-2-oxo-ethyl}-amide.

Example 42

Synthesis of 5-(2-Hydroxy-phenyl)-isoxazole-3-carboxylic acid {2-[4-(2-chloro-phenylamino)-piperidin-1-yl]-2-oxo-ethyl}-amide

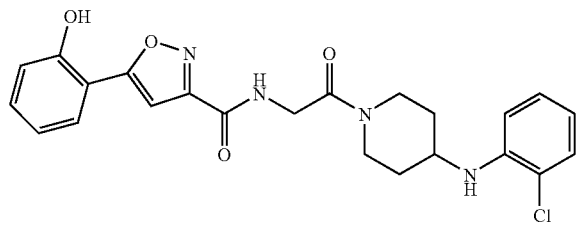

To a stirred solution of 5-(2-benzyloxy-phenyl)-isoxazole-3-carboxylic acid {2-[4-(2-chloro-phenylamino)-piperidin-1-yl]-2-oxo-ethyl}-amide (0.142 g, 0.00026 mole) in a mixture of methanol (60 mL) and THF (10 mL) was added 10% Pd/C (0.05 g) and the resulting mixture was stirred under an atmosphere of hydrogen for 1 hour. The mixture was then filtered through celite, the celite was washed with methanol and the organic layers were concentrated under reduced pressure. The resulting residue was recrystallized from ethyl acetate to afford 0.02 g (13%) of 5-(2-hydroxy-phenyl)-isoxazole-3-carboxylic acid {2-[4-(2-chloro-phenylamino)-piperidin-1-yl]-2-oxo-ethyl}-amide. LCMS: 455.14 (M+1)$^+$.

94.82%, $^1$H NMR (DMSO-d$_6$): δ 10.8 (s, 1H), 8.7 (t, 1H), 7.81 (d, 1H), 7.38 (t, 1H), 7.25 (d, 1H), 7.0 (m, 4H), 6.8 (d, 1H), 6.6 (t, 1H), 4.9 (d, 1H), 4.3 (d, 1H), 4.1 (d, 2H), 3.9 (d, 1H), 3.6 (s, 1H), 3.2 (m, 1H), 2.7 (m, 1H), 2.2 (m, 2H), 1.5 (m, 2H).

Intermediate 45

Synthesis of 5-(2-Benzyloxy-phenyl)-1H-pyrazole-3-carboxylic acid {2-[4-(2-chloro-phenylamino)-piperidin-1-yl]-2-oxo-ethyl}-amide

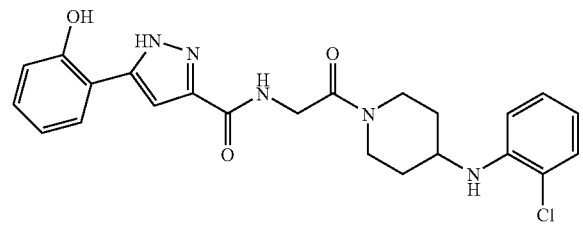

To a stirred solution of {[5-(2-benzyloxy-phenyl)-1H-pyrazole-3-carbonyl]-amino}-acetic acid (0.15 g, 0.00039 mol) in DMF (2 mL) was added DIPEA (0.224 g, 0.00174 mol), HOBt (0.065 g, 0.00048 mol) and EDCI.HCl (0.0925 g, 0.00048 mol) at ambient temperature. After 5 minutes (2-chloro-phenyl)-piperidin-4-yl-amine dihydrochloride (0.1 g, 0.00041 mol) was added to the reaction mixture continued stirring at the same temperature for overnight. The reaction mixture was diluted with cold water, filtered the solid precipitated and dried to afford 0.205 g (98%) of 5-(2-benzyloxy-phenyl)-1H-pyrazole-3-carboxylic acid {2-[4-(2-chloro-phenylamino)-piperidin-1-yl]-2-oxo-ethyl}-amide. LCMS: 544.2 (M+1)$^+$, 92.2%.

Example 43

Synthesis of 5-(2-Hydroxy-phenyl)-1H-pyrazole-3-carboxylic acid {2-[4-(2-chloro-phenylamino)-piperidin-1-yl]-2-oxo-ethyl}-amide To a stirred solution of 5-(2-benzyloxy-phenyl)-1H-pyrazole-3-carboxylic acid {2-[4-(2-chloro-phenylamino)-piperidin-1-yl]-2-oxo-ethyl}-amide (0.2 g, 0.00039 mole) in methanol (60 mL), added 10% Pd/C (0.04 g) and the resulting mixture was stirred under an atmosphere of hydrogen for 2 hours. The mixture was then filtered through celite, the celite was washed with methanol and the organic layers were concentrated under reduced pressure. The residue was recrystallized from a mixture of ethyl acetate and methanol to afford 0.055 g (32%) of 5-(2-hydroxy-phenyl)-1H-pyrazole-3-carboxylic acid {2-[4-(2-chloro-phenylamino)-piperidin-1-yl]-2-oxo-ethyl}-amide. LCMS: 454.16 (M+1)$^+$, 94.65%. $^1$H NMR (DMSO-d$_6$): δ 13.2 (s, 1H), 10.4 (s, 1H), 8.0 (s, 1H), 7.6 (d, 1H), 7.2 (m, 4H), 7.0 (d, 1H), 6.8 (m, 2H), 6.6 (t, 1H), 4.9 (d, 1H), 4.3 (d, 1H), 4.2 (d, 2H), 3.8 (d, 1H), 3.6 (m, 1H), 3.2 (t, 1H), 2.7 (t, 1H), 1.9 (m, 2H), 1.3 (m, 2H).

Intermediate 46

Synthesis of 5-(2-Benzyloxy-phenyl)-1H-pyrazole-3-carboxylic acid {2-[4-(2-chloro-phenoxy)-piperidin-1-yl]-2-oxo-ethyl}-amide

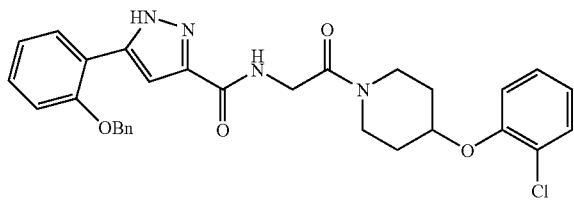

To a stirred solution of {[5-(2-benzyloxy-phenyl)-1H-pyrazole-3-carbonyl]-amino}-acetic acid (0.15 g, 0.00039 mol) in DMF (2 mL) was added DIPEA (0.224 g, 0.001736 mol), HOBt (0.065 g, 0.00048 mol) and EDCI.HCl (0.0925 g, 0.000482 mol) at ambient temperature. After 5 minutes (2-chlorophenoxy)-piperidin-4-yl-amine hydrochloride (0.1 g, 0.00041 mol) was added and the resulting mixture was stirred overnight. The reaction mixture was then diluted with cold water and the resulting precipitate was isolated by filtration and dried to afford 0.08 g (33%) of 5-(2-benzyloxy-phenyl)-1H-pyrazole-3-carboxylic acid {2-[4-(2-chloro-phenoxy)-piperidin-1-yl]-2-oxo-ethyl}-amide. LCMS: 544.2 (M+1)$^+$, 99.03%.

Example 44

Synthesis of 5-(2-Hydroxy-phenyl)-1H-pyrazole-3-carboxylic acid {2-[4-(2-chloro-phenoxy)-piperidin-1-yl]-2-oxo-ethyl}-amide

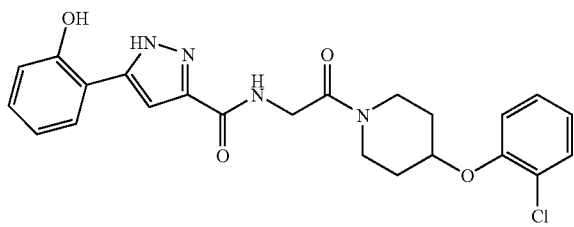

To a solution of 5-(2-benzyloxy-phenyl)-1H-pyrazole-3-carboxylic acid {2-[4-(2-chloro-phenoxy)-piperidin-1-yl]-2-oxo-ethyl}-amide (0.075 g, 0.00014 mole), in methanol (50 mL) was added 10% Pd/C (0.015 g) and the resulting mixture was stirred under an atmosphere of hydrogen for 1.5 hours. The mixture was then filtered through celite, the celite was washed with methanol and the organic layers were concentrated under reduced pressure. The resulting residue was recrystallized from a mixture of ethyl acetate and methanol to afford 0.052 g (83%) of 5-(2-hydroxy-phenyl)-1H-pyrazole-3-carboxylic acid {2-[4-(2-chloro-phenoxy)-piperidin-1-yl]-2-oxo-ethyl}-amide. LCMS: 455.16 (M+1)$^+$, 90.34%, $^1$H NMR (DMSO-d$_6$): δ 13.2 (s, 1H), 10.2 (s, 1H), 8.0 (s, 1H), 7.64 (m, 1H), 7.42 (m, 1H), 7.24 (m, 2H), 7.18 (m, 1H), 7.06 (s, 1H), 6.96 (m, 2H), 6.84 (t, 1H), 4.7 (m, 1H), 4.2 (d, 2H), 3.61 (m, 2H), 3.4 (m, 2H), 1.9 (m, 2H), 1.6 (m, 2H).

Intermediate 47

Synthesis of 6-Phenylamino-nicotinic acid

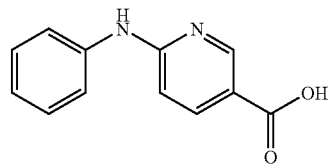

A mixture of 6-chloronicotinic acid ethyl ester (0.2 g, 0.00108 mole) and aniline (0.119 g, 0.00129 mole) in ethoxyethanol (10 mL) was heated to reflux for overnight. The mixture was then concentrated under reduced pressure and the residue was dissolved in ethyl acetate. The organic layer was washed with water, brine solution, dried over sodium sulfate and concentrated under reduced pressure. The resulting residue was purified by column chromatography using silica gel 60-120 mesh (5% ethyl acetate in hexane) to afford 0.23 g (88%) of 6-phenylamino-nicotinic acid ethyl ester. To a stirred solution 6-phenylamino-nicotinic acid ethyl ester (0.23 g, 0.00095 mol) in a mixture of THF (4 mL), methanol (4 mL) and H$_2$O (2 mL) was added LiOH.H$_2$O (0.159 g, 0.0038 mol) at ambient temperature and the resulting mixture was stirred overnight. Volatiles were then evaporated and the resulting residue was diluted with water, acidified with 10% aqueous citric acid solution. The resulting precipitate was isolated by filtration and dried to afford 0.174 g (85%) of 6-Phenylamino-nicotinic acid.

Intermediate 48

Synthesis of [(6-Phenylamino-pyridine-3-carbonyl)-amino]-acetic acid

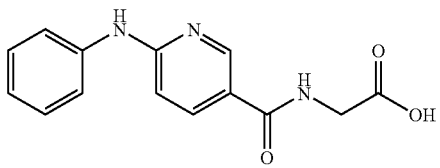

To a stirred solution of 6-phenylamino-nicotinic acid (0.1 g, 0.00047 mol) in DMF (2 mL), was added DIPEA (0.181 g, 0.001401 mol), HOBt (0.0756 g, 0.00056 mol) and EDCI.HCl (0.107 g, 0.00056 mol) at ambient temperature. After 2 minutes glycine ethyl ester hydrochloride (0.0782 g, 0.00056 mol) was added and the resulting mixture was stirred overnight. The reaction mixture was then diluted with cold water. The resulting precipitate was isolated by filtration and purified by column chromatography using silica gel 60-120 mesh (60% ethyl acetate in hexane) to afford 0.135 g (97%) of [(6-phenylamino-pyridine-3-carbonyl)-amino]-acetic acid ethyl ester. LCMS: 299.13 (M+1)$^+$, 99%. To a stirred solution of [(6-phenylamino-pyridine-3-carbonyl)-amino]-acetic acid ethyl ester (0.135 g, 0.00045 mol) in a mixture of THF (5 mL), methanol (7 mL) and H$_2$O (2 mL) was added LiOH.H$_2$O (0.0568 g, 0.00135 mol) at ambient temperature and the resulting mixture was stirred for 2 hours. Volatiles were then evaporated and the resulting residue was diluted with water, acidified with 10% aqueous HCl solution. The resulting precipitate was isolated by filtration and dried to afford 0.078 g (64%) of [(6-phenylamino-pyridine-3-carbonyl)-amino]-acetic acid.

Example 45

Synthesis of N-{2-[4-(2-Chloro-phenoxy)-piperidin-1-yl]-2-oxo-ethyl}-6-phenylamino-nicotinamide

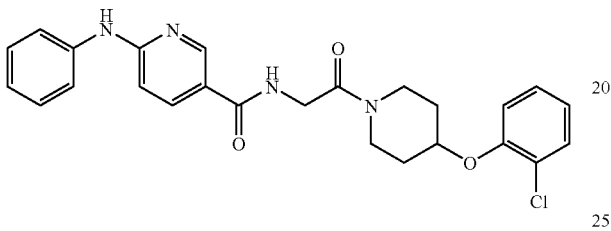

To a stirred solution of [(6-phenylamino-pyridine-3-carbonyl)-amino]-acetic acid (0.035 g, 0.00013 mol) in DMF (1 mL) was added DIPEA (0.05 g, 0.00039 mol), HOBt (0.0209 g, 0.00015 mol) and EDCI.HCl (0.029 g, 0.0001549 mol) at ambient temperature. After 2 minutes 4-(2-chloro-phenoxy)-piperidine hydrochloride (0.0382 g, 0.00015 mol) and the resulting mixture was stirred overnight. The reaction mixture was then diluted with cold water and the product was extracted with ethyl acetate. The ethyl acetate was washed with brine solution, dried over sodium sulfate and concentrated under reduced pressure. The resulting residue was purified by column chromatography using silica gel 60-120 mesh (70% ethyl acetate in hexane) to afford 0.037 g (62%) of N-{2-[4-(2-chloro-phenoxy)-piperidin-1-yl]-2-oxo-ethyl}-6-phenylamino-nicotinamide. LCMS: 465.16 (M+1)$^+$, 96.6%, $^1$H NMR (DMSO-d$_6$): δ 9.4 (s, 1H), 8.8 (s, 1H), 8.4 (t, 1H), 8.0 (dd, 1H), 7.7 (d, 2H), 7.45 (d, 1H), 7.4 (m, 4H), 7.0 (d, 2H), 6.8 (d, 1H), 4.7 (m, 1H), 4.25 (m, 2H), 3.7 (m, 2H), 3.5 (m, 2H), 2.0 (m, 2H), 1.7 (q, 2H).

Example 46

Synthesis of N-{2-[4-(2-Chloro-phenylamino)-piperidin-1-yl]-2-oxo-ethyl}-6-phenylamino-nicotinamide

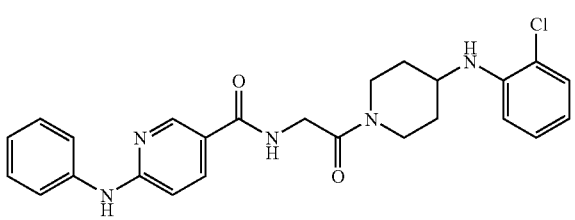

To a stirred solution of [(6-phenylamino-pyridine-3-carbonyl)-amino]-acetic acid (0.035 g, 0.00013 mol) in DMF (1 mL) was added DIPEA (0.05 g, 0.00039 mol), HOBt (0.0209 g, 0.00015 mol) and EDCI.HCl (0.029 g, 0.00015 mol) at ambient temperature. After 2 minutes (2-chloro-phenyl)-piperidin-4-yl-amine dihydrochloride (0.0382 g, 0.00015 mol) was added and the resulting mixture was stirred overnight. The reaction mixture was then diluted with cold water. The resulting precipitate was isolated by filtration and dried to afford 0.051 g (85%) of N-{2-[4-(2-chloro-phenylamino)-piperidin-1-yl]-2-oxo-ethyl}-6-phenylamino-nicotinamide. LCMS: 464.18 (M+1)$^+$, 98.3%, $^1$H NMR (DMSO-d$_6$): δ 9.4 (s, 1H), 8.7 (d, 1H), 8.4 (t, 1H), 8.0 (d, 1H), 7.7 (d, 2H), 7.3 (m, 3H), 7.15 (t, 1H), 7.0 (t, 1H), 6.85 (d, 2H), 6.4 (t, 1H), 4.9 (d, 1H), 4.35 (d, 1H), 4.1 (d, 2H), 3.9 (d, 1H), 3.6 (s, 1H), 3.2 (m, 1H), 2.8 (m, 1H), 2.0 (t, 2H), 1.5 (m, 1H), 1.4 (m, 1H).

Intermediate 49

Synthesis of 5-Phenylamino-pyridine-2-carboxylic acid

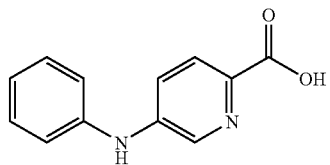

A mixture of BINAP (0.167 g, 0.00027 mole), palladium acetate (0.06 g, 0.00027 mole) and toluene (10 mL) was degassed with argon for 15 minutes. This mixture was then added to a mixture of aniline (0.5 g, 0.00537 mole), 3-chloro-6-cyanopyridine (0.893 g, 0.00645 mole) and cesium carbonate (3.49 g, 0.01075 mole) in toluene (10 mL). The resulting mixture was heated to reflux for 22 hours. The reaction mixture was then concentrated under reduced pressure and the residue was extracted with ethyl acetate. The ethyl acetate layer was washed with water, brine solution, dried over sodium sulfate and concentrated under reduced pressure. Purification of the residue by column chromatography using silica gel 60-120 mesh (15% ethyl acetate in hexane) afforded 0.4 g (38%) of 5-phenylamino-pyridine-2-carbonitrile. To a stirred solution of 5-phenylamino-pyridine-2-carbonitrile (0.4 g, 0.00205 mol) in EtOH (15 mL) was added NaOH (0.246 g, 0.0061 mol) and water (10 mL) and the resulting mixture was heated to reflux for 4 hours. The mixture was then concentrated under reduced pressure and the residue was diluted with cold water. The resulting precipitate was isolated by filtration and dried to afford 0.385 g (87%) of 5-phenylamino-pyridine-2-carboxylic acid Intermediate 50

Synthesis of [(5-Phenylamino-pyridine-2-carbonyl)-amino]-acetic acid

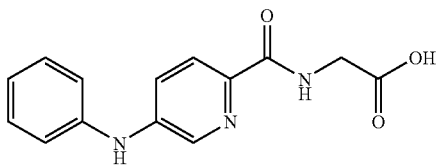

To a stirred solution of 5-phenylamino-pyridine-2-carboxylic acid (0.26 g, 0.00121 mol) in DMF (2 mL) was added DIPEA (0.471 g, 0.00364 mol), HOBt (0.196 g, 0.00145 mol) and EDCI.HCl (0.278 g, 0.00145 mol) at ambient temperature. After 2 minutes glycine ethyl ester hydrochloride (0.203 g, 0.00146 mol) was added and the resulting mixture was stirred overnight. The reaction mixture was then diluted with cold water. The resulting precipitate was isolated by filtration and purified by column chromatography using silica gel 60-120 mesh (60% ethyl acetate in hexane) to afford 0.32 g (88%) of [(5-phenylamino-pyridine-2-carbonyl)-amino]-acetic acid ethyl ester. LCMS: 300.13 (M+1)$^+$, 97%. To a stirred solution [(5-phenylamino-pyridine-2-carbonyl)-amino]-acetic acid ethyl ester (0.32 g, 0.00107 mol) in a mixture of THF (5 mL), methanol (10 mL) and H$_2$O (2 mL) was added LiOH.H$_2$O (0.134 g, 0.00321 mol) at ambient temperature and the resulting mixture was stirred for 2 hours. Volatiles were then evaporated and the resulting residue was diluted with water, acidified with 10% aqueous HCl solution. The resulting precipitate was isolated by filtration and dried to afford 0.26 g (90%) of [(5-phenylamino-pyridine-2-carbonyl)-amino]-acetic acid.

Example 47

Synthesis of 5-Phenylamino-pyridine-2-carboxylic acid {2-[4-(2-chloro-phenylamino)-piperidin-1-yl]-2-oxo-ethyl}-amide

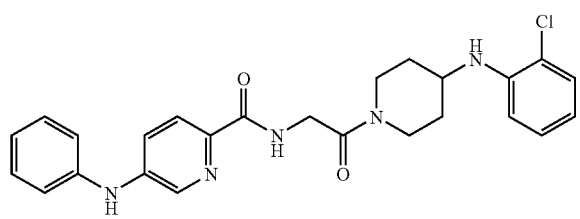

To a stirred solution of [(5-phenylamino-pyridine-2-carbonyl)-amino]-acetic acid (0.035 g, 0.00013 mol) in DMF (1 mL) was added DIPEA (0.05 g, 0.00039 mol), HOBt (0.0209 g, 0.00015 mol) and EDCI.HCl (0.0296 g, 0.00015 mol) at ambient temperature. After 2 minutes piperidin-4-yl-(2-chloro-phenyl)-amine dihydrochloride (0.0382 g, 0.00015 mol) was added and the resulting mixture was stirred overnight. The reaction mixture was then diluted with cold water and the resulting precipitate was isolated by filtration and dried to afford 0.038 g (64%) of 5-phenylamino-pyridine-2-carboxylic acid {2-[4-(2-chloro-phenylamino)-piperidin-1-yl]-2-oxo-ethyl}-amide. LCMS: 464.18 (M+1)$^+$, 92.88%, $^1$H NMR (DMSO-d$_6$): δ 8.9 (s, 1H), 8.5 (t, 1H), 8.3 (d, 1H), 7.9 (d, 1H), 7.55 (dd, 1H), 7.35 (t, 2H), 7.2 (m, 4H), 7.0 (t, 1H), 6.9 (d, 1H), 6.6 (t, 1H), 4.9 (d, 1H), 4.35 (d, 1H), 4.2 (d, 2H), 3.85 (d, 1H), 3.55 (s, 1H), 3.2 (m, 2H), 2.85 (m, 1H), 1.95 (t, 2H), 1.5 (m, 1H), 1.35 (m, 1H).

Example 48

Synthesis of 5-Phenylamino-pyridine-2-carboxylic acid {2-[4-(2-chloro-phenylamino)-piperidin-1-yl]-2-oxo-ethyl}-amide

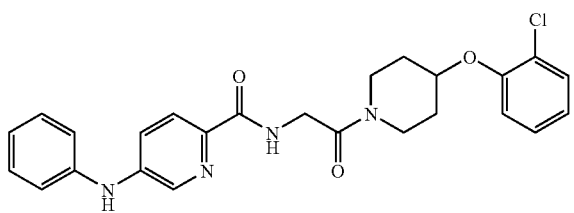

To a stirred solution of [(5-phenylamino-pyridine-2-carbonyl)-amino]-acetic acid (0.035 g, 0.00013 mol) in DMF (1 mL) was added DIPEA (0.05 g, 0.00039 mol), HOBt (0.0209 g, 0.00015 mol) and EDCI.HCl (0.0296 g, 0.00015 mol) at ambient temperature. After 2 minutes 4-(2-chloro-phenoxy)-piperidine hydrochloride (0.0382 g, 0.00015 mol) was added and the resulting mixture was stirred overnight. The reaction mixture was then diluted with cold water and the resulting precipitate was isolated by filtration and dried to afford 0.032 g (53%) of 5-phenylamino-pyridine-2-carboxylic acid {2-[4-(2-chloro-phenylamino)-piperidin-1-yl]-2-oxo-ethyl}-amide. LCMS: 465.16 (M+1)$^+$, 98.06%, $^1$H NMR (DMSO-d$_6$): δ 8.85 (s, 1H), 8.5 (t, 1H), 8.35 (d, 1H), 7.85 (d, 1H), 7.55 (dd, 1H), 7.4 (d, 1H), 7.3 (m, 4H), 7.2 (d, 2H), 7.0 (m, 2H), 4.75 (m, 1H), 4.2 (d, 2H), 3.7 (m, 2H), 3.5 (m, 2H), 1.95 (m, 3H), 1.7 (m, 2H).

Intermediate 51

Synthesis of N-Biphenyl-4-yl-malonamic acid

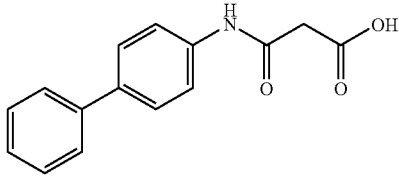

To a stirred solution of monoethyl malonate (0.86 g, 0.00649 mole) in DMF (20 mL) was added HOBt (0.795 g, 0.0059 mole) and DMAP (0.790 g, 0.00649 mole). The mixture was cooled to 10° C. and EDCI.HCl (1.7 g, 0.008 mole) followed by biphenyl-4-ylamine (1.0 g, 0.0059 mole) were added and the resulting mixture was stirred at the ambient temperature for overnight. The reaction mixture was then diluted with cold water and the resulting precipitate was isolated by filtration and dried to afford 1.76 g (94%) of N-biphenyl-4-yl-malonamic acid ethyl ester. To a solution of N-biphenyl-4-yl-malonamic acid ethyl ester (1.7 g, 0.0060 mole) in a mixture of methanol (5 mL), THF (10 mL) and H$_2$O (10 mL) was added LiOH.H$_2$O (0.5 g, 0.012 mole). The reaction mixture was stirred for 2 hours at ambient temperature. The mixture was then concentrated and the residue was diluted with water acidified with conc. HCl. The resulting precipitate was isolated by filtration and dried to afford 1.5 g (98%) of N-biphenyl-4-yl-malonamic acid. LC-MS purity: 95.4%, $^1$H NMR (DMSO-d$_6$): δ 10.3 (s, 1H), 7.7 (m, 6H), 7.4 (t, 2H), 7.32 (t, 1H).

Example 49

Synthesis of N-Biphenyl-4-yl-3-[4-(2-bromo-phenoxy)-piperidin-1-yl]-3-oxo-propionamide

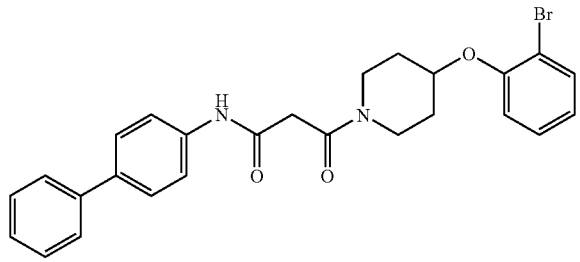

To a stirred solution of N-biphenyl-4-yl-malonamic acid (0.075 g, 0.00029 mole) in DMF (2.0 mL) was added HOBt (0.042 g, 0.00031 mole) and DIPEA (0.083 g, 0.00065 mole). The mixture was cooled to 10° C. and EDCI.HCl (0.060 g, 0.00031 mole) followed by 4-(2-bromo-phenoxy)-piperidin-1-ylamine trifluoroacetate (0.106 g, 0.00029 mole) were added. The mixture was stirred at the ambient temperature overnight. The mixture was then diluted with water and the product was extracted with ethyl acetate. The organic layer was washed with brine and concentrated. The resulting residue was purified by column chromatography using silica gel 60-120 mesh (40% ethyl acetate in hexane) to afford 0.045 g (31%) of N-biphenyl-4-yl-3-[4-(2-bromo-phenoxy)-piperidin-1-yl]-3-oxo-propionamide. LCMS: 493 (M+1)$^+$, 94.19%, $^1$H NMR (CDCl$_3$): δ 10.0 (s, 1H), 7.66 (d, 2H), 7.58 (m, 5H), 7.44 (t, 2H), 7.32 (m, 1H), 6.9 (m, 2H), 4.52 (m, 1H), 4.15 (m, 1H), 3.56 (m, 1H), 3.54 (m, 2H), 3.51 (d, 2H), 2.0 (m, 2H), 1.8 (m, 2H).

Example 50

Synthesis of N-Biphenyl-4-yl-3-[4-(2-chloro-5-fluoro-phenoxy)-piperidin-1-yl]-3-oxo-propionamide

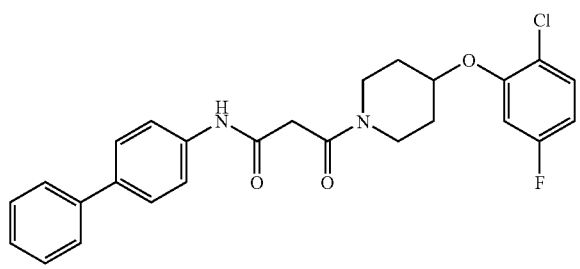

To a stirred solution of N-biphenyl-4-yl-malonamic acid (0.1 g, 0.00039 mole) in DMF (2 mL) was added HOBt (0.065 g, 0.00047 mole) and DIPEA (0.126 g, 0.00098 mole). The mixture was cooled to 10° C. and EDCI.HCl (0.090 g, 0.00047 mole) followed by 4-(2-chloro-5-fluoro-phenoxy)- piperidine hydrochloride (0.114 g, 0.00043 mole) were added. The resulting mixture was stirred at the ambient temperature overnight. The mixture was then diluted with cold water and the resulting precipitate was isolated by filtration. Purification by column chromatography using silica gel 60-120 mesh (35% ethyl acetate in hexane) afforded 0.024 g (13%) of N-biphenyl-4-yl-3-[4-(2-chloro-5-fluoro-phenoxy)-piperidin-1-yl]-3-oxo-propionamide. LCMS: 467 (M+1)$^+$, 97.5%, $^1$H NMR (CDCl$_3$): δ 10.0 (s, 1H), 7.66 (d, 2H), 7.58 (m, 4H), 7.42 (t, 2H), 7.34 (m, 2H), 6.68 (m, 2H), 4.64 (m, 1H), 4.3 (m, 1H), 3.7 (m, 3H), 3.52 (s, 2H), 1.96 (m, 4H).

Example 51

Synthesis of N-Biphenyl-4-yl-3-[4-(2-bromo-phenylamino)-piperidin-1-yl]-3-oxo-propionamide

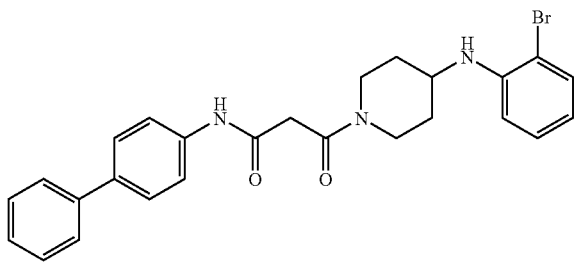

To a stirred solution of N-biphenyl-4-yl-malonamic acid (0.071 g, 0.00028 mole) in DMF (2 mL) was added DIPEA (0.089 g, 0.0007 mole), HOBt (0.046 g, 0.00034 mole) and EDCI.HCl (0.065 g, 0.00034 mole). After 2 minutes (2-bromo-phenyl)-piperidin-4-yl-amine dihydrochloride (0.082 g, 0.00028 mole) was added and the resulting mixture was stirred overnight. The reaction mixture was then diluted with cold water and the product was extracted with ethyl acetate. The organic layer was washed with aqueous sodium bicarbonate solution, brine and concentrated. The resulting residue was purified by column chromatography using silica gel 60-120 mesh (70% ethyl acetate in hexane) to afford 0.025 g (17%) of N-biphenyl-4-yl-3-[4-(2-bromo-phenylamino)-piperidin-1-yl]-3-oxo-propionamide. LC-MS purity: 492 (M+1)$^+$, 92.2%, $^1$H NMR (CDCl$_3$): δ 10.0 (s, 1H), 7.66 (d, 2H), 7.58 (m, 4H), 7.44 (t, 3H), 7.34 (t, 1H), 7.18 (t, 1H), 6.68

(d, 1H), 6.6 (t, 1H), 4.45 (d, 1H), 4.0 (d, 1H), 3.65 (bs, 1H), 3.5 (s, 2H), 3.35 (t, 1H), 3.1 (t, 1H), 2.2 (m, 2H), 1.5 (m, 2H).

Example 52

Synthesis of N-Biphenyl-4-yl-3-[4-(2-bromo-phenyl-sulfanyl)-piperidin-1-yl]-3-oxo-propionamide

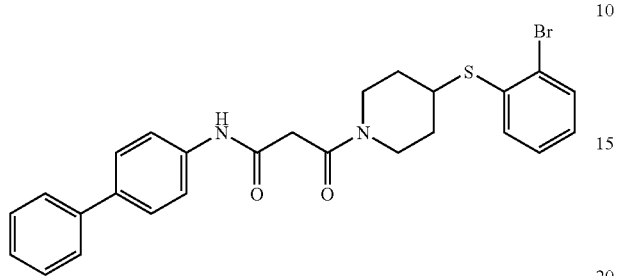

To a stirred solution of N-biphenyl-4-yl-malonamic acid (0.15 g, 0.00059 mole) in DMF (4 mL) was added DIPEA (0.226 g, 0.00176 mole), HOBt (0.095 g, 0.00071 mole) and EDCI.HCl (0.134 g, 0.00071 mole). After 2 minutes 4-(2-bromo-phenylsulfanyl)-piperidine hydrochloride (0.21 g, 0.00071 mole) was added and the resulting mixture was stirred overnight. The reaction mixture was then diluted with cold water and the resulting precipitate was isolated by filtration. Purification by column chromatography using silica gel 60-120 mesh (60% ethyl acetate in hexane) afforded 0.153 g (51%) of N-biphenyl-4-yl-3-[4-(2-bromo-phenylsulfanyl)-piperidin-1-yl]-3-oxo-propionamide. LC-MS purity: 509.08 (M+1)$^+$, 87.3%, $^1$H NMR (DMSO-d$_6$): δ 10.2 (s, 1H), 7.82-7.6 (m, 6H), 7.48-7.36 (m, 3H), 7.36-7.28 (m, 1H), 7.22-7.12 (m, 1H), 5.6-5.2 (d, 1H), 4.25 (d, 1H), 3.7 (m, 1H), 3.55 (s, 2H), 2.95 (m, 1H), 2.0 (m, 2H), 1.7-1.5 (m, 1H), 1.5-1.35 (m, 1H).

Example 53

Synthesis of N-Biphenyl-4-yl-3-oxo-3-(4-o-tolylamino-piperidin-1-yl)-propionamide

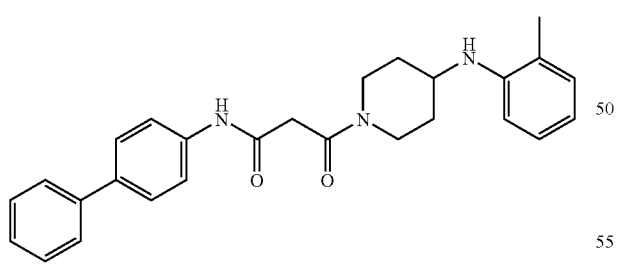

To a stirred solution of N-biphenyl-4-yl-malonamic acid (0.1 g, 0.00038 mole) in DMF (1 mL) was added DIPEA (0.245 g, 0.0019 mole), HOBt (0.056 g, 0.00042 mole) and EDCI.HCl (0.145 g, 0.00076 mole). After 2 minutes piperidin-4-yl-o-tolyl-amine dihydrochloride (0.106 g, 0.00042 mole) was added and the resulting mixture was stirred for 16 hours. The reaction mixture was then diluted with cold water and the resulting precipitate was isolated by filtration. Purification by column chromatography using silica gel (60-120 mesh) (1% methanol in chloroform) afforded 0.04 g (25%) of N-biphenyl-4-yl-3-oxo-3-(4-o-tolylamino-piperidin-1-yl)-propionamide. LC-MS purity: 428.23 (M+1)$^+$, 93.11%, $^1$H NMR (DMSO-d$_6$): δ 7.7 (m, 6H), 7.5 (t, 2H), 7.3 (t, 1H), 7.2 (q, 2H), 6.65 (q, 2H), 4.5 (d, 1H), 4.0 (d, 1H), 3.6 (m, 1H), 3.5 (s, 2H), 3.3 (s, 1H), 3.0 (t, 1H), 2.2 (m, 3H), 2.1 (s, 2H), 1.5 (t, 2H).

Example 54

Synthesis of N-Biphenyl-4-yl-3-[4-(2-nitro-phenoxy)-piperidin-1-yl]-3-oxo-propionamide

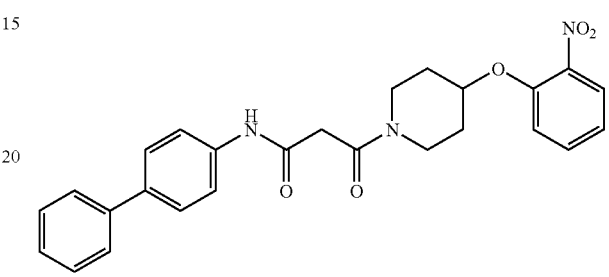

To a stirred solution of N-biphenyl-4-yl-malonamic acid (0.1 g, 0.00039 mole) in DMF (3 mL) was added DIPEA (0.176 g, 0.0014 mole), HOBt (0.078 g, 0.00058 mole) and EDCI.HCl (0.11 g, 0.00058 mole). After 2 minutes (2-nitro-phenoxy)-piperidine hydrochloride (0.12 g, 0.00046 mole) and the resulting mixture was stirred overnight. The reaction mixture was then diluted with cold water and the product was extracted with ethyl acetate. The organic layers were dried over sodium sulfate and concentrated under reduced pressure. The resulting residue was purified by column chromatography using neutral aluminium oxide (5% methanol in chloroform) to afford 0.130 g (72%) of N-biphenyl-4-yl-3-[4-(2-nitro-phenoxy)-piperidin-1-yl]-3-oxo-propionamide. LC-MS purity: 460.18 (M+1)$^+$, 95%, $^1$H NMR (DMSO-d$_6$): δ 7.9 (m, 1H), 7.7 (m, 7H), 7.5 (m, 3H), 7.3 (m, 1H), 7.1 (m, 1H), 5.0 (m, 1H), 3.6 (m, 6H), 2.0 (m, 2H), 1.8 (m, 2H).

Example 55

Synthesis of 3-[4-(2-Amino-phenoxy)-piperidin-1-yl]-N-biphenyl-4-yl-3-oxo-propionamide

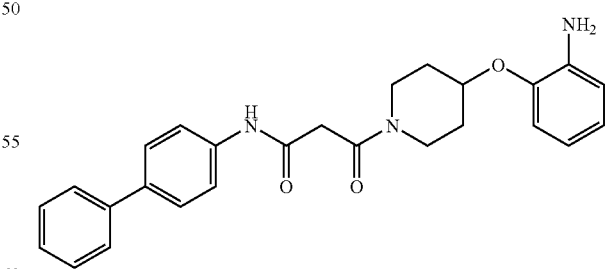

To a solution of N-biphenyl-4-yl-3-[4-(2-nitro-phenoxy)-piperidin-1-yl]-3-oxo-propionamide (0.09 g, 0.00019 mole) in methanol (10 mL) was added 10% Pd/C (0.015 g) and the resulting mixture was stirred under an atmosphere of hydrogen for 30 minutes. The mixture was then filtered through celite, the celite was washed with methanol and the organic layers were concentrated under reduced pressure. The resulting residue was recrystallized from a mixture of hexane and chloroform to afford 0.025 g (29%) of 3-[4-(2-amino-phenoxy)-piperidin-1-yl]-N-biphenyl-4-yl-3-oxo-propionamide. LC-MS purity: 430.21 (M+1)$^+$, 90.7%, $^1$H NMR (DMSO-d$_6$): δ 7.7 (m, 6H), 7.4 (m, 2H), 7.3 (m, 1H), 6.8 (m, 1H), 6.6 (m, 2H), 6.5 (m, 1H), 4.6 (bs, 2H), 4.5 (bs, 1H), 3.8 (m, 2H), 3.5 (m, 4H), 2.0 (m, 2H), 1.8 (m, 2H).

Example 56

Synthesis of N-Biphenyl-4-yl-3-[4-(2,3-dimethyl-phenylamino)-piperidin-1-yl]-3-oxo-propionamide

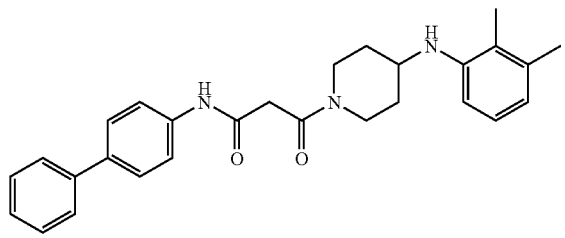

To a stirred solution of N-biphenyl-4-yl-malonamic acid (0.101 g, 0.00039 mole) in DMF (3 mL) was added DIPEA (0.233 g, 0.0018 mole), HOBt (0.053 g, 0.00039 mole) and EDCI.HCl (0.138 g, 0.00072 mole). After 2 minutes (2,3-dimethyl-phenyl)-piperidin-4-yl-amine dihydrochloride (0.1 g, 0.00036 mole) was added and the resulting mixture was stirred overnight. The reaction mixture was then diluted with cold water and the resulting precipitate was isolated by filtration. Purification by column chromatography using silica gel 60-120 mesh (1% methanol in chloroform) afforded 0.07 g (44%) of N-biphenyl-4-yl-3-[4-(2,3-dimethyl-phenylamino)-piperidin-1-yl]-3-oxo-propionamide. LC-MS purity: 442.24 (M+1)$^+$, 95.5%, $^1$H NMR (DMSO-d$_6$): δ 10.2 (s, 1H), 7.7 (m, 6H), 7.6 (t, 2H), 7.4 (d, 1H), 6.8 (t, 1H), 6.5 (d, 1H), 6.4 (d, 1H), 4.4 (t, 2H), 4.0 (d, 1H), 3.6 (bs, 3H), 3.2 (t, 1H), 2.8 (t, 1H), 2.2 (s, 3H), 2.0 (bs, 5H), 1.5 (d, 1H), 1.4 (d, 1H).

Example 57

Synthesis of N-Biphenyl-4-yl-3-[4-(2,4-dimethyl-phenylamino)-piperidin-1-yl]-3-oxo-propionamide

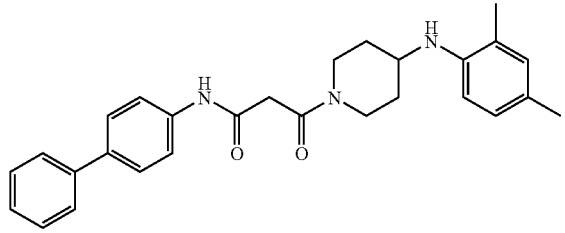

To a stirred solution of N-biphenyl-4-yl-malonamic acid (0.101 g, 0.00039 mole) in DMF (3 mL) was added DIPEA (0.233 g, 0.0018 mole), HOBt (0.053 g, 0.00039 mole) and EDCI.HCl (0.138 g, 0.000721 mole). After 2 minutes (2,4-dimethyl-phenyl)-piperidin-4-yl-amine dihydrochloride (0.1 g, 0.00036 mole was added and the resulting mixture was stirred overnight. The reaction mixture was then diluted with cold water and the resulting precipitate was isolated by filtration. Purification by column chromatography using silica gel 60-120 mesh (1% methanol in chloroform) afforded 0.07 g (44%) of N-biphenyl-4-yl-3-[4-(2,4-dimethyl-phenylamino)-piperidin-1-yl]-3-oxo-propionamide. LC-MS purity: 442.24 (M+1)$^+$, 98.89%, $^1$H NMR (DMSO-d$_6$): δ 10.2 (s, 1H), 7.8-7.6 (m, 6H), 7.5 (t, 2H), 7.4 (t, 3H), 6.8 (d, 2H), 6.6 (d, 1H), 4.3 (dd, 2H), 3.9 (d, 1H), 3.7 (s, 2H), 3.5 (bs, 1H), 3.2 (t, 1H), 2.7 (m, 1H), 2.2 (s, 3H), 2.1 (s, 3H), 1.9 (t, 2H), 1.5 (t, 1H), 1.3 (d, 1H).

Example 58

Synthesis of N-Biphenyl-4-yl-3-[4-(2,5-dimethyl-phenylamino)-piperidin-1-yl]-3-oxo-propionamide

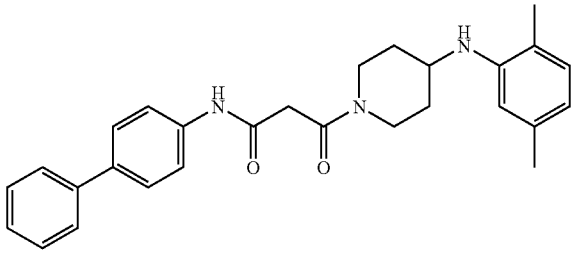

To a stirred solution of N-biphenyl-4-yl-malonamic acid (0.101 g, 0.00039 mole) in DMF (1 mL) was added DIPEA (0.233 g, 0.0018 mole), HOBt (0.053 g, 0.00039 mole) and EDCI.HCl (0.138 g, 0.00072 μmole). After 2 minutes (2,5-dimethyl-phenyl)-piperidin-4-yl-amine dihydrochloride (0.101 g, 0.00039 mole) was added and the resulting mixture was stirred overnight. The reaction mixture was then diluted with cold water and the resulting precipitate was isolated by filtration. Purification by column chromatography using silica gel 60-120 mesh (1% methanol in chloroform) afforded 0.025 g (16%) of N-biphenyl-4-yl-3-[4-(2,5-dimethyl-phenylamino)-piperidin-1-yl]-3-oxo-propionamide. LC-MS purity: 442.24 (M+1)$^+$, 97.08%, $^1$H NMR (DMSO-d$_6$): δ 10.1 (s, 1H), 7.7-7.5 (m, 6H), 7.4 (t, 2H), 7.35 (d, 1H), 6.9 (d, 1H), 6.5 (t, 2H), 4.5 (d, 1H), 4.0 (d, 1H), 3.7 (s, 1H), 3.5 (s, 2H), 3.4 (t, 2H), 3.1 (t, 1H), 2.3 (s, 3H), 2.2 (d, 2H), 2.1 (s, 3H), 1.5 (t, 2H).

Example 59

Synthesis of N-Biphenyl-4-yl-3-[4-(2-tert-butyl-phenylamino)-piperidin-1-yl]-3-oxo-propionamide

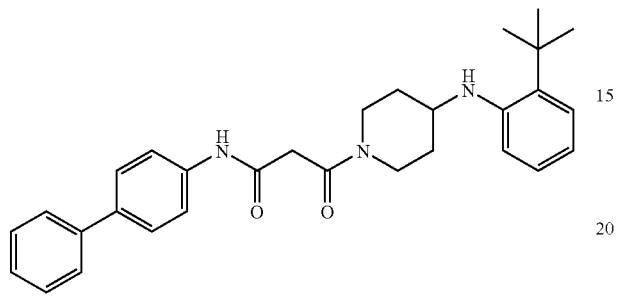

To a stirred solution of N-biphenyl-4-yl-malonamic acid (0.091 g, 0.00036 mole) in DMF (1 mL) was added DIPEA (0.211 g, 0.0016 mole), HOBt (0.048 g, 0.00036 mole) and EDCI.HCl (0.125 g, 0.00065 mole). After 2 minutes (2-tert-butyl-phenyl)-piperidin-4-yl-amine dihydrochloride (0.1 g, 0.00033 mole) was added and the resulting mixture was stirred overnight. The reaction mixture was then diluted with cold water and the resulting precipitate was isolated by filtration. Purification by column chromatography using silica gel 60-120 mesh (1% methanol in chloroform) afforded 0.062 g (40%) of N-biphenyl-4-yl-3-[4-(2-tert-butyl-phenylamino)-piperidin-1-yl]-3-oxo-propionamide. LC-MS purity: 470.27 (M+1)$^+$, 96.38%, $^1$H NMR (DMSO-d$_6$): δ 7.8-7.6 (m, 6H), 7.5 (t, 2H), 7.3 (d, 1H), 7.1 (d, 1H), 7.0 (t, 1H), 6.8 (d, 1H), 6.6 (t, 1H), 4.3 (d, 1H), 3.9 (d, 2H), 3.7 (s, 1H), 3.6 (s, 2H), 3.2 (t, 1H), 2.9 (t, 1H), 2.0 (t, 2H), 1.5 (t, 1H), 1.4 (s, 9H).

Example 60

Synthesis of N-Biphenyl-4-yl-3-[4-(2,5-difluoro-phenoxy)-piperidin-1-yl]-3-oxo-propionamide

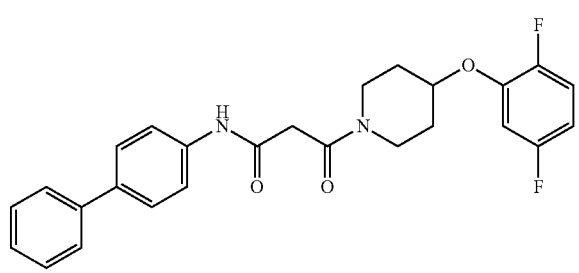

To a stirred solution of N-biphenyl-4-yl-malonamic acid (0.075 g, 0.0003 mole) in DMF (2 mL) was added, HOBt (0.06 g, 0.00045 mole) and DIPEA (0.135 g, 0.001 mole). The mixture was then cooled to 10° C. and EDCI.HCl (0.086 g, 0.00045 mole) followed by 4-(2,5-difluoro-phenoxy)-piperidine hydrochloride (0.073 g, 0.0003 mole) were added. The resulting mixture was stirred overnight. The reaction mixture was then diluted with cold water and the product was extracted with ethyl acetate. The organic layer was dried over sodium sulfate and concentrated under reduced pressure. The resulting residue was purified by column chromatography using neutral aluminium oxide (5% methanol in chloroform) to afford 0.03 g (22%) of N-biphenyl-4-yl-3-[4-(2,5-difluoro-phenoxy)-piperidin-1-yl]-3-oxo-propionamide. LC-MS purity: 451.18 (M+1)$^+$, 90.58%, $^1$H NMR (DMSO-d$_6$): δ 10.2 (s, 1H), 7.7 (m, 6H), 7.4 (m, 2H), 7.2 (m, 2H), 6.8 (m, 1H), 4.7 (m, 1H), 3.9 (m, 1H), 3.8 (m, 1H), 3.6 (s, 2H), 3.4 (m, 1H), 2.0 (m, 2H), 1.7 (m, 1H), 1.6 (m, 1H).

Intermediate 52

Synthesis of 6-Phenyl-pyridin-3-ylamine

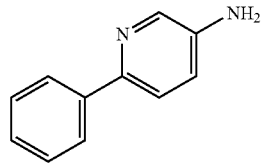

A mixture of toluene (15 mL) and water (5 mL) was degassed with argon for 5 minutes. Sodium carbonate (0.802 g, 0.00454 mole) was then added and the mixture was degassed with argon for 5 minutes. Phenylboronic acid (0.587 g, 0.00454 mole) and 2-chloro-5-nitro-pyridine (0.6 g, 0.00378 mole) were then added and the resulting mixture was degassed with argon for 5 minutes. Tetrakis(triphenylphosphine)palladium(0) (0.878 g, 0.00076 mole) was added and the mixture was degassed with argon for 5 minutes. The resulting mixture was then heated to reflux for 3 hours. The mixture was diluted with ethyl acetate, and the organic layer was washed with water followed by brine solution. The ethyl acetate layer was dried over sodium sulfate and concentrated under reduced pressure. Purification by column chromatography using silica gel 60-120 mesh (5% ethyl acetate in hexane) afforded 0.5 g (66%) of 5-nitro-2-phenyl-pyridine. LCMS purity: 201 (M+1)$^+$, 98.2%, $^1$H NMR (DMSO-d$_6$): δ 9.5 (s, 1H), 8.55 (dd, 1H), 8.1 (m, 2H), 7.9 (d, 1H), 7.55 (m, 3H). To a stirred solution of 5-nitro-2-phenyl-pyridine (0.5 g, 0.0025 mole) in THF (10 mL) was added ammonium chloride (1.1 g, 0.020 mole) dissolved in water (15 mL). Methanol (5 mL) was then added, resulting in a clear solution. Zinc powder (1.3 g, 0.020 mole) was then added portionwise and the resulting mixture was stirred for 1 hour. The mixture was filtered through a bed of celite and the filtrate was concentrated under reduced pressure. The residue was extracted with ethyl acetate, and the organic layer was washed with brine solution, dried over Na$_2$SO$_4$, and evaporated under reduced pressure to afford 0.35 g (82%) of 6-phenyl-pyridin-3-ylamine. LCMS purity: 171.08 (M+1)$^+$, 87.9%, $^1$H NMR (DMSO-d$_6$): δ 8.12 (d, 1H), 8.0 (d, 2H), 7.72 (d, 1H), 7.48 (t, 2H), 7.36 (t, 1H), 7.1 (dd, 1H), 5.6 (s, 2).

Intermediate 53

Synthesis of 3-[4-(2-Chloro-5-fluoro-phenoxy)-piperidin-1-yl]-3-oxo-propionic acid

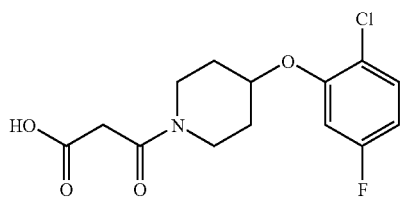

To a stirred solution of malonic acid monoethyl ester (0.5 g, 0.00377 mole) in DMF (10 mL) was added DIPEA (1.18 g, 0.0094 mole), HOBt (0.608 g, 0.0045 mole) and EDCI.HCl (0.865 g, 0.0045 mole). After 2 minutes 4-(2-chloro-5-fluoro-phenoxy)-piperidine hydrochloride (1 g, 0.003 7 mole) and the resulting mixture was stirred overnight. The reaction mixture was then diluted with cold water and the product was extracted with ethyl acetate. The organic layers were dried over sodium sulfate and concentrated under reduced pressure to get afford 0.9 g (70%) of 3-[4-(2-chloro-5-fluoro-phenoxy)-piperidin-1-yl]-3-oxo-propionic acid ethyl ester. LC-MS purity: 344.78 (M+1)$^+$, 82.56%. To a stirred solution of 3-[4-(2-chloro-5-fluoro-phenoxy)-piperidin-1-yl]-3-oxo-propionic acid ethyl ester (0.9 g, 0.0026 mole) in a mixture of THF (10 mL), methanol (3 mL) and H$_2$O (2 mL) was added LiOH.H$_2$O (0.218 g, 0.0052 mole) at ambient temperature and the resulting mixture was stirred for 30 minutes. Volatiles were then evaporated and the resulting residue was diluted with water, acidified with 10% aqueous HCl solution. The product was extracted with ethyl acetate, and the organic layer was washed with brine solution, dried over sodium sulfate and concentrated under reduced pressure to afford 0.6 g (73%) of 3-[4-(2-chloro-5-fluoro-phenoxy)-piperidin-1-yl]-3-oxo-propionic acid. LC-MS purity: 316.72 (M+1)$^+$, 75.8%.

Example 61

Synthesis of 3-[4-(2-Chloro-5-fluoro-phenoxy)-piperidin-1-yl]-3-oxo-N-(6-phenyl-pyridin-3-yl)-propionamide

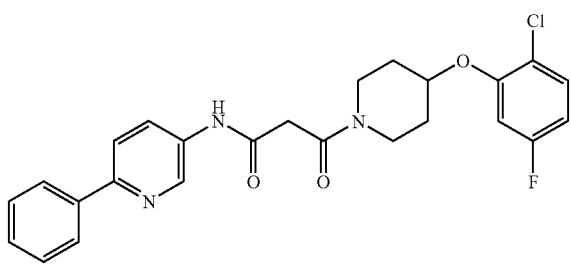

To a stirred solution of 3-[4-(2-chloro-5-fluoro-phenoxy)-piperidin-1-yl]-3-oxo-propionic acid (0.1 g, 0.00032 mole) in DMF (5 mL) was added DMAP (0.059 g, 0.00048 mole), HOBt (0.051 g, 0.00038 mole) and EDCI.HCl (0.073 g, 0.00038 mole). After 2 minutes 6-phenyl-pyridin-3-ylamine (0.06 g, 0.00035 mole) was added and the resulting mixture was stirred overnight. The reaction mixture was then diluted with cold water and the product was extracted with ethyl acetate. The organic layers were dried over sodium sulfate and concentrated under reduced pressure. The resulting residue was purified by column chromatography using silica gel 60-120 mesh (50% ethyl acetate in hexane) to afford 0.026 g (19%) of 3-[4-(2-chloro-5-fluoro-phenoxy)-piperidin-1-yl]-3-oxo-N-(6-phenyl-pyridin-3-yl)-propionamide. LC-MS purity: 468 (M+1)$^+$, 93.7%, $^1$H NMR (CDCl$_3$): δ 10.5 (s, 1H), 8.8 (s, 1H), 8.3 (d, 1H), 8.0 (d, 2H), 7.7 (d, 1H), 7.4 (m, 4H), 6.7 (m, 2H), 4.7 (m, 1H), 4.2 (m, 1H), 3.8 (m, 1H), 3.7 (m, 2H), 3.55 (s, 2H), 2.0 (m, 4H).

Intermediate 54

Synthesis of 5-Phenyl-pyridin-2-ylamine

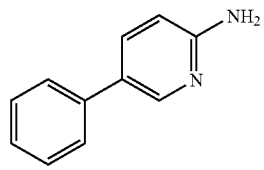

A mixture of toluene (80 mL) and water (20 mL) was degassed with argon for 5 minutes. Sodium carbonate (9.63 g, 0.0909 mole) was added and the mixture was degassed with argon for 5 minutes. Phenylboronic acid (6.65 g, 0.05454 mole) and 2-amino-5-iodo-pyridine (10.0 g, 0.04545 mole) were then added and the mixture was degassed with argon for 5 minutes. Tetrakis(triphenylphosphine)palladium(0) (5.252 g, 0.00454 mole) was added was degassed with argon for 5 minutes. The resulting mixture was then heated to reflux for 3 hours. The mixture was diluted with ethyl acetate, and the organic layer was washed with water followed by brine solution. The ethyl acetate layer was dried over sodium sulfate and concentrated under reduced pressure. Purification by column chromatography using silica gel 60-120 mesh (1% methanol in chloroform) afforded 3.2 g (41%) of 5-phenyl-pyridin-2-ylamine. LC-MS purity: 171.08 (M+1)$^+$, 87%.

Example 62

Synthesis of 3-[4-(2-Chloro-5-fluoro-phenoxy)-piperidin-1-yl]-3-oxo-N-(5-phenyl-pyridin-2-yl)-propionamide

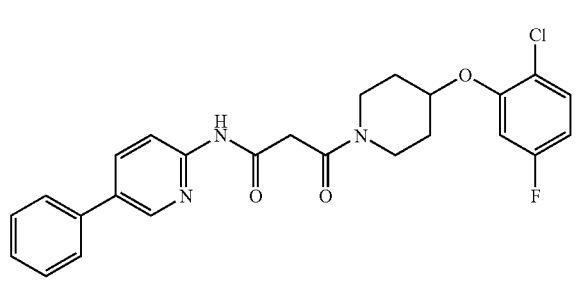

To a stirred solution of 5-phenyl-pyridin-2-ylamine (0.041 g, 0.00024 mole) in THF (3 mL) was added 3-[4-(2-chloro-5-fluoro-phenoxy)-piperidin-1-yl]-3-oxo-propionic acid (0.08 g, 0.00025 mole) followed by DIC (0.036 g, 0.00028 mole). The mixture was heated to reflux for 3 hours, and then concentrated under educed pressure. The resulting residue was stirred with cold ether. The organic layers were removed by filtration and concentrated under reduced pressure to afford 0.021 g (18%) of 3-[4-(2-chloro-5-fluoro-phenoxy)-piperidin-1-yl]-3-oxo-N-(5-phenyl-pyridin-2-yl)-propionamide. LC-MS purity: 468.14 (M+1)$^+$, 98%, $^1$H NMR (DMSO-d$_6$) δ 11.2 (bs, 1H), 8.2 (t, 2H), 8.0 (d, 1H), 7.4 (m, 4H), 7.1 (t, 1H), 6.6 (d, 2H), 4.6 (s, 1H), 4.0 (d, 1H), 3.7 (m, 1H), 3.6 (m, 3H), 2.1 (bs, 9H), 1.8 (t, 4H).

Intermediate 55

Synthesis of 3-[4-(2-Chloro-phenoxy)-piperidin-1-yl]-3-oxo-propionic acid

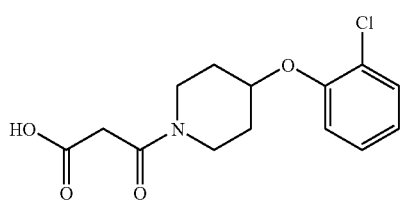

To a stirred solution of malonic acid monoethyl ester (1.2 g, 0.0089 mole) in DMF (10 mL) was added DIPEA (2.5 g, 0.02 mole), HOBt (1.3 g, 0.0097 mole) and EDCI.HCl (1.9 g, 0.0097 mole). After 2 minutes 4-(2-chloro-phenoxy)-piperidine hydrochloride (2 g, 0.0081 mole) was added and the resulting mixture was stirred overnight. The reaction mixture was then diluted with cold water and the product was extracted with ethyl acetate. The organic layers were dried over sodium sulfate and concentrated under reduced pressure. The resulting residue was purified by column chromatography using silica gel 60-120 mesh (60% ethyl acetate in hexane) to afford 1.1 g (42%) of 3-[4-(2-chloro-phenoxy)-piperidin-1-yl]-3-oxo-propionic acid ethyl ester. LC-MS purity: 326.11 (M+1)$^+$, 90.2%. To a stirred solution of 3-[4-(2-chloro-phenoxy)-piperidin-1-yl]-3-oxo-propionic acid ethyl ester (1.1 g, 0.0034 mole) in a mixture of THF (20 mL), methanol (4 mL) and H$_2$O (4 mL) was added LiOH.H$_2$O (0.286 g, 0.0068 mole) at ambient temperature. The resulting mixture was stirred for 30 minutes. Volatiles were then evaporated and the resulting residue was diluted with water, acidified with 10% aqueous HCl solution. The resulting precipitate was isolated by filtration and dried to afford 0.75 g (75%) of 3-[4-(2-chloro-phenoxy)-piperidin-1-yl]-3-oxo-propionic acid.

Example 63

Synthesis of 3-[4-(2-Chloro-phenoxy)-piperidin-1-yl]-3-oxo-N-(6-phenyl-pyridin-3-yl)-propionamide

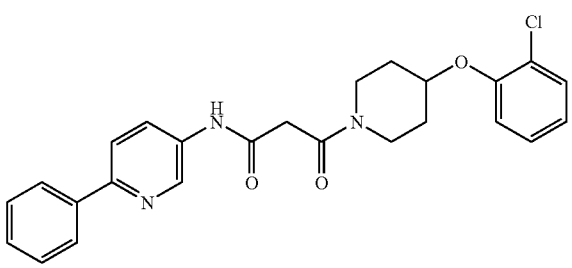

To a stirred solution of 3-[4-(2-chloro-phenoxy)-piperidin-1-yl]-3-oxo-propionic acid (0.08 g, 0.00027 mole) in DMF (3 mL) was added DMAP (0.049 g, 0.00040 mole), HOBt (0.043 g, 0.00032 mole) and EDCI.HCl (0.06 g, 0.00032 mole). After 2 minutes 6-phenyl-pyridin-3-ylamine (0.055 g, 0.00032 mole) was added and the resulting mixture was stirred overnight. The reaction mixture was then diluted with cold water and the product was extracted with ethyl acetate ethyl acetate. The organic layer was washed with brine solution, dried over sodium sulfate and concentrated under reduced pressure to afford 0.0642 g (53%) of 3-[4-(2-chloro-phenoxy)-piperidin-1-yl]-3-oxo-N-(6-phenyl-pyridin-3-yl)-propionamide. LC-MS purity: 450.15 (M+1)$^+$, 99.25%, $^1$H NMR (DMSO-d$_6$): δ 10.4 (s, 1H), 8.8 (s, 1H), 8.2 (dd, 1H), 8.1-8.0 (m, 2H), 8.0-7.9 (m, 1H), 7.5-7.2 (m, 6H), 7.0-6.9 (m, 1H), 4.8-4.7 (m, 1H), 3.8-3.7 (m, 2H), 3.7-3.6 (s, 2H), 3.6-3.5 (m, 2H), 2.1-1.5 (m, 4H).

Intermediate 56

Synthesis of N-(6-Phenyl-pyridin-3-yl)-malonamic acid

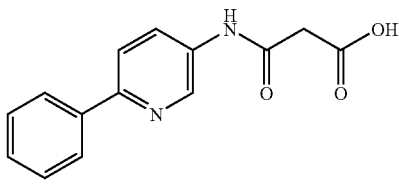

To a stirred solution of 5-amino-2-phenyl-pyridine (4.0 g, 0.0235 mol) in dichloromethane (40 mL) was added ethyl malonyl chloride (5.307 g, 0.035 mol) dropwise. The resulting mixture was stirred for 1 hour. The mixture was diluted with water and the product was extracted with dichloromethane. The organic layer was washed with saturated sodium bicarbonate solution, brine, dried over Na$_2$SO$_4$ and evaporated to afford 5.46 g (80%) of N-(6-phenyl-pyridin-3-yl)-malonamic acid ethyl ester. To a solution of N-(6-phenyl-pyridin-3-yl)-malonamic acid ethyl ester (5.46 g, 0.019 mol) in the mixture of methanol (27.5 mL), THF (55 mL) and H$_2$O (16.5 mL) was added LiOH.H$_2$O (1.212 g, 0.0288 mol). The resulting reaction mixture was stirred for 1 hour at ambient temperature then concentrated. The resulting residue was diluted with water, acidified with concentrated HCl and the product was extracted with ethyl acetate. The ethyl acetate was washed with brine, dried over $Na_2SO_4$ and evaporated under reduced pressure to afford 4.0 g (82%) of N-(6-phenyl-pyridin-3-yl)-malonamic acid.

Example 64

Synthesis of 3-[4-(2-Chloro-phenylamino)-piperidin-1-yl]-3-oxo-N-(6-phenyl-pyridin-3-yl)-propionamide

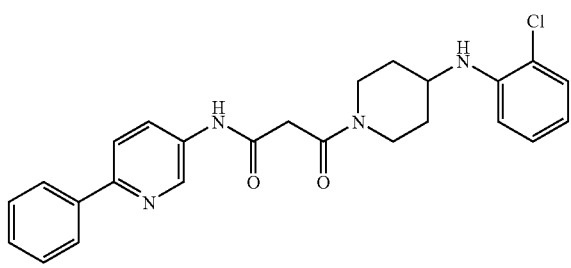

To a stirred solution of N-(6-phenyl-pyridin-3-yl)-malonamic acid (0.07 g, 0.00024 mole) in DMF (2 mL) was added, DIPEA (0.153 g, 0.00120 mole), HOBt (0.039 g, 0.00029 mole) and EDCI.HCl (0.055 g, 0.00029 mole). After 2 minutes (2-chloro-phenyl)-piperidin-4-yl-amine dihydrochloride (0.081 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 0.082 g (77%) of 3-[4-(2-chloro-phenylamino)-piperidin-1-yl]-3-oxo-N-(6-phenyl-pyridin-3-yl)-propionamide. LC-MS purity: 449.17 (M+1)$^+$, 98.46%, $^1$H NMR (DMSO-d$_6$): δ 10.5 (s, 1H), 8.8 (s, 1H), 8.2 (dd, 1H), 8.1 (d, 2H), 8.0 (d, 1H), 7.5-7.2 (m, 2H), 7.3 (d, 1H), 7.2 (t, 1H), 6.9 (d, 1H), 6.4 (t, 1H), 4.9 (d, 1H), 4.4 (d, 1H), 4.0 (d, 1H), 3.7-3.6 (m, 3H), 3.3-3.2 (m, 1H), 2.9-2.7 (m, 1H), 2.0 (t, 2H), 1.6-1.5 (m, 1H), 1.4-1.3 (m, 1H).

Example 65

Synthesis of 3-[4-(2-Bromo-phenylamino)-piperidin-1-yl]-3-oxo-N-(6-phenyl-pyridin-3-yl)-propionamide

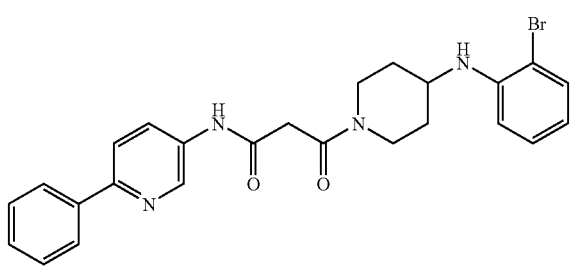

To a stirred solution of N-(6-phenyl-pyridin-3-yl)-malonamic acid (0.07 g, 0.00024 mole) in DMF (2 mL) was added DIPEA (0.153 g, 0.00120 mole), HOBt (0.039 g, 0.00029 mole) and EDCI.HCl (0.055 g, 0.00029 mole). After 2 minutes (2-bromo-phenyl)-piperidin-4-yl-amine dihydrochloride (0.093 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 77.9 mg (66%) of 3-[4-(2-bromo-phenylamino)-piperidin-1-yl]-3-oxo-N-(6-phenyl-pyridin-3-yl)-propionamide. LC-MS purity: 493.12 (M+1)$^+$, 99.22%, $^1$H NMR (DMSO-d$_6$): δ 10.5 (s, 1H), 8.8 (d, 1H), 8.2 (dd, 1H), 8.1 (d, 1H), 8.0 (d, 1H), 7.6-7.4 (m, 4H), 7.2 (t, 1H), 6.9 (d, 1H), 6.6 (t, 1H), 4.7 (d, 1H), 4.4 (d, 1H), 4.0 (d, 1H), 3.7-3.6 (m, 3H), 3.3-3.2 (m, 1H), 2.0 (t, 2H), 1.6-1.5 (m, 1H), 1.4-1.3 (m, 1H).

Example 66

Synthesis of 3-Oxo-N-(6-phenyl-pyridin-3-yl)-3-[4-(2-trifluoromethyl-phenylamino)-piperidin-1-yl]-propionamide

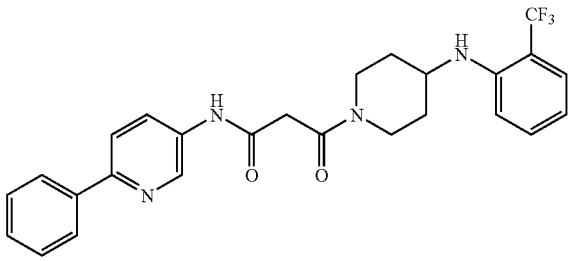

To a stirred solution of N-(6-phenyl-pyridin-3-yl)-malonamic acid (0.07 g, 0.00024 mole) in DMF (2 mL) was added DIPEA (0.153 g, 0.00120 mole), HOBt (0.039 g, 0.00029 mole) and EDCI.HCl (0.055 g, 0.00029 mole) After 2 minutes (2-trifluoromethyl-phenyl)-piperidin-4-yl-amine dihydrochloride (0.075 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 73.7 mg (64%) of 3-oxo-N-(6-phenyl-pyridin-3-yl)-3-[4-(2-trifluoromethyl-phenylamino)-piperidin-1-yl]-propionamide. LC-MS purity: 483.19 (M+1)$^+$, 95.78%, $^1$H NMR (DMSO-d$_6$) δ 10.5 (s, 1H), 8.8 (d, 1H), 8.2 (dd, 1H), 8.1 (d, 2H), 8.0 (d, 1H), 7.5-7.4 (m, 4H), 7.0 (d, 1H), 6.8 (t, 1H), 4.7 (d, 1H), 4.4 (d, 1H), 4.0 (d, 1H), 3.8-3.6 (m, 3H), 3.3-3.2 (m, 1H), 2.9-2.8 (m, 1H), 2.0 (m, 1H), 1.6-1.5 (m, 1H), 1.5-1.4 (m, 1H).

Example 67

Synthesis of 3-[4-(2-Chloro-phenylsulfanyl)-piperidin-1-yl]-3-oxo-N-(6-phenyl-pyridin-3-yl)-propionamide

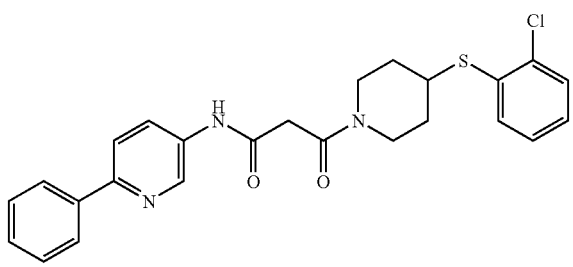

To a stirred solution of N-(6-phenyl-pyridin-3-yl)-malonamic acid (0.07 g, 0.00024 mole) in DMF (1 mL) was added DIPEA (0.153 g, 0.00120 mole), HOBt (0.039 g, 0.00029 mole) and EDCI.HCl (0.055 g, 0.00029 mole). After 2 minutes (2-chloro-phenylsulfanyl)-piperidin-4-yl-amine hydrochloride (0.076 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 0.07 g (63%) of 3-[4-(2-chloro-phenylsulfanyl)-piperidin-1-yl]-3-oxo-N-(6-phenyl-pyridin-3-yl)-propionamide. LC-MS purity: 466.13 (M+1)$^+$, 93.65%, $^1$H NMR (DMSO-d$_6$): δ 10.5 (s, 1H), 8.8 (d, 1H), 8.2 (d, 1H), 8.1 (d, 2H), 8.0 (d, 1H), 7.6-7.2 (m, 6H), 4.3 (d, 1H), 3.9 (d, 1H), 3.6-3.5 (m, 3H), 3.0 (t, 1H), 2.0 (m, 2H), 1.7-1.6 (m, 1H), 1.5-1.4 (m, 1H).

Example 68

Synthesis of 3-[4-(2-Bromo-phenylsulfanyl)-piperidin-1-yl]-3-oxo-N-(6-phenyl-pyridin-3-yl)-propionamide

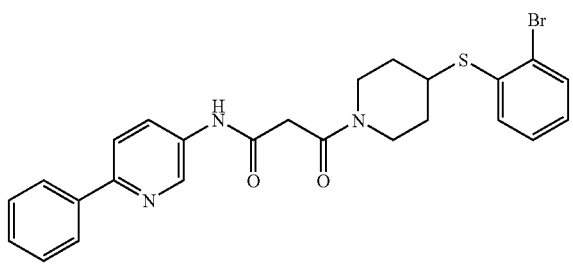

To a stirred solution of N-(6-phenyl-pyridin-3-yl)-malonamic acid (0.07 g, 0.00024 mole) in DMF (1 mL) was added DIPEA (0.153 g, 0.00120 mole), HOBt (0.039 g, 0.00029 mole) and EDCI.HCl (0.055 g, 0.00029 mole). After 2 minutes (2-bromo-phenylsulfanyl)-piperidin-4-yl-amine hydrochloride (0.088 g, 0.00028 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 73.2 mg (60%) of 3-[4-(2-bromo-phenylsulfanyl)-piperidin-1-yl]-3-oxo-N-(6-phenyl-pyridin-3-yl)-propionamide. LC-MS purity: 510.08 (M+1)$^+$, 93.64%, $^1$H NMR (DMSO-d$_6$): δ 10.5 (s, 1H), 8.8 (d, 1H), 8.2 (d, 1H), 8.1 (d, 2H), 8.0 (d, 1H), 7.84-7.7 (m, 2H), 7.7 (t, 1H), 7.54-7.36 (m, 4H), 4.3 (d, 1H), 3.9 (d, 1H), 3.8-3.7 (m, 1H), 3.6 (s, 2H), 3.3-3.2 (m, 1H), 3.0-2.9 (m, 1H), 2.0 (t, 2H), 1.6-1.5 (m, 1H), 1.5-1.4 (m, 1H).

Example 69

Synthesis of 3-Oxo-N-(6-phenyl-pyridin-3-yl)-3-[4-(2-trifluoromethyl-phenylsulfanyl)-piperidin-1-yl]-propionamide

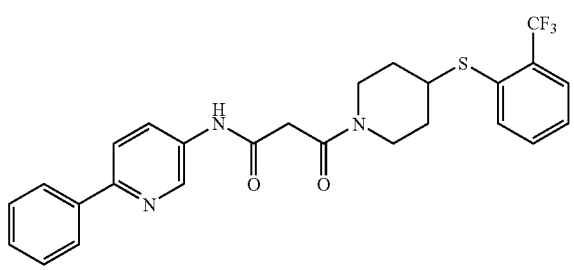

To a stirred solution of N-(6-phenyl-pyridin-3-yl)-malonamic acid (0.07 g, 0.00024 mole) in DMF (1 mL) was added DIPEA (0.153 g, 0.00120 mole), HOBt (0.039 g, 0.000286 mole) and EDCI.HCl (0.055 g, 0.00029 mole). After 2 minutes (2-trifluoromethyl-phenylsulfanyl)-piperidin-4-yl-amine hydrochloride (0.085 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 80.2 mg (67%) of 3-oxo-N-(6-phenyl-pyridin-3-yl)-3-[4-(2-trifluoromethyl-phenylsulfanyl)-piperidin-1-yl]-propionamide. LC-MS purity: 501.15 (M+1)$^+$, 95.38%, $^1$H NMR (DMSO-d$_6$): δ 10.5 (s, 1H), 8.8 (d, 1H), 8.2 (d, 1H), 8.1 (d, 2H), 8.0 (d, 1H), 7.7 (d, 1H), 7.6-7.4 (m, 5H), 7.2 (t, 1H), 4.3 (d, 1H), 3.9

(d, 1H), 3.7-3.6 (m, 3H), 3.3-3.2 (m, 1H), 3.0 (m, 1H), 2.0 (m, 2H), 1.7-1.6 (m, 1H), 1.5-1.4 (m, 1H).

Example 70

Synthesis of 3-Oxo-N-(6-phenyl-pyridin-3-yl)-3-[4-(2-trifluoromethyl-phenoxy)-piperidin-1-yl]-propionamide

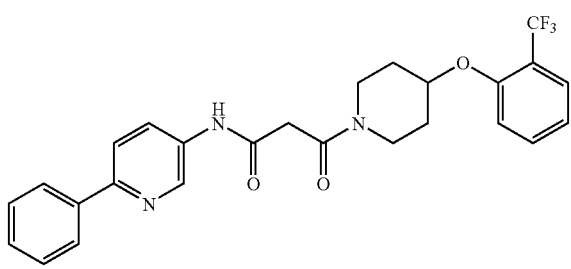

To a stirred solution of N-(6-phenyl-pyridin-3-yl)-malonamic acid (0.07 g, 0.00024 mole) in DMF (1 mL) was added DIPEA (0.153 g, 0.00120 mole), HOBt (0.039 g, 0.00029 mole) and EDCI.HCl (0.055 g, 0.00029 mole). After 2 minutes (2-trifluoromethyl-phenoxy)-piperidin-4-yl-amine hydrochloride (0.080 g, 0.00029 mole) was added and the resulting mixture was stirred overnight. The reaction mixture was then diluted with cold water and the product was extracted with ethyl acetate. The organic layer was washed with brine solution, dried over sodium sulfate and concentrated under reduced pressure to afford 57.5 mg (50%) of 3-oxo-N-(6-phenyl-pyridin-3-yl)-3-[4-(2-trifluoromethyl-phenoxy)-piperidin-1-yl]-propionamide. LC-MS purity: 484.18 (M+1)$^+$, 98.83%, $^1$H NMR (DMSO-d$_6$): δ 10.5 (s, 1H), 8.8 (d, 1H), 8.2 (d, 1H), 8.1 (d, 2H), 8.0 (d, 1H), 7.7-7.6 (m, 2H), 7.5-7.3 (m, 4H), 7.1 (t, 1H), 4.9 (m, 1H), 3.7-3.5 (m, 6H), 2.0-1.6 (m, 4H).

Example 71

Synthesis of 3-Oxo-N-(6-phenyl-pyridin-3-yl)-3-(4-o-tolylamino-piperidin-1-yl)-propionamide

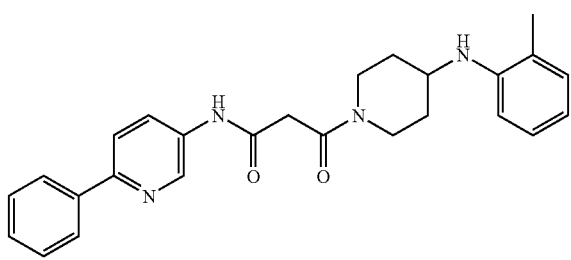

To a stirred solution of N-(6-phenyl-pyridin-3-yl)-malonamic (0.07 g, 0.00024 mole) in DMF (1 mL) was added DIPEA (0.153 g, 0.00120 mole), HOBt (0.039 g, 0.00029 mole) and EDCI.HCl (0.055 g, 0.00029 mole). After 2 minutes piperidin-4-yl-o-tolyl-amine dihydrochloride (0.075 g, 0.00029 mole) was added and the resulting mixture was stirred overnight. The reaction mixture was then diluted with cold water and the product was extracted with ethyl acetate. The organic layer was washed with water followed by brine solution, dried over sodium sulfate and concentrated under reduced pressure to afford 0.075 g (74%) of 3-oxo-N-(6-phenyl-pyridin-3-yl)-3-(4-o-tolylamino-piperidin-1-yl)-propionamide. LC-MS purity: 429.22 (M+1)$^+$, 98.41%, $^1$H NMR (DMSO-d$_6$): δ 10.5 (s, 1H), 8.8 (d, 1H), 8.2 (d, 1H), 8.1 (d, 2H), 8.0 (d, 1H), 7.5-7.3 (m, 2H), 7.0 (t, 2H), 6.7 (d, 1H), 6.5 (t, 1H), 4.5-4.3 (m, 2H), 4.0 (d, 1H), 3.7-3.5 (m, 3H), 3.3-3.2 (m, 1H), 2.9-2.8 (m, 1H), 2.1 (s, 3H) 2.0-1.9 (m, 2H).

Intermediate 57

Synthesis of N-(3-Phenyl-[1,2,4]thiadiazol-5-yl)-malonamic acid

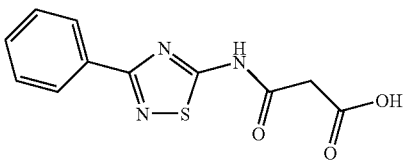

To a stirred solution of 3-phenyl-[1,2,4]thiadiazol-5-ylamine (0.25 g, 0.00141 mol) in chloroform (2.5 mL) was added mono ethylmalonylchloride (0.233 g, 0.00155 mol) dropwise, the resulting mixture was stirred for 3 hours. The mixture was then concentrated and the residue was stirred in ethyl acetate. The filtrate was removed and concentrated to afford 0.26 g (63%) of N-(3-phenyl-[1,2,4]thiadiazol-5-yl)-malonamic acid ethyl ester. LC-MS purity: 292.07 (M+1)$^+$, 67%. To a solution of N-(3-phenyl-[1,2,4]thiadiazol-5-yl)-malonamic acid ethyl ester (0.26 g, 0.00089 mol) in a mixture of methanol (3 mL) and H$_2$O (1 mL) was added LiOH.H$_2$O (0.112 g, 0.00267 mol). The reaction mixture was stirred for 4 hours at ambient temperature then concentrated. The resulting residue was diluted with cold water, acidified with 2NHCl and the product was extracted with ethyl acetate. The ethyl acetate layer washed with brine, dried over Na$_2$SO$_4$ and evaporated under reduced pressure to afford 0.105 g (45%) of N-(3-phenyl-[1,2,4]thiadiazol-5-yl)-malonamic acid. LCMS: 264.27 (M+1)$^+$: 97.64%.

Example 72

Synthesis of 3-[4-(2-Chloro-phenoxy)-piperidin-1-yl]-3-oxo-N-(3-phenyl-[1,2,4]thiadiazol-5-yl)-propionamide

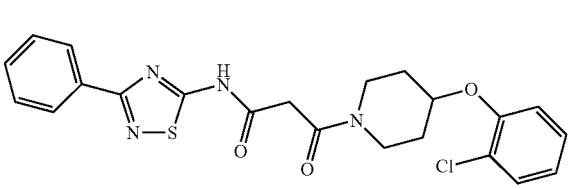

To a stirred solution of N-(3-phenyl-[1,2,4]thiadiazol-5-yl)-malonamic acid (0.07 g, 0.00027 mole) in THF (3 mL) was added, 4-(2-chloro-phenoxy)-piperidine hydrochloride (0.072 g, 0.00029 mol) followed by DIC (0.04 g, 0.00031 mole). The resulting mixture was heated to reflux for 4 hours then concentrated. The resulting residue was purified by column chromatography using neutral aluminium oxide (0.5% methanol in dichloromethane) to afford 0.045 g (37%) of 3-[4-(2-chloro-phenoxy)-piperidin-1-yl]-3-oxo-N-(3-phenyl-[1,2,4]thiadiazol-5-yl)-propionamide. LC-MS purity: 457.1 (M+1)$^+$, 84.85% $^1$H NMR (CDCl$_3$): δ 8.2 (s, 2H), 7.5 (m, 4H), 7.2 (m, 1H), 7.0 (d, 2H), 4.7 (s, 1H), 4.2 (d, 1H), 3.8 (m, 1H), 3.6 (m, 5H), 2.0 (dd, 4H), 2.6 (bs, 3H).

Intermediate 58

Synthesis of 4-[1,2,4]Oxadiazol-3-yl-phenylamine

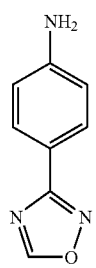

To a stirred solution of 4-nitrobenzonitrile (1 g, 0.0068 mol) in ethanol (20 mL) and water (8 mL) was added hydroxylamine hydrochloride (1.9 g, 0.0272 mol) followed by sodium carbonate (2.2 g, 0.0204 mol). The resulting mixture was heated to reflux at 85° C. under an atmosphere of nitrogen for 2 hours The reaction was monitored by TLC (50% Ethyl acetate in Hexane). The volatiles were evaporated and the residue was extracted with ethyl acetate. The ethyl acetate was washed with brine solution, dried over Na$_2$SO$_4$ and concentrated under reduced pressure to get afford 1.2 g (98%) of N-hydroxy-4-nitro-benzamidine. $^1$H NMR (DMSO-d$_6$): δ 10.2 (s, 1H), 8.24 (d, 2H), 7.97 (d, 2H), 6.03 (s, 2H). To a stirred solution of N-hydroxy-4-nitro-benzamidine (1.2 g, 0.0066 mol) in THF (15 mL) was added triethyl orthoformate (2.93 g, 0.0198 mol). The resulting mixture was cooled to between 0 and 5° C. Boron trifluoride dimethyl ether (0.9 g, 0.0079 mol) was then added dropwise and the resulting mixture was stirred at ambient temperature for 3 hours. Volatiles were evaporated under reduced pressure and the resulting residue was washed with ether and dried to afford 0.65 g (55%) of 3-(4-nitro-phenyl)-[1, 2, 4]oxadiazole. To a stirred solution of 3-(4-nitro-phenyl)-[1, 2, 4]oxadiazole (0.2 g, 0.001 mol) in THF (15 mL) was added ammonium chloride (0.214 g, 0.004 mol) in water (5 mL) followed by zinc powder (0.262 g, 0.004 mol) portionwise. The resulting mixture was stirred at ambient temperature for 1 hr and then heated to 65° C. for 5 hours. The mixture was then filtered through celite and the organic layers were concentrated under reduced pressure. The residue was extracted with ethyl acetate. The organic layers were washed with brine solution, dried over Na$_2$SO$_4$ and evaporated under reduced pressure to afford 0.155 g (92%) of 4-[1, 2, 4]oxadiazol-3-yl-phenylamine. $^1$H NMR (DMSO-d$_6$): δ 9.5 (s, 1H), 7.7 (d, 2H), 6.7 (d, 2H), 5.8 (s, 2H).

Example 73

Synthesis of 3-[4-(2-Chloro-phenoxy)-piperidin-1-yl]-N-(4-[1,2,4]oxadiazol-3-yl-phenyl)-3-oxo-propionamide

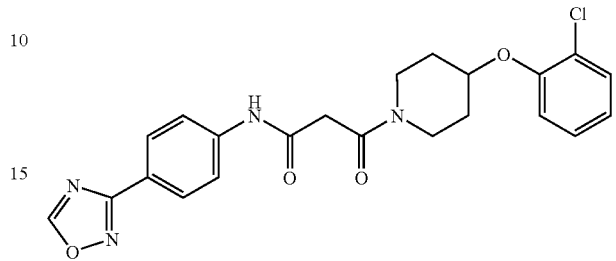

To a stirred solution of 3-[4-(2-chloro-phenoxy)-piperidin-1-yl]-3-oxo-propionic acid (0.1 g, 0.00034 mole) in DMF (2 mL) was added DMAP (0.063 g, 0.00051 mole), HOBt (0.055 g, 0.00041 mole) and EDCI.HCl (0.079 g, 0.00041 mole). After 2 minutes 4-[1, 2, 4]-oxadiazol-3-yl-phenylamine (0.06 g, 0.00037 mole) was added and the resulting mixture was stirred overnight. The reaction mixture was then diluted with cold water and the product was extracted with ethyl acetate. The ethyl acetate layer was dried over sodium sulfate and concentrated under reduced pressure to afford 0.09 g (61%) of 3-[4-(2-chloro-phenoxy)-piperidin-1-yl]-N-(4-[1,2,4]oxadiazol-3-yl-phenyl)-3-oxo-propionamide. LC-MS purity: 441 (M+1)$^+$, 94.4%, $^1$H NMR (CDCl$_3$): δ 10.5 (s, 1H), 8.8 (s, 1H), 8.1 (d, 2H), 7.74 (d, 2H), 7.4 (d, 1H), 7.2 (d, 1H), 6.96 (t, 2H), 4.7 (q, 1H), 4.1 (m, 1H), 3.8 (m, 1H), 3.6 (m, 2H), 3.55 (s, 2H), 2.0 (m, 5H).

Intermediate 59

Synthesis of N-(5-Phenyl-thiazol-2-yl)-malonamic acid

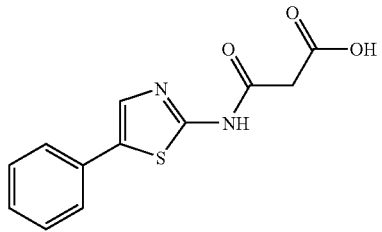

To a stirred solution of 5-phenyl-thiazol-2-ylamine (0.4 g, 0.0022 mol) and DIEA (0.73 g, 0.0056 mol) in chloroform (4 mL) was added mono-ethylmalonyl chloride (0.375 g, 0.0024 mol) dropwise at 0° C. and the resulting mixture was stirred at ambient temperature for 20 minutes. The reaction mixture was then diluted with cold water and the product was extracted with chloroform. The chloroform was washed with saturated sodium bicarbonate solution and brine, dried over Na$_2$SO$_4$ and evaporated under reduced pressure to afford 0.3 g (46%) of N-(5-phenyl-thiazol-2-yl)-malonamic acid ethyl ester. To a solution of N-(5-phenyl-thiazol-2-yl)-malonamic acid ethyl ester (0.292 g, 0.001 mol) in the mixture of methanol (1 mL), THF (1.5 mL) and H$_2$O (1 mL) was added LiOH.H$_2$O (0.084 g, 0.002 mol) and the resulting mixture was stirred for 1 hour. The reaction mixture was then concentrated. The residue was diluted with water, acidified with concentrated HCl and the product was extracted with ethylacetate. The ethyl acetate was washed with brine, dried over Na$_2$SO$_4$ and evaporated under reduced pressure to afford 0.23 g (87%) of N-(5-phenyl-thiazol-2-yl)-malonamic acid.

Example 74

Synthesis of 3-[4-(2-Chloro-phenoxy)-piperidin-1-yl]-3-oxo-N-(5-phenyl-thiazol-2-yl)-propionamide

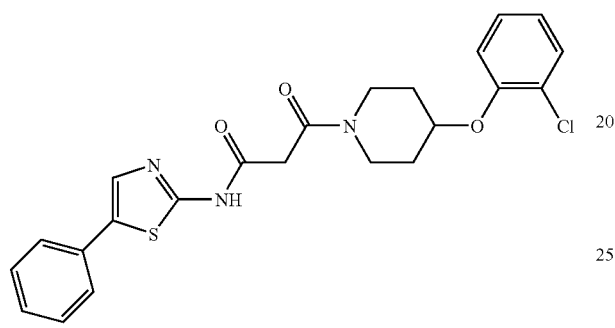

To a stirred solution of N-(5-phenyl-thiazol-2-yl)-malonamic acid (0.075 g, 0.00028 mole) in DMF (2 mL) was added DIPEA (0.11 g, 0.00085 mole), HOBt (0.038 g, 0.00028 mole) and EDCI.HCl (0.065 g, 0.00034 mole). After 2 minutes 4-(2-chloro-phenoxy)-piperidine hydrochloride (0.078 g, 0.00031 mole) was added and the resulting mixture was stirred overnight. The reaction mixture was then diluted with cold water and the product was extracted with ethyl acetate. The ethyl acetate layer was dried over sodium sulfate and concentrated under reduced pressure to afford 0.031 g (24%) of 3-[4-(2-chloro-phenoxy)-piperidin-1-yl]-3-oxo-N-(5-phenyl-thiazol-2-yl)-propionamide. LC-MS purity: 456.11 (M+1)$^+$, 93.27%, $^1$H NMR (CDCl$_3$): δ 11.6 (s, 1H), 7.9 (d, 2H), 7.44 (t, 3H), 7.3 (d, 1H), 7.22 (d, 1H), 7.14 (s, 1H), 6.92 (d, 2H), 4.7 (s, 1H), 4.1 (m, 1H), 3.8 (m, 1H), 3.7-3.5 (m, 4H), 2.0 (d, 4H).

Example 75

Synthesis of 3-[4-(2-Chloro-phenylamino)-piperidin-1-yl]-3-oxo-N-(5-phenyl-thiazol-2-yl)-propionamide

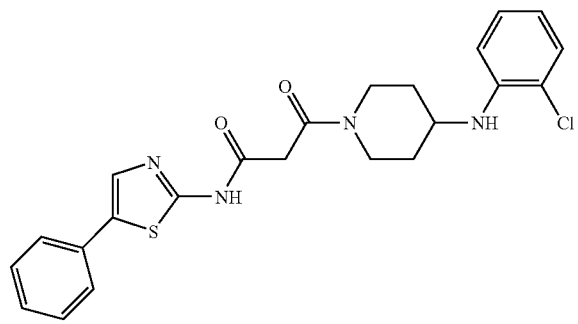

To a stirred solution of N-(5-phenyl-thiazol-2-yl)-malonamic acid (0.075 g, 0.00028 mole) in DMF (2 mL) was added DIPEA (0.11 g, 0.00085 mole), HOBt (0.038 g, 0.00028 mole) and EDCI.HCl (0.065 g, 0.00034 mol). After 2 minutes (2-chloro-phenyl)-piperidin-4-yl-amine dihydrochloride (0.077 g, 0.00031 mol) was added and the resulting mixture was stirred overnight. The reaction mixture was then diluted with cold water and the product was extracted with ethyl acetate. The ethyl acetate layer was dried over sodium sulfate and concentrated under reduced pressure. The residue was recrystallized from a mixture of ethyl acetate and hexane to afford 0.035 g (28%) of 3-[4-(2-chloro-phenylamino)-piperidin-1-yl]-3-oxo-N-(5-phenyl-thiazol-2-yl)-propionamide. LC-MS purity: 455.11 (M+1)$^+$, 98.03%, $^1$H NMR (CDCl$_3$): δ 11.6 (s, 1H), 7.9 (d, 2H), 7.4 (t, 3H), 7.3 (t, 2H), 7.2 (m, 2H), 7.1, 6.70 (m, 2H), 4.5 (d, 1H), 4.2 (d, 1H), 3.9 (d, 1H), 3.6 (s, 3H), 3.3 (t, 1H), 3.1 (t, 1H), 2.2 (s, 2H), 1.5 (m, 2H).

Intermediate 60

Synthesis of 1-(Biphenyl-4-ylcarbamoyl)-cyclopropanecarboxylic acid

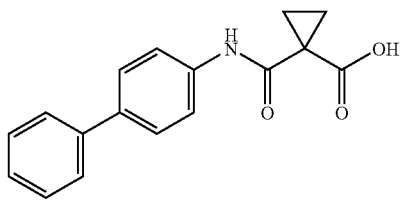

KOH (420 mg, 7.5 mmol) was added to a solution cyclopropane-1,1-dicarboxylic acid diethyl ester (1 g, 6.3 mmol) in methanol (7 mL). The reaction mixture was stirred for 4 hours at ambient temperature then concentrated. The resulting residue was diluted with water, acidified with conc. HCl and the product was extracted with dichloromethane. The dichloromethane layer was dried over sodium sulfate and concentrated under reduced pressure to afford 680 mg (75%) of cyclopropane-1,1-dicarboxylic acid methyl ester. HOBt (764 mg, 5.6 mmol), DMAP (1.72 g, 14.15 mmol) and EDCI.HCl (1.08 g, 5.6 mmol) followed by biphenyl-4-ylamine (957 mg, 5.6 mmol) were added to a stirred solution of cyclopropane-1,1-dicarboxylic acid methyl ester (680 mg, 4.7 mmol) in DMF (7 mL) and the resulting mixture was stirred at ambient temperature overnight. The mixture was then diluted with water and the product was extracted with ethyl acetate. The ethylacetate layer was washed with brine solution and concentrated to afford 1.1 g (79%) of 1-(biphenyl-4-ylcarbamoyl)-cyclopropanecarboxylic acid methyl ester. LiOH.H$_2$O (234 mg, 5.5 mmol) was added to a solution of 1-(biphenyl-4-ylcarbamoyl)-cyclopropanecarboxylic acid methyl ester (1.1 g, 3.7 mmol) in a mixture of methanol (5 mL), THF (11 mL) and H$_2$O (3 mL) and the resulting mixture was stirred for 2 hours at ambient temperature. The reaction mixture was then concentrated and the residue was diluted with water, acidified with conc. HCl. The resulting precipitate was isolated by filtration and dried to afford 340 mg (33%) of 1-(biphenyl-4-ylcarbamoyl)-cyclopropane carboxylic acid.

Example 76

Synthesis of 1-[4-(2-Chloro-phenoxy)-piperidine-1-carbonyl]-cyclopropane carboxylic acid biphenyl-4-ylamide

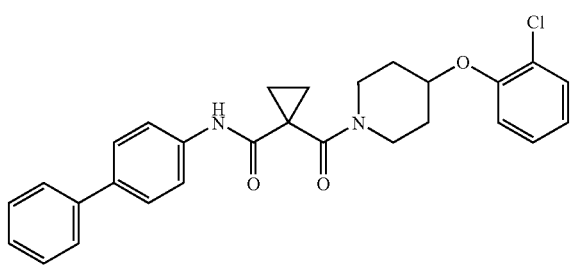

HOBt (57 mg, 0.42 mol) and DIPEA (137 mg, 1.06 mmole), EDCI.HCl (82 mg, 0.42 mol) followed by 4-(2-chloro-phenoxy)-piperidine hydrochloride (105 mg, 0.42 mol) were added to a stirred solution of 1-(biphenyl-4-ylcarbamoyl)-cyclopropanecarboxylic acid (100 mg, 0.35 mmol) in DMF (2.0 mL) and the resulting mixture was stirred at ambient temperature overnight. The reaction mixture was then diluted with water. The product was extracted with ethylacetate and the organic layers were washed with brine and concentrated to afford 78 mg (46%) of 1-[4-(2-chloro-phenoxy)-piperidine-1-carbonyl]-cyclopropanecarboxylic acid biphenyl-4-ylamide. LCMS: 475.17 (M+1)$^+$, 92.81%, $^1$H NMR (DMSO-d$_6$): δ 9.8 (s, 1H), 7.8-7.5 (d, 2H), 7.7-7.6 (t, 4H), 7.5-7.4 (m, 3H), 7.4-7.2 (m, 3H), 7.0-6.9 (m, 1H), 4.7 (m, 1H), 3.8-3.6 (m, 2H), 3.5 (m, 2H), 2.0-1.8 (m, 2H), 1.7-1.6 (m, 2H), 1.4 (m, 2H), 1.3-1.2 (m, 2H).

Example 77

Synthesis of 5-Phenyl-1H-pyrazole-3-carboxylic acid {2-[4-(5-bromo-2-methoxy-phenylamino)-piperidin-1-yl]-2-oxo-ethyl}-amide

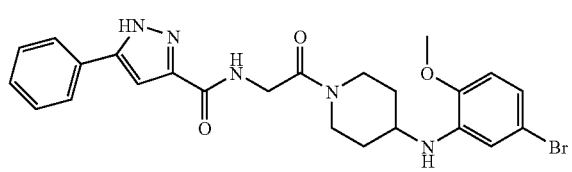

DIPEA (45 mg, 0.35 mmol) was added to a stirred solution of [(5-phenyl-1H-pyrazole-3-carbonyl)-amino]-acetic acid (26 mg, 0.1 mmol) in DMF (1 mL) followed by HOBt (20 mg, 0.15 mmol) and EDCI.HCl (28 mg, 0.15 mmol). After 2 minutes of stirring, 2-amino-1-[4-(5-bromo-2-methoxy-phenylamino)-piperidin-1-yl]-ethanone hydrochloride (prepared according to Step 2 and 5 of the General Scheme) (0.03 g, 0.0001 mmol) was added and stirring was continued at ambient temperature overnight. The reaction mixture was diluted with cold water extracted with ethyl acetate, dried over sodium sulfate and concentrated under reduced pressure Purification by column chromatography (using neutral alumina and 5% MeOH in CHCl$_3$ as eluent) to afford 60 mg (35% Yield) of 5-phenyl-1H-pyrazole-3-carboxylic acid {2-[4-(5-bromo-2-methoxy-phenylamino)-piperidin-1-yl]-2-oxo-ethyl}-amide. LC/MS [M+H]$^+$: 512.4, 91%, $^1$H NMR (300 MHz, DMSO-d$_6$): δ10.2 (m, 1H), 7.9 (m, 1H), 7.7 (m, 7H), 7.4 (m, 2H), 7.2 (m, 1H), 3.6 (m, 5H), 2.0 (m, 2H), 1.8 (m, 2H).

Example 78

Synthesis of 5-Phenyl-1H-pyrazole-3-carboxylic acid {2-oxo-2-[4-(3-trifluoromethyl-phenoxy)-piperidin-1-yl]-ethyl}-amide

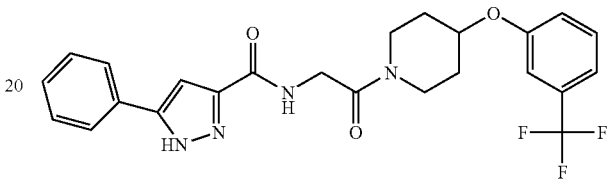

DIPEA (360 mg, 2.8 mmol) was added to a stirred solution of [(5-phenyl-1H-pyrazole-3-carbonyl)-amino]-acetic acid (200 mg, 0.8 mmol) in DMF (2 mL) followed by HOBt (131 mg, 0.97 mmol) and EDCI.HCl (187 mg, 00.97 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (200 mg, 0.8 mmol) was added and stirring was continued at ambient temperature overnight. The reaction mixture was diluted with cold water extracted with ethyl acetate, dried over sodium sulfate and concentrated under reduced pressure. Purification by column chromatography (using neutral alumina and 5% MeOH in CHCl$_3$ as eluent) to afford 62 mg (16.2% Yield) of 5-phenyl-1H-pyrazole-3-carboxylic acid {2-oxo-2-[4-(3-trifluoromethyl-phenoxy)-piperidin-1-yl]-ethyl}-amide.
LC/MS [M+H]$^+$: 473.17, 91%, $^1$H NMR (300 MHz, DMSO-d$_6$): δ8.1 (m, 1H), 7.8 (d, 2H), 7.5 (m, 3H), 7.4 (m, 4H), 7.1 (s, 1H), 4.8 (m, 1H), 4.2 (d, 2H), 3.8 (m, 1H), 3.6 (m, 1H), 3.5 (m, 2H), 2.0 (m, 2H), 1.6 (m, 2H).

Example 79

Synthesis of 5-Phenyl-1H-pyrazole-3-carboxylic acid {2-[4-(2-cyano-phenoxy)-piperidin-1-yl]-2-oxo-ethyl}-amide

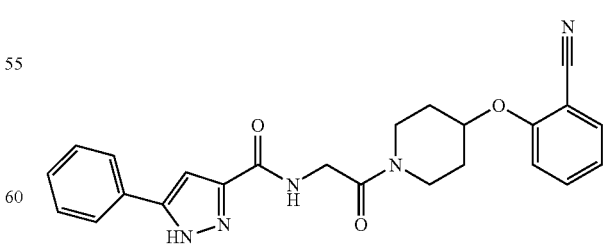

DIPEA (1.3 g, 0.01 mmol) was added to a stirred solution of [(5-phenyl-1H-pyrazole-3-carbonyl)-amino]-acetic acid (720 mg, 2.9 mmol) in DMF (4 mL) followed by HOBt (459 mg, 3.4 mmol) and EDCI.HCl (664 mg, 3.4 mmol). After 2 minutes of stirring, 2-[1-(2-amino-acetyl)-piperidin-4-yloxy]-benzonitrile hydrochloride (prepared by method used for the synthesis of Intermediate 15) (600 mg, 2.9 mmol) was added and stirring was continued at ambient temperature overnight. The reaction mixture was diluted with cold water extracted with ethyl acetate, dried over sodium sulfate and concentrated under reduced pressure. Purification by column chromatography (using neutral alumina and 5% MeOH in CHCl$_3$ as eluent) afforded 87 mg (6% Yield) of 5-phenyl-1H-pyrazole-3-carboxylic acid {2-[4-(2-cyano-phenoxy)-piperidin-1-yl]-2-oxo-ethyl}-amide. LC/MS [M+H]$^+$: 430.18, 96.4%, $^1$H NMR (300 MHz, DMSO-d$_6$): δ8.0 (m, 1H), 7.8 (m, 3H), 7.2 (m, 1H), 7.4 (m, 4H), 7.2 (m, 2H), 4.9 (m, 1H), 4.2 (bs, 2H), 3.7 (m, 2H), 3.5 (m, 2H), 2.0 (m, 2H), 1.6 (m, 2H).

Example 80

Synthesis of 5-(2-Fluoro-phenyl)-1H-pyrazole-3-carboxylic acid {2-[4-(2-chloro-phenylamino)-piperidin-1-yl]-2-oxo-ethyl}-amide

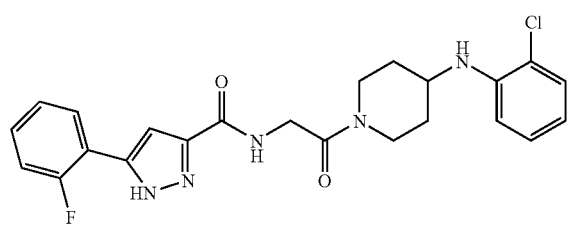

DIPEA (860 mg, 0.66 mmol) was added to a stirred solution of [(5-(2-fluoro-phenyl-1H-pyrazole-3-carbonyl)-amino]-acetic acid (prepared by the method used for the synthesis of Intermediate 30, starting from (2'-fluorophenyl) acetophenone) (50 mg, 0.19 mmol) in DMF (2 mL) followed by HOBt (27 mg, 0.19 mmol) and EDCI.HCl (39 mg, 0.19 mmol). After 2 minutes (2-chloro-phenyl)-piperidin-4-yl-amine dihydrochloride (47 mg, 0.189 mmol) was added and stirring was continued at ambient temperature overnight. The reaction mixture was diluted with cold water, the precipitate was collected to afford 44 mg (50.86% Yield) of 5-(2-fluoro-phenyl)-1H-pyrazole-3-carboxylic acid {2-[4-(2-chloro-phenylamino)-piperidin-1-yl]-2-oxo-ethyl}-amide. LC/MS [M+H]$^+$: 456.1, 94.91%, $^1$H NMR (300 MHz, DMSO-d$_6$): δ13.7 (d, 1H), 7.9 (m, 2H), 7.2 (m, 4H), 7.0 (m, 2H), 6.8 (m, 2H), 6.6 (m, 1H), 4.9 (d, 1H), 4.3 (d, 1H), 4.1 (d, 2H), 3.8 (m, 1H), 3.6 (m, 1H), 3.1 (m, 1H), 2.7 (m, 1H), 1.9 (m, 2H), 1.3 (m, 2H).

Example 81

Synthesis of 5-Phenyl-1H-pyrazole-3-carboxylic acid {2-[4-(2,4-difluoro-phenylamino)-piperidin-1-yl]-2-oxo-ethyl}-amide

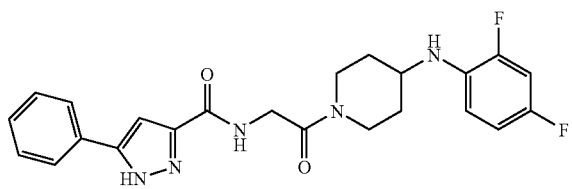

DIPEA (232 mg, 1.8 mmol) was added to a stirred solution of [(5-phenyl-1H-pyrazole-3-carbonyl)-amino]-acetic acid (148 mg, 0.6 mmol) in DMF (2 mL) followed by HOBt (95 mg, 0.7 mmol) and EDCI.HCl (137 mg, 0.7 mmol. After 2 minutes (2,4-difluoro-phenyl)-piperidin-4-yl-amine dihydrochloride (prepared by the method used for the synthesis of Intermediate 3) (150 mg, 0.6 mmol) was added to the reaction mixture and stirring was continued at ambient temperature overnight. The reaction mixture was diluted with cold water, extracted with ethyl acetate and dried over sodium sulfate. The organic layer thus collected was concentrated under reduced pressure. Purification by column chromatography (using 60-120 silica gel and 5% MeoH in CHCl$_3$ as eluent) to afford 43 mg (16.5% Yield) of 5-phenyl-1H-pyrazole-3-carboxylic acid {2-[4-(2,4-difluoro-phenylamino)-piperidin-1-yl]-2-oxo-ethyl}-amide. LC/MS [M+H]$^+$: 440.18, 94.52%. $^1$H NMR (300 MHz, DMSO-d$_6$): δ13.8 (s, 1H), 8.1 (m, 1H), 7.8 (m, 2H), 7.4 (m, 4H), 7.0 (m, 1H), 6.9 (m, 2H), 5.0 (m, 1H), 4.4 (m, 1H), 4.2 (m, 2H), 3.5 (m, 1H), 3.2 (m, 1H), 2.8 (m, 1H), 2.0 (m, 2H), 1.5 (m, 2H).

Example 82

Synthesis of 5-Phenyl-1H-pyrazole-3-carboxylic acid {2-[4-(5-fluoro-2-trifluoromethyl-phenylamino)-piperidin-1-yl]-2-oxo-ethyl}-amide

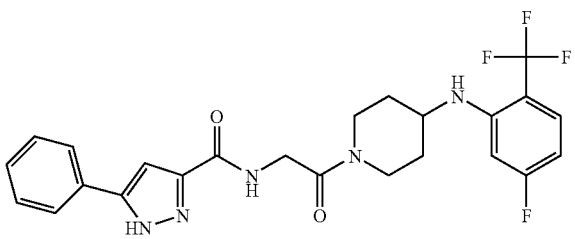

DIPEA (232 mg, 1.8 mmol) was added to a stirred solution of [(5-phenyl-1H-pyrazole-3-carbonyl)-amino]-acetic acid (148 mg, 0.6 mmol) in DMF (2 mL) followed by HOBt (95 mg, 0.7 mmol) and EDCI.HCl (137 mg, 0.7 mmol). After 2 minutes (5-fluoro-2-trifluoromethyl-phenyl)-piperidin-4-yl-amine dihydrochloride (prepared according to the method used for the synthesis of Intermediate 3) (150 mg, 0.6 mmol)

was added to the reaction mixture and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeoH in CHCl$_3$ as eluent) afforded 129 mg (44.4% Yield) of 5-phenyl-1H-pyrazole-3-carboxylic acid {2-[4-(5-fluoro-2-trifluoromethyl-phenylamino)-piperidin-1-yl]-2-oxo-ethyl}-amide. LC/MS [M+H]$^+$: 490.18, 95.08%. $^1$H NMR (300 MHz, DMSO-d$_6$): δ13.8 (s, 1H), 8.0 (bs, 1H), 7.8 (d, 2H), 7.5 (t, 4H), 7.1 (bs, 1H), 6.8 (d, 1H), 6.5 (t, 1H), 5.0 (d, 1H), 4.4 (d, 1H), 4.3 (d, 2H), 3.8 (m, 2H), 3.7 (m, 2H), 3.2 (t, 1H), 2.8 (t, 1H), 2.0 (m, 2H), 1.5 (m, 2H).

Example 83

Synthesis of 5-Phenyl-1H-pyrazole-3-carboxylic acid {2-[4-(4-fluoro-2-trifluoromethyl-phenylamino)-piperidin-1-yl]-2-oxo-ethyl}-amide

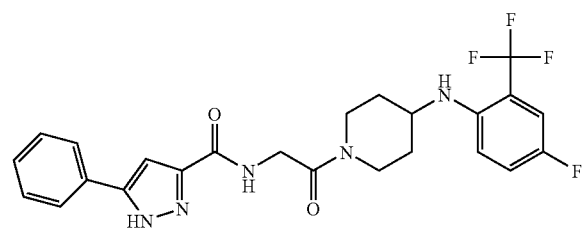

DIPEA (232 mg, 1.8 mmol) was added to a stirred solution of [(5-phenyl-1H-pyrazole-3-carbonyl)-amino]-acetic acid (140 mg, 0.6 mmol) in DMF (2 mL) followed by HOBt (97 mg, 0.7 mmol) and EDCI.HCl (137 mg, 0.7 mmol). After 2 minutes (4-fluoro-2-trifluoromethyl-phenyl)-piperidin-4-yl-amine dihydrochloride (prepared according to the method used for the synthesis of Intermediate 3) (150 mg, 0.6 mmol) was added and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeoH in CHCl$_3$ as eluent) to afford 105 mg (36% Yield) of 5-phenyl-1H-pyrazole-3-carboxylic acid {2-[4-(4-fluoro-2-trifluoromethyl-phenylamino)-piperidin-1-yl]-2-oxo-ethyl}-amide. LC/MS [M+H]$^+$: 490.18, 95.36%. $^1$H NMR (300 MHz, DMSO-d$_6$): δ13.8 (s, 1H), 8.0 (t, 1H), 7.8 (m, 2H), 7.4 (m, 6H), 7.1 (m, 2H), 4.6 (d, 1H), 4.4 (m, 1H), 4.2 (m, 2H), 3.9 (m, 1H), 3.7 (m, 1H), 3.2 (m, 1H), 2.8 (m, 1H), 2.0 (m, 2H), 1.5 (m, 2H), 1.4 (m, 1H).

Example 84

Synthesis of 5-Phenyl-1H-pyrazole-3-carboxylic acid {2-[4-(2-acetyl-phenoxy)-piperidin-1-yl]-2-oxo-ethyl}-amide

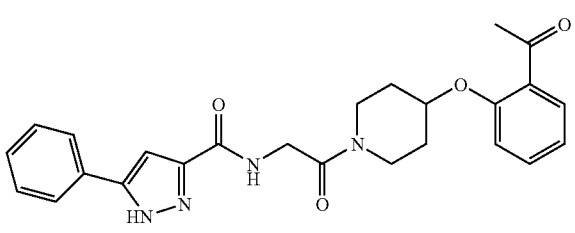

DIPEA (232 mg, 1.8 mmol) was added to a stirred solution of [(5-phenyl-1H-pyrazole-3-carbonyl)-amino]-acetic acid (144 mg, 0.6 mmol) in DMF (2 mL) followed by HOBt (97 mg, 0.7 mmol) and EDCI.HCl (137 mg, 0.7 mmol). After 2 minutes 1-[2-(piperidin-4-yloxy)-phenyl]-ethanone dihydrochloride (prepared according to Step 1 and 5 of the General Scheme) (150 mg, 0.6 mmol) was added and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeoH in CHCl$_3$ as eluent) to afford 112 mg (50.9% Yield) of 5-phenyl-1H-pyrazole-3-carboxylic acid {2-[4-(2-acetyl-phenoxy)-piperidin-1-yl]-2-oxo-ethyl}-amide. LC/MS [M+H]$^+$: 447.2, 95.68%. $^1$H NMR (300 MHz, DMSO-d$_6$): δ13.8 (s, 1H), 8.2 (bs, 1H), 7.8 (d, 2H), 7.5 (m, 4H), 7.4 (m, 1H), 7.3 (m, 1H), 7.2 (s, 1H), 7.0 (t, 1H), 4.8 (m, 1H), 4.4 (m, 2H), 3.8 (m, 1H), 3.4 (m, 1H), 3.5 (m, 2H), 2.5 (s, 3H), 2.0 (m, 2H), 1.7 (m, 2H).

Example 85

Synthesis of 5-Phenyl-1H-pyrazole-3-carboxylic acid {2-[4-(5-cyano-2-methyl-phenylamino)-piperidin-1-yl]-2-oxo-ethyl}-amide

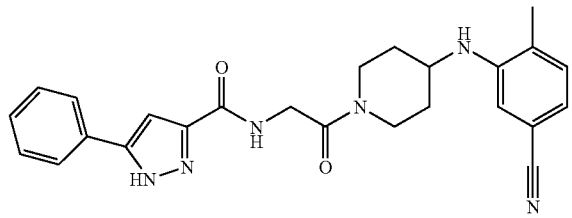

DIPEA (426 mg, 3.3 mmol) was added to a stirred solution of [(5-phenyl-1H-pyrazole-3-carbonyl)-amino]-acetic acid (285 mg, 1.1 mmol) in DMF (3 mL) followed by HOBt (175 mg, 1.3 mmol) and EDCI.HCl (252 mg, 1.3 mmol). After 2 minutes 4-methyl-3-(piperidin-4-ylamino)-benzonitrile dihydrochloride (250 mg, 1.1 mmol) (prepared according to the method used for the synthesis of Intermediate 3) was added and the stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeoH in CHCl₃ as eluent) afforded 100 mg (22.7% Yield) of 5-phenyl-1H-pyrazole-3-carboxylic acid {2-[4-(5-cyano-2-methyl-phenylamino)-piperidin-1-yl]-2-oxo-ethyl}-amide. LC/MS [M+H]⁺: 443.31, 91.96%. ¹H NMR (300 MHz, DMSO-d₆): δ13.8 (s, 1H), 8.1 (t, 1H), 7.8 (d, 2H), 7.4 (m, 4H), 7.2 (m, 2H), 7.0 (s, 1H), 6.9 (d, 1H), 5.0 (d, 1H), 4.4 (m, 1H), 4.2 (m, 2H), 3.9 (m, 1H), 3.7 (m, 1H), 3.2 (m, 1H), 2.8 (m, 1H), 2.2 (s, 3H), 2.0 (m, 2H), 1.7 (m, 2H).

Example 86

Synthesis of 5-Phenyl-1H-pyrazole-3-carboxylic acid {2-oxo-2-[4-(2-trifluoromethyl-benzenesulfinyl)-piperidin-1-yl]-ethyl}-amide

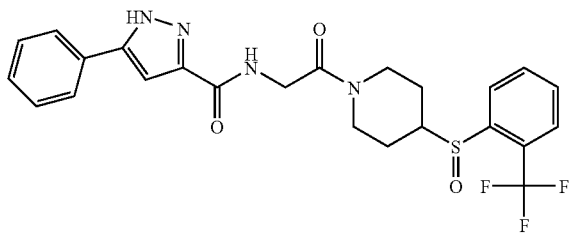

m-Chloroperbenzoic acid (18.5 mg, 0.1 mmol) was added to a cold (0-4° C.) solution of 5-phenyl-1H-pyrazole-3-carboxylic acid {2-oxo-2-[4-(2-trifluoromethyl-phenylsulfanyl)-piperidin-1-yl]-ethyl}-amide (50 mg, 0.1 mmol) in DCM (10 mL) and stirring was continued for 1 hr. The reaction mixture was concentrated. Purification by column chromatography (using 60-120 silica gel and 0.6% MeOH in CHCl₃ as eluent) afforded 30 mg (58.35% yield) of 5-phenyl-1H-pyrazole-3-carboxylic acid {2-oxo-2-[4-(2-trifluoromethyl-benzenesulfinyl)-piperidin-1-yl]-ethyl}-amide. LC/MS [M+H]⁺: 505.15, 95.9%. ¹H NMR (300 MHz, DMSO-d₆): δ 13.8 (s, 1H), 8.2-7.9 (m, 4H), 7.9-7.8 (m, 3H), 7.6-7.4 (t, 2H), 7.4 (t, 1H), 7.1 (s, 1H), 4.5 (d, 1H), 4.2 (d, 2H), 4.0 (d, 1H), 3.1 (m, 2H), 2.8-2.5 (m, 2H), 1.9 (d, 1H), 1.7 (dd, 1H), δ 1.6-1.4 (m, 2H).

Example 87

Synthesis of 5-Phenyl-1H-pyrazole-3-carboxylic acid {2-oxo-2-[4-(pyridin-4-yloxy)-piperidin-1-yl]-ethyl}-amide

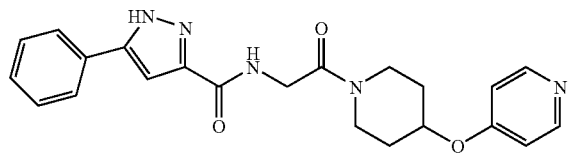

DIPEA (540 mg, 4.2 mmol) was added to a stirred solution of [(5-phenyl-1H-pyrazole-3-carbonyl)-amino]-acetic acid (344 mg, 1.4 mmol) in DMF (3 mL) followed by HOBt (229 mg, 1.7 mmol) and EDCI.HCl (321 mg, 1.7 mmol). After 2 minutes 2-amino-1-[4-(pyridin-4-yloxy)-piperidin-1-yl]-ethanone hydrochloride (250 mg, 1.4 mmol) (prepared according to Step 1 and 5 of the General Scheme) was added to the reaction mixture and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeOH in CHCl₃ as eluent) afforded 198 mg (% 34.9 Yield) of 5-phenyl-1H-pyrazole-3-carboxylic acid {2-oxo-2-[4-(pyridin-4-yloxy)-piperidin-1-yl]-ethyl}-amide. LC/MS [M+H]⁺: 406.18, 95.8%. ¹H NMR (300 MHz, DMSO-d₆): δ13.8 (m, 1H), 8.4 (m, 2H), 8.1 (m, 1H), 7.8 (m, 2H), 7.1 (m, 1H), 7.0 (s, 2H), 4.8 (m, 1H), 4.2 (m, 2H), 3.9 (m, 1H), 3.8 (m, 1H), 3.4 (m, 1H), 3.3 (m, 1H), 2.0 (m, 2H), 1.7 (m, 2H).

Example 88

Synthesis of 5-Phenyl-1H-pyrazole-3-carboxylic acid {2-[4-(5-chloro-pyridin-3-yloxy)-piperidin-1-yl]-2-oxo-ethyl}-amide

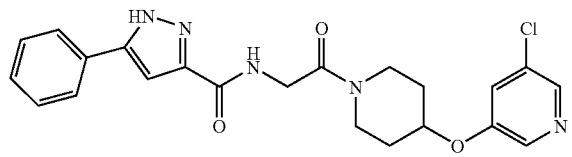

DIPEA (387 mg, 3.0 mmol) was added a stirred solution of [(5-phenyl-1H-pyrazole-3-carbonyl)-amino]-acetic acid (247 mg, 1.0 mmol) in DMF (2 mL) followed by HOBt (162 mg, 1.2 mmol) and EDCI.HCl (229 mg, 1.2 mmol). After 2 minutes 3-chloro-5-(piperidin-4-yloxy)-pyridine hydrochloride (prepared according to the method used for the synthesis of Intermediate 15) was added to the reaction mixture and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeOH in CHCl₃ as eluent) to afford 56 mg (12.71% Yield) of 5-phenyl-1H-pyrazole-3-carboxylic acid {2-[4-(5-chloro-pyridin-3-yloxy)-piperidin-1-yl]-2-oxo-ethyl}-amide. LC/MS [M+H]⁺: 440.14, 95.7%. ¹H NMR (300 MHz, DMSO-d₆): δ13.8 (s, 1H), 8.2 (m, 2H), 8.0 (m, 1H), 7.8 (m, 3H), 7.4 (m, 4H), 7.1 (m, 1H), 4.8 (m, 1H), 4.2 (m, 2H), 3.9 (m, 1H), 3.8 (m, 1H), 3.4 (m, 1H), 3.3 (m, 1H), 2.0 (m, 2H), 1.6 (m, 2H).

Example 89

Synthesis of 5-Phenyl-1H-pyrazole-3-carboxylic acid {2-[4-(2-hydroxy-phenoxy)-piperidin-1-yl]-2-oxo-ethyl}-amide

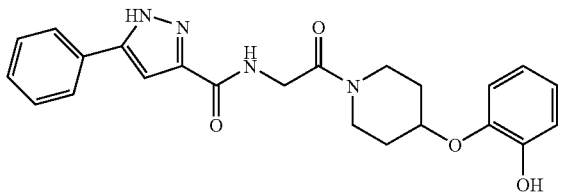

10% Pd/C (10 mg) was added to a stirred solution of 5-phenyl-1H-pyrazole-3-carboxylic acid {2-[4-(2-benzyloxy-phenoxy)-piperidin-1-yl]-2-oxo-ethyl}-amide (prepared from Intermediate 30 and (2-benzyloxyoxy-phenyl)-piperidin-4-yl-amine hydrochloride which was prepared according to the method used for the synthesis of Intermediate 15) (100 mg, 0.2 mmol) in a mixture of MeOH:$H_2O$ (1:1, 10 mL) under inert atmosphere and stirring was continued under $H_2$ gas atmosphere for 2 hr. The reaction mixture was filtered through celite. The filtrate collected was concentrated under reduced pressure to afford the residue. The residue was purified by preparative HPLC to afford 60 mg (71.5% Yield) of 5-phenyl-1H-pyrazole-3-carboxylic acid {2-[4-(2-hydroxy-phenoxy)-piperidin-1-yl]-2-oxo-ethyl}-amide.
LC/MS [M+H]$^+$: 421.8, 96.21%. $^1$H NMR (300 MHz, DMSO-$d_6$): δ13.8 (b, 1H), 8.9 (b, 1H), 8.2 (b, 1H), 7.8 (m, 2H), 7.5 (m, 3H), 7.2 (s, 1H), 7.0 (d, 1H), 6.8 (m, 3H), 4.5 (m, 1H), 4.2 (m, 2H), 3.8 (m, 2H), 3.3 (m, 2H), 1.9 (m, 2H), 1.6 (m, 2H).

Example 90

Synthesis of 5-Phenyl-1H-pyrazole-3-carboxylic acid {2-oxo-2-[4-(2-trifluoromethyl-benzenesulfonyl)-piperidin-1-yl]-ethyl}-amide

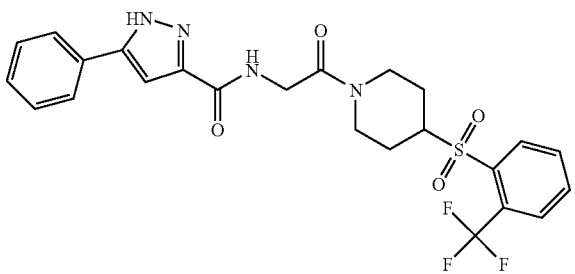

DIPEA (88 mg, 0.68 mmol) was added to a stirred solution of [(5-phenyl-1H-pyrazole-3-carbonyl)-amino]-acetic acid (36 mg, 0.15 mmol) in DMF (1 mL) followed by HOBt (20 mg, 0.15 mmol) and EDCI.HCl (39 mg, 0.2 mmol). After 2 minutes 4-(2-trifluoromethyl-benzenesulfonyl)-piperidine hydrochloride (250 mg, 1.0 mmol) (prepared from 4-(2-trifluoromethyl-phenylsulfanyl)-piperidine-1-carboxylic acid tert-butyl ester by means of oxidation with hydrogen peroxide and subsequent hydrolysis of the N-protection group with hydrochloric acid) was added to the reaction mixture and stirring was continued at ambient temperature overnight. The reaction mixture was diluted with cold water, the precipitate was collected. The solid obtained was purified by column chromatography (using 60-120 silica gel and 5% MeoH in DCM as eluent) to afford 21 mg (29.6% Yield) of 5-phenyl-1H-pyrazole-3-carboxylic acid {2-oxo-2-[4-(2-trifluoromethyl-benzenesulfonyl)-piperidin-1-yl]-ethyl}-amide.
LC/MS [M+H]$^+$: 521.14, $^1$H NMR (300 MHz, DMSO-$d_6$): δ13.8 (s, 1H), 8.2 (m, 5H), 7.7 (d, 2H), 7.5-7.3 (m, 3H), 7.1 (s, 1H), 4.5 (d, 1H), 4.2-4.0 (m, 2H), 4.0 (d, 1H), 3.7-3.5 (t, 1H), 3.1 (t, 1H), 2.7 (m, 1H), 1.9-1.7 (m, 2H), 1.7 (m, 1H), 1.5 (m, 1H).

Example 91

Synthesis of 5-Phenyl-1H-pyrazole-3-carboxylic acid {2-[4-(6-chloro-pyridin-2-yloxy)-piperidin-1-yl]-2-oxo-ethyl}-amide

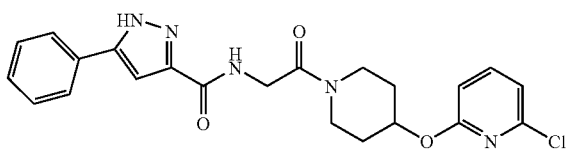

DIPEA (271 mg, 2.1 mmol) was added to a stirred solution of [(5-phenyl-1H-pyrazole-3-carbonyl)-amino]-acetic acid (162 mg, 0.7 mmol) in DMF (2 mL) followed by HOBt (94 mg, 0.7 mmol) and EDCI.HCl (134 mg, 0.7 mmol). After 2 minutes 2-chloro-6-(piperidin-4-yloxy)-pyridine hydrochloride (prepared according to the method used for the synthesis of Intermediate 15) (140 mg, 0.7 mmol) was added to the reaction mixture and stirring was continued at ambient temperature overnight. The reaction mixture was diluted with cold water, extracted with ethyl acetate and dried over sodium sulfate. The organic layer was concentrated under reduced pressure. Purification by column chromatography (using 60-120 silica gel and 5% MeoH in $CHCl_3$ as eluent) afforded 53 mg (18.27% Yield) of 5-phenyl-1H-pyrazole-3-carboxylic acid {2-[4-(6-chloro-pyridin-2-yloxy)-piperidin-1-yl]-2-oxo-ethyl}-amide. LC/MS [M+H]$^+$: 440.14, 90%. $^1$H NMR (300 MHz, DMSO-$d_6$): δ13.8 (s, 1H), 8.2 (b, 1H), 7.8 (m, 3H), 7.4 (m, 3H), 7.1 (m, 1H), 6.8 (m, 1H), 5.2 (m, 1H), 4.2 (m, 2H), 3.8 (m, 1H), 3.7 (m, 1H), 3.5 (m, 2H), 2.0 (m, 2H), 1.6 (m, 2H).

Example 92

Synthesis of 4-Methyl-3-(1-{2-[(5-phenyl-1H-pyrazole-3-carbonyl)-amino]-acetyl}-piperidin-4-yloxy)-benzoic acid methyl ester

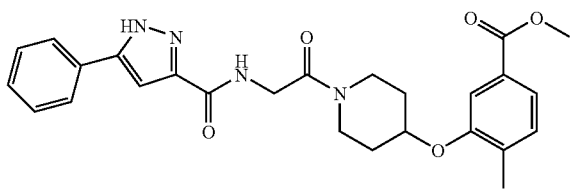

DIPEA (423 mg, 2.4 mmol) was added to a stirred solution of [(5-phenyl-1H-pyrazole-3-carbonyl)-amino]-acetic acid (200 mg, 0.81 mmol) in DMF (3 mL) followed by HOBt (130 mg, 0.93 mmol) and EDCI.HCl (187 mg, 0.93 mmol). After 2 minutes 4-methyl-3-(piperidin-4-yloxy)-benzoic acid methyl ester hydrochloride (prepared according to the method used for the synthesis of Intermediate 15) (280 mg, 0.97 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford 266 mg (68.55% Yield) of 4-methyl-3-(1-{2-[(5-phenyl-1H-pyrazole-3-carbonyl)-amino]-acetyl}-piperidin-4-yloxy)-benzoic acid methyl ester. LC/MS [M+H]$^+$: 477.21, 96.63%. $^1$H NMR (300 MHz, DMSO-d$_6$): δ13.8 (s, 1H), 8.1-8.0 (m, 1H), 7.8 (d, 2H), 7.54-7.28 (m, 6H), 7.1 (bs, 1H), 4.8 (m, 1H), 4.2 (d, 2H), 3.8 (s, 3H), 3.8-3.6 (m, 2H), 3.6-3.4 (m, 2H), 2.2 (s, 3H), 2.1-1.8 (m, 2H), 1.8-1.5 (m, 2H).

Example 92

Synthesis of 5-Phenyl-1H-pyrazole-3-carboxylic acid {2-[4-(2-fluoro-5-trifluoromethyl-phenoxy)-piperidin-1-yl]-2-oxo-ethyl}-amide

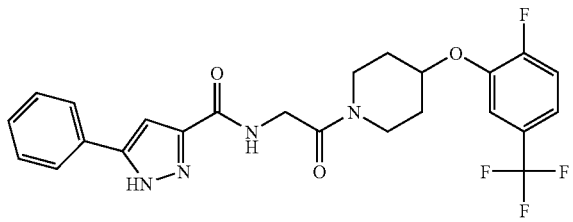

DIPEA (110 mg, 0.85 mmol) was added to a stirred solution of 5-phenyl-1H-pyrazole-3-carboxylic acid (50 mg, 0.24 mmol) in DMF (2 mL) followed by HOBt (33 mg, 0.24 mmol) and EDCI.HCl (49 mg, 0.25 mmol). After 2 minutes 2-amino-1-[4-(2-fluoro-5-trifluoromethyl-phenoxy)-piperidin-1-yl]-ethanone hydrochloride (prepared according to Step 1 and 5 of the General Scheme) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. The residue obtained was purified by recrystallisation using 25% EtOAc in hexane to afford 89 mg (80.9% Yield) of 5-phenyl-1H-pyrazole-3-carboxylic acid {2-[4-(2-fluoro-5-trifluoromethyl-phenoxy)-piperidin-1-yl]-2-oxo-ethyl}-amide. LC/MS [M+H]$^+$: 457, 90.38%. $^1$H NMR (300 MHz, DMSO-d$_6$): δ13.8 (s, 1H), 8.2 (bs, 1H), 7.9 (t, 1H), 7.1 (m, 7H), 4.61 (m, 1H), 4.4 (d, 2H), 3.7 (m, 2H), 3.3 (m, 2H), 1.9 (m, 2H), 1.5 (m, 2H).

Example 94

Synthesis of 5-(2-Fluoro-phenyl)-1H-pyrazole-3-carboxylic acid {2-[4-(2-chloro-phenoxy)-piperidin-1-yl]-2-oxo-ethyl}-amide

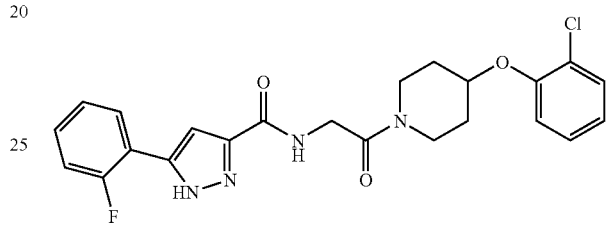

DIPEA (110 mg, 0.85 mmol) was added to a stirred solution of 5-(2-fluoro-phenyl)-1H-pyrazole-3-carboxylic acid (50 mg, 0.24 mmol) (prepared by the method used for the synthesis of Intermediate 29, starting from 2'-fluoroacetophenone) in DMF (2 mL) followed by HOBt (33 mg, 0.24 mmol) and EDCI.HCl (49 mg, 0.25 mmol). After 2 minutes 2-amino-1-[4-(2-chloro-phenoxy)-piperidin-1-yl]-ethanone hydrochloride (prepared according to Step 1 and 5 of the General Scheme) (75 mg, 0.24 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. Recrystallisation using 25% EtOAc in hexane afforded 89 mg (80.9% Yield) of 5-(2-fluoro-phenyl)-1H-pyrazole-3-carboxylic acid {2-[4-(2-chloro-phenoxy)-piperidin-1-yl]-2-oxo-ethyl}-amide. LC/MS [M+H]$^+$: 457, 90.38%. $^1$H NMR (300 MHz, DMSO-d$_6$): 613.8 (s, 1H), 8.2 (bs, 1H), 7.9 (t, 1H), 7.1 (m, 7H), 4.61 (m, 1H), 4.4 (d, 2H), 3.7 (m, 2H), 3.3 (m, 2H), 1.9 (m, 2H), 1.5 (m, 2H).

Example 95

Synthesis of 5-(2-Fluoro-phenyl)-1H-pyrazole-3-carboxylic acid {2-oxo-2-[4-(3-trifluoromethyl-phenoxy)-piperidin-1-yl]-ethyl}-amide

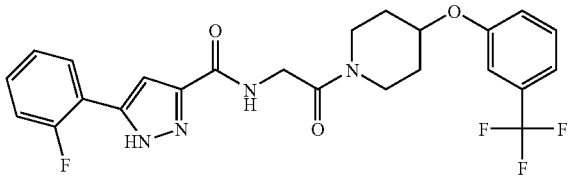

DIPEA (160 mg, 1.3 mmol) was added to a stirred solution of 5-(2-Fluoro-phenyl)-1H-pyrazole-3-carboxylic acid (77 mg, 0.37 mmol) (prepared by the method used for the synthesis of Intermediate 29, starting from 2'-fluoroacetophenone) in DMF (2 mL) followed by HOBt (52 mg, 0.39 mmol) and EDCI.HCl (74 mg, 0.39 mmol). After 2 minutes 2-amino-1-[4-(3-trifluoromethyl-phenoxy)-piperidin-1-yl]-ethanone hydrochloride (prepared according to Step 1 and 5 of the General Scheme) (125 mg, 0.37 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. Washing with ethyl acetate afforded 57 mg (31.67% Yield) of 5-(2-fluoro-phenyl)-1H-pyrazole-3-carboxylic acid {2-oxo-2-[4-(3-trifluoromethyl-phenoxy)-piperidin-1-yl]-ethyl}-amide. LC/MS [M+H]$^+$: 491, 93.63%. $^1$H NMR (300 MHz, DMSO-d$_6$): δ13.8 (d, 1H), 8.7 (m, 1H), 7.8 (m, 1H), 7.2 (m, 6H), 6.9 (m, 2H), 4.8 (m, 1H), 4.2 (d, 2H), 3.7 (m, 2H), 3.4 (m, 2H), 1.9 (m, 2H), 1.6 (m, 2H).

Example 96

Synthesis of 5-(4-Trifluoromethyl-phenyl)-1H-pyrazole-3-carboxylic acid {2-[4-(2-chloro-phenoxy)-piperidin-1-yl]-2-oxo-ethyl}-amide

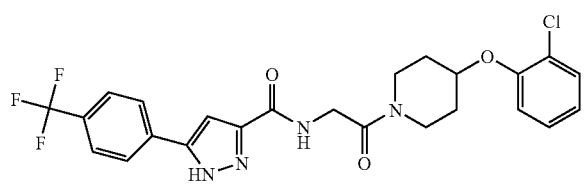

DIPEA (150 mg, 1.15 mmol) was added to a stirred solution of 5-(4-trifluoromethyl-phenyl)-1H-pyrazole-3-carboxylic acid (84 mg, 0.33 mmol) (prepared by the method used for the synthesis of Intermediate 29, starting from (p-trifluoromethyl)acetophenone) in DMF (2 mL) followed by HOBt (46 mg, 0.34 mmol) and EDCI.HCl (66 mg, 0.34 mmol). After 2 minutes 2-amino-1-[4-(2-chloro-phenoxy)-piperidin-1-yl]-ethanone hydrochloride (prepared according to Step 1 and 5 of the General Scheme) (100 mg, 0.33 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. The residue was purified by washing with mixture of ethyl acetate and methanol to afford 80 mg (48.2% Yield) of 5-(4-trifluoromethyl-phenyl)-1H-pyrazole-3-carboxylic acid {2-[4-(2-chloro-phenoxy)-piperidin-1-yl]-2-oxo-ethyl}-amide. LC/MS [M+H]$^+$: 507, 92.02%. $^1$H NMR (300 MHz, DMSO-d$_6$): δ13.7 (d, 1H), 8.0 (m, 3H), 7.8 (m, 2H), 7.44 (d, 1H), 7.24 (m, 3H), 6.96 (m, 1H), 4.7 (m, 1H), 4.2 (d, 2H), 3.7 (m, 2H), 3.4 (m, 2H), 1.9 (m, 2H), 1.6 (m, 2H).

Example 97

Synthesis of 5-(3-Fluoro-phenyl)-1H-pyrazole-3-carboxylic acid {2-oxo-2-[4-(3-trifluoromethyl-phenoxy)-piperidin-1-yl]-ethyl}-amide

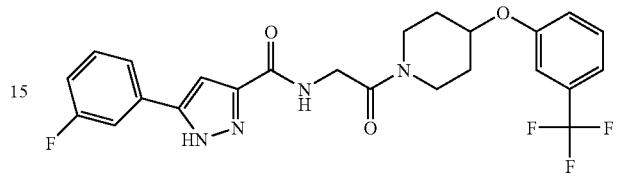

DIPEA (165 mg, 1.3 mmol) was added to a stirred solution of 5-(3-fluoro-phenyl)-1H-pyrazole-3-carboxylic acid (75 mg, 0.36 mmol) (prepared by the method used for the synthesis of Intermediate 29, starting from 3'-fluoroacetophenone) in DMF (2 mL) followed by HOBt (51 mg, 0.38 mmol) and EDCI.HCl (73 mg, 0.38 mmol). After 2 minutes 2-amino-1-[4-(3-trifluoromethyl-phenoxy)-piperidin-1-yl]-ethanone hydrochloride (prepared according to Step 1 and 5 of the General Scheme) (120 mg, 0.36 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. The residue was purified by dissolving in ethyl acetate and then reprecipitating with hexane to afford 103 mg (57.86% Yield) of 5-(3-fluoro-phenyl)-1H-pyrazole-3-carboxylic acid {2-oxo-2-[4-(3-trifluoromethyl-phenoxy)-piperidin-1-yl]-ethyl}-amide. LC/MS [M+H]$^+$: 491, 92.15%. $^1$H NMR (300 MHz, DMSO-d$_6$): δ13.8 (s, 1H), 8.1 (m, 1H), 7.46 (m, 4H), 7.1 (m, 5H), 4.8 (m, 1H), 4.2 (d, 2H), 3.9 (m, 1H), 3.7 (m, 1H), 3.4 (m, 1H), 3.3 (m, 1H), 1.9 (m, 2H), 1.6 (m, 2H).

Example 98

Synthesis of 5-(3-Fluoro-phenyl)-1H-pyrazole-3-carboxylic acid {2-[4-(2-chloro-phenylamino)-piperidin-1-yl]-2-oxo-ethyl}-amide

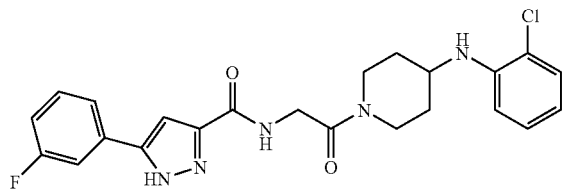

DIPEA (165 mg, 1.3 mmol) was added to a stirred solution of 5-(3-fluoro-phenyl)-1H-pyrazole-3-carboxylic acid (75 mg, 0.36 mmol) (prepared by the method used for the synthesis of Intermediate 29, starting from 3'-fluoroacetophenone) in DMF (2 mL) followed by HOBt (51 mg, 0.38 mmol) and EDCI.HCl (73 mg, 0.38 mmol). After 2 minutes 2-amino-1-[4-(2-chloro-phenylamino)-piperidin-1-yl]-ethanone hydrochloride (120 mg, 0.36 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. Washing with methanol afforded 76 mg (43.1% Yield) of 5-(3-fluoro-phenyl)-1H-pyrazole-3-carboxylic acid {2-[4-(2-chloro-phenylamino)-piperidin-1-yl]-2-oxo-ethyl}-amide. LC/MS [M+H]$^+$: 456, 100%. $^1$H NMR (300 MHz, DMSO-d$_6$): δ13.8 (s, 1H), 8.06 (t, 1H), 7.44 (m, 4H), 7.12 (m, 4H), 6.84 (d, 1H), 6.58 (m, 1H), 4.9 (d, 1H), 4.3 (d, 1H), 4.2 (m, 2H), 3.7 (m, 1H), 3.6 (m, 1H), 3.2 (m, 1H), 2.8 (m, 1H), 1.9 (m, 2H), 1.4 (m, 2H).

Example 99

Synthesis of 5-(2-Trifluoromethyl-phenyl)-1H-pyrazole-3-carboxylic acid {2-oxo-2-[4-(3-trifluoromethyl-phenoxy)-piperidin-1-yl]-ethyl}-amide

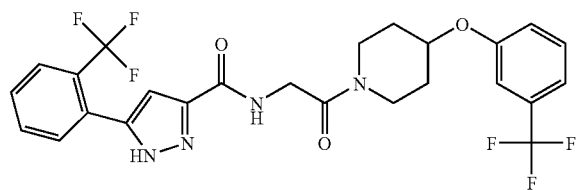

DIPEA (76 mg, 0.59 mmol) was added to a stirred solution of 5-(2-trifluoromethyl-phenyl)-1H-pyrazole-3-carboxylic acid (43 mg, 0.167 mmol) (prepared by the method used for the synthesis of Intermediate 29, starting from (o-trifluoromethyl)acetophenone) in DMF (2 mL) followed by HOBt (24 mg, 0.176 mmol) and EDCI.HCl (34 mg, 0.176 mmol). After 2 minutes 2-amino-1-[4-(3-trifluoromethyl-phenoxy)-piperidin-1-yl]-ethanone hydrochloride (prepared according to Step 1 and 5 of the General Scheme) (0.057 mg, 0.167 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. The residue was purified by washing with chloroform to afford 51 mg (56% Yield) of 5-(2-trifluoromethyl-phenyl)-1H-pyrazole-3-carboxylic acid {2-oxo-2-[4-(3-trifluoromethyl-phenoxy)-piperidin-1-yl]-ethyl}-amide. LC/MS [M+H]$^+$: 541, 87.52%. $^1$H NMR (300 MHz, DMSO-d$_6$): δ13.8 (d, 1H), 8.1 (m, 1H), 7.6 (m, 4H), 7.5 (t, 1H), 7.3 (t, 3H), 6.76 (s, 1H), 4.8 (m, 1H), 4.1 (d, 2H), 3.7 (m, 2H), 3.4 (m, 1H), 3.2 (m, 1H), 1.9 (m, 2H), 1.6 (m, 2H).

Example 100

Synthesis of 5-(4-Hydroxy-phenyl)-1H-pyrazole-3-carboxylic acid {2-oxo-2-[4-(3-trifluoromethyl-phenoxy)-piperidin-1-yl]-ethyl}-amide

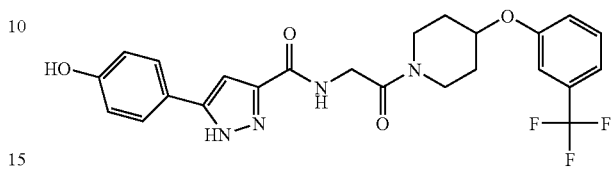

DIPEA (150 mg, 1.2 mmol) was added to a stirred solution of 5-(4-hydroxy-phenyl)-1H-pyrazole-3-carboxylic acid (70 mg, 0.34 mmol) in DMF (2 mL) followed by HOBt (48 mg, 0.36 mmol) and EDCI.HCl (69 mg, 0.36 mmol). After 2 minutes 2-amino-1-[4-(3-trifluoromethyl-phenoxy)-piperidin-1-yl]-ethanone hydrochloride (prepared according to Step 1 and 5 of the General Scheme) (116 mg, 0.34 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. The residue was purified by washing with 1% MeOH in EtOAc to afford 92 mg (55% Yield) of 5-(4-hydroxy-phenyl)-1H-pyrazole-3-carboxylic acid {2-oxo-2-[4-(3-trifluoromethyl-phenoxy)-piperidin-1-yl]-ethyl}-amide. LC/MS [M+H]$^+$: 489, 96%. $^1$H NMR (300 MHz, DMSO-d$_6$): δ13.8 (s, 1H), 9.8 (s, 1H), 8.02 (t, 1H), 7.5 (m, 3H), 7.28 (t, 3H), 6.8 (m, 3H), 4.8 (m, 1H), 4.2 (d, 2H), 3.9 (m, 1H), 3.6 (m, 1H), 3.4 (m, 1H), 3.2 (m, 1H), 2.0 (m, 2H), 1.7 (m, 2H).

Example 101

Synthesis of 5-(3-Hydroxy-phenyl)-1H-pyrazole-3-carboxylic acid {2-oxo-2-[4-(3-trifluoromethyl-phenoxy)-piperidin-1-yl]-ethyl}-amide

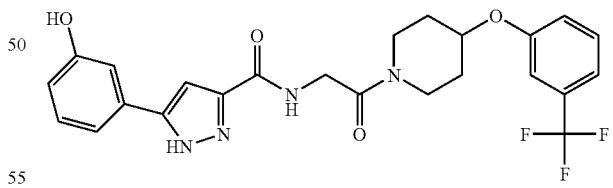

DIPEA (133 mg, 1.03 mmol) was added to a stirred solution of 5-(3-hydroxy-phenyl)-1H-pyrazole-3-carboxylic acid (60 mg, 0.294 mmol) (prepared from 5-(3-benzyloxy-phenyl)-1H-pyrazole-3-carboxylic acid ethyl ester) in DMF (2 mL) followed by HOBt (41.7 mg, 0.308 mmol) and EDCI.HCl (59 mg, 0.308 mmol). After 2 minutes 2-amino-1-[4-(3-trifluoromethyl-phenoxy)-piperidin-1-yl]-ethanone hydrochloride (prepared according to Step 1 and 5 of the General Scheme) (99 mg, 0.294 mmol) was added to the reaction mixture and stirring was continued at ambient temperature overnight. The reaction mixture was diluted with cold water, extracted with ethyl acetate and dried over sodium sulfate. The organic layer was concentrated under reduced pressure to afford the residue. Washing with ethyl acetate afforded 74 mg (51.7% Yield) of 5-(3-hydroxy-phenyl)-1H-pyrazole-3-carboxylic acid {2-oxo-2-[4-(3-trifluoromethyl-phenoxy)-piperidin-1-yl]-ethyl}-amide. LC/MS [M+H]+: 489, 96%. 1H NMR (300 MHz, DMSO-d6): δ13.6 (s, 1H), 9.6 (s, 1H), 8.0 (t, 1H), 7.5 (t, 1H), 7.1 (m, 7H), 6.9 (d, 1H), 6.8 (m, 1H), 4.8 (m, 1H), 4.2 (d, 2H), 3.9 (m, 1H), 3.7 (m, 1H), 3.4 (m, 2H), 2.0 (m, 2H), 1.6 (m, 2H).

Example 102

Synthesis of 5-(4-Fluoro-phenyl)-1H-pyrazole-3-carboxylic acid {2-oxo-2-[4-(3-trifluoromethyl-phenoxy)-piperidin-1-yl]-ethyl}-amide

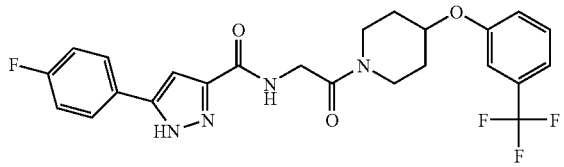

DIPEA (131 mg, 1.0 mmol) was added to a stirred solution of 5-(4-fluoro-phenyl)-1H-pyrazole-3-carboxylic acid (60 mg, 0.29 mmol) (prepared by the method used for the synthesis of Intermediate 29, starting from 4'-fluoroacetophenone) in DMF (2 mL) followed by HOBt (41 mg, 0.305 mmol) and EDCI.HCl (59 mg, 0.306 mmol). After 2 minutes 2-amino-1-[4-(3-trifluoromethyl-phenoxy)-piperidin-1-yl]-ethanone hydrochloride (98 mg, 0.294 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure The residue was purified by washing with 1% MeOH in EtOAc to afford 97 mg (68.3% Yield) of 5-(4-fluoro-phenyl)-1H-pyrazole-3-carboxylic acid {2-oxo-2-[4-(3-trifluoromethyl-phenoxy)-piperidin-1-yl]-ethyl}-amide. LC/MS [M+H]+: 491, 92.85%. 1H NMR (300 MHz, DMSO-d6): δ13.8 (s, 1H), 8.1 (t, 1H), 7.9 (m, 2H), 7.5 (t, 1H), 7.24 (m, 5H), 7.1 (d, 1H), 4.8 (m, 1H), 4.2 (d, 2H), 3.9 (m, 1H), 3.7 (m, 1H), 3.4 (m, 2H), 2.0 (m, 2H), 1.6 (m, 2H).

Example 103

Synthesis of 5-(4-Fluoro-phenyl)-1H-pyrazole-3-carboxylic acid {2-[4-(2-chloro-pyridin-3-yloxy)-piperidin-1-yl]-2-oxo-ethyl}-amide

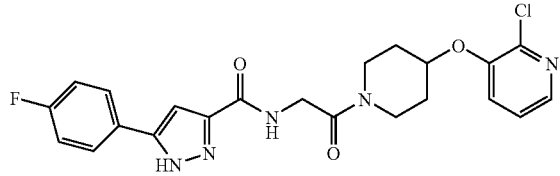

DIPEA (226 mg, 1.75 mmol) was added to a stirred solution of {[5-(4-fluoro-phenyl)-1H-pyrazole-3-carbonyl]-amino}-acetic acid (130 mg, 0.5 mmol) (prepared by the method used for the synthesis of Intermediate 30, starting from (4-fluorophenyl)acetophenone) in DMF (2 mL) followed by HOBt (71 mg, 0.52 mmol) and EDCI.HCl (100 mg, 0.52 mmol). After 2 minutes 3-chloro-5-(piperidin-4-yloxy)-pyridine hydrochloride (125 mg, 0.5 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure The residue was purified by column chromatography (using 60-120 silica gel and 40% ethyl acetate in hexane as eluent) to afford 134 mg (58.5% Yield) of 5-(4-fluoro-phenyl)-1H-pyrazole-3-carboxylic acid {2-[4-(2-chloro-pyridin-3-yloxy)-piperidin-1-yl]-2-oxo-ethyl}-amide. LC/MS [M+H]+: 458, 93.27%. 1H NMR (300 MHz, DMSO-d6): δ13.8 (s, 1H), 8.0 (m, 2H), 7.8 (m, 2H), 7.7 (d, 1H), 7.4 (m, 1H), 7.25 (m, 2H), 7.1 (m, 1H), 4.8 (m, 1H), 4.2 (d, 2H), 3.7 (m, 2H), 3.5 (m, 2H), 1.9 (m, 2H), 1.7 (m, 2H).

Example 104

Synthesis of 5-(4-Fluoro-phenyl)-1H-pyrazole-3-carboxylic acid {2-[4-(5-chloro-pyridin-3-yloxy)-piperidin-1-yl]-2-oxo-ethyl}-amide

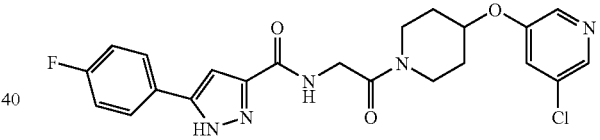

DIPEA (200 mg, 1.6 mmol) was added to a stirred solution of {[5-(4-fluoro-phenyl)-1H-pyrazole-3-carbonyl]-amino}-acetic acid (120 mg, 0.45 mmol) (prepared by the method used for the synthesis of Intermediate 30, starting from (4'-fluorophenyl)acetophenone) in DMF (2 mL) followed by HOBt (65 mg, 0.48 mmol) and EDCI.HCl (92 mg, 0.48 mmol). After 2 minutes 3-chloro-5-(piperidin-4-yloxy)-pyridine hydrochloride (0.114 g, 0.00045 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure The residue was purified by column chromatography (using 60-120 silica gel and 50% ethyl acetate in hexane as eluent) to afford 111 mg (55.5% Yield) of 5-(4-fluoro-phenyl)-1H-pyrazole-3-carboxylic acid {2-[4-(5-chloro-pyridin-3-yloxy)-piperidin-1-yl]-2-oxo-ethyl}-amide. LC/MS [M+H]+: 458, 97.78%. 1H NMR (300 MHz, DMSO-d6): δ13.8 (s, 1H), 8.3 (m, 1H), 8.21 (m, 1H), 8.04 (m, 1H), 7.8 (m, 2H), 7.7 (m, 1H), 7.3 (m, 2H), 7.1 (s, 1H), 4.8 (m, 1H), 4.2 (d, 2H), 3.9 (m, 2H), 3.7 (m, 1H), 3.4 (m, 1H), 3.2 (m, 1H), 2.0 (m, 2H), 1.6 (m, 2H).

Example 105

Synthesis of 5-Phenyl-1H-pyrazole-3-carboxylic acid {2-[4-(3-chloro-phenoxy)-piperidin-1-yl]-2-oxo-ethyl}-amide

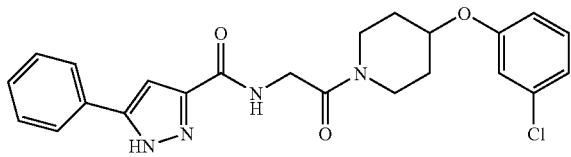

DIPEA (155 mg, 1.2 mmol) was added to a stirred solution of [(5-phenyl-1H-pyrazole-3-carbonyl)-amino]-acetic acid (99 mg, 0.4 mmol) in DMF (2 mL) followed by HOBt (54 mg, 0.4 mmol) and EDCI.HCl (84 mg, 0.44 mmol). After 2 minutes 4-(3-chloro-phenoxy)-piperidine hydrochloride (100 mg, 0.4 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure The residue was purified by washing with methanol to afford 67 mg (39.4% Yield) 5-phenyl-1H-pyrazole-3-carboxylic acid {2-[4-(3-chloro-phenoxy)-piperidin-1-yl]-2-oxo-ethyl}-amide. LC/MS [M+H]$^+$: 439, 92.8%. $^1$H NMR (300 MHz, DMSO-d$_6$): δ13.8 (m, 1H), 8.0 (m, 1H), 7.8 (m, 2H), 7.5 (m, 2H), 7.4 (m, 1H), 7.3 (m, 2H), 7.1 (m, 2H), 7.0 (m, 2H), 4.7 (m, 1H), 4.2 (m, 2H), 4.0 (m, 1H), 3.7 (m, 1H), 3.4 (m, 1H), 3.2 (m, 1H), 2.0 (m, 2H), 1.5 (m, 2H).

Example 106

Synthesis of 3-(1-{2-[(5-Phenyl-1H-pyrazole-3-carbonyl)-amino]-acetyl}-piperidin-4-yloxy)-benzoic acid

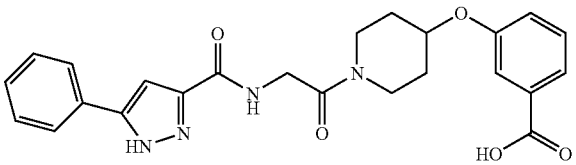

LiOH.H$_2$O (44 mg, 1.0 mmol) was added to a stirred mixture of 3-(1-{2-[(5-phenyl-1H-pyrazole-3-carbonyl)-amino]-acetyl}-piperidin-4-yloxy)-benzoic acid methyl ester (prepared by the method used to generate Example 92) (99 mg, 0.2 mmol) in MeOH:H$_2$O (1:1, 4 mL) was added, and the resulting mixture was stirred at ambient temperature overnight. The reaction mixture was concentrated under reduced pressure. Cold water was then added and acidified it with 10% aqueous HCl and extracted with ethyl acetate, dried over sodium sulfate and concentrated under reduced pressure The residue was purified by washing with diethyl ether to afford 87 mg (97.7% Yield) 3-(1-{2-[(5-phenyl-1H-pyrazole-3-carbonyl)-amino]-acetyl}-piperidin-4-yloxy)-benzoic acid. LC/MS [M+H]$^+$: 463, 96.9%. $^1$H NMR (300 MHz, DMSO-d$_6$): δ13.8 (b, 1H), 13.6 (b, 1H), 8.1 (b, 1H), 7.8 (q, 2H), 7.5 (m, 6H), 7.3 (m, 1H), 7.1 (b, 1H), 4.8 (m, 1H), 4.2 (m, 2H), 3.9 (m, 1H), 3.8 (m, 1H), 3.4 (m, 2H), 2.0 (m, 2H), 1.7 (m, 1H).

Example 107

Synthesis of 5-(3-Fluoro-phenyl)-1H-pyrazole-3-carboxylic acid {2-[4-(5-chloro-pyridin-3-yloxy)-piperidin-1-yl]-2-oxo-ethyl}-amide

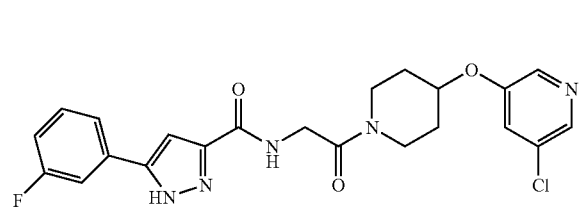

DIPEA (253 mg, 1.96 mmol) was added to a stirred solution of 5-(3-fluoro-phenyl)-1H-pyrazole-3-carboxylic acid (81 mg, 0.39 mmol) (prepared by the method used for the synthesis of Intermediate 29, starting from 3'-fluoroacetophenone) in DMF (2 mL) followed by HOBt (56 mg, 0.41 mmol) and EDCI.HCl (79 mg, 0.41 mmol). After 2 minutes 2-amino-1-[4-(5-chloro-pyridin-3-yloxy)-piperidin-1-yl]-ethanone hydrochloride (120 mg, 0.39 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure The residue was purified by washing with ethyl acetate to afford 78 mg (43.5% Yield) of 5-(3-fluoro-phenyl)-1H-pyrazole-3-carboxylic acid {2-[4-(5-chloro-pyridin-3-yloxy)-piperidin-1-yl]-2-oxo-ethyl}-amide. LC/MS [M+H]$^+$: 458, 90%. $^1$H NMR (300 MHz, DMSO-d$_6$): δ 13.8 (s, 1H), 8.3 (d, 1H), 8.22 (d, 1H), 8.04 (m, 1H), 7.6 (m, 3H), 7.5 (m, 2H), 7.18 (m, 2H), 4.8 (m, 1H), 4.2 (m, 2H), 3.9 (m, 1H), 3.7 (m, 1H), 3.4 (m, 1H), 3.2 (m, 1H), 2.0 (m, 2H), 1.6 (m, 2H).

Example 108

Synthesis of 5-Phenyl-1H-pyrazole-3-carboxylic acid [2-oxo-2-(4-m-tolyloxy-piperidin-1-yl)-ethyl]-amide

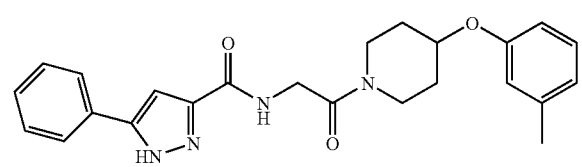

DIPEA (155 mg, 1.2 mmol) was added to a stirred solution of [(5-phenyl-1H-pyrazole-3-carbonyl)-amino]-acetic acid (100 mg, 0.4 mmol) in DMF (2 mL) followed by HOBt (54 mg, 0.4 mmol) and EDCI.HCl (84 mg, 0.44 mmol). After 2 minutes 4-m-tolyloxy-piperidine hydrochloride (107 mg, 0.4 mmol) (prepared by method used for the synthesis of Intermediate 15) was added to the reaction mixture and stirring was continued at ambient temperature overnight. The reaction mixture was diluted with cold water, the solid collected.

The solid was purified by washing with 10% MeOH in CHCl₃ to afford 92 mg (56% Yield) 5-phenyl-1H-pyrazole-3-carboxylic acid [2-oxo-2-(4-m-tolyloxy-piperidin-1-yl)-ethyl]-amide. LC/MS [M+H]⁺: 419, 95.4%. ¹H NMR (300 MHz, DMSO-d₆): δ13.8 (m, 1H), 8.6 (m, 1H), 8.0 (m, 2H), 7.8 (m, 2H), 7.4 (m, 4H), 7.2 (m, 2H), 6.8 (m, 3H), 4.6 (m, 1H), 4.2 (m, 2H), 3.8 (m, 1H), 3.6 (m, 1H), 3.4 (m, 1H), 3.3 (m, 1H), 2.3 (s, 3H), 2.0 (m, 2H), 1.6 (m, 2H).

Example 109

Synthesis of 5-Phenyl-1H-pyrazole-3-carboxylic acid {2-[4-(2-methyl-pyridin-3-yloxy)-piperidin-1-yl]-2-oxo-ethyl}-amide

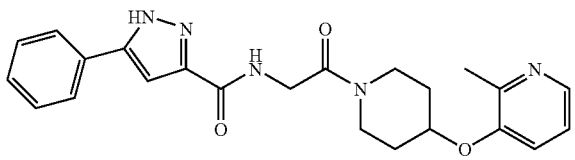

DIPEA (193 mg, 1.5 mmol) was added to a stirred solution of [(5-phenyl-1H-pyrazole-3-carbonyl)-amino]-acetic acid (127 mg, 0.5 mmol) in DMF (2 mL) followed by HOBt (67 mg, 0.5 mmol) and EDCI.HCl (105 mg, 0.55 mmol). After 2 minutes 2-methyl-3-(piperidin-4-yloxy)-pyridine hydrochloride (100 mg, 0.5 mmol) (prepared by method used for the synthesis of Intermediate 15) was added to the reaction mixture and stirring was continued at ambient temperature overnight. The reaction mixture was diluted with cold water, and the solid was collected. Purification of the solid by washing with 10% MeOH in CHCl₃ afforded 95 mg (47.5% Yield) of 5-phenyl-1H-pyrazole-3-carboxylic acid {2-[4-(2-methyl-pyridin-3-yloxy)-piperidin-1-yl]-2-oxo-ethyl}-amide. LC/MS [M+H]⁺: 420, 96.7%. ¹H NMR (300 MHz, DMSO-d₆): δ 8.3 (m, 1H), 8.2 (b, 1H), 8.0 (m, 1H), 7.8 (m, 2H), 7.6 (m, 1H), 7.5 (m, 2H), 7.4 (m, 1H), 7.2 (b, 1H), 4.9 (m, 1H), 4.2 (m, 2H), 3.8 (m, 2H), 3.5 (m, 2H), 2.5 (m, 3H), 2.0 (m, 2H), 1.8 (m, 2H).

Example 110

Synthesis of 5-Pyridin-2-yl-1H-pyrazole-3-carboxylic acid {2-[4-(2-chloro-phenoxy)-piperidin-1-yl]-2-oxo-ethyl}-amide

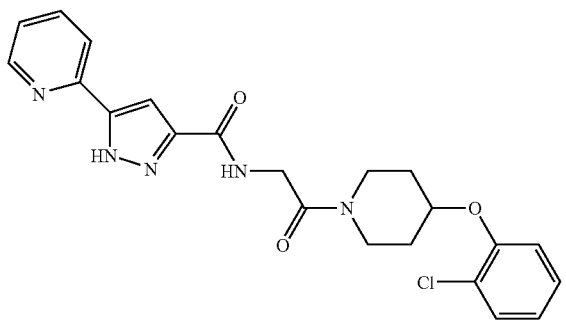

DIPEA (287 mg, 2.2 mmol) was added to a stirred solution of 5-pyridin-2-yl-1H-pyrazole-3-carboxylic acid hydrochloride (100 mg, 0.44 mmol) (prepared by the method used for the synthesis of Intermediate 29, starting from 2-acetylpyridine) in DMF (2 mL) followed by HOBt (63 mg, 0.46 mmol) and EDCI.HCl (89 mg, 0.46 mmol). After 2 minutes 2-amino-1-[4-(2-chloro-phenoxy)-piperidin-1-yl]-ethanone hydrochloride (135 mg, 0.44 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure The residue was purified by filtering through 60-120 silica gel column and filtrate collected was concentrated under reduced pressure to afford 145 mg (74.3% Yield) of 5-pyridin-2-yl-1H-pyrazole-3-carboxylic acid {2-[4-(2-chloro-phenoxy)-piperidin-1-yl]-2-oxo-ethyl}-amide. LC/MS [M+H]⁺: 440, 90%. ¹H NMR (300 MHz, DMSO-d₆): δ 13.9 (s, 1H), 8.6 (d, 1H), 8.1 (bs, 1H), 7.84 (m, 2H), 7.24 (m, 5H), 6.94 (m, 2H), 4.75 (m, 1H), 4.15 (d, 2H), 3.6 (m, 2H), 3.4 (m, 2H), 1.9 (m, 2H), 1.6 (m, 2H).

Example 111

Synthesis of 3-(5-{2-Oxo-2-[4-(3-trifluoromethyl-phenoxy)-piperidin-1-yl]-ethylcarbamoyl}-1H-pyrazol-3-yl)-benzoic acid

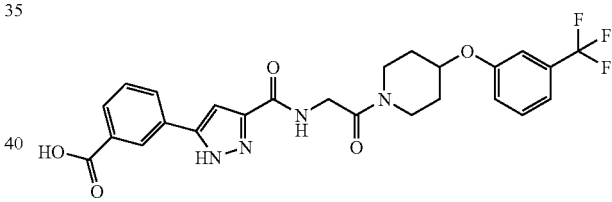

LiOH.H₂O (32 mg, 0.76 mmol) was added to a stirred mixture of 3-(5-{2-oxo-2-[4-(3-trifluoromethyl-phenoxy)-piperidin-1-yl]-ethylcarbamoyl}-1H-pyrazol-3-yl)-benzoic acid methyl ester (99 mg, 0.2 mmol) (prepared by the method used for the synthesis of Example 102, starting, alternatively from methyl 3-acetylbenzoate to generate the 1H-pyrazole intermediate) in THF:MeOH:H₂O (3:2:1, 38 mL) was added, and the resulting mixture was stirred at ambient temperature overnight. The reaction mixture was concentrated under reduced pressure Cold water was then added and the contents were acidified with 10% aqueous HCl, the precipitate was filtered. The solid obtained was purified by recrystallisation form methanol to afford 50 mg (38.1% Yield) of 3-(5-{2-oxo-2-[4-(3-trifluoromethyl-phenoxy)-piperidin-1-yl]-ethylcarbamoyl}-2H-pyrazol-3-yl)-benzoic acid. LC/MS [M+H]⁺: 517, 95.29%. ¹H NMR (300 MHz, DMSO-d₆): δ13.8 (s, 1H), 13.2 (s, 1H), 8.38 (s, 1H), 8.04 (d, 1H), 7.9 (d, 1H), 7.5 (m, 2H), 7.26 (t, 3H), 7.18 (bs, 1H), 4.8 (m, 1H), 4.2 (d, 2H), 3.9 (m, 1H), 3.7 (m, 1H), 3.4 (m, 2H), 1.9 (m, 2H), 1.6 (m, 2H).

Example 112

Synthesis of 5-Pyridin-3-yl-1H-pyrazole-3-carboxylic acid {2-oxo-2-[4-(3-trifluoromethyl-phenoxy)-piperidin-1-yl]-ethyl}-amide

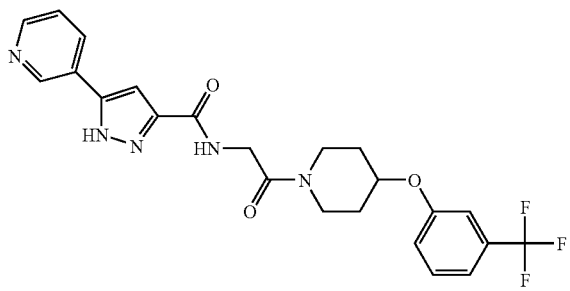

DIPEA (290 mg, 2.26 mmol) was added to a stirred solution of 5-pyridin-3-yl-1H-pyrazole-3-carboxylic acid hydrochloride (prepared by the method used for the synthesis of Intermediate 29, starting from 3-acetylpyridine) (100 mg, 0.44 mmol) in DMF (2 mL) followed by HOBt (63 mg, 0.46 mmol) and EDCI.HCl (90 mg, 0.46 mmol). After 5 minutes 2-amino-1-[4-(3-trifluoromethyl-phenoxy)-piperidin-1-yl]-ethanone hydrochloride (150 mg, 0.44 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure The residue was purified by filtering through 60-120 silica gel column and filtrate collected was concentrated under reduced pressure to afford 138 mg (66% Yield) of 5-pyridin-3-yl-1H-pyrazole-3-carboxylic acid {2-oxo-2-[4-(3-trifluoromethyl-phenoxy)-piperidin-1-yl]-ethyl}-amide. LC/MS [M+H]$^+$: 474, 94.7%. $^1$H NMR (300 MHz, DMSO-d$_6$): δ 13.8 (s, 1H), 9.4 (s, 1H), 8.56 (d, 1H), 8.16 (m, 1H), 7.46 (m, 2H), 7.22 (m, 4H), 4.8 (m, 1H), 4.2 (d, 2H), 3.9 (m, 1H), 3.7 (m, 1H), 3.44 (m, 2H), 1.9 (m, 2H), 1.6 (m, 2H).

Example 113

Synthesis of 5-Pyridin-3-yl-1H-pyrazole-3-carboxylic acid {2-[4-(2-chloro-phenoxy)-piperidin-1-yl]-2-oxo-ethyl}-amide

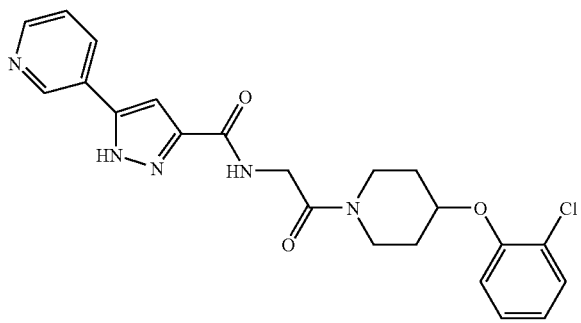

DIPEA (290 mg, 2.26 mmol) to a stirred solution of 5-pyridin-3-yl-1H-pyrazole-3-carboxylic acid hydrochloride (100 mg, 0.44 mmol) (prepared by the method used for the synthesis of Intermediate 29, starting from 3-acetylpyridine) in DMF (2 mL) followed by HOBt (63 mg, 0.46 mmol) and EDCI.HCl (90 mg, 0.46 mmol). After 2 minutes 2-amino-1-[4-(2-chloro-phenoxy)-piperidin-1-yl]-ethanone hydrochloride (150 mg, 0.44 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 10% EtOAc in hexane afforded 100 mg (51.5% Yield) of 5-pyridin-3-yl-1H-pyrazole-3-carboxylic acid {2-[4-(2-chloro-phenoxy)-piperidin-1-yl]-2-oxo-ethyl}-amide. LC/MS [M+H]$^+$: 440, 96.47%. $^1$H NMR (300 MHz, DMSO-d$_6$): δ 13.9 (s, 1H), 9.0 (m, 1H), 8.5 (m, 1H), 8.1 (m, 2H), 7.4 (m, 2H), 7.2 (m, 3H), 6.9 (m, 1H), 4.75 (m, 1H), 4.2 (m, 2H), 3.65 (m, 2H), 3.4 (m, 2H), 1.9 (m, 2H), 1.7 (m, 2H).

Example 114

Synthesis of 5-Phenyl-1H-pyrazole-3-carboxylic acid {2-[4-(4-methyl-pyridin-3-yloxy)-piperidin-1-yl]-2-oxo-ethyl}-amide

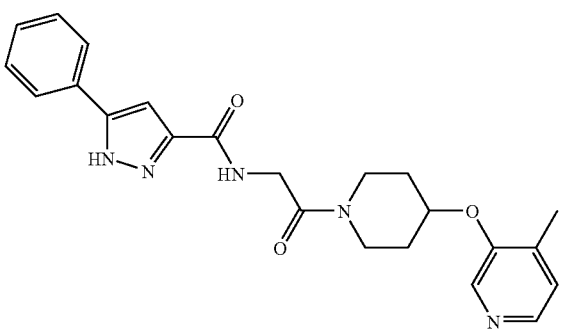

DIPEA (154 mg, 1.4 mmol) was added to a stirred solution of [(5-phenyl-1H-pyrazole-3-carbonyl)-amino]-acetic acid (107 mg, 0.4 mmol) in DMF (2 mL) followed by HOBt (54 mg, 0.4 mmol) and EDCI.HCl (84 mg, 0.44 mmol). After 2 minutes 4-methyl-3-(piperidin-4-yloxy)-pyridine hydrochloride (100 mg, 0.4 mmol) (prepared by method used for the synthesis of Intermediate 15) was added to the reaction mixture and stirring was continued at ambient temperature overnight. The reaction mixture was diluted with cold water, the solid collected. Purification of the solid by washing with 10% MeOH in CHCl$_3$ afforded 106 mg (66% Yield) of 5-phenyl-1H-pyrazole-3-carboxylic acid {2-[4-(4-methyl-pyridin-3-yloxy)-piperidin-1-yl]-2-oxo-ethyl}-amide. LC/MS [M+H]$^+$: 420, 98.9%. $^1$H NMR (300 MHz, DMSO-d$_6$): δ 14.0 (b, 1H), 8.6 (s, 1H), 8.4 (d, 1H), 8.2 (b, 1H), 7.8 (m, 3H), 7.5

(m, 2H), 7.4 (m, 1H), 7.2 (s, 1H), 4.9 (m, 1H), 4.2 (m, 2H), 3.8 (m, 2H), 3.5 (m, 2H), 2.4 (s, 3H), 2.0 (m, 2H), 1.7 (m, 2H).

Example 115

Synthesis of 5-Phenyl-1H-pyrazole-3-carboxylic acid {2-oxo-2-[4-(5-trifluoromethyl-pyridin-3-yloxy)-piperidin-1-yl]-ethyl}-amide

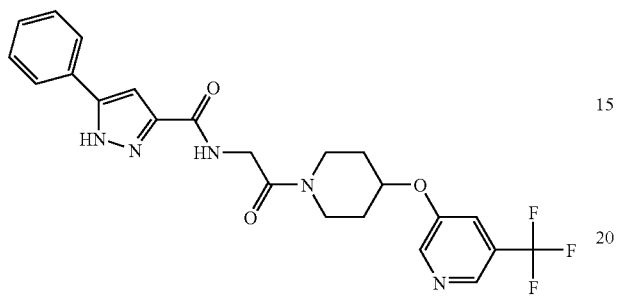

DIPEA (140 mg, 1.1 mmol) was added to a stirred solution of [(5-phenyl-1H-pyrazole-3-carbonyl)-amino]-acetic acid (87 mg, 0.35 mmol) in DMF (2 mL) followed by HOBt (47 mg, 0.35 mmol) and EDCI.HCl (73 mg, 0.38 mmol). After 2 minutes 3-(piperidin-4-yloxy)-5-trifluoromethyl-pyridine hydrochloride (100 mg, 0.35 mmol) (prepared by method used for the synthesis of Intermediate 15) was added to the reaction mixture and stirring was continued at ambient temperature overnight. The reaction mixture was diluted with cold water, the solid was collected. Purification of the solid by washing with 10% MeOH in CHCl₃ afforded 76 mg (47.5% Yield) of 5-phenyl-1H-pyrazole-3-carboxylic acid {2-oxo-2-[4-(5-trifluoromethyl-pyridin-3-yloxy)-piperidin-1-yl]-ethyl}-amide. LC/MS [M+H]$^+$: 474, 99%. $^1$H NMR (300 MHz, DMSO-d$_6$): δ 13.8 (m, 1H), 8.68 (m, 1H), 8.58 (s, 1H), 8.1 (m, 1H), 7.9 (m, 1H), 7.8 (m, 2H), 7.4 (m, 4H), 7.1 (m, 1H), 5.0 (m, 1H), 4.2 (m, 2H), 4.0 (m, 1H), 3.8 (m, 1H), 3.4 (m, 1H), 3.3 (m, 1H), 2.0 (m, 2H), 1.7 (m, 2H).

Example 116

Synthesis of 5-(5-Chloro-thiophen-2-yl)-1H-pyrazole-3-carboxylic acid {2-oxo-2-[4-(3-trifluoromethyl-phenoxy)-piperidin-1-yl]-ethyl}-amide

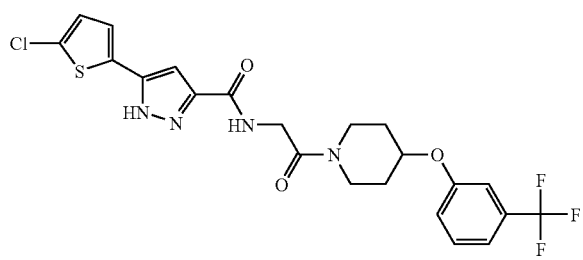

DIPEA (200 mg, 1.5 mmol) was added to a stirred solution of 5-(5-chloro-thiophen-2-yl)-1H-pyrazole-3-carboxylic acid (100 mg, 0.44 mmol) (prepared by the method used for the synthesis of Intermediate 29, starting from 2-acetyl-5-chlorothiophene) in DMF (2 mL) followed by HOBt (63 mg, 0.46 mmol) and EDCI.HCl (90 mg, 0.46 mmol). After 5 minutes 2-amino-1-[4-(3-trifluoromethyl-phenoxy)-piperidin-1-yl]-ethanone hydrochloride (140 mg, 0.44 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 10% EtOAc in hexane afforded 146 mg (65.1% Yield) of 5-(5-chloro-thiophen-2-yl)-1H-pyrazole-3-carboxylic acid {2-oxo-2-[4-(3-trifluoromethyl-phenoxy)-piperidin-1-yl]-ethyl}-amide. LC/MS [M+H]$^+$: 513, 98.3%. $^1$H NMR (300 MHz, DMSO-d$_6$): δ 13.7 (s, 1H), 8.64 (m, 1H), 7.5 (t, 1H), 7.3 (m, 3H), 7.2 (m, 2H), 6.9 (m, 1H), 4.7 (m, 1H), 4.2 (m, 2H), 3.9 (m, 1H), 3.7 (m, 1H), 3.4 (m, 1H), 3.3 (m, 1H), 1.9 (m, 2H), 1.6 (m, 2H).

Example 117

Synthesis of 5-(5-Chloro-thiophen-2-yl)-1H-pyrazole-3-carboxylic acid {2-[4-(2,5-difluoro-phenoxy)-piperidin-1-yl]-2-oxo-ethyl}-amide

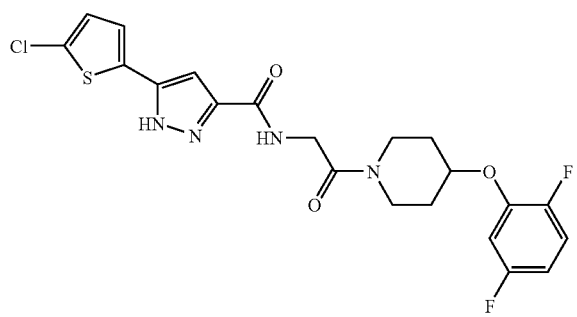

DIPEA (120 mg, 0.98 mmol) was added to a stirred solution of {[5-(5-chloro-thiophen-2-yl)-1H-pyrazole-3-carbonyl]-amino}-acetic acid (80 mg, 0.28 mmol) (prepared by the method used for the synthesis of Intermediate 30, starting from 2-acetyl-5-chlorothiophene) in DMF (2 mL) followed by HOBt (40 mg, 0.29 mmol) and EDCI.HCl (56 mg, 0.29 mmol). After 5 minutes 4-(2,5-difluoro-phenoxy)-piperidine hydrochloride (70 mg, 0.28 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 10% EtOAc in hexane afforded 84 mg (65.1% Yield) of 5-(5-chloro-thiophen-2-yl)-1H-pyrazole-3-carboxylic acid {2-[4-(2,5-difluoro-phenoxy)-piperidin-1-yl]-2-oxo-ethyl}-amide. LC/MS [M+H]$^+$: 481, 90.38%. $^1$H NMR (300 MHz, DMSO-d$_6$): δ 13.6 (s, 1H), 8.6 (m, 1H), 7.18

(m, 4H), 7.1 (m, 1H), 6.8 (m, 1H), 4.7 (m, 1H), 4.2 (d, 2H), 3.8 (m, 1H), 3.7 (m, 1H), 1.9 (m, 2H), 1.6 (m, 2H).

Example 118

Synthesis of 5-(2-Hydroxy-phenyl)-1H-pyrazole-3-carboxylic acid {2-oxo-2-[4-(3-trifluoromethyl-phenoxy)-piperidin-1-yl]-ethyl}-amide

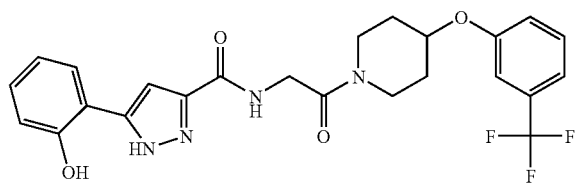

10% Pd/C (50 mg) was added to a stirred solution of 5-(2-benzyloxy-phenyl)-1H-pyrazole-3-carboxylic acid {2-oxo-2-[4-(3-trifluoromethyl-phenoxy)-piperidin-1-yl]-ethyl}-amide (195 mg, 0.34 mmol) (prepared by method used for the synthesis of Intermediate 45) in methanol (30 mL) under inert atmosphere and stirred under H$_2$ atmosphere with pressure for 3 hrs. The reaction mixture was filtered through celite, the celite was washed with methanol and the filtrate was concentrated under reduced pressure Washing with ethyl acetate afforded 58 mg (35% Yield) of 5-(2-hydroxy-phenyl)-1H-pyrazole-3-carboxylic acid {2-oxo-2-[4-(3-trifluoromethyl-phenoxy)-piperidin-1-yl]-ethyl}-amide. LC/MS [M+H]$^+$: 489, 91.45%. $^1$H NMR (300 MHz, DMSO-d$_6$): δ8.2 (m, 1H), 7.64 (d, 1H), 7.5 (t, 1H), 7.26 (t, 2H), 7.1 (m, 2H), 6.94 (m, 1H), 6.84 (t, 1H), 4.8 (m, 1H), 4.2 (d, 2H), 3.9 (m, 1H), 3.7 (m, 1H), 3.4 (m, 2H), 1.9 (m, 2H), 1.6 (m, 2H).

Synthesis of 4-(2-methanesulfonyl-phenoxy)-piperidine hydrochloride

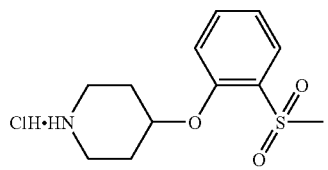

m-Chloroperbenzoic acid (280 mg, 1.62 mmol) was added to a cold (0-4° C.) solution of 1-methoxy-2-methylsulfanyl-benzene (100 mg, 0.64 mmol) in DCM (3 mL) and stirring was continued for 1 hr. The reaction mixture was diluted with water and extracted with dichloromethane. The organic layer was washed with saturated brine solution, dried over sodium sulfate and concentrated under reduced pressure to afford 110 mg (91.6% Yield) of 1-methanesulfonyl-2-methoxy-benzene. Boron tribromide (370 mg, 1.47 mmol) was added to a cold solution (–70° C.) solution of 1-methanesulfonyl-2-methoxy-benzene (10 mg, 0.591 mmol) in DCM (2 mL) and stirring was continued for 10 minutes. After which the reaction mixture was stirred at ambient temperature overnight. The reaction mixture was diluted with water and extracted with dichloromethane. The organic layer was washed with saturated brine solution, dried over sodium sulfate and concentrated under reduced pressure to afford 65 mg (64.35% Yield) of 2-methanesulfonyl-phenol. 2-Methylsulfonyl-phenol was converted to 4-(2-methanesulfonyl-phenoxy)-piperidine hydrochloride according to Step 1 of the General Scheme).

Example 119

Synthesis of 5-Phenyl-1H-pyrazole-3-carboxylic acid {2-[4-(2-methanesulfonyl-phenoxy)-piperidin-1-yl]-2-oxo-ethyl}-amide

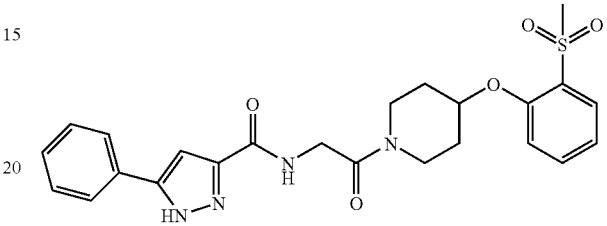

DIPEA (63 mg, 0.48 mmol) was added to a stirred solution of [(5-phenyl-1H-pyrazole-3-carbonyl)-amino]-acetic acid (40 mg, 0.163 mmol) in DMF (1 mL) followed by HOBt (26 mg, 0.195 mmol) and EDCI.HCl (37 mg, 0.195 mmol). After 2 minutes 4-(2-methanesulfonyl-phenoxy)-piperidine hydrochloride (57 mg, 0.195 mmol) was added to the reaction mixture and stirring was continued at ambient temperature overnight. The reaction mixture was diluted with cold water and extracted with ethyl acetate. The ethyl acetate was washed with brine solution, dried over sodium sulfate and concentrated under reduced pressure The residue was purified by preparative HPLC to afford 28 mg (26.66% Yield) of 5-phenyl-1H-pyrazole-3-carboxylic acid {2-[4-(2-methanesulfonyl-phenoxy)-piperidin-1-yl]-2-oxo-ethyl}-amide. LC/MS [M+H]$^+$: 483, 98.59%. $^1$H NMR (300 MHz, CDCl$_3$): δ 8.8 (bs, 1H), 8.0 (m, 1H), 7.7-7.6 (d, 2H), 7.6-7.5 (m, 1H), 7.5-7.3 (m, 3H), 7.2-7.0 (m, 3H), 5.1-4.9 (m, 3H), 4.6-4.5 (dd, 1H), 4.2-4.1 (m, 2H), 3.9-3.4 (m, 3H), 3.2 (s, 3H), 2.1-1.9 (m, 4H).

Example 120

Synthesis of 5-(2-Fluoro-phenyl)-isoxazole-3-carboxylic acid {2-[4-(2-chloro-phenylamino)-piperidin-1-yl]-2-oxo-ethyl}-amide

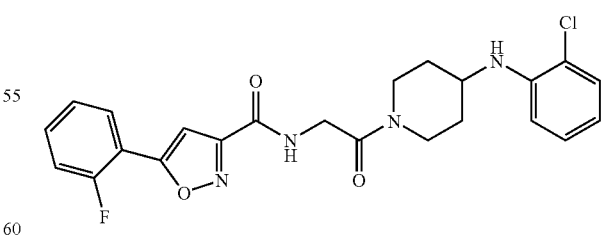

DIPEA (328 mg, 2.5 mmol) to a stirred solution of 5-(2-fluoro-phenyl)-1H-pyrazole-3-carboxylic acid (150 mg, 0.724 mmol) (prepared by the method used for the synthesis of Intermediate 29, starting from 2'fluoroacetophenone) in DMF (5 mL) followed by HOBt (100 mg, 0.76 mmol) and EDCI.HCl (140 mg, 0.76 mmol). After 2 minutes 2-amino- 1-[4-(2-chloro-phenylamino)-piperidin-1-yl]-ethanone dihydrochloride (220 mg, 0.724 mmol) was added to the reaction mixture and stirring was continued at ambient temperature overnight. The reaction mixture was diluted with cold water, the precipitate was collected. The solid was purified by recrystallisation from ethyl acetate The residue obtained was again purified by column chromatography (using 60-120 silica gel and 60% EtOAc in hexane as eluent) to afford 88 mg (26.6% Yield) of 5-(2-fluoro-phenyl)-isoxazole-3-carboxylic acid {2-[4-(2-chloro-phenylamino)-piperidin-1-yl]-2-oxo-ethyl}-amide. LC/MS [M+H]+: 457, 91.47%. 1H NMR (300 MHz, DMSO-d6): δ8.75 (t, 1H), 8.0 (m, 1H), 7.6 (m, 1H), 7.38 (m, 2H), 7.1 (m, 3H), 6.82 (d, 1H), 6.6 (m, 1H), 4.8 (m, 1H), 4.3 (d, 1H), 4.1 (d, 2H), 3.8 (d, 1H), 3.6 (m, 1H), 3.1 (t, 1H), 2.8 (t, 1H), 1.9 (t, 2H), 1.45 (m, 2H).

Example 121

Synthesis of 5-Phenyl-isoxazole-3-carboxylic acid {2-oxo-2-[4-(3-trifluoromethyl-phenoxy)-piperidin-1-yl]-ethyl}-amide

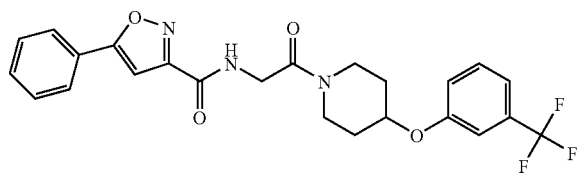

DIPEA (96 mg, 0.745 mmol) was added to a stirred solution of [(5-phenyl-isoxazole-3-carbonyl)-amino]-acetic acid (67 mg, 0.27 mmol) in DMF (3 mL) followed by HOBt (36 mg, 0.273 mmol) and EDCI.HCl (62 mg, 0.32 mmol). After 2 minutes 4-(3-trifluoromethyl-phenoxy)-piperidine hydrochloride (70 mg, 0.248 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure The residue was purified by column chromatography (using 60-120 silica gel and 50% EtOAc in hexane as eluent) to afford 60 mg (34% Yield) of 5-phenyl-isoxazole-3-carboxylic acid {2-oxo-2-[4-(3-trifluoromethyl-phenoxy)-piperidin-1-yl]-ethyl}-amide. LC/MS [M+H]+: 474, 70.17%. 1H NMR (300 MHz, DMSO-d6): δ8.7-8.6 (t, 1H), 8.0-7.9 (m, 2H), 7.6-7.5 (m, 4H), 7.4 (s, 1H), 7.3-7.26 (t, 3H), 4.8 (m, 1H), 4.2 (d, 2H), 3.9 (m, 1H), 3.7 (m, 1H), 3.5 (m, 1H), 3.3 (m, 1H), 2.0 (m, 2H), 1.8-1.4 (m, 2H).

Example 122

Synthesis of 5-(2-Fluoro-phenyl)-isoxazole-3-carboxylic acid {2-oxo-2-[4-(3-trifluoromethyl-phenoxy)-piperidin-1-yl]-ethyl}-amide

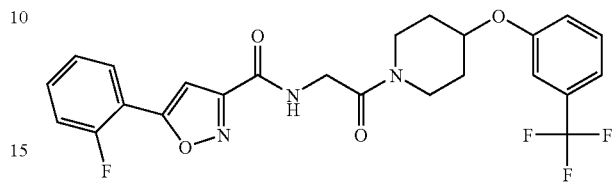

DIPEA (167 mg, 1.3 mmol) was added to a stirred solution of 5-(2-fluoro-phenyl)-isoxazole-3-carboxylic acid (76 mg, 0.37 mmol) in DMF (2 mL) (prepared by the method used for the synthesis of Intermediate 25, starting from 2'-fluoroacetophenone) followed by HOBt (52 mg, 0.38 mmol) and EDCI.HCl (74 mg, 0.39 mmol). After 2 minutes 2-amino-1-[4-(3-trifluoromethyl-phenoxy)-piperidin-1-yl]-ethanone hydrochloride (125 mg, 0.37 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. The residue was purified by washing with methanol to afford the 40 mg (34% Yield) of 5-(2-fluoro-phenyl)-isoxazole-3-carboxylic acid {2-oxo-2-[4-(3-trifluoromethyl-phenoxy)-piperidin-1-yl]-ethyl}-amide. LC/MS [M+H]+: 492, 92.84%. 1H NMR (300 MHz, DMSO-d6): δ8.8 (t, 1H), 8.0 (m, 1H), 7.6 (m, 1H), 7.4 (m, 3H), 7.25 (m, 3H), 7.2 (d, 1H), 4.8 (m, 1H), 4.2 (m, 2H), 3.7 (m, 2H), 3.4 (m, 2H), 1.9 (m, 2H), 1.6 (m, 2H).

Example 123

Synthesis of 5-(2-Hydroxy-phenyl)-isoxazole-3-carboxylic acid {2-oxo-2-[4-(3-trifluoromethyl-phenoxy)-piperidin-1-yl]-ethyl}-amide

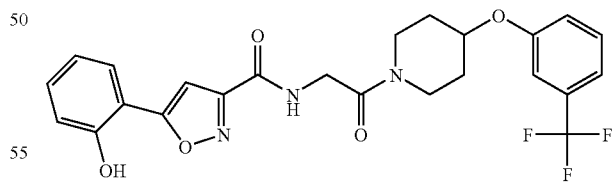

10% Pd/C (50 mg) was added to a stirred solution of 5-(2-benzyloxy-phenyl)-isoxazole-3-carboxylic acid {2-oxo-2-[4-(3-trifluoromethyl-phenoxy)-piperidin-1-yl]-ethyl}-amide (192 mg, 0.33 mmol) (prepared by the method used to generate Intermediate 43) in methanol (50 mL) and stirred under H2 atmosphere with pressure for 3 hrs. The reaction mixture was filtered through celite, the celite was washed with methanol and the filtrate was concentrated under reduced pressure. Washing with ethyl acetate afforded the residue. The residue was purified by preparative HPLC to afford 31 mg (19.1% Yield) of 5-(2-hydroxy-phenyl)-isoxazole-3-carboxylic acid {2-oxo-2-[4-(3-trifluoromethyl-phenoxy)-piperidin-1-yl]-ethyl}-amide. LC/MS [M+H]+: 490, 96.83%. ¹H NMR (300 MHz, DMSO-$d_6$): δ10.8 (s, 1H), 8.68 (t, 1H), 7.8 (m, 1H), 7.5 (t, 1H), 7.3 (m, 4H), 7.18 (s, 1H), 7.04 (d, 1H), 6.94 (t, 1H), 4.8 (m, 1H), 4.2 (d, 2H), 3.8 (m, 1H), 3.7 (m, 1H), 3.4 (m, 1H), 3.25 (m, 1H), 1.9 (m, 2H), 1.65 (m, 2H).

Example 124

Synthesis of 5-(3-Hydroxy-phenyl)-isoxazole-3-carboxylic acid {2-oxo-2-[4-(3-trifluoromethyl-phenoxy)-piperidin-1-yl]-ethyl}-amide

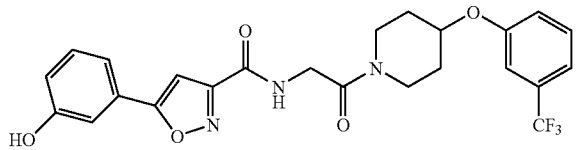

DIPEA (133 mg, 1.03 mmol) was added to a stirred solution of 5-(3-hydroxy-phenyl)-isoxazole-3-carboxylic acid (61 mg, 0.294 mmol)) (prepared by the method used for the synthesis of Intermediate 25, starting from 2'-benzyloxyacetophenone) in DMF (2 mL) followed by HOBt (41.7 mg, 0.308 mmol) and EDCI.HCl (59 mg, 0.308 mmol). After 2 minutes 2-amino-1-[4-(3-trifluoromethyl-phenoxy)-piperidin-1-yl]-ethanone hydrochloride (99 mg, 0.294 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure The residue was purified by washing with ethylacetate to afford 54 mg (37.7% Yield) of 5-(3-hydroxy-phenyl)-isoxazole-3-carboxylic acid {2-oxo-2-[4-(3-trifluoromethyl-phenoxy)-piperidin-1-yl]-ethyl}-amide. LC/MS [M+H]⁺: 490, 94.4%. ¹H NMR (300 MHz, DMSO-$d_6$): δ9.9 (s, 1H), 8.65 (t, 1H), 7.5 (t, 1H), 7.3 (m, 7H), 6.95 (m, 1H), 4.8 (m, 1H), 4.2 (d, 2H), 3.9 (s, 1H), 3.7 (m, 1H), 3.4 (m, 2H), 2.0 (m, 2H), 1.6 (m, 2H).

Example 125

Synthesis of 5-(4-Hydroxy-phenyl)-isoxazole-3-carboxylic acid {2-oxo-2-[4-(3-trifluoromethyl-phenoxy)-piperidin-1-yl]-ethyl}-amide

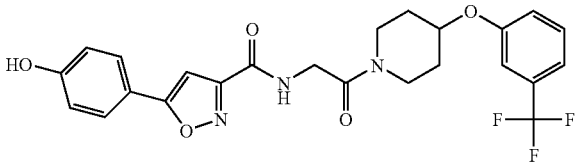

DIPEA (133 mg, 1.03 mmol) was added to a stirred solution of 5-(4-hydroxy-phenyl)-isoxazole-3-carboxylic acid (61 mg, 0.294 mmol) (prepared by the method used for the synthesis of Intermediate 25, starting from 3'benzyloxyacetophenone) in DMF (2 mL) followed by HOBt (41.7 mg, 0.308 mmol) and EDCI.HCl (59 mg, 0.308 mmol). After 2 minutes 2-amino-1-[4-(3-trifluoromethyl-phenoxy)-piperidin-1-yl]-ethanone hydrochloride (99 mg, 0.294 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 110% EtOAc in hexane afforded 74 mg (51.3% Yield) of 5-(4-hydroxy-phenyl)-isoxazole-3-carboxylic acid {2-oxo-2-[4-(3-trifluoromethyl-phenoxy)-piperidin-1-yl]-ethyl}-amide. LC/MS [M+H]⁺: 490, 90.53%. ¹H NMR (300 MHz, DMSO-$d_6$): δ10.2 (s, 1H), 8.6 (s, 1H), 7.78 (d, 2H), 7.5 (t, 1H), 7.3 (t, 3H), 7.16 (s, 1H), 6.9 (m, 2H), 4.7 (m, 1H), 4.2 (d, 2H), 3.9 (m, 1H), 3.7 (m, 1H), 3.4 (m, 2H), 2.0 (m, 2H), 1.6 (m, 2H).

Example 126

Synthesis of 5-(3-Fluoro-phenyl)-isoxazole-3-carboxylic acid {2-oxo-2-[4-(3-trifluoromethyl-phenoxy)-piperidin-1-yl]-ethyl}-amide

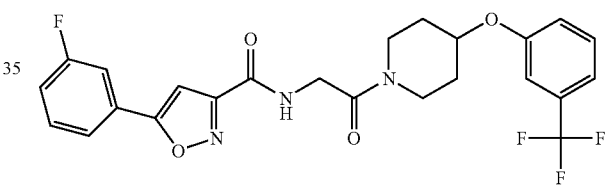

DIPEA (131 mg, 1.0 mmol) was added to a stirred solution of 5-(3-fluoro-phenyl)-isoxazole-3-carboxylic acid (60 mg, 0.29 mmol) (prepared by the method used for the synthesis of Intermediate 25, starting from 3'-fluoroacetophenone) in DMF (2 mL) followed by HOBt (41 mg, 0.3 mmol) and EDCI.HCl (58 mg, 0.3 mmol). After 2 minutes 2-amino-1-[4-(3-trifluoromethyl-phenoxy)-piperidin-1-yl]-ethanone hydrochloride (125 mg, 0.37 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from methanol afforded 84 mg (59.15% Yield) of 5-(3-fluoro-phenyl)-isoxazole-3-carboxylic acid {2-oxo-2-[4-(3-trifluoromethyl-phenoxy)-piperidin-1-yl]-ethyl}-amide. LC/MS [M+H]⁺: 492, 70.25%. ¹H NMR (300 MHz, DMSO-$d_6$): δ8.6 (t, 1H), 7.8 (m, 2H), 7.5 (m, 3H), 7.24 (m, 4H), 4.7 (m, 1H), 4.2 (d, 2H), 3.9 (m, 1H), 3.7 (m, 1H), 3.4 (m, 2H), 2.0 (m, 2H), 1.6 (m, 2H).

Example 127

Synthesis of 5-(4-Fluoro-phenyl)-isoxazole-3-carboxylic acid {2-oxo-2-[4-(3-trifluoromethyl-phenoxy)-piperidin-1-yl]-ethyl}-amide

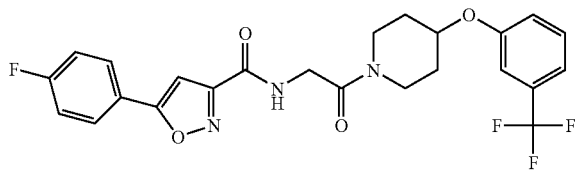

DIPEA (131 mg, 1.0 mmol) was added to a stirred solution of 5-(4-fluoro-phenyl)-isoxazole-3-carboxylic acid (60 mg, 0.29 mmol) (prepared by the method used for the synthesis of Intermediate 25, starting from 4'-fluoroacetophenone) in DMF (2 mL) followed by HOBt (41 mg, 0.3 mmol) and EDCI.HCl (58 mg, 0.3 mmol). After 2 minutes 2-amino-1-[4-(3-trifluoromethyl-phenoxy)-piperidin-1-yl]-ethanone hydrochloride (125 mg, 0.37 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from chloroform afforded 77 mg (54.2% Yield) of 5-(4-fluoro-phenyl)-isoxazole-3-carboxylic acid {2-oxo-2-[4-(3-trifluoromethyl-phenoxy)-piperidin-1-yl]-ethyl}-amide. LC/MS [M+H]$^+$: 492, 96.7%. $^1$H NMR (300 MHz, DMSO-d$_6$): δ8.62 (t, 1H), 8.0 (m, 2H), 7.5 (t, 1H), 7.38 (m, 3H), 7.26 (t, 3H), 4.8 (m, 1H), 4.2 (d, 2H), 3.7 (m, 4H), 3.4 (m, 2H), 2.0 (m, 2H), 1.6 (m, 2H).

Example 128

Synthesis of 5-(4-Fluoro-phenyl)-isoxazole-3-carboxylic acid {2-[4-(5-chloro-pyridin-3-yloxy)-piperidin-1-yl]-2-oxo-ethyl}-amide

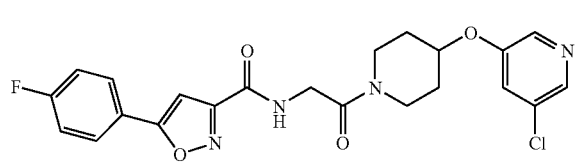

DIPEA (253 mg, 1.96 mmol) was added to a stirred solution of 5-(4-fluoro-phenyl)-isoxazole-3-carboxylic acid (81 mg, 0.39 mmol) (prepared by the method used for the synthesis of Intermediate 25, starting from 4'-fluoroacetophenone) in DMF (2 mL), followed by HOBt (56 mg, 0.41 mmol) and EDCI.HCl (79 mg, 0.41 mmol). After 2 minutes 2-amino-1-[4-(5-chloro-pyridin-3-yloxy)-piperidin-1-yl]-ethanone hydrochloride (120 mg, 0.39 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 10% ethyl acetate in hexane afforded 32 mg (17.8% Yield) of 5-(4-fluoro-phenyl)-isoxazole-3-carboxylic acid {2-[4-(5-chloro-pyridin-3-yloxy)-piperidin-1-yl]-2-oxo-ethyl}-amide. LC/MS [M+H]$^+$: 459, 92.84%. $^1$H NMR (300 MHz, CDCl$_3$): δ8.2 (s, 2H), 7.86 (m, 1H), 7.76 (m, 2H), 7.14 (m, 3H), 6.9 (s, 1H), 4.7 (m, 1H), 4.3 (m, 2H), 3.7 (m, 3H), 3.5 (m, 1H), 1.9 (m, 4H).

Example 129

Synthesis of 5-(4-Fluoro-phenyl)-isoxazole-3-carboxylic acid {2-[4-(2-chloro-pyridin-3-yloxy)-piperidin-1-yl]-2-oxo-ethyl}-amide

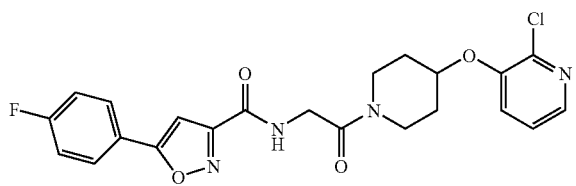

DIPEA (186 mg, 1.43 mmol) was added to a stirred solution of {[5-(4-fluoro-phenyl)-isoxazole-3-carbonyl]-amino}-acetic acid (76 mg, 0.29 mmol) (prepared by the method used for the synthesis of Intermediate 26, starting from 4'-fluoroacetophenone) in DMF (2 mL) followed by HOBt (41 mg, 0.3 mmol) and EDCI.HCl (58 mg, 0.3 mmol). After 2 minutes 2-chloro-3-(piperidin-4-yloxy)-pyridine hydrochloride (72 mg, 0.29 mmol) (prepared by method used for the synthesis of Intermediate 15) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 10% ethyl acetate in hexane to afford 66 mg (50% Yield) of 5-(4-fluoro-phenyl)-isoxazole-3-carboxylic acid {2-[4-(2-chloro-pyridin-3-yloxy)-piperidin-1-yl]-2-oxo-ethyl}-amide. LC/MS [M+H]$^+$: 459, 94.53%. $^1$H NMR (300 MHz, DMSO-d$_6$): δ 8.65 (s, 1H), 7.98 (m, 3H), 7.72 (m, 1H), 7.38 (m, 4H), 4.8 (m, 1H), 4.2 (d, 2H), 3.7 (m, 2H), 3.4 (m, 2H), 1.9 (m, 2H), 1.6 (m, 2H).

Example 130

Synthesis of 5-(3-Fluoro-phenyl)-isoxazole-3-carboxylic acid {2-[4-(5-chloro-pyridin-3-yloxy)-piperidin-1-yl]-2-oxo-ethyl}-amide

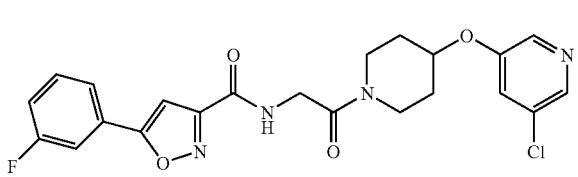

DIPEA (253 mg, 1.96 mmol) was added to a stirred solution 5-(3-fluoro-phenyl)-isoxazole-3-carboxylic acid (81 mg, 0.39 mmol) (prepared by the method used for the synthesis of Intermediate 25, starting from 3'-fluoroacetophenone) in DMF (2 mL) followed by HOBt (56 mg, 0.41 mmol) and EDCI.HCl (79 mg, 0.41 mmol). After 2 minutes 2-amino-1-[4-(5-Chloro-pyridin-3-yloxy)-piperidin-1-yl]-ethanone hydrochloride (120 mg, 0.38 mmol) (prepared according to Step 1 and 5 of the General Scheme) was added to the reaction mixture and stirring was continued at ambient temperature overnight. The reaction mixture was diluted with cold water, extracted with ethyl acetate, dried over sodium sulfate and concentrated under reduced pressure. Purification by recrystallisation from 1% methanol in ethyl acetate to afford 35 mg (19.5% Yield) of 5-(3-fluoro-phenyl)-isoxazole-3-carboxylic acid {2-[4-(5-chloro-pyridin-3-yloxy)-piperidin-1-yl]-2-oxo-ethyl}-amide. LC/MS [M+H]$^+$: 459, 100%. $^1$H NMR (300 MHz, DMSO-d$_6$): δ 8.7 (t, 1H), 8.32 (d, 1H), 8.22 (s, 1H), 7.78 (t, 2H), 7.72 (s, 1H), 7.58 (m, 1H), 7.5 (s, 1H), 7.36 (m, 1H), 4.8 (m, 1H), 4.2 (d, 2H), 3.9 (m, 1H), 3.7 (m, 2H), 3.4 (m, 1H), 3.2 (m, 1H), 2.0 (m, 2H), 1.6 (m, 2H).

Intermediate 61

Synthesis of 1-Phenyl-1H-pyrazole-4-carboxylic acid

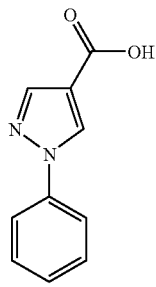

1-Phenyl-1H-pyrazole (250 mg, 1.7 mmol) was added to a cold (0-4° C.) solution of DMF (1.5 g, 1.6 mL, 9.7 mmol) and POCl$_3$ (1.86 g, 1.1 mL, 19.2 mmol) and stirring continued for 10 minutes. The resulting mixture was heated at 106° C. for 2.5 hrs. The reaction mixture was cooled and quenched with ice cold water, basified with 20% aqueous NaOH solution, the solid was collected to afford 330 mg (crude) of 1-phenyl-1H-pyrazole-4-carbaldehyde. $^1$H NMR (300 MHz, CDCl$_3$): δ 10.0 (s, 1H), 8.45 (s, 1H), 8.2 (s, 1H), 7.75 (d, 2H), 7.55 (t, 2H), 7.45 (t, 1H). Sulphamic acid (253 mg, 2.6 mmol) in water (0.5 mL) was added at 0° C. to a mixture of phenyl-1H-pyrazole-4-carbaldehyde (0.5 g, 2.34 mmol) in acetone (3 mL). After 2 minutes sodium chlorite (315 mg, 3.5 mmol) was added and the resulting mixture was stirred at 0° C. for 30 minutes. Water was added and the solid obtained was isolated by filtration to afford 140 mg (85% yield) of 1-phenyl-1H-pyrazole-4-carboxylic acid.

Example 131

Synthesis of 1-Phenyl-1H-pyrazole-4-carboxylic acid {2-[4-(2-chloro-phenoxy)-piperidin-1-yl]-2-oxo-ethyl}-amide

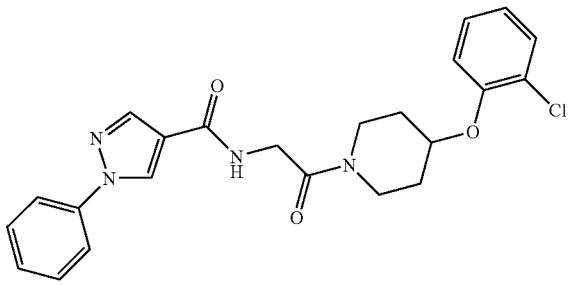

DIPEA (223 mg, 0.3 mL, 1.72 mmol) was added to a stirred solution of 1-phenyl-1H-pyrazole-4-carboxylic acid (65 mg, 0.34 mmol) in DMF (5 mL) followed by HOBt (51 mg, 0.38 mmol) and EDCI (165 mg, 0.86 mmol). After 2 minutes of stirring, 2-amino-1-[4-(2-chloro-phenoxy)-piperidin-1-yl]-ethanone hydrochloride salt (116 mg, 0.38 mmol) (prepared according to Step 1 and 5 of the General Scheme) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure. The residue was purified by column chromatography (using 60-120 silica gel and 70% EtOAc in hexane as eluent) to afford 70 mg (46.35% yield) of 1-phenyl-1H-pyrazole-4-carboxylic acid {2-[4-(2-chloro-phenoxy)-piperidin-1-yl]-2-oxo-ethyl}-amide. LC/MS [M+H]$^+$: 439.15, 95.23%. $^1$H NMR (300 MHz, CDCl$_3$): δ 8.4 (s, 1H), 8.06 (s, 1H), 7.76 (d, 2H), 7.54 (t, 2H), 7.42 (m, 2H), 7.2 (d, 1H), 7.1 (t, 1H), 7.0 (t, 2H), 4.7 (t, 1H), 4.4-4.2 (m, 2H), 4.1 (m, 1H), 3.8-3.5 (m, 2H), δ 3.5 (m, 1H), 2.1-1.8 (m, 4H).

Example 132

Synthesis of 2-[(Biphenyl-4-ylmethyl)-amino]-1-[4-(2-chloro-phenoxy)-piperidin-1-yl]-ethanone

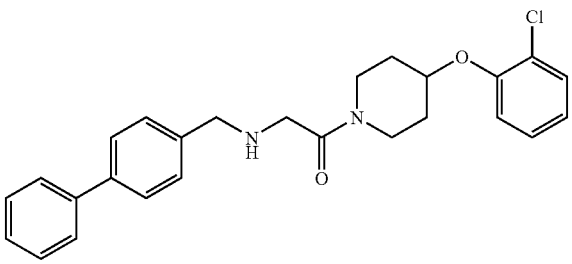

A mixture of biphenyl-4-yl-methanol (250 mg, 1.35 mmol) and aqueous HBr (48%) (3 mL) was stirred at 10° C. for 3 hrs. After completion of the reaction, the mixture was diluted with cold water, extracted with ethyl acetate and dried over sodium sulfate. The organic layer collected was concentrated under reduced pressure to afford 330 mg (98.5% Yield) 4-bromomethyl-biphenyl. 4-Bromomethyl-biphenyl (120 mg, 0.485 mmol) was added to a stirred mixture of 2-amino-1-[4-(2- chloro-phenoxy)-piperidin-1-yl]-ethanone hydrochloride (134 mg, 0.44 mmol) (prepared according to Step 1 and 5 of the General Scheme), LiOH.H$_2$O (40 mg, 0.97 mmol) and 4 Å molecular sieves (350 mg) in DMF (4 mL) and stirring was continued overnight. The reaction mixture was filtered and filtrate was diluted with cold water, extracted with ethyl acetate and organic layer was dried over sodium sulfate. The organic layer was concentrated under reduced pressure. Purification by column chromatography (using neutral alumina and 5% MeOH in DCM as eluent) to afford 22 mg (11.4% Yield) of 2-[(biphenyl-4-ylmethyl)-amino]-1-[4-(2-chloro-phenoxy)-piperidin-1-yl]-ethanone. LC/MS [M+H]$^+$: 435, 90.56%. $^1$H NMR (CDCl$_3$): δ7.64-7.52 (m, 4H), 7.5-7.3 (m, 6H), 7.24-7.15 (dt, 1H), 7.0-6.86 (m, 2H), 4.6 (q, 1H), 4.0-3.8 (m, 3H), 3.7-3.6 (m, 3H), 3.5 (s, 2H), 3.4-3.3 (m, 1H), 2.0-1.8 (m, 4H).

Intermediate 62

Synthesis of 4-[1,3,4]Oxadiazol-2-yl-benzoic acid

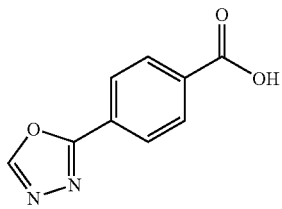

Hydrazine hydrate was added to a solution of terephthalic acid monomethyl ester (1 g, 5.5 mmol) in MeOH (10 mL) and stirring was continued for 1 hr. The reaction mixture was concentrated to afford 900 mg (90.09% Yield) of 4-hydrazinocarbonyl-benzoic acid. p-Toluene sulfonic acid (48 mg, 0.277 mmol) was added to a solution of 4-hydrazinocarbonyl-benzoic acid (500 mg, 2.77 mmol) in triethylorthoformate (7.5 mL, 44.0 mmol) and stirring was continued with heating at 100° C. for 3 hrs. The reaction mixture was diluted with water, the solid was collected to afford 200 mg (37.9% Yield) of 4-[1,3,4]oxadiazol-2-yl-benzoic acid.

Example 133

Synthesis of N-{2-[4-(2-Chloro-phenoxy)-piperidin-1-yl]-2-oxo-ethyl}-4-[1,3,4]oxadiazol-2-yl-benzamide

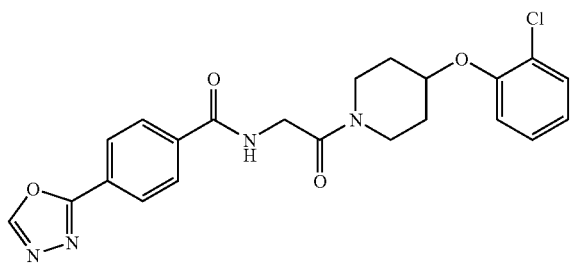

DIPEA (203 mg, 0.27 mL, 1.57 mmol) was added to a stirred solution of 4-[1,3,4]oxadiazol-2-yl-benzoic acid (100 mg, 0.52 mmol) in DMF (2 mL) followed by HOBt (85 mg, 0.63 mmol) and EDCI (121 mg, 0.63 mmol). After 2 minutes of stirring, 2-amino-1-[4-(2-chloro-phenoxy)-piperidin-1-yl]-ethanone hydrochloride (192 mg, 0.63 mmol) (prepared according to Step 1 and 5 of the General Scheme) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to afford 88 mg (38.09% yield) of N-{2-[4-(2-chloro-phenoxy)-piperidin-1-yl]-2-oxo-ethyl}-4-[1,3,4]oxadiazol-2-yl-benzamide. LC/MS [M+H]$^+$: 441.13, 95.23%. $^1$H NMR (300 MHz, DMSO-d$_6$): δ 9.4 (s, 1H), 8.8 (t, 1H), 8.1 (q, 4H), 7.4 (m, 1H), 7.3 (m, 2H), 7.0 (m, 1H), 4.8 (m, 1H), 4.2 (m, 2H), 3.7 (m, 2H), 3.5 (m, 2H), 2.18 (m, 2H), 1.8-1.5 (m, 4H).

Intermediate 63

Synthesis of 4-Phenyl-11H-pyrazole hydrochloride

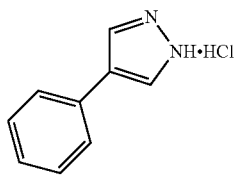

Trityl chloride (1.58 g, 5.67 mmol) was added to a stirred cold (0-5° C.) solution of 4-iodo pyrazole (1 g, 5.15 mmol) and triethylamine (1.04 g, 10.3 mmol) in DCM (12 mL). Stirring was continued at room temperature overnight. Cold water was then added and the product was extracted with DCM and the organic layer was washed with saturated sodium bicarbonate solution followed by brine. The organic phase collected was dried over Na$_2$SO$_4$ and concentrated under reduced pressure The residue was purified by column chromatography (using neutral alumina and 2% EtOAc in hexane as eluent) to afford 1.9 g (84.4% Yield) of 4-iodo-1-trityl-1H-pyrazole. Na$_2$CO$_3$ (727 mg, 6.86 mmol) was added to a stirred solution of 4-iodo-1-trityl-1H-pyrazole (1.5 g, 3.43 mmol) in toluene: H$_2$O (4:1, 20 mL). Pd(PPh$_3$)$_4$ (790 mg, 0.686 mmol) and phenylboronic acid (838 mg, 6.86 mmol) were then added and the reaction mixture was heated to reflux for 2 hrs. The reaction mixture was then diluted with water and the product was extracted with ethyl acetate. The organic layer was washed with saturated brine solution, dried over sodium sulfate and concentrated to in vacuo. Purification by column chromatography (using neutral alumina and 5% EtOAc in hexane as eluent) afforded 790 mg (59.4% Yield) of 4-phenyl-1-trityl-1H-pyrazole. $^1$H NMR (300 MHz, CDCl$_3$): δ 7.96-7.94 (s, 1H), 7.64-7.6 (s, 1H), 7.46-7.4 (d, 2H), 7.36-7.0 (m, 11H), 7.24-7.16 (m, 7H). A solution of 4-phenyl-1-trityl-1H-pyrazole (785 mg, 2.03 mmol) in ether.HCl (15 mL) was stirred for 1 hr. The reaction mixture was then concentrated under reduced pressure and washed with hexane to afford 320 mg (87.4% Yield) of 4-phenyl-1H-pyrazole hydrochloride. $^1$H NMR (300 MHz, DMSO-d$_6$): δ 8.1-8.08 (s, 2H), 7.64 (d, 2H), 7.38 (t, 2H), 7.22 (t, 1H).

Example 134

Synthesis of 4-Phenyl-pyrazole-1-carboxylic acid {2-[4-(2-chloro-phenoxy)-piperidin-1-yl]-2-oxo-ethyl}-amide

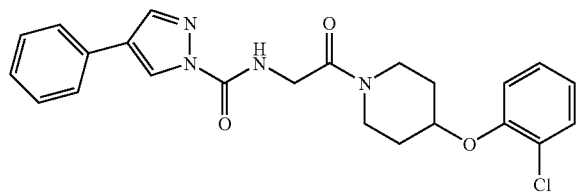

A mixture of 4-phenyl-1H-pyrazole hydrochloride (70 mg, 0.387 mmol), DIPEA (100 mg, 0.81 mmol) and DCM (5 mL) was added to a stirred solution of triphosgene (36 mg, 0.12 mmol) in DCM (2 mL) at room temperature. After 30 minutes, to the above solution, a mixture of 2-amino-1-[4-(2-chloro-phenoxy)-piperidin-1-yl]-ethanone hydrochloride (prepared by method used for the synthesis of Intermediate 15) 118 mg, 0.3875 mmol), DIPEA (100 mg, 0.81 mmol) and DCM (5 mL) was added and the resulting mixture was stirred at room temperature for 1 hr. Cold water was then added and the product was extracted with EtOAc and the organic layer was washed with brine. The organic phase was dried over Na$_2$SO$_4$ and concentrated under reduced pressure The residue was purified by preparative HPLC to afford 60 mg (17.6% Yield) of 4-phenyl-pyrazole-1-carboxylic acid {2-[4-(2-chloro-phenoxy)-piperidin-1-yl]-2-oxo-ethyl}-amide. LC/MS [M+H]+$^+$: 439.15, 93.19%. $^1$H NMR (300 MHz, DMSO-d$_6$): δ 8.8 (s, 1H), 8.4 (t, 1H), 8.35-8.3 (s, 1H), 7.8-7.72 (d, 2H), 7.48-7.38 (m, 3H), 7.35-7.24 (m, 3H), 7.0 (t, 1H), 4.8 (m, 1H), 4.2 (d, 2H), 3.8-3.6 (m, 2H), 3.6-3.4 (m, 2H), 2.1-1.8 (m, 2H), 1.8-1.6 (m, 2H).

Intermediate 64

Synthesis of 1-Phenyl-1H-[1,2,3]triazole-4-carboxylic acid

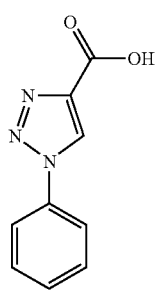

Oxalyl chloride (4.7 g, 30.1 mL, 37.0 mmol) was added to a cold (0-4° C.) solution of DMF (2.25 g, 2.4 mL, 30.8 mmol) in CHCl$_3$ (20 mL) and stirring was continued for 10 minutes. The reaction mixture was heated at 40° C. for 10 minutes and cooled to −10° C. Diazoacetic acid ethyl ester (3.5 g, 3.5 mL, 30.6 mmol) was then added and stirred at room temperature for 1 hr. The reaction mixture was concentrated ether was then added, the precipitate was collected and dissolved in 10% aq Hac (10 mL) and stirring was continued for 1 hr. The reaction mixture was extracted with ether, washed with saturated sodium bicarbonate solution and brine. The organic phase was dried over Na$_2$SO$_4$ and concentrated under reduced pressure to afford 590 mg (21% Yield) of 2-diazo-3-oxo-propionic acid ethyl ester. $^1$H NMR (300 MHz, CDCl$_3$): δ 9.7 (s, 1H), 4.4 (q, 2H), 1.4 (t, 3H). Aniline (143 mg, 1.5 mmol) was added to a solution of 2-diazo-3-oxo-propionic acid ethyl ester (200 mg, 1.4 mmol) and HOAc (0.2 mL) in EtOH (0.5 mL) and stirring was at room temperature overnight. The reaction mixture was concentrated and cold water was then added, the solid was collected to afford 264 mg (87.41% Yield) of 1-phenyl-1H-[1,2,3]triazole-4-carboxylic acid ethyl ester. $^1$H NMR (300 MHz, CDCl$_3$): δ 8.5 (s, 1H), 7.8 (d, 2H), 7.6-7.48 (m, 3H), 4.5 (q, 2H), 1.4 (t, 3H). LiOH.H$_2$O (80 mg, 1.9 mmol) was added to a stirred solution of 1-phenyl-1H-[1,2,3]triazole-4-carboxylic acid ethyl ester (130 mg, 0.6 mmol) in THF:H$_2$O (1:1, 4 mL), and the resulting mixture was stirred at room temperature for 45 min. The reaction mixture was concentrated under reduced pressure. Cold water was then added and it was acidified with 10% aqueous HCl, the solid was collected to afford 40 mg (35.4% yield) of 1-phenyl-1H-[1,2,3]triazole-4-carboxylic acid. $^1$H NMR (300 MHz, DMSO-d$_6$): δ 13.4 (bs, 1H), 9.4 (s, 1H), 8.0 (d, 2H), 7.7 (t, 2H), 7.6 (t, 1H).

Example 135

Synthesis of 1-Phenyl-1H-[1,2,3]triazole-4-carboxylic acid {2-[4-(2-chloro-phenoxy)-piperidin-1-yl]-2-oxo-ethyl}-amide

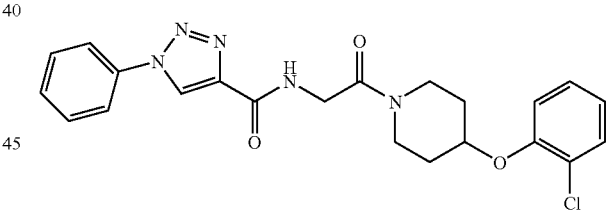

DIPEA (200 mg, 0.27 mL, 1.55 mmol) was added to a stirred solution of 1-phenyl-1H-[1,2,3]triazole-4-carboxylic acid (60 mg, 0.32 mmol) in DMF (5 mL) followed by HOBt (47.6 mg, 0.35 mmol) and EDCI (153 mg, 0.8 mmol). After 2 minutes of stirring, 2-amino-1-[4-(2-chloro-phenoxy)-piperidin-1-yl]-ethanone hydrochloride (prepared according to Step 1 and 5 of the General Scheme) (107 mg, 0.35 mmol) was added and the resulting mixture was stirred at room temperature overnight. Cold water was then added and the precipitate formed was collected to afford 108 mg (76.6% Yield) of 1-phenyl-1H-[1,2,3]triazole-4-carboxylic acid {2-[4-(2-chloro-phenoxy)-piperidin-1-yl]-2-oxo-ethyl}-amide. LC/MS [M+H]$^+$: 440.14, 95.71%. $^1$H NMR (300 MHz, DMSO-d$_6$): δ 9.36 (s, 1H), 8.5 (t, 1H), 8.02 (d, 2H), 7.68 (m, 3H), 7.48 (d, 1H), 7.36-7.22 (m, 2H), 7.0 (t, 1H), 4.8 (m, 1H), 4.3 (d, 2H), 3.8 (t, 2H), 3.6 (s, 2H), 2.1 (d, 2H), 1.8 (d, 2H).

Example 136

Synthesis of 1-Phenyl-1H-[1,2,3]triazole-4-carboxylic acid {2-[4-(2-chloro-phenoxy)-piperidin-1-yl]-2-oxo-ethyl}-amide

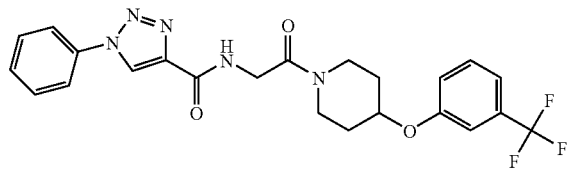

DIPEA (137 mg, 11.0 mmol) was added to stirred solution of 1-phenyl-1H-[1,2,3]triazole-4-carboxylic acid (50 mg, 0.26 mmol) in DMF (3 mL) followed by HOBT (39 mg, 0.29 mmol) and EDCI (100 mg, 0.53 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (90 mg, 0.26 mmol) was added and the resulting mixture was stirred at room temperature overnight. The reaction mixture was diluted with cold water and extracted with ethyl acetate. The organic layer collected was dried over sodium sulfate and concentrated under reduced pressure afforded residue. The residue was purified by column chromatography (using 60-120 silica gel and 50% EtOAc in hexane as eluent) afforded 63 mg (50% Yield) of 1-phenyl-1H-[1,2,3]triazole-4-carboxylic acid {2-[4-(2-chloro-phenoxy)-piperidin-1-yl]-2-oxo-ethyl}-amide. LC/MS [M+H]$^+$: 474.14, 94.1%. $^1$H NMR (300 MHz, DMSO-d$_6$): δ 9.38 (s, 1H), 8.5 (t, 1H), 8.0 (d, 2H), 7.7-7.6 (t, 2H), 7.6-7.5 (t, 2H), 7.36-7.24 (t, 3H), 4.8 (q, 1H), 4.25 (d, 2H), 4.0-3.8 (m, 1H), 3.8-3.7 (m, 1H), 3.5 (m, 2H), 2.0 (m, 2H), 1.8-1.5 (m, 2H).

Example 137

Synthesis of 1-(3-Fluoro-phenyl)-1H-[1,2,3]triazole-4-carboxylic acid {2-oxo-2-[4-(3-trifluoromethyl-phenoxy)-piperidin-1-yl]-ethyl}-amide

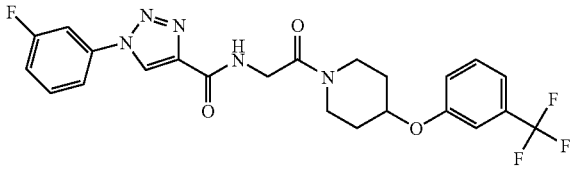

DIPEA (168 mg, 1.3 mmol) was added to a stirred solution of 1-(3-fluoro-phenyl)-1H-[1,2,3]triazole-4-carboxylic acid (prepared by the method used for the synthesis of Intermediate 64, starting from 3-fluoroaniline) (60 mg, 0.29 mmol) in DMF (5 mL) followed by, HOBt (43 mg, 0.32 mmol) and EDCI (139 mg, 0.72 mmol). After 2 minutes of stirring, 2-amino-1-[4-(3-trifluoromethyl-phenoxy)-piperidin-1-yl]-ethanone hydrochloride salt (prepared according to Step 1 and 5 of the General Scheme) (108 mg, 0.32 mmol) was added and the resulting mixture was stirred at room temperature overnight. Cold water was then added and the precipitate formed was collected to afford 110 mg (77.46% Yield) of 1-(3-fluoro-phenyl)-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 492.16, 90.71%. $^1$H NMR (300 MHz, DMSO-d6): δ 9.4 (s, 1H), 8.56 (t, 1H), 8.0 (q, 2H), 7.74 (q, 1H), 7.58 (t, 1H), 7.46-7.24 (m, 4H), 4.9 (m, 1H), 4.3 (d, 2H), 4.0 (bs, 1H), 3.8 (bs, 1H), 3.5 (bs, 2H), 2.1 (d, 2H), 1.8 (d, 2H).

Example 138

Synthesis of 1-(3-Fluoro-phenyl)-1H-[1,2,3]triazole-4-carboxylic acid {2-[4-(2-chloro-5-fluoro-phenoxy)-piperidin-1-yl]-2-oxo-ethyl}-amide

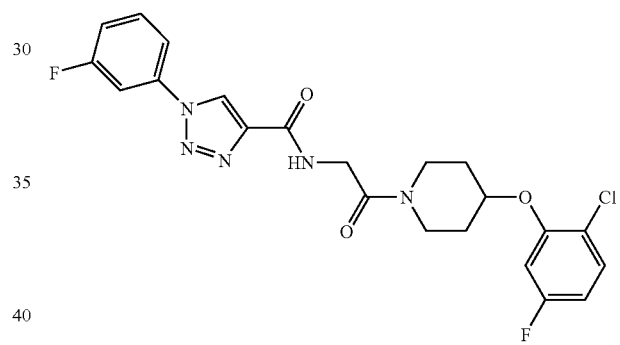

DIPEA (168 mg, 1.3 mmol) was added to a stirred solution of 1-(3-fluoro-phenyl)-1H-[1,2,3]triazole-4-carboxylic acid (60 mg, 0.29 mmol) (prepared by the method used for the synthesis of Intermediate 64, starting from 3-fluoroaniline) in DMF (5 mL) followed by HOBt (43 mg, 0.32 mmol) and EDCI (139 mg, 0.72 mmol). After 2 minutes of stirring, 2-amino-1-[4-(2-chloro-5-fluoro-phenoxy)-piperidin-1-yl]-ethanone hydrochloride (103 mg, 0.32 mmol) was added and the resulting mixture was stirred at ambient temperature overnight. Cold water was then added and the solid was collected to afford 128 mg (92.75% Yield) of 1-(3-fluoro-phenyl)-1H-[1,2,3]triazole-4-carboxylic acid {2-[4-(2-chloro-5-fluoro-phenoxy)-piperidin-1-yl]-2-oxo-ethyl}-amide. LC/MS [M+H]$^+$: 476, 96.08%. $^1$H NMR (300 MHz, DMSO-d$_6$): δ 9.4 (s, 1H), 8.54 (t, 1H), 8.0-7.96 (t, 2H), 7.72 (q, 1H), 7.54-7.34

(m, 2H), 7.34 (d, 1H), 6.9 (t, 1H), 4.9 (s, 1H), 4.3 (d, 2H), 3.8 (bs, 2H), 3.55 (bs, 2H), 2.05 (d, 2H), 1.8 (d, 2H).

Example 139

Synthesis of 1-m-Tolyl-1H-[1,2,3]triazole-4-carboxylic acid {2-oxo-2-[4-(3-trifluoromethyl-phenoxy)-piperidin-1-yl]-ethyl}-amide

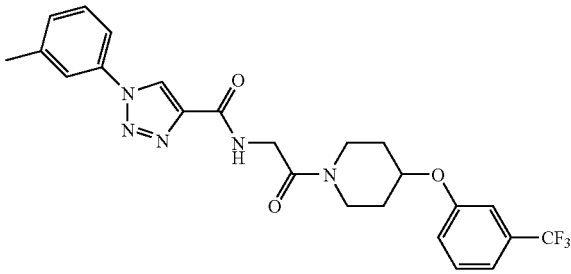

DIPEA (171 mg, 1.32 mmol) was added to a stirred solution of 1-m-Tolyl-1H-[1,2,3]triazole-4-carboxylic acid (60 mg, 0.29 mmol) (prepared by the method used for the synthesis of Intermediate 64, starting from 3-methylaniline) in DMF (5 mL) followed by HOBt (44 mg, 0.32 mmol) and EDCI (141 mg, 0.73 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (110 mg, 0.32 mmol) was added and the resulting mixture was stirred at ambient temperature overnight. Cold water was then added and the solid was collected to afford the crude solid. The crude solid obtained was purified by recrystallisation from a solvent system (3:7:0.2), EtOAc:hexane:MeOH to afford 100 mg (70.5% Yield) of 1-m-tolyl-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 488, 96.08%. $^1$H NMR (300 MHz, DMSO-d6): δ 9.3 (s, 1H), 8.5 (t, 1H), 7.84 (s, 1H), 7.8 (d, 1H), 7.56-7.44 (m, 2H), 7.38-7.24 (m, 4H), 4.8 (m, 1H), 4.2 (d, 2H), 3.9 (s, 1H), 3.8 (s, 1H), 3.5 (s, 1H), 3.3 (s, 1H), 2.4 (s, 3H), 2.1 (t, 2H), 1.8 (d, 2H).

Example 140

Synthesis of 1-m-Tolyl-1H-[1,2,3]triazole-4-carboxylic acid {2-[4-(2-chloro-5-fluoro-phenoxy)-piperidin-1-yl]-2-oxo-ethyl}-amide

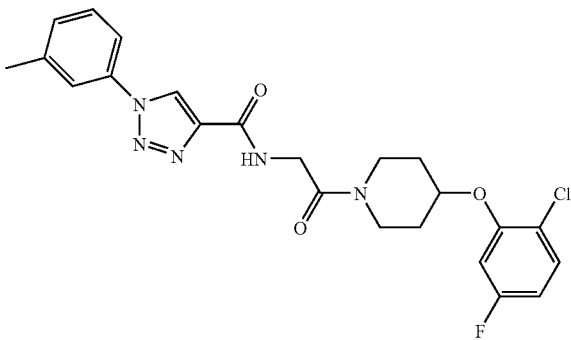

DIPEA (171 mg, 1.32 mmol) was added to a stirred solution of 1-m-tolyl-1H-[1,2,3]triazole-4-carboxylic acid (60 mg, 0.29 mmol) (prepared by the method used for the synthesis of Intermediate 64, starting from 3-methylaniline) in DMF (5 mL) followed by HOBt (44 mg, 0.32 mmol) and EDCI (141 mg, 0.73 mmol). After 2 minutes of stirring, 2-amino-1-[4-(2-chloro-5-fluoro-phenoxy)-piperidin-1-yl]-ethanone (105 mg, 0.32 mmol) was added and the resulting mixture was stirred at ambient temperature overnight. Cold water was then added and the precipitate was collected The solid obtained was purified by recrystallisation from a solvent system EtOAc:hexane:MeOH (2:8:0.2) to afford 103 mg (74.1% Yield) of 1-m-tolyl-1H-[1,2,3]triazole-4-carboxylic acid {2-[4-(2-chloro-5-fluoro-phenoxy)-piperidin-1-yl]-2-oxo-ethyl}-amide. LC/MS [M+H]$^+$: 472, 96.02%. $^1$H NMR (300 MHz, DMSO-d6): δ 8.5 (t, 1H), 7.86 (s, 1H), 7.8 (d, 1H), 7.54-7.44 (m, 2H), 7.38-7.24 (m, 4H), 6.88 (t, 1H), 4.9 (m, 1H), 4.3 (d, 2H), 3.8 (m, 2H), 3.5 (s, 2H), 2.4 (s, 3H), 2.1 (d, 2H), 1.8 (d, 2H).

Example 141

Synthesis of 1-(2-Cyano-phenyl)-1H-[1,2,3]triazole-4-carboxylic acid {2-oxo-2-[4-(3-trifluoromethyl-phenoxy)-piperidin-1-yl]-ethyl}-amide

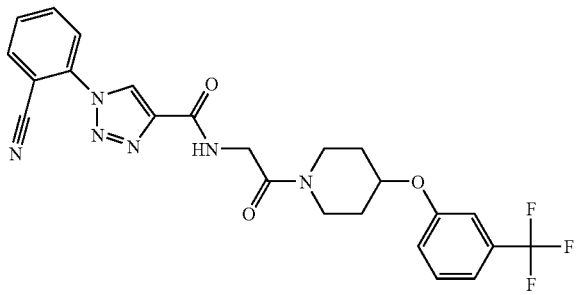

DIPEA (163 mg, 1.26 mmol) was added to a stirred solution of 1-(2-cyano-phenyl)-1H-[1,2,3]triazole-4-carboxylic acid (60 mg, 0.28 mmol) (prepared by the method used for the synthesis of Intermediate 64, starting from 2-aminobenzonitrile) in DMF (5 mL) followed by HOBt (41 mg, 0.3 mmol) and EDCI (134 mg, 0.7 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (104 mg, 0.3 mmol) was added and the resulting mixture was stirred at ambient temperature overnight. Cold water was then added and the solid was collected. The solid obtained was purified by column chromatography (using 60-120 silica gel and 30-70% EtOAc in hexane as eluent) to afford 52 mg (37.6% Yield) of 1-(2-cyano-phenyl)-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 499, 96.38%. $^1$H NMR (300 MHz, DMSO-d6): δ 9.3 (s, 1H), 8.64 (t, 1H), 8.22 (d, 1H), 8.02 (t, 2H), 7.84 (t, 1H), 7.6 (t, 1H), 7.4 (t, 3H), 4.9 (m, 1H), 4.3 (d, 2H), 4.0 (s, 1H), 3.8 (s, 1H), 3.5 (s, 1H), 2.1 (t, 2H), 1.8 (d, 2H).

Example 142

Synthesis of 1-(2-Cyano-phenyl)-1H-[1,2,3]triazole-4-carboxylic acid {2-oxo-2-[4-(3-trifluoromethyl-phenoxy)-piperidin-1-yl]-ethyl}-amide

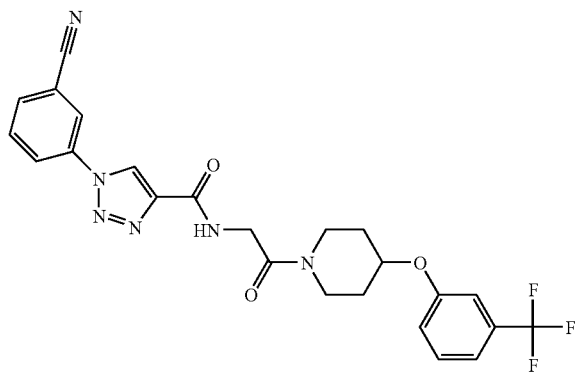

DIPEA (61 mg, 4.7 mmol) was added to a stirred solution of 1-(3-cyano-phenyl)-1H-[1,2,3]triazole-4-carboxylic acid (202 mg, 0.94 mmol) (prepared by the method used for the synthesis of Intermediate 64, starting from 3-aminobenzonitrile) in DMF (5 mL) followed by HOBt (14 mg, 1.03 mmol) and EDCI (452 mg, 2.36 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (351 mg, 1.03 mmol) was added and the resulting mixture was stirred at ambient temperature overnight. Cold water was then added and the solid was collected. The solid obtained was purified by column chromatography (using 60-120 silica gel and 30-70% EtOAc in hexane as eluent) to afford 75 mg (16% Yield) of 1-(2-cyano-phenyl)-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 499, 99.08%. $^1$H NMR (300 MHz, DMSO-d$_6$): δ 9.48 (s, 1H), 8.58 (t, 2H), 8.4 (d, 1H), 8.06 (d, 1H), 7.9 (t, 1H), 7.38 (t, 3H), 4.9 (m, 1H), 4.3 (d, 2H), 4.0 (s, 1H), 3.8 (s, 1H), 3.5 (m, 2H), 2.1 (t, 2H), 1.8 (s, 1H), 1.6 (s, 1H).

Example 143

Synthesis of 1-o-Tolyl-1H-[1,2,3]triazole-4-carboxylic acid {2-oxo-2-[4-(3-trifluoromethyl-phenoxy)-piperidin-1-yl]-ethyl}-amide

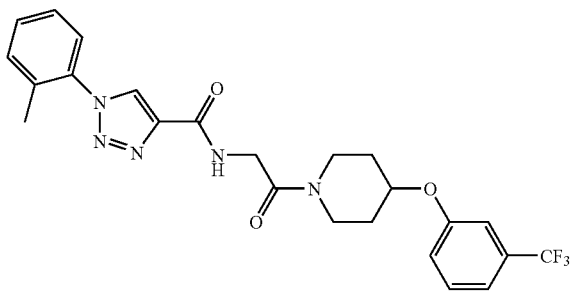

DIPEA (171 mg, 1.32 mmol) was added to a stirred solution of 1-o-tolyl-1H-[1,2,3]triazole-4-carboxylic acid (60 mg, 0.29 mmol) (prepared by the method used for the synthesis of Intermediate 64, starting from 2-methylaniline) in DMF (5 mL) followed by HOBt (44 mg, 0.32 mmol) and EDCI (141 mg, 0.73 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (110 mg, 0.32 mmol) was added and the resulting mixture was stirred at ambient temperature overnight. Cold water was then added and the solid was collected. The solid obtained was purified by recrystallisation from a solvent system (3:7:0.2), EtOAc:hexane:MeOH to afford 124 mg (86.17% Yield) 1-o-tolyl-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 488, 98.68%. $^1$H NMR (300 MHz, DMSO-d6): δ 9.0 (s, 1H), 8.5 (t, 1H), 7.6-7.48 (m, 4H), 7.48 (m, 1H), 7.36 (t, 3H), 4.9 (m, 1H), 4.3 (d, 2H), 4.0 (s, 1H), 3.8 (s, 1H), 3.6 (m, 2H), 2.2 (s, 3H), 2.1 (t, 2H), 1.7 (s, 1H), 1.6 (s, 1H).

Example 144

Synthesis of 1-Pyridin-3-yl-1H-[1,2,3]triazole-4-carboxylic acid {2-[4-(2-chloro-phenoxy)-piperidin-1-yl]-2-oxo-ethyl}-amide

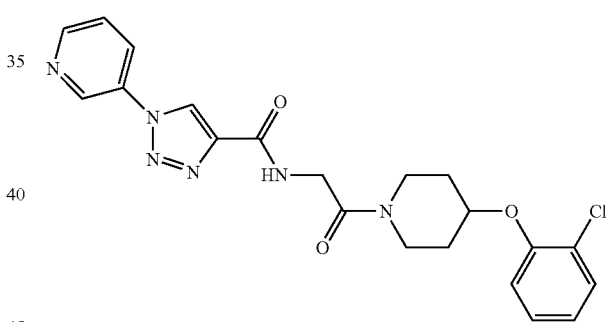

DIPEA (215 mg, 1.66 mmol) was added to a stirred solution of 1-pyridin-3-yl-1H-[1,2,3]triazole-4-carboxylic acid (70 mg, 0.37 mmol) (prepared by the method used for the synthesis of Intermediate 64, starting from 3-aminopyridine) in DMF (5 mL) followed by HOBt (55 mg, 0.41 mmol) and EDCI (177 mg, 0.92 mmol) and stirring was continued at ambient temperature. After 2 minutes of stirring, 2-amino-1-[4-(2-chloro-phenoxy)-piperidin-1-yl]-ethanone hydrochloride (prepared according to Step 1 and 5 of the General Scheme) (124 mg, 0.4 mmol) was added and the resulting mixture was stirred at ambient temperature overnight. Cold water was then added and filtered the precipitate was filtered to afford 147 mg (90.74% Yield) of 1-pyridin-3-yl-1H-[1,2,3]triazole-4-carboxylic acid {2-[4-(2-chloro-phenoxy)-piperidin-1-yl]-2-oxo-ethyl}-amide. LC/MS [M+H]$^+$: 441, 98.31%. $^1$H NMR (300 MHz, DMSO-d6): δ 9.5 (s, 1H), 9.24 (d, 1H), 8.76 (d, 1H), 8.56 (t, 1H), 8.46 (d, 1H), 7.74 (d, 1H), 7.48 (d, 1H), 7.36 (q, 2H), 7.02 (t, 1H), 4.8 (m, 1H), 4.4 (d, 2H), 3.8 (t, 2H), 3.6 (t, 2H), 2.1 (d, 2H), 1.8 (d, 2H).

Example 145

Synthesis of 1-Cyclopentyl-1H-[1,2,3]triazole-4-carboxylic acid {2-[4-(5-chloro-pyridin-3-yloxy)-piperidin-1-yl]-2-oxo-ethyl}-amide

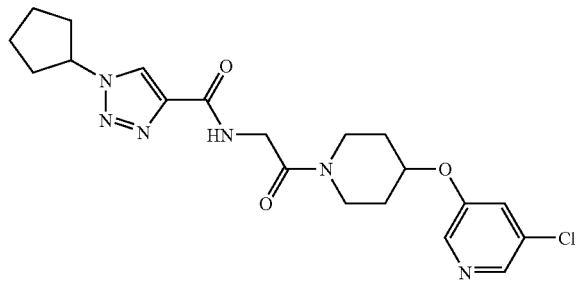

DIPEA (300 mg, 2.3 mmol) was added to a stirred solution of 1-Cyclopentyl-1H-[1,2,3]triazole-4-carboxylic acid (75 mg, 0.41 mmol (prepared by the method used for the synthesis of Intermediate 64, starting from cyclopentylamine) in DMF (5 mL) followed by HOBt (61 mg, 0.4 mmol) and EDCI (200 mg, 1 mmol). After 2 minutes of stirring, 2-amino-1-[4-(5-chloro-pyridin-3-yloxy)-piperidin-1-yl]-ethanone hydrochloride (prepared according to Step 1 and 5 of the General Scheme) (156 mg, 0.5 mmol) was added and the resulting mixture was stirred at ambient temperature overnight. Cold water was then added and filtered the precipitate was filtered. The solid obtained was purified by recrystallisation from a solvent system EtOAc:hexane:MeOH (3:7:0.2) to afford 98 mg (55% Yield) of 1-cyclopentyl-1H-[1,2,3]triazole-4-carboxylic acid {2-[4-(5-chloro-pyridin-3-yloxy)-piperidin-1-yl]-2-oxo-ethyl}-amide. LC/MS [M+H]$^+$ 433, 98.59%. $^1$H NMR (300 MHz, DMSO-d6): δ 8.7 (s, 1H), 8.34 (m, 2H), 8.24 (s, 1H), 7.74 (s, 1H), 5.1 (m, 1H), 4.9 (m, 1H), 4.2 (d, 2H), 4.0 (bs, 1H), 3.8 (bs, 1H), 3.4 (s, 1H), 3.3 (m, 1H), 2.3 (m, 2H), 2.1 (m, 4H), 1.9-1.5 (m, 6H).

Example 146

Synthesis of 1-(5-Fluoro-pyridin-3-yl)-1H-[1,2,3]triazole-4-carboxylic acid {2-[4-(2-chloro-phenoxy)-piperidin-1-yl]-2-oxo-ethyl}-amide

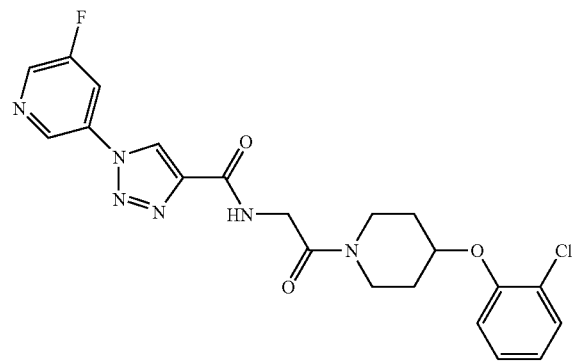

DIPEA (195 mg, 1.66 mmol) was added to a stirred solution of 1-(5-fluoro-pyridin-3-yl)-1H-[1,2,3]triazole-4-carboxylic acid (70 mg, 0.33 mmol) (prepared by the method used for the synthesis of Intermediate 64, starting from 3-amino-5-fluoropyridine) in DMF (5 mL) followed by HOBt (55 mg, 0.41 mmol) and EDCI (177 mg, 0.92 mmol). After 2 minutes of stirring, 2-amino-1-[4-(2-chloro-phenoxy)-piperidin-1-yl]-ethanone hydrochloride (prepared according to Step 1 and 5 of the General Scheme) (124 mg, 0.4 mmol) was added and the resulting mixture was stirred at ambient temperature overnight. Cold water was then added and the solid was collected to afford 147 mg (90.74% Yield) of 1-(5-fluoro-pyridin-3-yl)-1H-[1,2,3]triazole-4-carboxylic acid {2-[4-(2-chloro-phenoxy)-piperidin-1-yl]-2-oxo-ethyl}-amide. LC/MS [M+H]$^+$: 441 (M+1), 98.31%. $^1$H NMR (300 MHz, DMSO-d6): δ 9.5 (s, 1H), 9.24 (d, 1H), 8.76 (d, 1H), 8.56 (t, 1H), 8.46 (d, 1H), 7.74 (d, 1H), 7.48 (d, 1H), 7.36 (q, 2H), 7.02 (t, 1H), 4.8 (m, 1H), 4.4 (d, 2H), 3.8 (t, 2H), 3.6 (t, 2H), 2.1 (d, 2H), 1.8 (d, 2H).

Intermediate 65

Synthesis of 4-(5-Methyl-[1,3,4]oxadiazol-2-yl)-benzoic acid

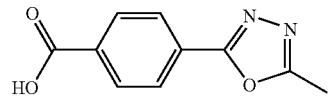

Oxalyl chloride (1.05 g, 8.3 mmol) was added to a stirred solution of terephthalic acid monomethyl ester (1 g, 5.55 mmol) in DCM (12 mL) and stirring was continued at ambient temperature for 4 hr. The reaction mixture was concentrated under reduced pressure to afford the residue. The residue was dissolved in DCM (4 mL) and to the resulting solution was added, acetic acid hydrazide (490 mg, 6.66 mmol), Et$_3$N (670 mg, 6.66 mmol) and stirring was continued at temperature overnight. The reaction mixture was diluted with water and extracted with ethylacetate, dried over sodium sulfate and concentrated under reduced pressure to afford 1 g (76.39% Yield) of 4-(N'-acetyl-hydrazinocarbonyl)-benzoic acid methyl ester. A stirred solution of 4-(N'-acetyl-hydrazinocarbonyl)-benzoic acid methyl ester (500 mg, 5.55 mmol) in POCl$_3$ (12 mL) was heated at 100° C. for 3 hr. The reaction mixture was concentrated under reduced pressure to afford the residue. The residue was diluted with cold water, extracted with ethyl acetate, washed the organic layer with sodium bicarbonate solution, saturated brine solution and dried over sodium sulfate. The organic layer was concentrated under reduced pressure to 350 mg (75.92% Yield) of afford 4-(5-methyl-[1,3,4]oxadiazol-2-yl)-benzoic acid methyl ester. LiOH.H$_2$O (330 mg, 8 mmol) was added to a solution of 4-(5-methyl-[1,3,4]oxadiazol-2-yl)-benzoic acid methyl ester (350 mg, 1.6 mmol) in the mixture of methanol (4 mL), THF (10 mL) and H$_2$O (4 mL). The resulting reaction mixture was stirred at ambient temperature for 2 hrs. The reaction mixture was concentrated The residue was diluted with water, acidified with aqueous citric acid solution, extracted with ethyl acetate and dried over sodium sulfate.

The organic layer was concentrated under reduced pressure to afford 280 mg (87.46% Yield) of 4-(5-methyl-[1,3,4]oxadiazol-2-yl)-benzoic acid.

Example 147

Synthesis of N-{2-[4-(2-Chloro-phenoxy)-piperidin-1-yl]-2-oxo-ethyl}-4-(5-methyl-[1,3,4]oxadiazol-2-yl)-benzamide

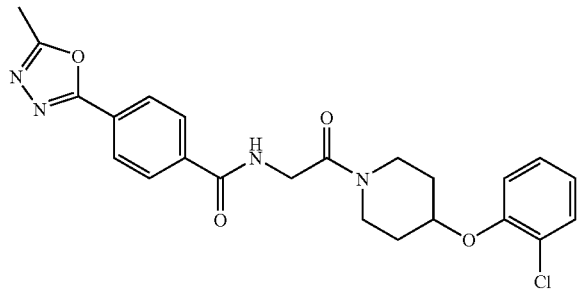

DIPEA (180 mg, 1.47 mmol) was added to a stirred solution of 1 4-(5-methyl-[1,3,4]oxadiazol-2-yl)-benzoic acid (100 mg, 0.48 mmol) in DMF (2 mL) followed by HOBt (79 mg, 0.58 mmol) and EDCI (113 mg, 0.587 mmol). After 2 minutes of stirring, 2-amino-1-[4-(2-chloro-phenoxy)-piperidin-1-yl]-ethanone hydrochloride (179 mg, 0.587 mmol) (prepared according to Step 1 and 5 of the General Scheme) was added and the resulting mixture was stirred at room temperature overnight. Cold water was then added and the product was extracted with EtOAc and the organic layer was washed with brine. The organic phase was dried over $Na_2SO_4$ and concentrated under reduced pressure The residue was purified by preparative HPLC to afford 50 mg (22.52% Yield) of N-{2-[4-(2-chloro-phenoxy)-piperidin-1-yl]-2-oxo-ethyl}-4-(5-methyl-[1,3,4]oxadiazol-2-yl)-benzamide. LC/MS [M+H]$^+$: 93.97%. $^1$H NMR (300 MHz, DMSO-$d_6$): δ 8.8 (s, 1H), 8.2-7.9 (m, 4H), 7.5-7.2 (m, 3H), 7.0 (bt, 1H), 4.8 (bs, 1H), 4.2 (bs, 2H), 3.7 (bs, 2H), 3.5 (m, 2H), 2.7-2.5 (m, 3H), 2.1-1.5 (m, 4H).

Example 148

Synthesis of 3'-Dimethylamino-biphenyl-4-carboxylic acid {2-[4-(2-chloro-phenoxy)-piperidin-1-yl]-2-oxo-ethyl}-amide

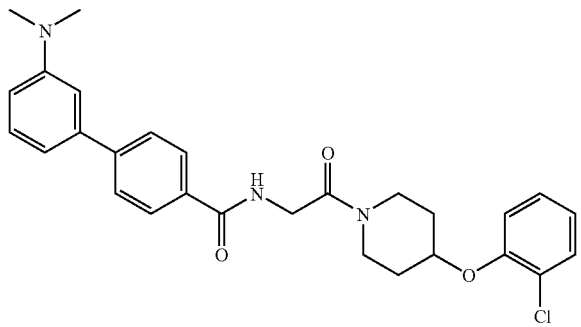

DIPEA (170 mg, 1.3 mmol) was added to a stirred solution of to a stirred solution of 3'-dimethylamino-biphenyl-4-carboxylic acid (80 mg, 0.33 mmol) (generated from methyl 3'-amino(1,1'-biphenyl)-4-carboxylate) in DMF (2 mL) followed by HOBt (49 mg, 0.36 mmol) and EDCI (126 mg, 0.66 mmol). After 2 minutes of stirring, 2-amino-1-[4-(2-chloro-phenoxy)-piperidin-1-yl]-ethanone hydrochloride (110 mg, 0.36 mmol) (prepared according to Step 1 and 5 of the General Scheme) was added and the resulting mixture was stirred at room temperature overnight. Cold water was then added and the product was extracted with EtOAc and the organic layer was washed with brine. The organic phase was dried over $Na_2SO_4$ and concentrated under reduced pressure The residue was purified by preparative HPLC to afford 36 mg (22% Yield) of 3'-dimethylamino-biphenyl-4-carboxylic acid {2-[4-(2-chloro-phenoxy)-piperidin-1-yl]-2-oxo-ethyl}-amide. LC/MS [M+H]$^+$: 492, 86.69%. $^1$H NMR (300 MHz, DMSO-$d_6$): δ 8.6 (t, 1H), 8.0-7.9 (d, 2H), 7.8-7.7 (d, 3H), 7.5-7.4 (d, 1H), 7.36-7.24 (m, 3H), 7.1-7.0 (m, 2H), 7.0-6.94 (m, 1H), 6.88-6.8 (d, 1H), 4.8 (q, 1H), 4.2 (d, 2H), 4.0-3.7 (m, 4H), 3.5 (m, 3H), 3.0 (s, 6H), 2.0-1.8 (m, 3H), 1.8-1.6 (m, 3H).

Intermediate 66

Synthesis of 4-(Pyrrolidine-1-carbonyl)-benzoic acid

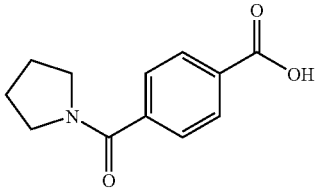

DIPEA (1.26 g, 9.7 mmol) was added to a stirred solution of terephthalic acid monomethyl ester (500 mg, 2.77 mmol) in DMF (3 mL) followed by HOBt (410 mg, 3.0 mmol) and EDCI (1.32 g, 7.0 mmol). After 2 minutes of stirring, pyrrolidine (215 mg, 3.0 mmol) was added and the resulting mixture was stirred at room temperature overnight. The reaction mixture was diluted with cold water, the precipitate was collected to afford 53 mg (81.9% Yield) of 4-(pyrrolidine-1-carbonyl)-benzoic acid methyl ester. LiOH.H$_2$O (285 mg, 6.8 mmol) was added to a solution of 4-(pyrrolidine-1-carbonyl)-benzoic acid methyl ester (530 mg, 2.27 mmol) in a mixture of methanol (2 mL), THF (6 mL) and H$_2$O (2 mL). The reaction mixture was stirred at ambient temperature for 3 hrs. The reaction mixture was concentrated, the residue was diluted with water, and acidified with conc. HCl. The solid was filtered and dried to afford 41 mg (82.32% Yield).

Example 149

Synthesis of N-{2-Oxo-2-[4-(3-trifluoromethyl-phenoxy)-piperidin-1-yl]-ethyl}-4-(pyrrolidine-1-carbonyl)-benzamide

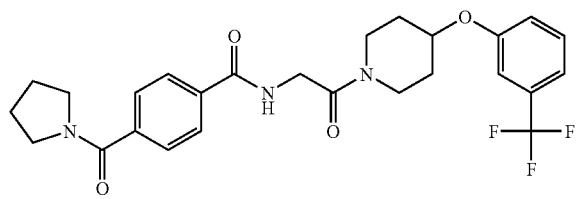

DIPEA (200 mg, 1.5 mmol) was added to a stirred solution of 4-(pyrrolidine-1-carbonyl)-benzoic acid (75 g, 0.34 mmol) in DMF (5 mL) followed by HOBt (50 mg, 0.37 mmol) and EDCI (164 mg, 0.85 mmol). After 2 minutes of stirring, 2-amino-1-[4-(3-trifluoromethyl-phenoxy)-piperidin-1-yl]-ethanone hydrochloride (127 mg, 0.37 mmol) (prepared according to Step 1 and 5 of the General Scheme) was added and the resulting mixture was stirred at room temperature overnight. The reaction mixture was diluted with cold water, the precipitate was collected to afford 130 mg (75.58% Yield) of N-{2-oxo-2-[4-(3-trifluoromethyl-phenoxy)-piperidin-1-yl]-ethyl}-4-(pyrrolidine-1-carbonyl)-benzamide. LC/MS [M+H]$^+$: 504, 94.9%. $^1$H NMR (300 MHz, DMSO-d$_6$): δ 7.2 (t, 1H), 7.96 (d, 2H), 7.64-7.48 (m, 3H), 7.36 (t, 3H), 4.9 (b, 1H), 4.2 (d, 2H), 4.0 (d, 2H), 3.5 (t, 2H), 3.4 (t, 2H), 2.1-1.8 (m, 6H), 1.7 (m, 3H).

Intermediate 67

Synthesis of 9H-Carbazole-3-carboxylic acid

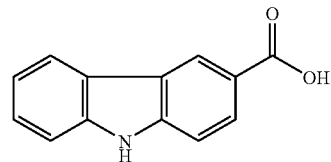

A mixture of dicylcohexylphosphino-2',3'-dimethoxy biphenyl (17 mg, 0.04 mmol), palladium(II) acetate (5 mg, 0.02 mmol) in toluene (20 mL) was degassed with argon gas for 15 min. To the resulting mixture was added aniline (136 mg, 1.4 mmol), K$_3$PO$_4$ (636 mg, 3.0 mmol), and 4-bromobenzoic acid methyl ester (300 mg, 1.4 mmol) and stirring was continued at reflux temperature overnight. After completion of the reaction, the reaction mixture was filtered through celite and the filtrate collected was concentrated under reduced pressure. Purification by column chromatography (using 60-120 silica gel and 15% ethyl acetate in hexane as eluent) to afford 200 mg (63.4% Yield) of 4-phenylamino-benzoic acid methyl ester. A stirred solution of 4-phenylamino-benzoic acid methyl ester (98 mg, 0.43 mmol), Palladium acetate (193 mg, 0.86 mmol) in acetic acid (2 mL) was heated at 110° C. for 15 hr. After completion of the reaction, the reaction mixture was diluted with water, extracted with ethyl acetate and washed with sodium bicarbonate solution. The organic layer collected was dried over sodium sulfate and concentrated under reduced pressure. Purification by column chromatography (using 60-120 silica gel and 10% ethyl acetate in hexane as eluent) to afford 120 mg (60.3% Yield) of 9H-carbazole-3-carboxylic acid methyl ester. LiOH.H$_2$O (680 mg, 16.2 mmol) was added to a stirred solution of 9H-carbazole-3-carboxylic acid methyl ester (120 mg, 0.53 mmol) in the mixture of methanol (1 mL), THF (3 mL) and H$_2$O (1 mL). The reaction mixture was stirred at 60° C. for 3 hrs. The reaction mixture was concentrated. The residue was diluted with water, acidified with aqueous 10% aqueous HCl solution, filtered the solid to afford 104 mg (92.85% Yields) of 9H-carbazole-3-carboxylic acid.

Example 150

Synthesis of 9H-Carbazole-3-carboxylic acid {2-oxo-2-[4-(3-trifluoromethyl-phenoxy)-piperidin-1-yl]-ethyl}-amide

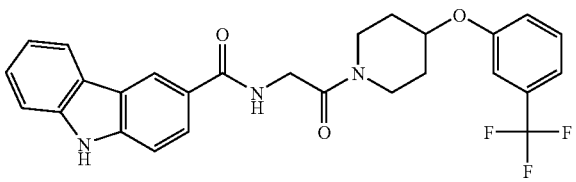

DIPEA (137 mg, 1.0 mmol) was added to a stirred solution of to a stirred solution of 9H-carbazole-3-carboxylic acid (50 mg, 0.23 mmol) in DMF (4 mL) followed by HOBt (35 mg, 0.26 mmol) and EDCI (116 mg, 0.59 mmol). After 2 minutes, 2-amino-1-[4-(3-trifluoromethyl-phenoxy)-piperidin-1-yl]-ethanone hydrochloride (88 mg, 0.26 mmol) (prepared according to Step 1 and 5 of the General Scheme) was added and the resulting mixture was stirred at ambient temperature overnight. The reaction mixture was diluted with cold water and the precipitate was filtered. The solid obtained was purified by recrystallisation from a mixture of 10% ethyl acetate in hexane and 50% MeOH in H$_2$O to afford 81 mg (69.23% Yield) of 9H-carbazole-3-carboxylic acid {2-oxo-2-[4-(3-trifluoromethyl-phenoxy)-piperidin-1-yl]-ethyl}-amide.
LC/MS [M+H]$^+$: 496, 91.03%. $^1$H NMR (300 MHz, DMSO-d$_6$): δ 11.6 (s, 1H), 8.8 (s, 1H), 8.6 (t, 1H), 8.1 (d, 1H), 8.0 (d, 1H), 7.6 (d, 2H), 7.46 (t, 1H), 7.36 (t, 2H), 7.24 (t, 1H), 4.9 (b, 1H), 4.3 (d, 3H), 4.0 (d, 2H), 3.5 (d, 2H), 2.1 (t, 2H), 1.7 (d, 2H).

167

Intermediate 68

Synthesis of 1-Phenyl-1H-imidazole-4-carboxylic acid

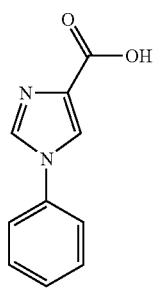

A stirred solution of 1H-imidazole-4-carboxylic acid (0.5 g, 0.00446 mmol), concentrated sulfuric acid (0.5 mL) and MeOH (20 mL) was heated to reflux overnight. The reaction mixture was concentrated under reduced pressure. The residue was diluted with cold water, extracted with ethyl acetate and washed the organic layer with sodium bicarbonate. The organic layer was dried over sodium sulfate and concentrated under reduced pressure to afford 325 mg (58% Yield) of 1H-imidazole-4-carboxylic acid methyl ester. A mixture of 1H-imidazole-4-carboxylic acid methyl ester (225 mg, 1.8 mmol), cuprous oxide (225 mg, 1.8 mmol), iodobenzene (736 mg, 3.6 mmol), 1,10-phenanthroline (320 mg, 1.8 mmol) and cesium carbonate (1.74 g, 5.3 mmol) in DMSO (2 mL) in a seal tube was subjected to reaction in a microwave reactor (time: 5 min, temp: 90° C., power: zero) The reaction mixture was filtered through celite and the filtrate collected was concentrated under reduced pressure. The residue was diluted with cold water, extracted with ethyl acetate, dried over sodium sulfate and concentrated under reduced pressure to afford the residue. Purification by column chromatography (using 60-120 silica gel and 50% ethyl acetate in hexane as eluent) to afford 200 mg (55% Yield) of 1-phenyl-1H-imidazole-4-carboxylic acid methyl ester. LiOH.H$_2$O (143 mg, 3.4 mmol) was added to a stirred solution of 1-phenyl-1H-imidazole-4-carboxylic acid methyl ester (231 mg, 1.1 mmol) in a mixture of THF (3 mL), MeOH (1 mL), H$_2$O (1 mL) and stirring was continued at ambient temperature for 3 hrs. The reaction mixture was concentrated under reduced pressure. Cold water was then added and acidified it with 10% aqueous HCl, the solid was collected to afford 180 mg (83.7% Yield) of 1-phenyl-1H-imidazole-4-carboxylic acid.

Example 151

1-Phenyl-1H-imidazole-4-carboxylic acid {2-oxo-2-[4-(3-trifluoromethyl-phenoxy)-piperidin-1-yl]-ethyl}-amide

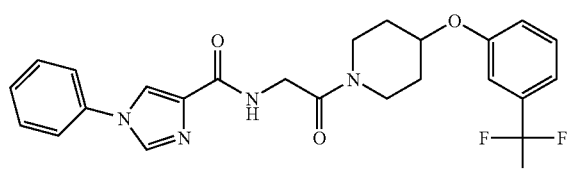

DIPEA (186 mg, 1.4 mmol) was added to a stirred solution of 1-phenyl-1H-imidazole-4-carboxylic acid (60 mg, 0.32 mmol) in DMF (5 mL) followed by HOBt (47 mg, 0.35 mmol) and EDCI (153 mg, 0.8 mmol). After 2 minutes of stirring, 2-amino-1-[4-(3-trifluoromethyl-phenoxy)-piperidin-1-yl]-ethanone hydrochloride (119 mg, 0.35 mmol) (prepared according to Step 1 and 5 of the General Scheme) was added and the resulting mixture was stirred at ambient temperature overnight. The reaction mixture was diluted with cold water, the solid was collected to afford the 129 mg (86% Yield) of 1-phenyl-1H-imidazole-4-carboxylic acid {2-oxo-2-[4-(3-trifluoromethyl-phenoxy)-piperidin-1-yl]-ethyl}-amide. LC/MS [M+H]$^+$: Purity: 473 (M+1), 96.61%. $^1$H NMR (300 MHz, DMSO-d$_6$): δ 8.4 (s, 1H), 8.32 (s, 1H), 8.08 (t, 1H), 7.8 (d, 2H), 7.6-7.48 (t, 3H), 7.46 (t, 1H), 7.36-7.24 (t, 3H), 4.9 (s, 1H), 4.2 (d, 2H), 4.0 (bs, 1H), 3.8 (bs, 1H), 3.5 (d, 2H), 2.1 (t, 2H), 1.8 (d, 2H).

Example 152

Synthesis of 1-Phenyl-1H-imidazole-4-carboxylic acid {2-[4-(2-chloro-5-fluoro-phenoxy)-piperidin-1-yl]-2-oxo-ethyl}-amide

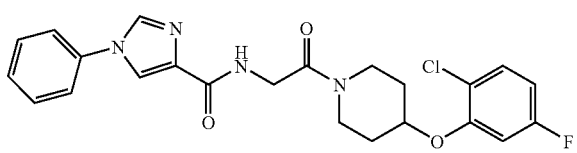

DIPEA (186 mg, 1.44 mmol) was added to a stirred solution of 1-phenyl-1H-imidazole-4-carboxylic acid (60 mg, 0.32 mmol) in DMF (5 mL) followed by HOBt (47 mg, 0.35 mmol) and EDCI (153 mg, 0.8 mmol). After 2 minutes of stirring, 2-amino-1-[4-(2-chloro-5-fluoro-phenoxy)-piperidin-1-yl]-ethanone hydrochloride (prepared according to Step 1 and 5 of the General Scheme) (119 mg, 0.37 mmol) was added and the resulting mixture was stirred at ambient temperature overnight. Cold water was added and the precipitate formed was collected to afford the residue. The residue was purified by preparative HPLC to afford 80 mg (55% Yield) of 1-phenyl-1H-imidazole-4-carboxylic acid {2-[4-(2-chloro-5-fluoro-phenoxy)-piperidin-1-yl]-2-oxo-ethyl}-amide. LC/MS [M+H]$^+$: 457.14, 96.27%. $^1$H NMR (300 MHz, DMSO-d$_6$): δ 8.46 (s, 1H), 8.14 (s, 1H), 8.1 (t, 2H), 7.8 (d, 2H), 7.6-7.4 (m, 4H), 7.32 (d, 1H), 6.9 (t, 1H), 4.9 (bs, 1H), 4.2 (d, 2H), 3.8 (b, 2H), 3.55 (b, 2H), 2.1 (d, 2H), 1.8 (d, 2H).

Example 153

Synthesis of 5-Phenyl-1H-pyrazole-3-carboxylic acid {2-[4-(2-formyl-phenoxy)-piperidin-1-yl]-2-oxo-ethyl}-amide

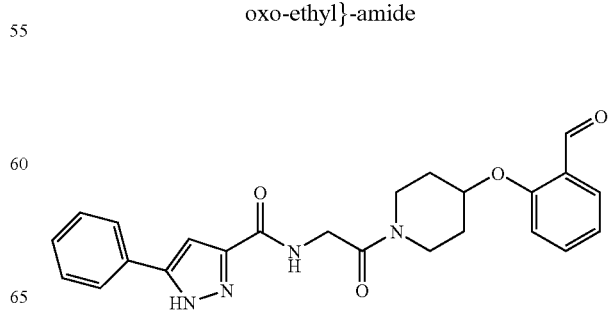

DIPEA (360 mg, 2.8 mmol) was added to a stirred solution of [(5-phenyl-1H-pyrazole-3-carbonyl)-amino]-acetic acid (190 mg, 0.8 mmol) in DMF (2.0 mL) followed by HOBt (160 mg, 1.2 mmol) and EDCI.HCl (230 mg, 1.2 mmol). After 2 minutes of stirring, 2-(piperidin-4-yloxy)-benzaldehyde hydrochloride (200 mg, 0.8 mmol) (prepared according to Step 1 and 5 of the General Scheme) was added and stirring was continued at ambient temperature overnight. The reaction mixture was diluted with water, extracted with ethyl acetate, washed with brine and concentrated The residue was purified by column chromatography (using neutral alumina and 5% MeOH in CHCl$_3$) to afford 150 mg (44% Yield) of 5-phenyl-1H-pyrazole-3-carboxylic acid {2-[4-(2-formyl-phenoxy)-piperidin-1-yl]-2-oxo-ethyl}-amide. LC/MS [M+H]$^+$: 433.18, 98.8%, $^1$H NMR (300 MHz, DMSO-d$_6$): δ13.8 (m, 1H), 10.3 (s, 1H), 8.2 (m, 1H), 7.8 (m, 2H), 7.7 (m, 2H), 7.5 (m, 2H), 7.4 (m, 2H), 7.1 (m, 2H), 5.0 (m, 1H), 4.2 (m, 2H), 3.7 (m, 2H), 3.5 (m, 2H), 2.0 (m, 2H), 1.8 (m, 2H).

Example 154

Synthesis of 2-(1-{2-[(5-Phenyl-1H-pyrazole-3-carbonyl)-amino]-acetyl}-piperidin-4-yloxy)-benzoic acid

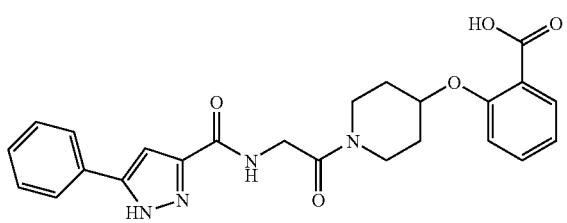

Sulphamic acid (34 mg, 0.3 mmol) was added to stirred a mixture of 5-phenyl-1H-pyrazole-3-carboxylic acid {2-[4-(2-formyl-phenoxy)-piperidin-1-yl]-2-oxo-ethyl}-amide (50 mg, 0.1 mmol) in acetone (1 mL). After 2 minutes, sodium chlorite (36 mg, 0.4 mmol) was added and the resulting mixture was stirred at ambient temperature for 1 hour. Water was added and the solid obtained was isolated by filtration to afford 24 mg (53% yield) of 2-(1-{2-[(5-phenyl-1H-pyrazole-3-carbonyl)-amino]-acetyl}-piperidin-4-yloxy)-benzoic acid. LC/MS [M+H]$^+$: 449.17, 90.6%, $^1$H NMR (300 MHz, DMSO-d$_6$): δ13.8 (b, 1H), 12.8 (b, 1H), 8.1 (m, 1H), 7.8 (m, 2H), 7.6 (m, 1H), 7.5 (m, 3H), 7.4 (m, 1H), 7.2 (m, 1H), 7.1 (m, 1H), 7.0 (m, 1H), 4.8 (m, 1H), 4.2 (m, 2H), 3.7 (m, 3H), 3.5 (m, 1H), 2.0 (m, 1H), 1.7 (m, 3H).

Example 155

Synthesis of 5-Phenyl-1H-pyrazole-3-carboxylic acid {2-[4-(2-hydroxymethyl-phenoxy)-piperidin-1-yl]-2-oxo-ethyl}-amide

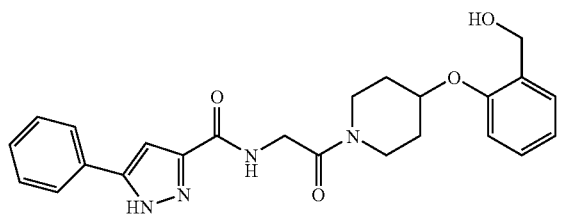

NaBH$_4$ (5 mg, 0.12 mmol) was added to stirred a mixture of 5-phenyl-1H-pyrazole-3-carboxylic acid {2-[4-(2-formyl-phenoxy)-piperidin-1-yl]-2-oxo-ethyl}-amide (50 mg, 0.1 mmol) in MeOH (2 mL) and stirring was continued for 1 hr. The reaction mixture was diluted with water, extracted with ethyl acetate and dried over sodium sulfate. The organic layer was concentrated under reduced pressure to afford the residue. The residue was purified by recrystallisation from CHCl$_3$ in hexane mixture to afford 25 mg (58% yield) of 5-phenyl-1H-pyrazole-3-carboxylic acid {2-[4-(2-hydroxymethyl-phenoxy)-piperidin-1-yl]-2-oxo-ethyl}-amide. LC/MS [M+H]$^+$: 435.2, 93.8%, $^1$H NMR (300 MHz, DMSO-d$_6$): δ13.8 (m, 1H), 8.0 (m, 1H), 7.8 (m, 2H), 7.5 (m, 2H), 7.4 (m, 2H), 7.2 (m, 1H), 7.1 (m, 1H), 7.0 (m, 1H), 6.9 (m, 1H), 5.0 (m, 1H), 4.7 (m, 1H), 4.5 (m, 2H), 3.7 (m, 3H), 3.5 (m, 2H), 2.0 (m, 2H), 1.7 (m, 2H).

Example 155

Synthesis of 5-Phenyl-1H-pyrazole-3-carboxylic acid {2-oxo-2-[4-(3,4,5-trifluoro-phenoxy)-piperidin-1-yl]-ethyl}-amide

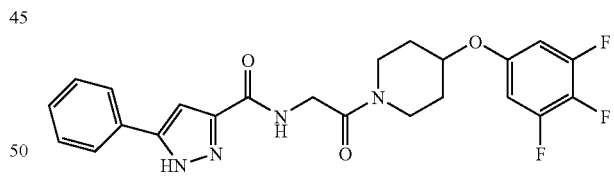

DIPEA (135 mg, 1.0 mmol) was added to a stirred solution of [(5-phenyl-1H-pyrazole-3-carbonyl)-amino]-acetic acid (69 mg, 0.3 mmol) in DMF (2.0 mL) followed by HOBt (61 mg, 0.45 mmol) and EDCI.HCl (85 mg, 0.45 mmol). After 2 minutes of stirring, 4-(3,4,5-trifluoro-phenoxy)-piperidine hydrochloride (75 mg, 0.3 mmol) (prepared according to Step 1 and 5 of the General Scheme) was added and stirring was continued at ambient temperature overnight. The reaction mixture was diluted with water, extracted with ethyl acetate, washed with brine and concentrated The residue was purified by column chromatography (using neutral alumina and 5% MeOH in CHCl$_3$) to afford 26 mg (19% Yield) of 5-phenyl-1H-pyrazole-3-carboxylic acid {2-oxo-2-[4-(3,4,5-trifluoro-phenoxy)-piperidin-1-yl]-ethyl}-amide. LC/MS [M+H]$^+$: 459.16, 97.98%, $^1$H NMR (300 MHz, DMSO-d$_6$): δ13.8 (m, 1H), 8.1 (m, 1H), 7.8 (m, 2H), 7.4 (m, 4H), 7.1 (m, 1H), 4.7 (m, 1H), 4.2 (m, 2H), 3.9 (m, 1H), 3.7 (m, 1H), 2.0 (m, 3H), 1.7 (m, 3H).

Example 156

Synthesis of 5-Phenyl-1H-pyrazole-3-carboxylic acid (2-{4-[2-(hydroxyimino-methyl)-phenoxy]-piperidin-1-yl}-2-oxo-ethyl)-amide

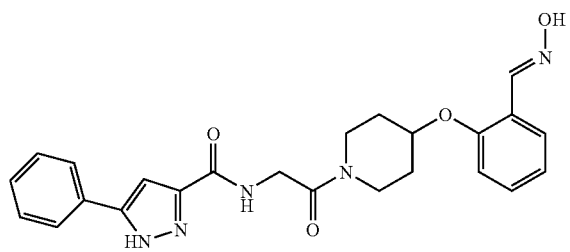

Hydroxylamine hydrochloride (33 mg, 0.5 mmol) was added to a stirred cold (0° C.) mixture of 5-phenyl-1H-pyrazole-3-carboxylic acid {2-[4-(2-formyl-phenoxy)-piperidin-1-yl]-2-oxo-ethyl}-amide (150 mg, 0.4 mmol) and sodium acetate (65 mg, 0.8 mmol) in MeOH (3 mL) and stirring was continued at ambient temperature for 4 hrs. The reaction mixture was diluted with water, extracted with ethyl acetate and dried over sodium sulfate. The organic layer was concentrated under reduced pressure to afford 25 mg (58% yield) of 5-phenyl-1H-pyrazole-3-carboxylic acid {2-[4-(2-hydroxymethyl-phenoxy)-piperidin-1-yl]-2-oxo-ethyl}-amide. LC/MS [M+H]$^+$: 435.2, 93.8%, $^1$H NMR (300 MHz, DMSO-d$_6$): δ8.3 (s, 1H), 8.2 (b, 1H), 7.8 (d, 2H), 7.7 (d, 1H), 7.5 (t, 2H), 7.4 (t, 2H), 7.2 (d, 2H), 7.0 (t, 1H), 4.8 (m, 1H), 4.2 (m, 2H), 3.8 (m, 2H), 3.5 (m, 2H), 2.0 (m, 2H), 1.8 (m, 2H).

Example 157

Synthesis of 5-Phenyl-1H-pyrazole-3-carboxylic acid {2-oxo-2-[4-(2-trifluoromethyl-phenoxy)-piperidin-1-yl]-ethyl}-amide

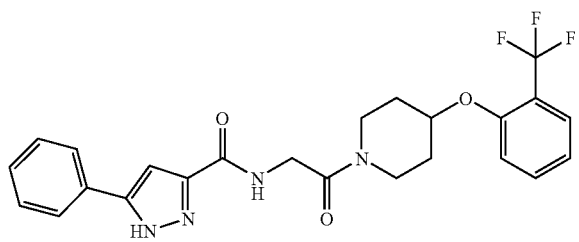

DIPEA (154 mg, 1.2 mmol) was added to a stirred solution of [(5-phenyl-1H-pyrazole-3-carbonyl)-amino]-acetic acid (100 mg, 0.4 mmol) in DMF (2.0 mL) followed by HOBt (60 mg, 0.49 mmol) and EDCI.HCl (93 mg, 0.49 mmol). After 2 minutes of stirring, 4-(2-trifluoromethyl-phenoxy)-piperidine trifluoroacetate (167 mg, 0.49 mmol) (prepared according to Step 1 and 5 of the General Scheme) was added and stirring was continued at ambient temperature overnight. The reaction mixture was diluted with water, extracted with ethylacetate, washed with brine and concentrated to afford 111 mg (57.81% Yield) of 5-phenyl-1H-pyrazole-3-carboxylic acid {2-oxo-2-[4-(2-trifluoromethyl-phenoxy)-piperidin-1-yl]-ethyl}-amide. LC/MS [M+H]$^+$: 473.17, 97.38%, $^1$H NMR (300 MHz, DMSO-d$_6$): δ13.8 (m, 1H), 8.1 (bs, 1H), 7.9-7.3 (m, 8H), 7.2-7.0 (m, 2H), 4.9 (bs, 1H), 4.2 (m, 2H), 3.8-2.9 (m, 4H), 2.0-1.7 (m, 3H).

Example 158

Synthesis of 5-Phenyl-1H-pyrazole-3-carboxylic acid {2-[4-(3-cyano-phenoxy)-piperidin-1-yl]-2-oxo-ethyl}-amide

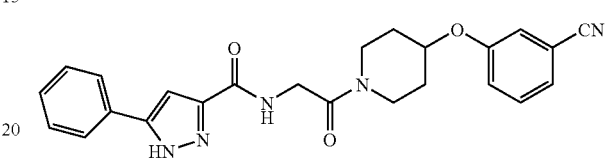

DIPEA (316 mg, 2.5 mmol) was added to a stirred solution of [(5-phenyl-1H-pyrazole-3-carbonyl)-amino]-acetic acid (181 mg, 0.7 mmol) in DMF (3 mL) followed by HOBt (108 mg, 0.8 mmol) and EDCI.HCl (160 mg, 0.8 mmol). After 2 minutes of stirring, 3-(piperidin-4-yloxy)-benzonitrile hydrochloride (50 mg, 0.7 mmol) (prepared according to Step 1 and 5 of the General Scheme) was added and stirring was continued at ambient temperature overnight. The reaction mixture was diluted with water, extracted with ethyl acetate, washed with brine and concentrated The residue was purified by column chromatography (using neutral alumina and 5% MeOH in CHCl$_3$) afford 44 mg (14.3% Yield) of 5-phenyl-1H-pyrazole-3-carboxylic acid {2-[4-(3-cyano-phenoxy)-piperidin-1-yl]-2-oxo-ethyl}-amide. LC/MS [M+H]$^+$: 473.17, 99.16%, $^1$H NMR (300 MHz, DMSO-d$_6$): δ 8.1 (m, 1H), 7.8 (m, 2H), 7.6 (m, 4H), 7.4 (m, 3H), 7.1 (b, 1H), 4.8 (m, 1H), 4.2 (m, 2H), 4.0 (m, 1H), 3.8 (m, 1H), 2.0 (m, 2H), 1.5 (m, 2H).

Example 159

Synthesis of 5-Phenyl-1H-pyrazole-3-carboxylic acid (2-{4-[2-(methoxyimino-methyl)-phenoxy]-piperidin-1-yl}-2-oxo-ethyl)-amide

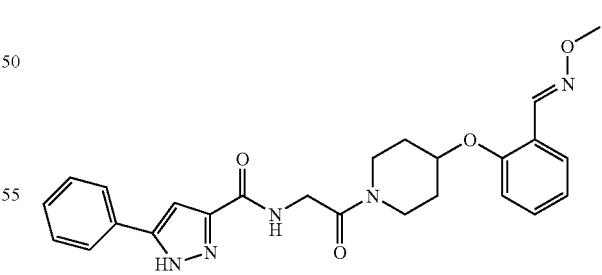

O-Methyl-hydroxylamine hydrochloride (23 mg, 0.27 mmol) was added to a stirred cold (0° C.) mixture of 5-phenyl-1H-pyrazole-3-carboxylic acid {2-[4-(2-formyl-phenoxy)-piperidin-1-yl]-2-oxo-ethyl}-amide (100 mg, 0.23 mmol) and sodium acetate (56 mg, 0.7 mmol) in MeOH (10 mL) and stirring was continued at ambient temperature for 4 hrs. The reaction mixture was diluted with water, extracted with ethyl acetate, dried over sodium sulfate, and the organic layer was concentrated under reduced pressure. The residue was purified by preparative HPLC to afford 33 mg (31.13% yield) of 5-phenyl-1H-pyrazole-3-carboxylic acid (2-{4-[2-(methoxyimino-methyl)-phenoxy]-piperidin-1-yl}-2-oxo-ethyl)-amide. LC/MS [M+H]$^+$: 462.2, 96.3%. $^1$H NMR (300 MHz, DMSO-d$_6$): δ13.7 (s, 1H), 8.4 (s, 1H), 8.1 (t, 1H), 7.8 (t, 2H), 7.7 (d, 1H), 7.5-7.34 (m, 4H), 7.2 (d, 1H), 7.1 (s, 1H), 7.0 (t, 1H), 4.8 (bs, 1H), 4.2 (b, 2H), 3.9 (s, 3H), 3.8-3.6 (bs, 2H), 3.5 (b, 2H), 2.1-1.9 (b, 2H), 1.8-1.6 (b, 2H).

Example 160

Synthesis of 5-Phenyl-1H-pyrazole-3-carboxylic acid {2-[4-(2-methylcarbamoyl-phenoxy)-piperidin-1-yl]-2-oxo-ethyl}-amide

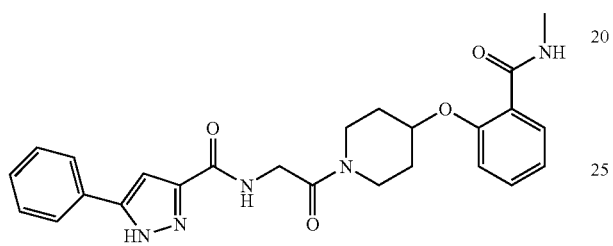

DIPEA (72 mg, 0.56 mmol) was added to a stirred solution of 2-(1-{2-[(5-phenyl-1H-pyrazole-3-carbonyl)-amino]-acetyl}-piperidin-4-yloxy)-benzoic acid (75 mg, 0.16 mmol) in DMF (2 mL) followed by HOBt (33 mg, 0.24 mmol) and EDCI.HCl (46 mg, 0.24 mmol). After 2 minutes of stirring, methyl amine hydrochloride (11 mg, 0.16 mmol) was added and stirring was continued at ambient temperature overnight. The reaction mixture was diluted with water, extracted with ethyl acetate, washed with brine and concentrated The residue was purified by column chromatography (using neutral alumina and 5% MeOH in CHCl$_3$) afford 23 mg (31.5% Yield) of 5-phenyl-1H-pyrazole-3-carboxylic acid {2-[4-(2-methylcarbamoyl-phenoxy)-piperidin-1-yl]-2-oxo-ethyl}-amide. LC/MS [M+H]$^+$: 462.2, 96.9%. $^1$H NMR (300 MHz, DMSO-d$_6$): δ 8.1 (m, 1H), 8.0 (m, 1H), 7.8 (m, 2H), 7.6 (m, 1H), 7.4 (m, 4H), 7.2 (m, 1H), 7.1 (b, 1H), 7.0 (m, 1H), 4.8 (b, 1H), 4.2 (m, 2H), 3.6 (m, 3H), 2.8 (d, 3H), 2.0 (m, 2H), 1.8 (m, 2H).

Example 161

Synthesis of 5-Phenyl-1H-pyrazole-3-carboxylic acid {2-[4-(2-carbamoyl-phenoxy)-piperidin-1-yl]-2-oxo-ethyl}-amide

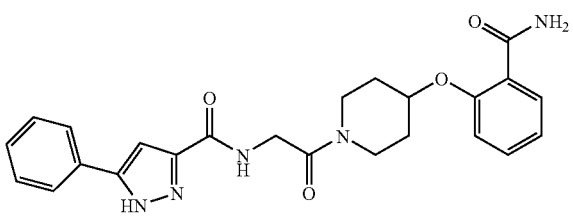

N-Methyl morpholine (28 mg, 0.28 mmol) was added to a cold (−70° C.) solution of 2-(1-{2-[(5-phenyl-1H-pyrazole-3-carbonyl)-amino]-acetyl}-piperidin-4-yloxy)-benzoic acid (100 mg, 0.2 mmol) in THF (2 mL) followed by isobutyl chloroformate (41 mg, 0.3 mmol) and stirring was continued at the at −70° C. for 1 hr. After complete formation of anhydride, ammonia gas was bubbled through the reaction mixture at −70° C. for 10 minutes. The resulting mixture was then stirred at room temperature for 1 hr. Water (10 mL) was added, the precipitated was filtered and dried to afford 54 mg (60.6% yield) of 5-phenyl-1H-pyrazole-3-carboxylic acid {2-[4-(2-carbamoyl-phenoxy)-piperidin-1-yl]-2-oxo-ethyl}-amide. LC/MS [M+H]$^+$: 448.18, 93.4%. $^1$H NMR (300 MHz, DMSO-d$_6$): δ 7.9 (m, 1H), 7.8 (m, 2H), 7.5 (m, 3H), 7.4 (m, 1H), 7.3 (m, 1H), 7.1 (m, 2H), 4.3 (s, 2H), 4.0 (m, 1H), 3.8 (m, 1H), 3.5 (m, 2H), 2.1 (m, 3H), 1.9 (m, 3H), 1.1 (m, 1H).

Example 162

Synthesis of 5-(2-Trifluoromethyl-phenyl)-1H-pyrazole-3-carboxylic acid {2-[4-(2-chloro-phenylamino)-piperidin-1-yl]-2-oxo-ethyl}-amide

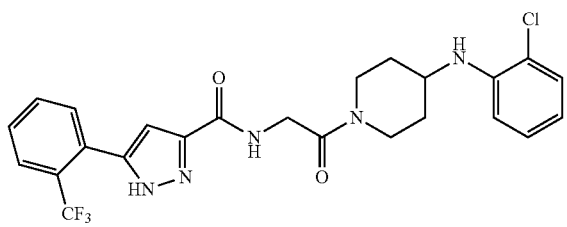

DIPEA (137 mg, 1.06 mmol) was added to a stirred solution {[5-(2-trifluoromethyl-phenyl)-1H-pyrazole-3-carbonyl]-amino}-acetic acid (95 mg, 0.3 mmol) (prepared by the method used for the synthesis of Intermediate 30, starting from (2'-trifluoromethyl)acetophenone) in DMF (2.0 mL) followed by HOBt (47 mg, 0.35 mmol) and EDCI.HCl (67 mg, 0.35 mmol). After 2 minutes of stirring, (2-chloro-phenyl)-piperidin-4-yl-amine dihydrochloride (75 mg, 0.3 mmol) was added and stirring was continued at ambient temperature overnight. The reaction mixture was diluted with water, extracted with ethyl acetate, washed with brine and concentrated under reduced pressure. The residue was purified washing with diethyl ether to afford 67 mg (43.5% Yield) of 5-(2-trifluoromethyl-phenyl)-1H-pyrazole-3-carboxylic acid {2-[4-(2-chloro-phenylamino)-piperidin-1-yl]-2-oxo-ethyl}-amide. LC/MS [M+H]$^+$: 506.12, 97.9%, $^1$H NMR (300 MHz, DMSO-d$_6$): δ13.2 (d, 1H), 8.2 (m, 1H), 7.5 (m, 5H), 7.2 (m, 2H), 6.85 (m, 1H), 6.5 (m, 2H), 4.8 (m, 1H), 4.3

(m, 1H), 4.1 (d, 2H), 4.0 (m, 1H), 3.6 (m, 1H), 3.2 (m, 1H), 2.7 (m, 1H), 1.9 (m, 2H), 1.3 (m, 2H).

Example 163

Synthesis of 5-Phenyl-1H-pyrazole-3-carboxylic acid {2-[4-(3-cyano-phenylamino)-piperidin-1-yl]-2-oxo-ethyl}-amide

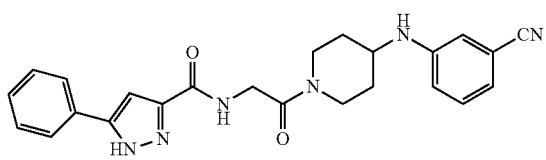

DIPEA (135 mg, 1.0 mmol) was added to a stirred of [(5-phenyl-1H-pyrazole-3-carbonyl)-amino]-acetic acid (150 mg, 0.7 mmol) in DMF (4 mL) followed by HOBt (108 mg, 0.8 mmol) and EDCI.HCl (160 mg, 0.8 mmol). After 2 minutes of stirring 3-(piperidin-4-ylamino)-benzonitrile dihydrochloride (prepared according to Step 2 and 5 of the General Scheme) was added and stirring was continued at ambient temperature overnight. The reaction mixture was diluted with water, extracted with ethyl acetate, washed with brine and concentrated. The residue was purified by column chromatography (using neutral alumina and 5% MeOH in $CHCl_3$) to afford 91 mg (42% Yield) of 5-phenyl-1H-pyrazole-3-carboxylic acid {2-[4-(3-cyano-phenylamino)-piperidin-1-yl]-2-oxo-ethyl}-amide. LC/MS [M+H]$^+$: 429.2, 92.9%, $^1$H NMR (300 MHz, DMSO-$d_6$): δ 8.0 (m, 1H), 7.8 (m, 2H), 7.5 (m, 2H), 7.4 (m, 1H), 7.2 (m, 1H), 7.1 (b, 1H), 6.9 (m, 2H), 6.2 (m, 1H), 4.3 (m, 1H), 4.2 (m, 1H), 3.8 (m, 1H), 3.6 (m, 1H), 3.4 (m, 1H), 2.8 (m, 1H), 2.0 (m, 2H), 1.4 (m, 1H), 1.2 (m, 1H).

Intermediate 69

Synthesis of 4-(Adamantan-2-ylamino)-piperidine dihydrochloride

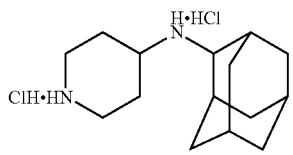

Ammonium formate (300 mg, 4.8 mmol) was added to a stirred solution of 4-oxo-piperidine-1-carboxylic acid tert-butyl ester (250 mg, 1.2 mmol) in methanolic ammonia (2.5 mL) followed by 10% Pd/C (50 mg) and stirring was continued at room temperature overnight. The above mixture was filtered through celite, filtrate was collected, and concentrated under reduced pressure to furnish a crude residue. The residue was treated with 2N aqueous NaOH solution, extracted with EtOAc, dried over $Na_2SO_4$ and concentrated under reduced pressure to afford 200 mg (83% yield) of (4-amino-piperidine-1-carboxylic acid tert-butyl ester. Titanium isopropoxide (756 mg, 2.66 mmol) was added to a stirred solution of 4-amino-piperidine-1-carboxylic acid tert-butyl ester (293 mg, 1.46 mmol) and adamantan-2-one (200 mg, 1.33 mmol) in EtOH (5 mL) and stirring was continued at room temperature overnight. $NaBH_4$ (100 mg, 2.64 mmol) was added in portionwise and the resulting mixture was stirred at room temperature for 10 hrs. The reaction mixture was quenched with 2N aqueous $NH_3$ solution and filtered. The filtrate was extracted with EtOAc, dried over $Na_2SO_4$ and concentrated under reduced pressure The residue was purified by column chromatography (using neutral alumina and 20% EtOAc in hexane as eluent) to afford 420 mg (94.4% Yield) of 4-(adamantan-2-ylamino)-piperidine-1-carboxylic acid tert-butyl ester. $^1$H NMR (300 MHz, $CDCl_3$): δ 4.0 (s, 2H), 2.9-2.4 (m, 4H), 2.0-1.6 (m, 9H), 1.7 (s, 4H), 1.6-1.5 (d, 4H), 1.45 (s, 9H), 1.35-1.2 (m, 3H). A mixture of 4-(adamantan-2-ylamino)-piperidine-1-carboxylic acid tert-butyl ester (420 mg, 1.25 mmol) in dioxane.HCl (20 mL) was stirred at ambient temperature for 2 hrs. The reaction mixture was concentrated under reduced pressure to get the residue, which was washed with ether to afford 363 mg (93.8% Yield) of 4-(adamantan-2-ylamino)-piperidine dihydrochloride. $^1$H NMR (300 MHz, DMSO-$d_6$): δ 9.2 (s, 1H), 9.0 (s, 3H), 3.8 (s, 4H), 3.5-3.3 (m, 4H), 3.0-2.8 (m, 2H), 2.4 (d, 2H), 2.3 (d, 3H), 2.0 (t, 2H), 1.9-1.8 (m, 5H), 1.7 (s, 2H), 1.6-1.5 (d, 2H).

Example 164

Synthesis of 5-Phenyl-1H-pyrazole-3-carboxylic acid {2-[4-(adamantan-2-ylamino)-piperidin-1-yl]-2-oxo-ethyl}-amide

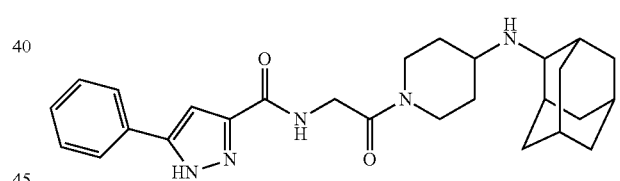

DIPEA (150 mg, 3.5 mmol) was added to a stirred solution [(5-phenyl-1H-pyrazole-3-carbonyl)-amino]-acetic acid (150 mg, 0.53 mmol) in DMF (4 mL) followed by HOBt (82 mg, 0.61 mmol) and EDCI.HCl (270 mg, 1.4 mmol). After 2 minutes of stirring, adamantan-2-yl-piperidin-4-yl-amine dihydrochloride (150 mg, 0.59 mmol) was added and stirring was continued at ambient temperature overnight. The reaction mixture was diluted with water and the precipitate was filtered to afford 200 mg (81.63% Yield) of 5-phenyl-1H-pyrazole-3-carboxylic acid {2-[4-(adamantan-2-ylamino)-piperidin-1-yl]-2-oxo-ethyl}-amide. LC/MS [M+H]$^+$: 462.28, 91.77%. $^1$H NMR (300 MHz, DMSO-$d_6$): δ8.2-8.0 (bs, 1H), 7.82-7.76 (d, 2H), 7.5-7.42 (t, 2H), 7.4-7.34 (t, 1H), 7.2-7.1 (bs, 1H), 4.3-4.1 (m, 3H), 3.8 (d, 1H), 3.1 (t, 1H), 2.9-2.7 (m, 3H), 2.1 (d, 2H), 1.9-1.6 (m, 1H), 1.4-1.3 (d, 3H), 1.2-1.1 (m, 2H).

Example 165

Synthesis of N-Biphenyl-4-yl-3-oxo-3-[4-(3,4,5-trifluoro-phenoxy)-piperidin-1-yl]-propionamide

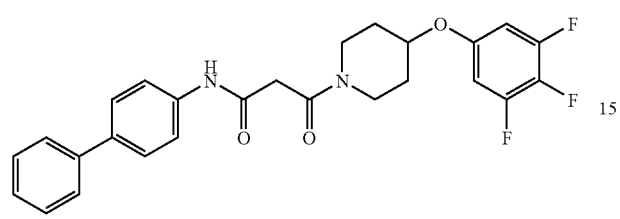

DIPEA (170 mg, 1.3 mmol) was added to a stirred solution of N-biphenyl-4-yl-malonamic acid (100 mg, 0.4 mmol) in DMF (2.0 mL) followed by HOBt (81 mg, 0.6 mmol) and EDCI.HCl (114 mg, 0.6 mmol). After 2 minutes of stirring, 4-(3,4,5-trifluoro-phenoxy)-piperidine hydrochloride (100 mg, 0.4 mmol) (prepared according to Step 1 and 5 of the General Scheme) was added and stirring was continued at ambient temperature overnight. The reaction mixture was diluted with water, extracted with ethylacetate, washed with brine and concentrated. The remaining residue was purified by column chromatography (using neutral alumina and 5% MeOH in CHCl$_3$) to afford 30 mg (17% Yield) of N-biphenyl-4-yl-3-oxo-3-[4-(3,4,5-trifluoro-phenoxy)-piperidin-1-yl]-propionamide. LC/MS [M+H]$^+$: 469.17, 98.06%, $^1$H NMR (300 MHz, DMSO-d$_6$): δ7.6 (m, 6H), 7.4 (m, 2H), 7.3 (m, 1H), 7.1 (m, 2H), 4.6 (m, 1H), 3.9 (m, 1H), 3.8 (m, 1H), 3.6 (m, 2H), 3.4 (m, 1H), 3.2 (m, 1H), 2.0 (m, 2H), 1.7 (m, 1H), 1.5 (m, 1H).

Example 166

Synthesis of N-Biphenyl-4-yl-3-[4-(3-cyano-phenoxy)-piperidin-1-yl]-3-oxo-propionamide

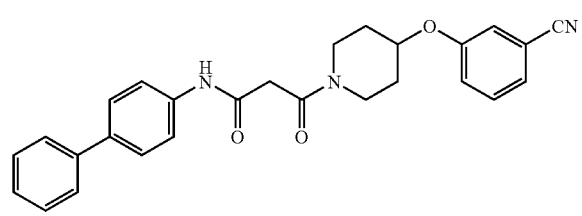

DIPEA (135 mg, 11.0 mmol) was added to a stirred solution of N-biphenyl-4-yl-malonamic acid (64 mg, 0.3 mmol) in DMF (2.0 mL) followed by HOBt (61 mg, 0.45 mmol) and EDCI.HCl (85 mg, 0.45 mmol). After 2 minutes of stirring, 3-(piperidin-4-yloxy)-benzonitrile hydrochloride (60 mg, 0.3 mmol) (prepared according to Step 1 and 5 of the General Scheme) was added and stirring was continued at ambient temperature overnight. The reaction mixture was diluted with water, extracted with ethylacetate, washed with brine and concentrated The residue was purified by column chromatography (using neutral alumina and 5% MeOH in CHCl$_3$) to afford 27 mg (19.7% Yield) of N-biphenyl-4-yl-3-[4-(3-cyano-phenoxy)-piperidin-1-yl]-3-oxo-propionamide. LC/MS [M+H]$^+$: 440.2, 98.14%, $^1$H NMR (300 MHz, DMSO-d$_6$): δ10.2 (s, 1H), 7.7 (m, 5H), 7.5 (m, 5H), 7.3 (m, 2H), 4.8 (m, 1H), 4.0 (m, 1H), 3.8 (m, 1H), 3.6 (m, 2H), 3.3 (m, 2H), 2.0 (m, 2H), 1.7 (m, 1H), 1.6 (m, 1H).

Example 167

Synthesis of 5-(2-Methoxy-phenyl)-1H-pyrazole-3-carboxylic acid {2-[4-(2-chloro-phenylamino)-piperidin-1-yl]-2-oxo-ethyl}-amide

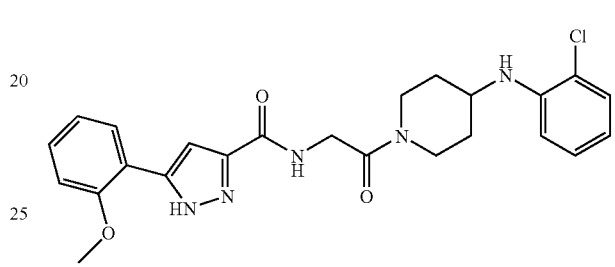

DIPEA (99 mg, 0.76 mmol) was added to a stirred solution {[5-(2-methoxy-phenyl)-1H-pyrazole-3-carbonyl]-amino}-acetic acid (60 mg, 0.22 mmol) (prepared by the method used for the synthesis of Intermediate 30, starting from (2'-methoxy)acetophenone) in DMF (2.0 mL) followed by HOBt (34 mg, 0.25 mmol) and EDCI.HCl (49 mg, 0.25 mmol). After 2 minutes of stirring, (2-chloro-phenyl)-piperidin-4-yl-amine dihydrochloride (54 mg, 0.22 mmol) was added and stirring was continued at ambient temperature overnight. The reaction mixture was diluted with water, extracted with ethyl acetate, washed with brine and concentrated. The residue was purified washing with diethyl ether to afford 67 mg (43.5% Yield) of 5-(2-methoxy-phenyl)-1H-pyrazole-3-carboxylic acid {2-[4-(2-chloro-phenylamino)-piperidin-1-yl]-2-oxo-ethyl}-amide. LC/MS [M+H]$^+$: 468.2, 98.33%. $^1$H NMR (300 MHz, DMSO-d$_6$): δ13.6 (S, 1H), 8.05 (m, 1H), 7.7 (m, 1H), 7.35 (m, 1H), 7.24 (m, 1H), 7.12 (m, 2H), 7.0 (m, 2H), 6.82 (m, 1H), 4.85 (d, 1H), 4.3 (d, 1H), 4.1 (d, 2H), 3.9 (s, 3H), 3.85 (m, 1H), 3.6 (m, 1H), 3.1 (m, 1H), 2.7 (m, 1H), 1.9 (m, 2H), 1.4 (m, 2H).

Intermediate 70

Synthesis of 3-Hydroxy-4-methyl-benzonitrile

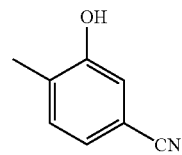

K$_2$CO$_3$ (18.1 g, 131.2 mmol) was added to a stirred solution of 3-hydroxy-4-methyl-benzoic acid (5 g, 33 mmol) in DMF (50 mL) followed by benzyl bromide (11.8 g, 69 mmol) and the resulting mixture was stirred at room temperature overnight. The reaction mixture was filtered, the filterate was diluted with water and extracted with EtOAc. The organic layer was collected, dried over sodium sulfate and concentrated under reduced pressure to afford 11.3 g (crude) of 3-benzyloxy-4-methyl-benzoic acid benzyl ester which was such taken for the next step without purification. NaOH (4.0 g, 102 mmol) was added to a stirred solution of 3-benzyloxy-4-methyl-benzoic acid benzyl ester (11.3 g, 34 mmol) in a mixture of MeOH (50 mL) and H₂O (50 mL), stirring was continued at ambient temperature for 2 hrs. The reaction mixture was concentrated under reduced pressure Cold water was then added and acidified it with 10% aqueous HCl, the precipitate was collected to afford 7.21 g (87.8% Yield) of 3-benzyloxy-4-methyl-benzoic acid. A mixture of 3-benzyloxy-4-methyl-benzoic acid (7.21 g, 29.7 mmol) in thionyl chloride (50 mL) was stirred at 79° C. for 4 hrs. The reaction mixture was concentrated under reduced pressure to afford 7.75 g (crude) of 3-benzyloxy-4-methyl-benzoyl chloride. A solution of 3-benzyloxy-4-methyl-benzoyl chloride (7.75 g) in THF (10 mL) was poured to cold aqueous solution of ammonia (50 mL) with stirring, The precipitate was collected to afford 6.7 g (94% Yield) of 3-benzyloxy-4-methyl-benzamide. A solution of 3-benzyloxy-4-methyl-benzamide (3.0 g, 12.4 mmol) in pyridine (4 mL) was cooled to −30° C. Imidazole (1.68 g, 24.8 mmol) followed by POCl₃ (2.64 g, 49.6 mmol) were added to the cold solution with stirring and the reaction was continued at the same temperature for 30 minutes. The reaction mixture was diluted with ethyl acetate. The organic layer was washed with water followed by 110% aqueous HCl solution. The organic layer separated was dried over sodium sulfate and concentrated under reduced pressure to afford 2.46 g (89% Yield) of 3-benzyloxy-4-methyl-benzonitrile. Pd/C (476 mg) was added to a stirred solution of 3-benzyloxy-4-methyl-benzonitrile (2.46 g, 11.0 mmol) in MeOH (25 mL) in an inert atmosphere and stirring was continued under H₂ gas atmosphere at ambient temperature, overnight. The reaction mixture was filtered through celite. The filtrate collected was concentrated under reduced pressure to afford 1.367 g (93.6% Yield) of 3-hydroxy-4-methyl-benzonitrile.

Intermediate 71

Synthesis of 3-(3-Trifluoromethyl-phenoxy)-azetidine hydrochloride

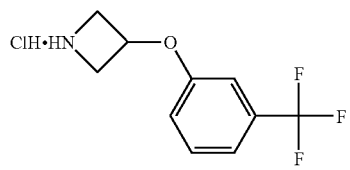

Pd(OH)₂ (100 mg) was added to a stirred solution of 1-benzhydryl-3-(3-trifluoromethyl-phenoxy)-azetidine (506 mg, 1.32 mmol) (prepared according to Step 1 and 5 of the General Scheme from 1-(diphenylmethyl)-3-azetidinyl methanesulfonate) in EtOH (50 mL) in an inert atmosphere and shaken in a Parr apparatus under H₂ atmosphere (60 psi) for 7 hrs. The reaction mixture was filtered through celite. The filtrate collected was concentrated under reduced pressure. The residue thus collected was stirred in EtOAc.HCl for 5 minutes, the supernatant liquid was decanted, and it was dried to afford 160 mg (47.9% Yield) of 3-(3-trifluoromethyl-phenoxy)-azetidine hydrochloride.

Intermediate 72

Synthesis of 3-(3-Trifluoromethyl-phenoxy)-pyrrolidine

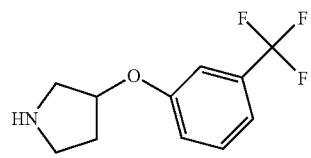

Pd(OH)₂ (125 mg) was added to a stirred solution of 1-benzyl-3-(3-trifluoromethyl-phenoxy)-pyrrolidine (prepared according to Step 1 and 5 of the General Scheme from 1-benzylpyrrolidin-3-ol) (125 mg, 0.4 mmol) in MeOH (15 mL) in an inert atmosphere and stirring was continued under H₂ gas atmosphere overnight. The reaction mixture was filtered through celite. The filtrate collected was concentrated under reduced pressure to afford 811 mg (85.9% Yield) of 3-(3-Trifluoromethyl-phenoxy)-pyrrolidine.

Example 168

Synthesis of 1-Pyrrolidin-3-yl-1H-[1,2,3]triazole-4-carboxylic acid {2-oxo-2-[4-(3-trifluoromethyl-phenoxy)-piperidin-1-yl]-ethyl}-amide

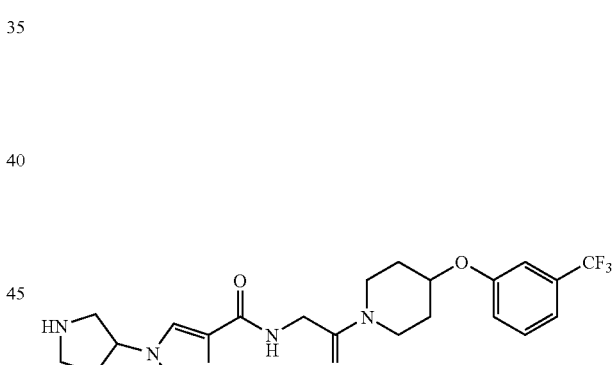

Pd(OH)₂ (80 mg) was added to a stirred solution of 1-(1-benzyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide (prepared by the method used for the synthesis of Example 136, starting from 1-benzyl-3-aminopyrrolidine) (407 mg, 0.73 mmol) in MeOH (4 mL) in an inert atmosphere and stirring was continued under H₂ gas atmosphere for 6 hrs. The reaction mixture was filtered through celite. The filtrate collected was concentrated under reduced pressure to afford 260 mg (80.2% Yield) of 1-pyrrolidin-3- yl-1H-[1,2,3]triazole-4-carboxylic acid {2-oxo-2-[4-(3-trifluoromethyl-phenoxy)-piperidin-1-yl]-ethyl}-amide. LC/MS [M+H]+: 467.19.

Example 169

Synthesis of 1-(1-Methyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide

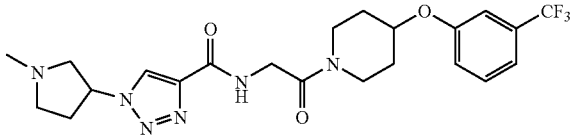

37% Aqueous formaldehyde (12 mg, 0.4 mmol) solution was added to a stirred solution of 1-pyrrolidin-3-yl-1H-[1,2,3]triazole-4-carboxylic acid {2-oxo-2-[4-(3-trifluoromethyl-phenoxy)-piperidin-1-yl]-ethyl}-amide (100 mg, 0.15 mmol) in a mixture of acetic acid (37.62 mg, 0.62 mmol) and H₂O (0.5 mL) and stirring was continued at ambient temperature for 5 minutes. To the above mixture was added, Zinc powder (39.23 mg, 0.6 mmol) and stirring was continued at ambient temperature for 1 hr. The reaction mixture was cooled, basified with aqueous ammonia solution and extracted with DCM. The organic layer thus collected was dried over sodium sulfate and concentrated under reduced pressure to afford 88 mg (88% Yield) of 1-(1-methyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide. LC/MS [M+H]+: 481.2. ¹H NMR (300 MHz, DMSO-d₆): δ 11.2-11.0 (b, 1H), 8.85 (s, 1H), 8.4 (s, 1H), 7.5 (t, 1H), 7.3 (t, 3H), 5.51 (b, 1H), 4.7 (m, 2H), 4.4 (d, 2H), 3.8 (m, 1H), 3.7 (m, 2H), 3.4 (m, 2H), 2.9 (s, 3H), 2.5 (m, 2H), 2.0 (m, 2H), 1.7-1.5 (m, 2H).

Example 170

Synthesis of 1-(3,5-Difluoro-phenyl)-1H-[1,2,3]triazole-4-carboxylic acid {2-[4-(2-chloro-phenoxy)-piperidin-1-yl]-2-oxo-ethyl}-amide

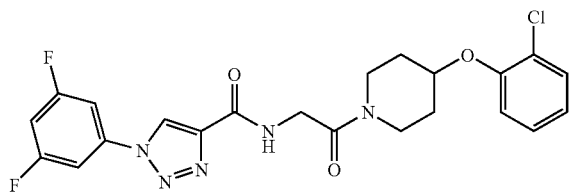

DIPEA (160.7 mg, 1.24 mmol) was added to a stirred solution of 1-(3,5-difluoro-phenyl)-1H-[1,2,3]triazole-4-carboxylic acid (prepared by the method used for the synthesis of Intermediate 64, starting from 3,5-difluoroaniline) (70 mg, 0.31 mmol) in DMF (2 mL) followed by HOBt (46.2 mg, 0.34 mmol) and EDCI (119 mg, 0.62 mmol). After 2 minutes of stirring, 2-amino-1-[4-(2-chloro-phenoxy)-piperidin-1-yl]-ethanone hydrochloride (94.8 mg, 0.31 mmol) (prepared according to Step 1 and 5 of the General Scheme) was added and the resulting mixture was stirred at room temperature overnight. Cold water was added and the precipitate was collected. The crude solid was stirred in a mixture of 30% EtOAc in hexane and MeOH (0.5 mL) for 1 hr and filtered to afford 95 mg (64.19% Yield) of 1-(3,5-difluoro-phenyl)-1H-[1,2,3]triazole-4-carboxylic acid {2-[4-(2-chloro-phenoxy)-piperidin-1-yl]-2-oxo-ethyl}-amide. LC/MS [M+H]+: 476.12, 98.71%. ¹H NMR (300 MHz, DMSO-d₆): δ 9.5 (s, 1H), 8.5 (t, 1H), 7.9 (m, 2H), 7.6-7.4 (m, 2H), 7.4-7.2 (m, 2H), 7.0 (m, 1H), 4.8 (m, 1H), 4.2 (d, 2H), 3.8-3.6 (m, 2H), 3.6-3.4 (m, 2H), 2.1-1.8 (m, 2H), 1.8-1.5 (m, 2H).

Example 171

Synthesis of 1-(3,5-Difluoro-phenyl)-1H-[1,2,3]triazole-4-carboxylic acid {2-[4-(5-chloro-pyridin-3-yloxy)-piperidin-1-yl]-2-oxo-ethyl}-amide

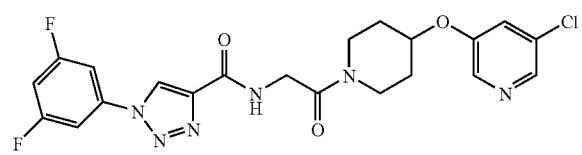

DIPEA (149.2 mg, 1.15 mmol) was added to a stirred solution of 1-(3,5-difluoro-phenyl)-1H-[1,2,3]triazole-4-carboxylic acid (65 mg, 0.28 mmol) in DMF (2 mL) followed by HOBt (43 mg, 0.31 mmol) and EDCI (110 mg, 0.57 mmol). After 2 minutes of stirring, 2-amino-1-[4-(5-chloro-pyridin-3-yloxy)-piperidin-1-yl]-ethanone hydrochloride (prepared according to Step 1 and 5 of the General Scheme) (88.4 mg, 0.28 mmol) was added and the resulting mixture was stirred at room temperature overnight. Cold water was added and the precipitate was collected. The crude solid was purified by recrystallisation from a mixture of DCM and hexane to afford 95 mg (54.4% Yield) of 1-(3,5-difluoro-phenyl)-1H-[1,2,3]triazole-4-carboxylic acid {2-[4-(5-chloro-pyridin-3-yloxy)-piperidin-1-yl]-2-oxo-ethyl}-amide. LC/MS [M+H]+: 477.12, 98.45%. ¹H NMR (300 MHz, DMSO-d₆): δ 9.5 (s, 1H), 8.5 (t, 1H), 8.3 (d, 1H), 8.2 (d, 1H), 7.9 (d, 2H), 7.75 (t, 1H), 7.58-7.5 (m, 1H), 4.8 (m, 1H), 4.2 (d, 2H), 4.0-3.8 (m, 1H), 3.8-3.6 (m, 1H), 3.4 (m, 1H), 3.2 (m, 1H), 2.1-1.9 (m, 2H), 1.9-1.5 (m, 2H).

Example 172

Synthesis of 1-Piperidin-4-yl-1H-[1,2,3]triazole-4-carboxylic acid {2-oxo-2-[4-(3-trifluoromethyl-phenoxy)-piperidin-1-yl]-ethyl}-amide hydrochloride

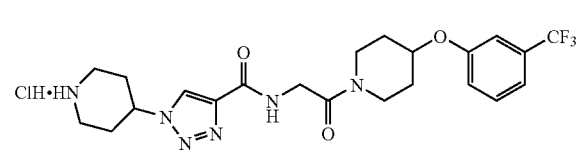

A mixture of 4-(4-{2-oxo-2-[4-(3-trifluoromethyl-phenoxy)-piperidin-1-yl]-ethylcarbamoyl}-[1,2,3]triazol-1-yl)-piperidine-1-carboxylic acid tert-butyl ester (prepared by the method used for the synthesis of Example 136, starting from 1-Boc-4-aminopiperidine) (380 mg, 0.65 mmol) in dioxane-.HCl (5 mL) was stirred at ambient temperature for 1 hr. The reaction mixture was concentrated under reduced pressure to get the crude solid which was purified by recrystallisation from a mixture of MeOH and diethyl ether to afford 252 mg

Example 173

Synthesis of 1-(1-Methyl-piperidin-4-yl)-1H-[1,2,3]triazole-4-carboxylic acid {2-oxo-2-[4-(3-trifluoromethyl-phenoxy)-piperidin-1-yl]-ethyl}-amide

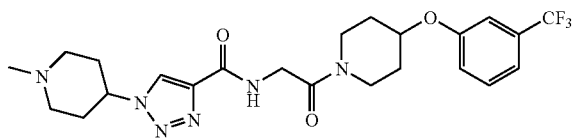

37% Aqueous formaldehyde (29.22 mg, 0.97 mmol) solution was added to a stirred solution of 1-piperidin-4-yl-1H-[1,2,3]triazole-4-carboxylic acid {2-oxo-2-[4-(3-trifluoromethyl-phenoxy)-piperidin-1-yl]-ethyl}-amide hydrochloride (252 mg, 0.48 mmol) in a mixture of acetic acid (240 mg, 4.0 mmol) and H$_2$O (2 mL) and stirring was continued at ambient temperature for 5 minutes. Zinc dust was added to the reaction mixture (94.1 mg, 1.44 mmol) and stirring was continued at ambient temperature for 1 hr. The reaction mixture was cooled, basified with aqueous ammonia solution and extracted with DCM. The organic layer was collected and dried over sodium sulfate and concentrated under reduced pressure to afford 110 mg (45.6% Yield) of 1-(1-methyl-piperidin-4-yl)-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 495.2. $^1$H NMR (300 MHz, DMSO-d$_6$): δ 8.7 (s, 1H), 8.3 (t, 1H), 7.5 (t, 1H), 7.3 (t, 3H), 4.8 (m, 1H), 4.5 (m, 1H), 4.2 (d, 2H), 3.9 (m, 1H), 3.7 (m, 1H), 3.4 (m, 2H), 2.9 (m, 2H), 2.2 (s, 3H), 2.1 (m, 6H), 1.95 (m, 2H).

Example 174

Synthesis of 1-Pyridin-3-yl-1H-[1,2,3]triazole-4-carboxylic acid {2-[4-(2,5-difluoro-phenoxy)-piperidin-1-yl]-2-oxo-ethyl}-amide

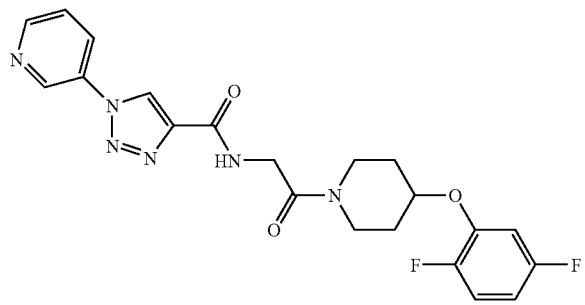

DIPEA (135.9 mg, 1.05 mmol) was added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (65 mg, 0.26 mmol) in DMF (2 mL) followed by HOBt (39 mg, 0.29 mmol) and EDCI (101 mg, 0.52 mmol). After 2 minutes of stirring, 4-(2,5-difluoro-phenoxy)-piperidine hydrochloride (prepared by the method used for the synthesis of Intermediate 15) (65.6 mg, 0.26 mmol) was added and the resulting mixture was stirred at room temperature overnight. Cold water was then added and the resultant was extracted with DCM. The organic layer was collected and dried over sodium sulfate and concentrated under reduced pressure The residue obtained was purified by stirring in mixture of 30% EtOAc in hexane (10 mL), H$_2$O (0.5 mL) and MeOH (0.5 mL) for 30 minutes. Filtered the mixture to afford 54 mg (46.5% Yield) of 1-pyridin-3-yl-1H-[1,2,3]triazole-4-carboxylic acid {2-[4-(2,5-difluoro-phenoxy)-piperidin-1-yl]-2-oxo-ethyl}-amide. LC/MS [M+H]$^+$: 443.16, 92.48%. $^1$H NMR (300 MHz, DMSO-d$_6$): δ 9.45 (s, 1H), 9.2 (d, 1H), 8.75 (m, 1H), 8.5 (t, 1H), 8.4 (m, 1H), 7.7 (q, 1H), 7.32-7.2 (m, 2H), 6.7-6.4 (m, 1H), 4.8-4.7 (m, 1H), 4.25 (d, 2H), 4.0-3.8 (m, 1H), 3.8-3.7 (m, 1H), 3.4 (m, 1H), 3.3 (m, 1H), 2.1-1.9 (m, 2H), 1.8-1.5 (m, 2H).

Example 175

Synthesis of 1-Pyridin-3-yl-1H-[1,2,3]triazole-4-carboxylic acid {2-[4-(5-cyano-2-methyl-phenoxy)-piperidin-1-yl]-2-oxo-ethyl}-amide

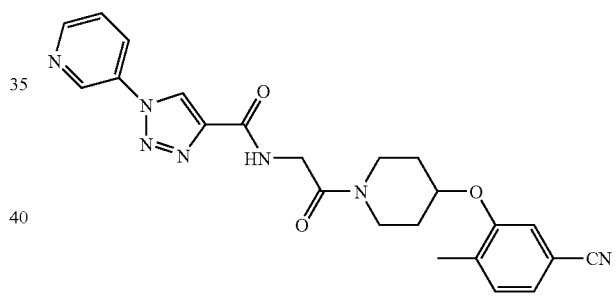

DIPEA (94.1 mg, 0.72 mmol) was added to a stirred solution of [(1-pyridin-3-yl-1H-[1,2,3]triazole-4-carbonyl)-amino]-acetic acid (45 mg, 0.18 mmol) (prepared by the method used for the synthesis of Intermediate 64, starting from 3-aminopyridine, and subsequently, application of Step 3 of the General Scheme) in DMF (2 mL) followed by HOBt (27 mg, 0.2 mmol) and EDCI (69.8 mg, 0.366 mmol). After 2 minutes of stirring, 4-methyl-3-(piperidin-4-yloxy)-benzonitrile hydrochloride (prepared by the method used for the synthesis of Intermediate 15) (50.6 mg, 0.2 mmol) was added and the resulting mixture was stirred at room temperature overnight. Cold water was added and the precipitate was collected. The solid was purified by stirring in mixture of DCM in hexane to afford 40 mg (49.2% Yield) of 1-pyridin-3-yl-1H-[1,2,3]triazole-4-carboxylic acid {2-[4-(5-cyano-2-methyl-phenoxy)-piperidin-1-yl]-2-oxo-ethyl}-amide. LC/MS [M+H]$^+$: 446.19, 96.84%. $^1$H NMR (300 MHz, DMSO-d$_6$): δ 9.45 (s, 1H), 9.2 (d, 1H), 8.75 (d, 1H), 8.55-8.45 (t, 1H), 8.4 (m, 1H), 7.72-7.64 (m, 1H), 7.55 (s, 1H), 7.4-7.3

(q, 2H), 4.8 (m, 1H), 4.25 (d, 2H), 3.8-3.6 (m, 2H), 3.5-3.4 (m, 2H), 2.25 (s, 3H), 2.1-1.8 (m, 2H), 1.8-1.5 (m, 2H).

Example 176

Synthesis of 5-Phenyl-1H-pyrazole-3-carboxylic acid {2-oxo-2-[3-(3-trifluoromethyl-phenoxy)-pyrrolidin-1-yl]-ethyl}-amide

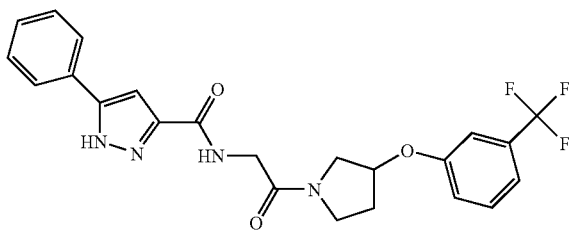

DIPEA (167.7 mg, 1.29 mmol) was added to a stirred solution of [(5-phenyl-1H-pyrazole-3-carbonyl)-amino]-acetic acid (106 mg, 0.43 mmol) in DMF (4 mL) followed by HOBt (70.13 mg, 0.52 mmol) and EDCI (99.5 mg, 0.52 mmol). After 2 minutes of stirring, 3-(3-trifluoromethyl-phenoxy)-pyrrolidine (100 mg, 0.43 mmol) was added and the resulting mixture was stirred at room temperature overnight. Cold water was added and the precipitate was collected to afford 122 mg (61.5% Yield) of 5-phenyl-1H-pyrazole-3-carboxylic acid {2-oxo-2-[3-(3-trifluoromethyl-phenoxy)-pyrrolidin-1-yl]-ethyl}-amide. LC/MS [M+H]+: 459.16, 96.52%. $^1$H NMR (300 MHz, DMSO-$d_6$): δ 13.8 (s, 1H), 8.05 (bs, 1H), 7.8 (db, 2H), 7.7-7.6 (m, 7H), 7.05 (bs, 1H), 5.4 (s, 1H), 5.3 (s, 1H), 4.1 (m, 2H), 3.9 (m, 1H), 3.8-3.6 (m, 3H), 3.4 (m, 1H), 2.3-2.0 (m, 2H).

Intermediate 73

Synthesis of 4-(2-Oxo-pyrrolidin-1-yl)-benzoic acid

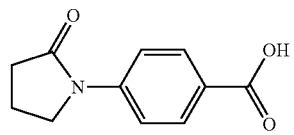

A mixture of pyrrolidin-2-one (500 mg, 5.9 mmol), 4-bromo benzoic acid methyl ester (1.5 g, 6.97 mmol), Pd$_2$(dba)$_3$ (135 mg, 0.14 mmol), xantphos (256 mg, 0.44 mmol) and cesium carbonate (2.7 g, 8.28 mmol) in dioxane (2 mL) in a sealed tube was subjected to reaction in a microwave reactor (time: 20 min, temp: 105° C., power: zero). The reaction mixture was filtered through celite and the filtrate collected was concentrated under reduced pressure. The residue was diluted with cold water, extracted with ethyl acetate, dried over sodium sulfate and concentrated under reduced pressure to afford the residue. The residue obtained was purified by column chromatography (using 60-120 silica gel and 50% ethyl acetate in hexane as eluent) to afford 485 mg (37.89% Yield) of 4-(2-oxo-pyrrolidin-1-yl)-benzoic acid methyl ester. NaOH (295 mg, 7.4 mmol) was added to a stirred mixture of 4-(2-oxo-pyrrolidin-1-yl)-benzoic acid methyl ester (485 mg, 2.2 mmol) in a mixture of MeOH (5 mL) and H$_2$O (5 mL), stirring was continued at 60° C. for 1 hr. After completion of the reaction, the reaction mixture was concentrated under reduced pressure to get the residue, which was acidified with 10% aqueous HCl solution, the precipitate was collected to afford 300 mg (66% Yield) of 4-(2-oxo-pyrrolidin-1-yl)-benzoic acid.

Example 177

Synthesis of 4-(2-Oxo-pyrrolidin-1-yl)-N-{2-oxo-2-[4-(3-trifluoromethyl-phenoxy)-piperidin-1-yl]-ethyl}-benzamide

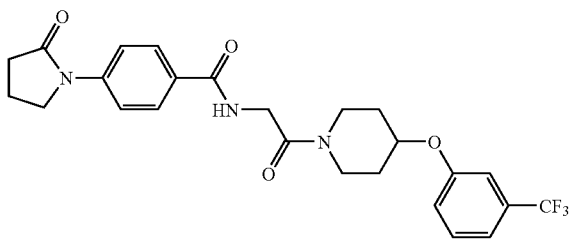

DIPEA (200 mg, 1.55 mmol) was added to a stirred solution of 4-(2-oxo-pyrrolidin-1-yl)-benzoic acid (70 mg, 0.34 mmol) in DMF (5 mL) followed by HOBt (50 mg, 0.37 mmol) and EDCI (163 mg, 0.85 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (127 mg, 0.37 mmol) was added and the resulting mixture was stirred at room temperature overnight. Cold water was then added and the precipitate was filtered off. The solid obtained was purified by column chromatography (using 60-120 silica gel and 70% ethyl acetate in hexane as eluent) to afford 94 mg (56.62% Yield) of 4-(2-oxo-pyrrolidin-1-yl)-N-{2-oxo-2-[4-(3-trifluoromethyl-phenoxy)-piperidin-1-yl]-ethyl}-benzamide. LC/MS [M+H]+: 490.19, 98.95%. $^1$H NMR (300 MHz, DMSO-$d_6$): δ 8.6 (t, 1H), 7.94 (d, 2H), 7.8 (d, 2H), 7.6 (t, 1H), 7.38 (t, 3H), 4.8 (m, 1H), 4.2 (d, 1H), 4.0 (t, 3H), 3.8 (d, 1H), 3.5 (d, 1H), 3.3 (bs, 1H), 2.5 (bs, 2H), 2.1 (m, 2H), 2.0 (d, 2H), 1.7 (d, 2H).

Example 178

Synthesis of 1-Cyclopropyl-1H-[1,2,3]triazole-4-carboxylic acid {2-oxo-2-[4-(3-trifluoromethyl-phenoxy)-piperidin-1-yl]-ethyl}-amide

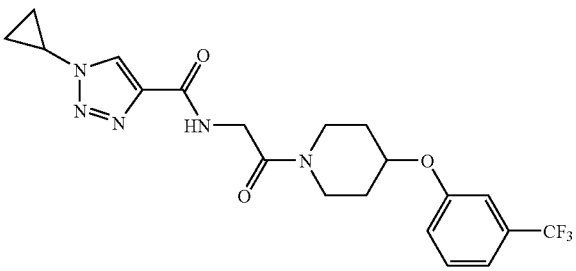

DIPEA (190 mg, 1.47 mmol) was added to a stirred solution of 1-cyclopropyl-1H-[1,2,3]triazole-4-carboxylic acid (prepared by the method used for the synthesis of Intermediate 64, starting from cyclopropylamine) (50 mg, 0.32 mmol) in DMF (5 mL) followed by HOBt (48 mg, 0.35 mmol) and EDCI (156 mg, 0.81 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (127 mg, 0.37 mmol) was added and the resulting mixture was stirred at room temperature overnight. Cold water was added and the solid precipitate was filtered. The solid was purified by column chromatography (using 60-120 silica gel and 70% ethyl acetate in hexane as eluent) to afford 94 mg (56.62% Yield) of 4-(2-oxo-pyrrolidin-1-yl)-N-{2-oxo-2-[4-(3-trifluoromethyl-phenoxy)-piperidin-1-yl]-ethyl}-benzamide. LC/MS [M+H]$^+$: 490.19, 98.95%. $^1$H NMR (300 MHz, DMSO-d$_6$): δ 8.6 (t, 1H), 7.94 (d, 2H), 7.8 (d, 2H), 7.6 (t, 1H), 7.38 (t, 3H), 4.8 (m, 1H), 4.2 (d, 1H), 4.0 (t, 3H), 3.8 (d, 1H), 3.5 (d, 1H), 3.3 (bs, 1H), 2.5 (bs, 2H), 2.1 (m, 2H), 2.0 (d, 2H), 1.7 (d, 2H).

Example 179

Synthesis of 1-Morpholin-4-yl-1H-[1,2,3]triazole-4-carboxylic acid {2-oxo-2-[4-(3-trifluoromethyl-phenoxy)-piperidin-1-yl]-ethyl}-amide

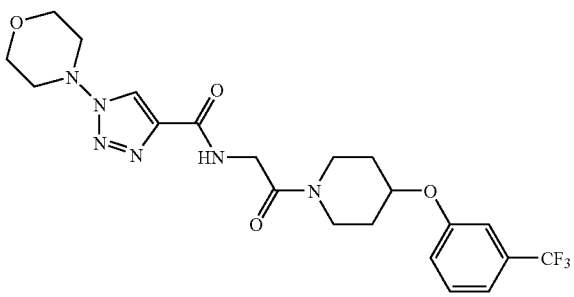

DIPEA (200 mg, 1.54 mmol) was added to a stirred solution of 1-morpholin-4-yl-1H-[1,2,3]triazole-4-carboxylic acid (prepared by the method used for the synthesis of Intermediate 64, starting from 4-aminomorpholine) (70 mg, 0.35 mmol) in DMF (5 mL) followed by HOBt (52 mg, 0.38 mmol) and EDCI (170 mg, 0.88 mmol). After 2 minutes of stirring, 2-amino-1-[4-(3-trifluoromethyl-phenoxy)-piperidin-1-yl]-ethanone hydrochloride (prepared according to Step 1 and 5 of the General Scheme) (120 mg, 0.35 mmol) was added and the resulting mixture was stirred at room temperature overnight. Cold water was then added and the precipitate was collected out. The solid obtained was purified by recrystallisation from a mixture of 20% ethyl acetate in hexane and MeOH to afford 144 mg (84.7% Yield) of 1-morpholin-4-yl-1H-[1,2,3]triazole-4-carboxylic acid {2-oxo-2-[4-(3-trifluoromethyl-phenoxy)-piperidin-1-yl]-ethyl}-amide. LC/MS [M+H]$^+$: 483.19, 92.7%. $^1$H NMR (300 MHz, DMSO-d$_6$): δ 8.82 (s, 1H), 8.4 (t, 1H), 7.6 (t, 1H), 7.36 (t, 3H), 4.9 (m, 1H), 4.2 (d, 2H), 4.0-3.6 (m, 6H), 3.4 (m, 2H), 3.2 (m, 2H), 2.1 (t, 2H), 1.7 (d, 2H).

Synthesis of 1-Morpholin-4-yl-1H-[1,2,3]triazole-4-carboxylic acid {2-[4-(2-chloro-5-fluoro-phenoxy)-piperidin-1-yl]-2-oxo-ethyl}-amide

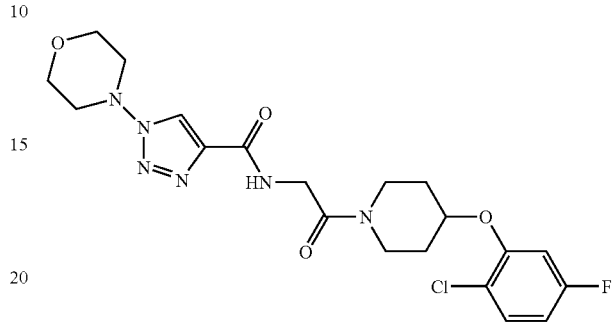

DIPEA (200 mg, 1.54 mmol) was added to a stirred solution of 1-morpholin-4-yl-1H-[1,2,3]triazole-4-carboxylic acid (prepared by the method used for the synthesis of Intermediate 64, starting from 4-aminomorpholine) (70 mg, 0.35 mmol) in DMF (5 mL) followed by HOBt (52 mg, 0.38 mmol) and EDCI (170 mg, 0.88 mmol). After 2 minutes of stirring, 2-amino-1-[4-(2-chloro-5-fluoro-phenoxy)-piperidin-1-yl]-ethanone hydrochloride (prepared according to Step 1 and 5 of the General Scheme) (125 mg, 0.38 mmol) was added and the resulting mixture was stirred at room temperature overnight. Cold water was then added and the precipitate was collected. The solid was purified by recrystallizing from a mixture of 20% ethyl acetate in hexane and MeOH to afford 116 mg (70.3% Yield) of 1-morpholin-4-yl-1H-[1,2,3]triazole-4-carboxylic acid {2-[4-(2-chloro-5-fluoro-phenoxy)-piperidin-1-yl]-2-oxo-ethyl}-amide. LC/MS [M+H]$^+$: 467.15, 96.7%. $^1$H NMR (300 MHz, DMSO-d$_6$): δ 8.8 (s, 1H), 8.4 (t, 1H), 7.5 (t, 1H), 7.3 (d, 1H), 6.8 (t, 1H), 4.9 (m, 1H), 4.2 (d, 2H), 3.85 (t, 4H), 3.7 (d, 2H), 3.5 (b, 2H), 3.3 (bs, 4H), 2.0 (d, 2H), 1.8 (d, 2H).

Example 180

Synthesis of 1-Phenyl-1H-[1,2,3]triazole-4-carboxylic acid {2-[4-(3-cyano-phenoxy)-piperidin-1-yl]-2-oxo-ethyl}-amide

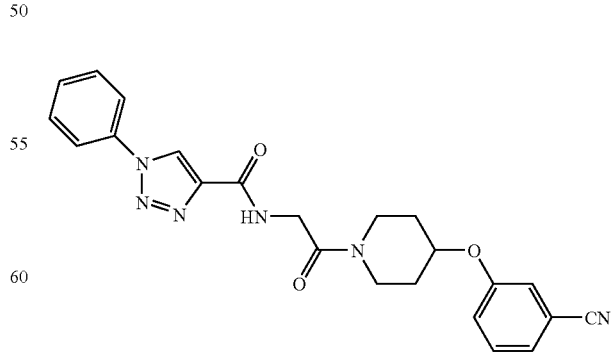

DIPEA (167.9 mg, 1.3 mmol) was added to a stirred solution of [(1-phenyl-1H-[1,2,3]triazole-4-carbonyl)-amino]-acetic acid (80 mg, 0.32 mmol) in DMF (3 mL) followed by HOBt (48.2 mg, 0.35 mmol) and EDCI (124.5 mg, 0.65 mmol). After 2 minutes of stirring, 3-(piperidin-4-yloxy)-benzonitrile hydrochloride (prepared by the method used for the synthesis of Intermediate 15) (77.5 mg, 0.32 mmol) was added and the resulting mixture was stirred at room temperature overnight. Cold water was added and precipitate was collected. The solid was purified by column chromatography (using 70% ethyl acetate in hexane as eluent) to afford 45 mg (32.6% Yield) of 1-phenyl-1H-[1,2,3]triazole-4-carboxylic acid {2-[4-(3-cyano-phenoxy)-piperidin-1-yl]-2-oxo-ethyl}-amide. LC/MS [M+H]$^+$: 431.18, 85.06%. $^1$H NMR (300 MHz, DMSO-d$_6$): δ 9.35 (s, 1H), 8.5 (t, 1H), 8.0 (d, 2H), 7.7-7.6 (m, 2H), 7.58-7.45 (m, 3H), 7.45-7.32 (m, 2H), 4.75 (m, 1H), 4.2 (d, 2H), 4.0-3.9 (m, 1H), 3.8-3.7 (m, 1H), 2.1-1.9 (m, 2H), 1.75-1.5 (m, 2H).

Example 181

Synthesis of 1-Pyridin-3-yl-1H-[1,2,3]triazole-4-carboxylic acid {2-[3-(2,5-difluoro-phenoxy)-pyrrolidin-1-yl]-2-oxo-ethyl}-amide

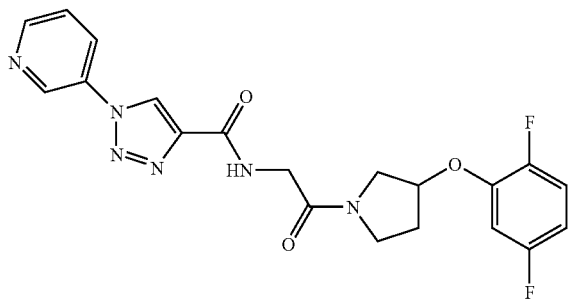

DIPEA (156.8 mg, 1.2 mmol) was added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (75 mg, 0.3 mmol) in DMF (3 mL) followed by HOBt (45 mg, 0.33 mmol) and EDCI (116 mg, 0.6 mmol). After 2 minutes of stirring, 3-(2,5-difluoro-phenoxy)-pyrrolidine hydrochloride (prepared by the method used for the synthesis of Intermediate 72) (71.5 mg, 0.3 mmol) was added and the resulting mixture was stirred at room temperature overnight. Cold water was then added and precipitate was collected to afford 48 mg (37.2% Yield) of 1-pyridin-3-yl-1H-[1,2,3]triazole-4-carboxylic acid {2-[3-(2,5-difluoro-phenoxy)-pyrrolidin-1-yl]-2-oxo-ethyl}-amide. LC/MS [M+H]$^+$: 429.14, 92.32%. $^1$H NMR (300 MHz, DMSO-d$_6$): δ 9.5 (s, 1H), 9.2 (d, 1H), 8.75 (d, 1H), 8.6 (m, 1H), 8.4 (m, 1H), 7.7 (q, 1H), 7.3-7.2 (m, 2H), 6.9-6.7 (m, 1H), 5.3-5.1 (d, 1H), 4.25-4.1 (m, 2H), 4.0-3.5 (m, 4H), 2.3-2.2 (m, 1H), 2.2-2.05 (m, 1H).

Example 182

Synthesis of 5-Phenyl-1H-pyrazole-3-carboxylic acid {2-oxo-2-[3-(3-trifluoromethyl-phenoxy)-azetidin-1-yl]-ethyl}-amide

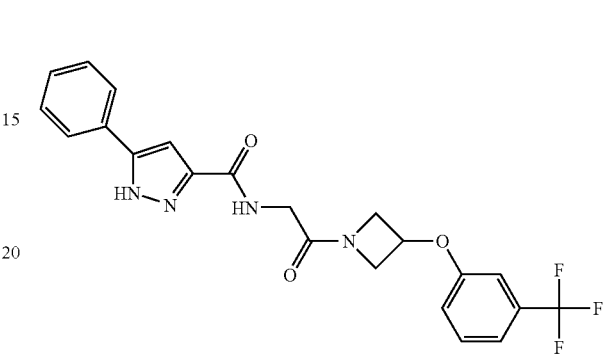

DIPEA (158.2 mg, 1.22 mmol) was added to a stirred solution of [(5-phenyl-1H-pyrazole-3-carbonyl)-amino]-acetic acid (75 mg, 0.30 mmol) in DMF (2 mL) followed by HOBt (43.4 mg, 0.32 mmol) and EDCI (61.6 mg, 0.32 mmol). After 2 minutes of stirring, 3-(3-trifluoromethyl-phenoxy)-azetidine hydrochloride (77.5 mg, 0.3 mmol) was added and the resulting mixture was stirred at room temperature overnight. Cold water was added followed by extraction with ethyl acetate. The organic phase was dried over sodium sulfate and concentrated under reduced pressure to afford the residue. The residue was purified by column chromatography (using silica gel 60- and 100% ethyl acetate as eluent) to afford 69 mg (51.1% Yield) of 5-phenyl-1H-pyrazole-3-carboxylic acid {2-oxo-2-[3-(3-trifluoromethyl-phenoxy)-azetidin-1-yl]-ethyl}-amide. LC/MS [M+H]$^+$: 445.14, 90.72%. $^1$H NMR (300 MHz, DMSO-d$_6$): δ 14.8 (s, 1H), 8.2 (t, 1H), 7.78 (t, 2H), 7.5 (t, 1H), 7.3 (m, 5H), 7.16 (d, 2H), 7.1 (d, 1H), 5.18 (m, 1H), 4.64 (q, 1H), 4.36 (m, 1H), 4.18 (m, 1H), 3.84 (m, 3H).

Example 183

Synthesis of 5-Pyridin-3-yl-1H-pyrazole-3-carboxylic acid {2-oxo-2-[3-(3-trifluoromethyl-phenoxy)-azetidin-1-yl]-ethyl}-amide

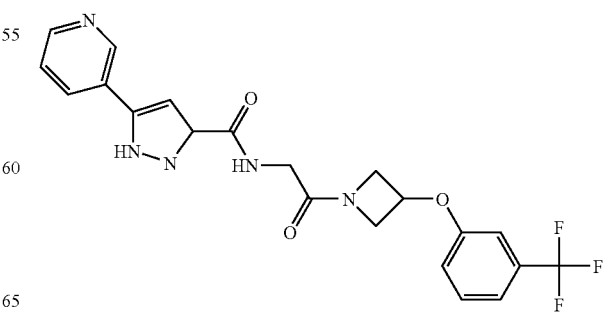

DIPEA (158.2 mg, 1.22 mmol) was added to a stirred solution of [(5-pyridin-3-yl-1H-pyrazole-3-carbonyl)-amino]-acetic acid (prepared by the method used for the synthesis of Intermediate 30, starting from 3-acetylpyridine) (76 mg, 0.30 mmol) in DMF (2 mL) followed by HOBt (43.4 mg, 0.32 mmol) and EDCI (61.6 mg, 0.32 mmol). After 2 minutes of stirring, 3-(3-trifluoromethyl-phenoxy)-azetidine hydrochloride (77.5 mg, 0.3 mmol) was added and the resulting mixture was stirred at room temperature overnight. Cold water was added and extracted with ethyl acetate. The organic layer was dried over sodium sulfate and concentrated under reduced pressure The residue obtained purified by column chromatography (using silica gel 60- and 100% ethyl acetate as eluent) to afford 43 mg (32% Yield) of 5-pyridin-3-yl-1H-pyrazole-3-carboxylic acid {2-oxo-2-[3-(3-trifluoromethyl-phenoxy)-azetidin-1-yl]-ethyl}-amide. LC/MS [M+H]+: 446.14, 93.76%. 1H NMR (300 MHz, DMSO-d6): δ 9.44 (s, 1H), 9.2 (d, 1H), 8.72 (m, 2H), 8.38 (m, 1H), 7.64 (m, 1H), 7.52 (t, 1H), 7.35 (d, 1H), 7.16 (m, 2H), 5.2 (m, 1H), 4.7 (m, 1H), 4.3 (m, 1H), 4.2 (m, 1H), 3.95 (d, 2H), 3.8 (m, 1H).

Example 184

Synthesis of 5-Phenyl-1H-pyrazole-3-carboxylic acid {2-[3-(2,5-difluoro-phenoxy)-pyrrolidin-1-yl]-2-oxo-ethyl}-amide

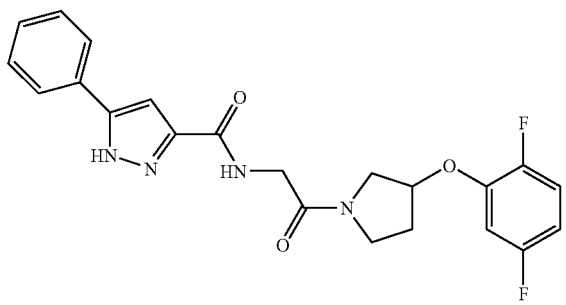

DIPEA (166 mg, 1.28 mmol) was added to a stirred solution of [(5-phenyl-1H-pyrazole-3-carbonyl)-amino]-acetic acid (70 mg, 0.28 mmol) in DMF (5 mL) followed by HOBt (42 mg, 0.31 mmol) and EDCI (136 mg, 0.71 mmol). After 2 minutes of stirring, 3-(2,5-difluoro-phenoxy)-pyrrolidine hydrochloride (prepared by the method used for the synthesis of Intermediate 72) (74 mg, 0.3 mmol) was added and the resulting mixture was stirred at room temperature overnight. Cold water was added and the precipitate was collected. The solid was purified by recrystallisation from a mixture of 20% ethyl acetate in hexane (15 mL), water (0.5 mL) and MeOH (0.03 mL) to afford 92 mg (76% Yield) of 5-phenyl-1H-pyrazole-3-carboxylic acid {2-[3-(2,5-difluoro-phenoxy)-pyrrolidin-1-yl]-2-oxo-ethyl}-amide. LC/MS [M+H]+: 427.15. 1H NMR (300 MHz, DMSO-d6): δ 13.8 (s, 1H), 8.1 (s, 1H), 7.84 (d, 2H), 7.54-7.12 (m, 6H), 7.14 (s, 1H), 6.88 (t, 1H), 5.3 (d, 1H), 4.1 (d, 2H), 3.9-3.5 (m, 4H), 2.3 (s, 1H), 2.1 (s, 1H).

Example 185

Synthesis of 1-Phenyl-1H-imidazole-4-carboxylic acid {2-[4-(2,5-difluoro-phenoxy)-piperidin-1-yl]-2-oxo-ethyl}-amide

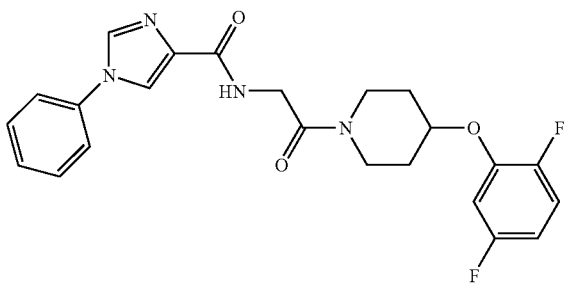

DIPEA (170 mg, 1.3 mmol) was added to a stirred solution of 1-phenyl-1H-imidazole-4-carboxylic acid (55 mg, 0.29 mmol) in DMF (5 mL) followed by HOBt (43 mg, 0.32 mmol) and EDCI (140 mg, 0.7 mmol). After 2 minutes of stirring, 2-amino-1-[4-(2,5-difluoro-phenoxy)-piperidin-1-yl]-ethanone hydrochloride (prepared according to Step 1 and 5 of the General Scheme) (98.5 mg, 0.32 mmol) was added and the resulting mixture was stirred at ambient temperature overnight. The reaction mixture was diluted with cold water, extracted with ethyl acetate, dried over sodium sulfate and concentrated under reduced pressure. The residue obtained was purified by washing with ether to afford 63.5 mg (49.6% Yield) of 1-phenyl-1H-imidazole-4-carboxylic acid {2-[4-(2,5-difluoro-phenoxy)-piperidin-1-yl]-2-oxo-ethyl}-amide. LC/MS [M+H]+: 441.17. 1H NMR (300 MHz, DMSO-d6): δ 8.4 (s, 1H), 8.3 (s, 1H), 8.08 (t, 1H), 7.8 (d, 2H), 7.6 (t, 2H), 7.44 (t, 1H), 7.3 (m, 1H), 6.84 (m, 1H), 4.8 (m, 1H), 4.2 (d, 2H), 4.0 (bs, 1H), 3.8 (bs, 1H), 3.7 (bs, 2H), 3.5 (bs, 1H), 2.1 (t, 2H), 1.8 (d, 2H).

Example 186

Synthesis of 1-Phenyl-1H-imidazole-4-carboxylic acid {2-[4-(2-chloro-phenoxy)-piperidin-1-yl]-2-oxo-ethyl}-amide

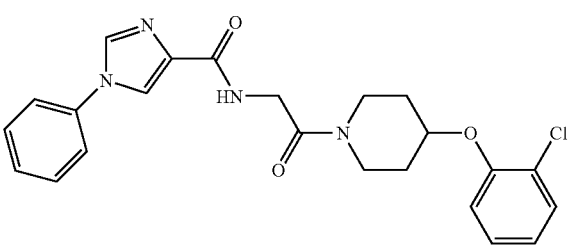

DIPEA (170 mg, 1.3 mmol) was added to a stirred solution of [(1-phenyl-1H-imidazole-4-carbonyl)-amino]-acetic acid (prepared from Intermediate 68 by means of Step 3 of the General Scheme) (55 mg, 0.29 mmol) in DMF (5 mL) followed by HOBt (43 mg, 0.32 mmol) and EDCI (140 mg, 0.7 mmol). After 2 minutes of stirring, 4-(2-chloro-phenoxy)-piperidine hydrochloride (98 mg, 0.32 mmol) was added and the resulting mixture was stirred at ambient temperature overnight. The reaction mixture was diluted with cold water and the precipitate was collected. The precipitate was purified by recrystallisation from a mixture of 20% EtOAc in hexane (15 mL) and MeOH (0.1 mL) to afford the 80 mg (62.5% Yield) of 1-phenyl-1H-imidazole-4-carboxylic acid {2-[4-(2-chloro-phenoxy)-piperidin-1-yl]-2-oxo-ethyl}-amide. LC/MS [M+H]$^+$: 439.15, 98.75%. $^1$H NMR (300 MHz, DMSO-d$_6$): δ 8.4 (s, 1H), 8.3 (s, 1H), 8.08 (t, 1H), 7.8 (d, 2H), 7.6 (t, 2H), 7.48 (m, 2H), 7.34 (m, 2H), 7.1 (t, 1H), 4.8 (m, 1H), 4.2 (d, 2H), 3.8 (t, 2H), 3.6 (t, 2H), 2.0 (d, 2H), 1.8 (d, 2H).

Synthesis of 1-Phenyl-1H-imidazole-4-carboxylic acid {2-oxo-2-[4-(2-trifluoromethyl-phenoxy)-piperidin-1-yl]-ethyl}-amide DIPEA (236 mg, 1.826 mmol) was added to a stirred solution of [(1-Phenyl-1H-imidazole-4-carbonyl)-amino]-acetic acid (prepared from Intermediate 68 by means of Step 3 of the General Scheme) (100 mg, 0.4 mmol) in DMF (5 mL) followed by HOBt (60.5 mg, 0.4 mmol) and EDCI (195 mg, 1.02 mmol). After 2 minutes of stirring, 4-(2-trifluoromethyl-phenoxy)-piperidine trifluoroacetate (126 mg, 0.45 mmol) was added and the resulting mixture was stirred at ambient temperature overnight. The reaction mixture was diluted with cold water, and the precipitate was filtered. The precipitate was purified by recrystallisation from a mixture of 20% EtOAc in hexane (15 mL) and MeOH (0.1 mL) to afford 113 mg (58.2% Yield) of 1-phenyl-1H-imidazole-4-carboxylic acid {2-oxo-2-[4-(2-trifluoromethyl-phenoxy)-piperidin-1-yl]-ethyl}-amide. LC/MS [M+H]$^+$: 473, 96.85%. $^1$H NMR (300 MHz, DMSO-d$_6$): δ 8.4 (s, 1H), 8.3 (s, 1H), 8.08 (t, 1H), 7.8 (d, 2H), 7.68-7.6 (t, 2H), 7.6 (t, 2H), 7.4-7.34 (m, 2H), 7.14 (t, 1H), 5.0 (m, 1H), 4.2 (d, 2H), 3.7-3.4 (m, 4H), 2.1 (d, 2H), 1.8 (d, 2H).

Example 187

Synthesis of 1-Phenyl-1H-imidazole-4-carboxylic acid {2-[4-(5-cyano-2-methyl-phenoxy)-piperidin-1-yl]-2-oxo-ethyl}-amide

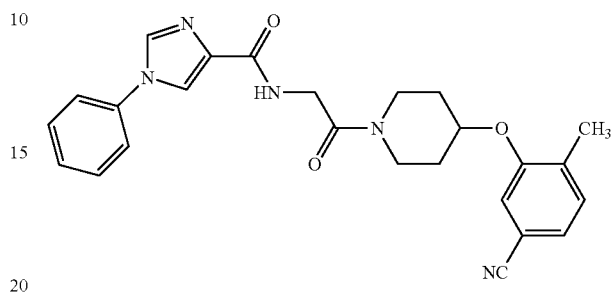

DIPEA (236 mg, 1.826 mmol) was added to a stirred solution of [(1-phenyl-1H-imidazole-4-carbonyl)-amino]-acetic acid (prepared from Intermediate 68 by means of Step 3 of the General Scheme) (100 mg, 0.4 mmol) in DMF (5 mL) followed by HOBt (60.5 mg, 0.4 mmol) and EDCI (195 mg, 1.02 mmol). After 2 minutes of stirring, 4-methyl-3-(piperidin-4-yloxy)-benzonitrile hydrochloride (113 mg, 0.45 mmol) (prepared by the method used for the synthesis of Intermediate 15) was added and the resulting mixture was stirred at ambient temperature overnight. The reaction mixture was diluted with cold water, the precipitate was collected and purified by recrystallisation from a mixture of diethyl ether (15 mL) and MeOH (0.1 mL) to afford 149 mg (82.7% Yield) of 1-phenyl-1H-imidazole-4-carboxylic acid {2-[4-(5-cyano-2-methyl-phenoxy)-piperidin-1-yl]-2-oxo-ethyl}-amide. LC/MS [M+H]$^+$: 443, 98.73%. $^1$H NMR (300 MHz, DMSO-d$_6$): δ 8.4 (s, 1H), 8.3 (s, 1H), 8.08 (t, 1H), 7.8 (d, 2H), 7.6 (t, 3H), 7.4-7.18 (m, 3H), 4.85 (m, 1H), 4.2 (d, 2H), 3.85-3.6 (d, 2H), 3.5 (bs, 2H), 2.3 (s, 3H), 2.1 (d, 2H), 1.8 (d, 2H).

Example 188

Synthesis of 1-Phenyl-1H-imidazole-4-carboxylic acid {2-[3-(3-fluoro-5-trifluoromethyl-phenoxy)-azetidin-1-yl]-2-oxo-ethyl}-amide

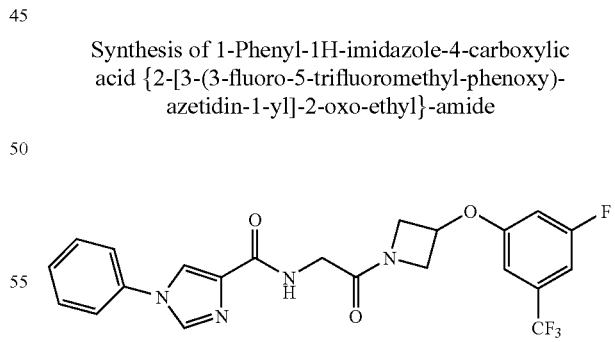

DIPEA (143 mg, 1.1 mmol) was added to a stirred solution of [(1-phenyl-1H-imidazole-4-carbonyl)-amino]-acetic acid (prepared from Intermediate 68 by means of Step 3 of the General Scheme) (68 g, 0.27 mmol) in DMF (2 mL) followed by HOBt (39 mg, 0.29 mmol) and EDCI (56 mg, 0.29 mmol). After 2 minutes of stirring, 3-(3-fluoro-5-trifluoromethyl-phenoxy)-azetidine hydrochloride (prepared by the method used for the synthesis of Intermediate 71) (75 mg, 0.27 mmol)

was added and it was stirred overnight at ambient temperature. Partitioning with cold water and ethyl acetate and concentration of the organic layer after drying over sodium sulfate afforded a residue which was purified by preparative HPLC to give 40 mg (31.4% Yield) of 1-phenyl-1H-imidazole-4-carboxylic acid {2-[3-(3-fluoro-5-trifluoromethyl-phenoxy)-azetidin-1-yl]-2-oxo-ethyl}-amide. LC/MS [M+H]$^+$: 463, 99.18%. $^1$H NMR (300 MHz, DMSO-d$_6$): δ 8.44 (d, 1H), 8.34 (d, 1H), 8.2 (t, 1H), 7.8 (d, 2H), 7.56 (t, 2H), 7.44 (m, 1H), 7.34 (d, 1H), 7.12 (m, 2H), 5.25 (m, 1H), 4.7 (m, 1H), 4.4 (m, 1H), 4.3 (m, 1H), 3.9 (m, 3H).

Example 189

Synthesis of 1-Phenyl-1H-imidazole-4-carboxylic acid {2-[4-(3-fluoro-5-trifluoromethyl-phenoxy)-piperidin-1-yl]-2-oxo-ethyl}-amide

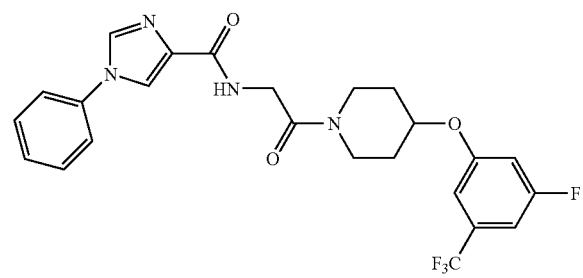

DIPEA (97 mg, 0.75 mmol) was added to a stirred solution of [(1-phenyl-1H-imidazole-4-carbonyl)-amino]-acetic acid (prepared from Intermediate 68 by means of Step 3 of the General Scheme) (61 mg, 0.25 mmol) in DMF (2 mL) followed by HOBt (35 mg, 0.26 mmol) and EDCI (50 mg, 0.26 mmol). After 2 minutes of stirring, 4-(3-fluoro-5-trifluoromethyl-phenoxy)-piperidine hydrochloride (prepared by the method used for the synthesis of Intermediate 15) (75 mg, 0.25 mmol) was added and the resulting mixture was stirred at ambient temperature overnight. The reaction mixture was diluted with cold water and extracted with ethyl acetate. The organic layer was dried over sodium sulfate, concentrated under reduced pressure The residue obtained was purified by column chromatography (using silica gel 60-120 and 40% EtOAc in hexane as eluent) to afford 66 mg (54% Yield) of 1-phenyl-1H-imidazole-4-carboxylic acid {2-[4-(3-fluoro-5-trifluoromethyl-phenoxy)-piperidin-1-yl]-2-oxo-ethyl}-amide. LC/MS [M+H]$^+$: 491, 96%. $^1$H NMR (300 MHz, DMSO-d$_6$): δ 8.4 (m, 1H), 8.3 (m, 1H), 8.03 (m, 1H), 7.78 (m, 2H), 7.58 (m, 2H), 7.4 (m, 1H), 7.3 (m, 1H), 7.2 (m, 2H), 4.8 (m, 1H), 4.2 (m, 2H), 3.9 (m, 1H), 3.7 (m, 1H), 3.4 (m, 2H), 2.0 (m, 2H), 1.6 (m, 2H).

Example 190

Synthesis of 1-Phenyl-1H-imidazole-4-carboxylic acid {2-[4-(4-fluoro-3-trifluoromethyl-phenoxy)-piperidin-1-yl]-2-oxo-ethyl}-amide

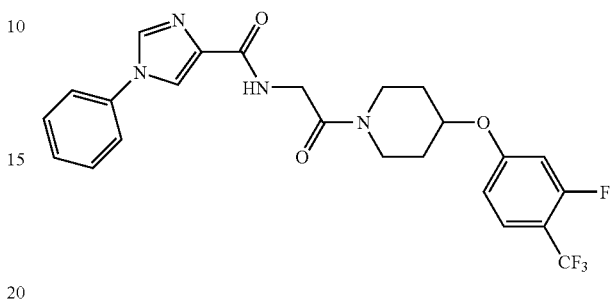

DIPEA (97 mg, 0.75 mmol) was added to a stirred solution of [(1-phenyl-1H-imidazole-4-carbonyl)-amino]-acetic acid (prepared from Intermediate 68 by means of Step 3 of the General Scheme) (61 mg, 0.25 mmol) in DMF (2 mL) followed by HOBt (35 mg, 0.26 mmol) and EDCI (50 mg, 0.26 mmol). After 2 minutes of stirring, 4-(4-fluoro-3-trifluoromethyl-phenoxy)-piperidine hydrochloride (prepared by the method used for the synthesis of Intermediate 15) (75 mg, 0.25 mmol) was added and the resulting mixture was stirred at ambient temperature overnight. The reaction mixture was diluted with cold water and extracted with ethyl acetate. The organic layer was dried over sodium sulfate, concentrated under reduced pressure. The residue obtained was purified by column chromatography (using silica gel 60-120 and 40% EtOAc in hexane as eluent) to afford 59.3 mg (49% Yield) of 1-phenyl-1H-imidazole-4-carboxylic acid {2-[4-(4-fluoro-3-trifluoromethyl-phenoxy)-piperidin-1-yl]-2-oxo-ethyl}-amide. LC/MS [M+H]$^+$: 491, 96%. $^1$H NMR (300 MHz, DMSO-d$_6$): δ 8.4 (m, 1H), 8.3 (m, 1H), 8.05 (m, 1H), 7.75 (m, 2H), 7.55 (m, 2H), 7.4 (m, 4H), 4.8 (m, 1H), 4.2 (m, 2H), 3.9 (m, 1H), 3.6 (m, 1H), 3.4 (b, 1H), 3.3 (m, 1H), 2.0 (m, 2H), 1.6 (m, 2H).

Example 191

Synthesis of 1-Phenyl-1H-imidazole-4-carboxylic acid {2-[3-(2-chloro-phenoxy)-azetidin-1-yl]-2-oxo-ethyl}-amide

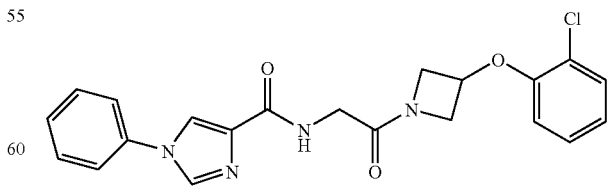

DIPEA (141 mg, 1.09 mmol) was added to a stirred solution of [(1-phenyl-1H-imidazole-4-carbonyl)-amino]-acetic acid (prepared from Intermediate 68 by means of Step 3 of the General Scheme) (67 mg, 0.27 mmol) in DMF (3 mL) followed by HOBt (39 mg, 0.28 mmol) and EDCI (56 mg, 0.28 mmol). After 2 minutes of stirring, 3-(2-chloro-phenoxy)-azetidine hydrochloride (prepared by the method used for the synthesis of Intermediate 71) (60 mg, 0.27 mmol) was added and the resulting mixture was stirred at ambient temperature overnight. Partitioning with cold water and ethyl acetate and concentration of the organic layer after drying over sodium sulfate afforded a residue which was purified by column chromatography (using silica gel 60-120 and 100% EtOAc as eluent) to afford 30 mg (26.7% Yield) of 1-phenyl-1H-imidazole-4-carboxylic acid {2-[3-(2-chloro-phenoxy)-azetidin-1-yl]-2-oxo-ethyl}-amide. LC/MS [M+H]$^+$: 411, 98.45%. $^1$H NMR (300 MHz, DMSO-d$_6$): δ 8.34 (d, 1H), 8.28 (d, 1H), 8.12 (t, 1H), 7.72 (d, 1H), 7.44 (m, 3H), 7.38 (m, 1H), 7.26 (m, 1H), 6.8 (m, 1H), 6.7 (d, 1H), 5.1 (m, 1H), 4.7 (m, 1H), 4.4 (m, 1H), 4.2 (m, 1H), 3.8 (m, 3H).

Example 192

Synthesis of 1-Phenyl-1H-imidazole-4-carboxylic acid {2-[3-(5-cyano-2-methyl-phenoxy)-azetidin-1-yl]-2-oxo-ethyl}-amide

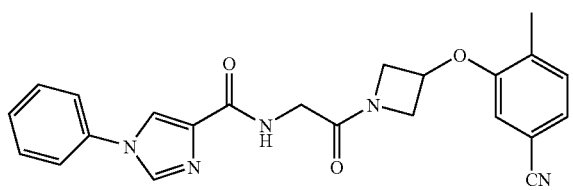

DIPEA (193.9 mg, 1.5 mmol) was added to a stirred solution of [(1-phenyl-1H-imidazole-4-carbonyl)-amino]-acetic acid (prepared from Intermediate 68 by means of Step 3 of the General Scheme) (92 mg, 0.37 mmol) in DMF (3 mL) followed by HOBt (53.2 mg, 0.39 mmol) and EDCI (75.5 mg, 0.39 mmol). After 2 minutes of stirring, 3-(azetidin-3-yloxy)-4-methyl-benzonitrile hydrochloride (prepared by the method used for the synthesis of Intermediate 71) (84 mg, 0.37 mmol) was added and the resulting mixture was stirred at ambient temperature overnight. Partitioning with cold water and ethyl acetate and concentration of the organic layer after drying over sodium sulfate afforded a residue which was purified by preparative HPLC to afford 29 mg (18.7% Yield) of 1-phenyl-1H-imidazole-4-carboxylic acid {2-[3-(5-cyano-2-methyl-phenoxy)-azetidin-1-yl]-2-oxo-ethyl}-amide. LC/MS [M+H]$^+$: 416, 98.6%. $^1$H NMR (300 MHz, DMSO-d$_6$): δ 8.38 (d, 1H), 8.28 (d, 1H), 8.12 (t, 1H), 7.7 (d, 2H), 7.5 (t, 2H), 7.38 (m, 3H), 7.16 (s, 1H), 5.2 (m, 1H), 4.7 (t, 1H), 4.4 (m, 1H), 4.2 (m, 1H), 3.8 (m, 3H).

Example 193

Synthesis of 1-Phenyl-1H-imidazole-4-carboxylic acid {2-[3-(2-chloro-phenoxy)-pyrrolidin-1-yl]-2-oxo-ethyl}-amide

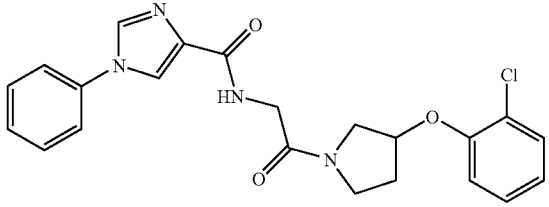

DIPEA (167.9 mg, 1.3 mmol) was added to a stirred solution of [(1-phenyl-1H-imidazole-4-carbonyl)-amino]-acetic acid (prepared from Intermediate 68 by means of Step 3 of the General Scheme) (80 mg, 0.32 mmol) in DMF (2 mL) followed by HOBt (48.3 mg, 0.35 mmol) and EDCI (124 mg, 0.65 mmol). After 2 minutes of stirring, 3-(2-chloro-phenoxy)-pyrrolidine hydrochloride (prepared by the method used for the synthesis of Intermediate 72) (76 mg, 0.32 mmol) was added and the resulting mixture was stirred at ambient temperature overnight. The reaction mixture was diluted with cold water, extracted with ethyl acetate, dried over sodium sulfate, and concentrated under reduced pressure. Purification by recrystallisation from a mixture of DCM in hexane afforded 48 mg (34.7% Yield) of 1-phenyl-1H-imidazole-4-carboxylic acid {2-[3-(2-chloro-phenoxy)-pyrrolidin-1-yl]-2-oxo-ethyl}-amide. LC/MS [M+H]$^+$: 425, 93.15%. $^1$H NMR (300 MHz, DMSO-d$_6$): δ 8.4 (s, 1H), 8.3 (s, 1H), 8.1-8.0 (t, 1H), 7.8-7.7 (t, 2H), 7.5-7.4 (m, 2H), 7.4-7.2 (m, 2H), 7.06-7.0 (m, 1H), 5.3-5.1 (d, 1H), 4.2-4.0 (m, 2H), 4.0-3.5 (m, 4H), 2.3-2.2 (m, 1H), 2.2-2.0 (m, 1H).

Example 194

Synthesis of 5-Phenyl-isoxazole-3-carboxylic acid {2-[3-(2,5-difluoro-phenoxy)-pyrrolidin-1-yl]-2-oxo-ethyl}-amide

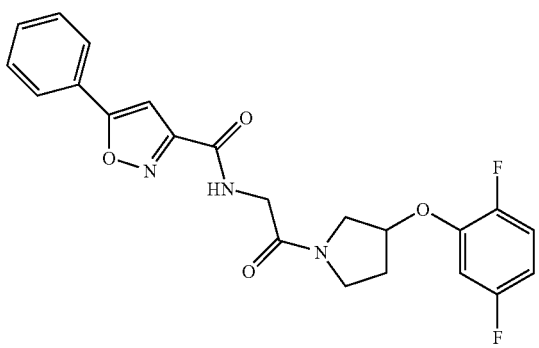

DIPEA (153.5 mg, 1.2 mmol) followed by HOBt (44.1 mg, 0.32 mmol) and EDCI (113.8 mg, 0.59 mmol) were added to a stirred solution of [(5-phenyl-isoxazole-3-carbonyl)- amino]-acetic acid (73.4 mg, 0.29 mmol) in DMF (2 mL). After 2 minutes of stirring, 3-(2,5-difluoro-phenoxy)-pyrrolidine hydrochloride (prepared by the method used for the synthesis of Intermediate 15) (70 mg, 0.29 mmol) was added and the resulting mixture was stirred at ambient temperature overnight. The reaction mixture was partitioned between ethyl acetate and water. The organic layer was dried over sodium sulfate, concentrated under reduced pressure. Purification by column chromatography (using silica gel 60-120 and 50% EtOAc in hexane) afforded 45 mg (35.4% Yield) of 5-phenyl-isoxazole-3-carboxylic acid {2-[3-(2,5-difluoro-phenoxy)-pyrrolidin-1-yl]-2-oxo-ethyl}-amide. LC/MS [M+H]$^+$: 428, 91.77%. $^1$H NMR (300 MHz, DMSO-d$_6$): δ 8.8-8.68 (m, 1H), 8.0-7.9 (m, 2H), 7.6-7.5 (m, 3H), 7.4 (s, 1H), 7.34-7.2 (m, 2H), 6.9-6.75 (m, 1H), 5.3-5.0 (m, 2H), 4.2-4.0 (m, 2H), 3.9 (m, 1H), 3.8-3.7 (m, 1H), 3.7-3.5 (m, 2H), 2.3-2.2 (m, 1H), 2.1 (m, 1H).

Intermediate 74

Synthesis of
2-Phenyl-4H-thieno[3,2-b]pyrrole-5-carboxylic acid

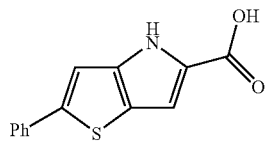

Thionyl chloride (350 mg, 3.0 mmol) was added to cold (0° C.) solution of 5-bromo-thiophene-2-carboxylic acid (100 mg, 0.4 mmol) in MeOH (2 mL) and stirred at ambient temperature overnight. The reaction mixture was concentrated under reduced pressure The residue was diluted with ethylacetate. The organic layer was washed with water followed by saturated brine solution, dried over sodium sulfate and concentrated under reduced pressure to afford 200 mg of 5-bromo-thiophene-2-carboxylic acid methyl ester. Aqueous 2M Na$_2$CO$_3$ solution (7.35 mL) was added to a stirred solution of 5-bromo-thiophene-2-carboxylic acid methyl ester (1.0 g, 4.5 mmol) and phenylboronic acid (660 mg, 5.4 mmol) in DME (15 mL) purged with N$_2$ for 10 minutes. Pd (PPh$_3$)$_4$ (250 mg, 0.22 mmol) was added and the reaction mixture was heated to reflux for 2 hrs. The reaction mixture was diluted with water and the product was extracted with ethyl acetate. The organic layer was washed with saturated brine solution, dried over sodium sulfate and concentrated. Purification by column chromatography (using silica gel 60-120 and 2% EtOAc in hexane as eluent) afforded 900 mg (92% Yield) of 5-phenyl-thiophene-2-carboxylic acid methyl ester. A solution of 5-phenyl-thiophene-2-carboxylic acid methyl ester (800 mg, 3.9 mmol) in THF (3 mL) was added dropwise to reaction flask containing LAH (299 mg, 7.9 mmol) at 0° C. and stirring was continued at ambient temperature for 3 hrs. The reaction mixture was quenched with aqueous NaOH solution and filtered through celite. The filtrated was collected was extracted with ethyl acetate, dried over sodium sulfate and concentrated to afford 710 mg (91.1% Yield) of (5-phenyl-thiophen-2-yl)-methanol IBX (3.0 g, 11.0 mmol) was added to a stirred solution of (5-phenyl-thiophen-2-yl)-methanol (700 mg, 3.6 mmol) in THF (10 mL) and stirring was continued at ambient temperature overnight. The reaction mixture was filtered through celite, filtrated was collected, diluted with water and extracted with ethyl acetate. The organic layer was washed with saturated brine solution, dried over sodium sulfate and concentrated. Purification by column chromatography (using silica gel 60-120 and 5% EtOAc in hexane as eluent) afforded 600 mg (89.5% Yield) of 5-phenyl-thiophene-2-carbaldehyde. 5-phenyl-thiophene-2-carbaldehyde (500 mg, 2.6 mmol) and azido-acetic acid ethyl ester (1.3 g, 10.4 mmol) were added to a stirred solution of sodium metal (240 mg, 10.4 mmol) dissolved in EtOH (10 mL) and cooled to 0° C. while stirring under N$_2$ atmosphere. Stirring was continued at 11° C. for 1.5 hrs. The reaction mixture was quenched with saturated NH$_4$Cl solution and extracted with ethyl acetate. The organic layer was washed with saturated brine solution, dried over sodium sulfate and concentrated to afford 500 mg (crude) of 2-azido-3-(5-phenyl-thiophen-2-yl)-acrylic acid ethyl ester. A mixture of 2-azido-3-(5-phenyl-thiophen-2-yl)-acrylic acid ethyl ester (350 mg, crude) in xylene (5 mL) was stirred at reflux temperature for 30 minutes. The reaction mixture was concentrated. Purification by column chromatography (using silica gel 60-120 and 15% EtOAc in hexane as eluent) afforded 75 mg of 2-phenyl-4H-thieno[3,2-b]pyrrole-5-carboxylic acid ethyl ester. LiOH.H$_2$O (17 mg, 0.4 mmol) was added to a stirred solution of 2-phenyl-4H-thieno[3,2-b]pyrrole-5-carboxylic acid ethyl ester (55 mg, 0.2 mmol) in a mixture of methanol (0.5 mL), THF (11 mL) and H$_2$O (1 mL). The reaction mixture was stirred at ambient temperature for 2 hrs. The reaction mixture was concentrated. The residue was diluted with water, acidified with conc. HCl, and extracted with ethyl acetate. The organic layer collected was dried over sodium sulfate and concentrated under reduced pressure to afford 42 mg (87.5%) of 2-phenyl-4H-thieno[3,2-b]pyrrole-5-carboxylic acid.

Example 195

Synthesis of 2-Phenyl-4H-thieno[3,2-b]pyrrole-5-carboxylic acid {2-[4-(2-chloro-5-fluoro-phenoxy)-piperidin-1-yl]-2-oxo-ethyl}-amide

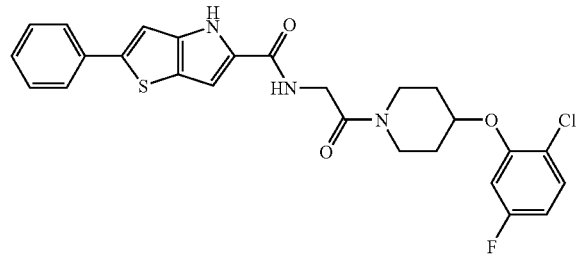

DIPEA (62 mg, 0.48 mmol) followed by HOBt (23 mg, 0.16 mmol) and EDCI (32 mg, 0.16 mmol) were added to a stirred solution of 2-phenyl-4H-thieno[3,2-b]pyrrole-5-carboxylic acid (40 mg, 0.16 mmol) in DMF (2 mL). After 2 minutes of stirring, 2-amino-1-[4-(2-chloro-phenoxy)-piperidin-1-yl]-ethanone hydrochloride (prepared according to Step 1 and 5 of the General Scheme) (51 mg, 0.16 mmol) was added and the resulting mixture was stirred at ambient temperature overnight. The reaction mixture was diluted with cold water, extracted with ethyl acetate, dried over sodium sulfate, and concentrated under reduced pressure. Purification by column chromatography (using silica gel 60-120 and 40% EtOAc in hexane as eluent) afforded 18.5 mg (23% Yield) of 2-phenyl-4H-thieno[3,2-b]pyrrole-5-carboxylic acid {2-[4-(2-chloro-5-fluoro-phenoxy)-piperidin-1-yl]-2- oxo-ethyl}-amide. LC/MS [M+H]⁺: 512, 97.8%. ¹H NMR (300 MHz, DMSO-d₆): δ 11.9 (s, 1H), 8.4 (m, 1H), 7.7 (m, 2H), 7.4 (m, 4H), 7.3 (m, 2H), 7.17 (m, 1H), 6.8 (m, 1H), 4.8 (m, 1H), 4.2 (m, 2H), 3.6 (m, 2H), 3.5 (m, 2H), 2.0 (m, 2H), 1.7 (m, 2H).

Intermediate 75

Synthesis of 6-Pyrazol-1-yl-imidazo[1,2-a]pyridine-2-carboxylic

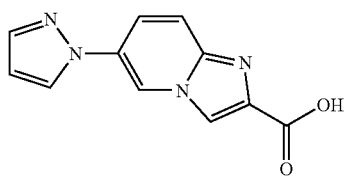

A mixture of sulfuric acid (0.5 mL), acetic acid (12 mL) and water (2 mL) was added to a reaction flask containing 2-aminopyridine (2.0 g, 21.26 mmol) and the solution was stirred for 5 minutes. NaIO₄ (1.81 g, 8.5 mmol) followed by 12 (2.16 g, 8.5 mmol) was added into the reaction flask and stirred at 80° C. for 4 hrs. The reaction mixture was cooled to ambient temperature, diluted with cold water, basified with 20% aqueous KOH solution and extracted with DCM. The organic layer was washed with brine solution, dried over sodium sulfate and concentrated under reduced pressure to obtain the crude residue. Purification by column chromatography (using silica gel 60-120 and 8% EtOAc in hexane as eluent) and subsequent recrystallisation from ethanol afforded 53 g (58.6% Yield) of 5-iodo-pyridin-2-ylamine. Ethyl bromopyruvate (4.89 g, 25.11 mmol) was added to solution of 5-iodo-pyridin-2-ylamine (5.0 g, 22.83 mmol) in DMF (25 mL) and stirring was continued at 80° C. for 2 hrs. The reaction mixture was diluted with cold water and extracted with ethyl acetate. The organic layer was washed with brine solution, dried over sodium sulfate and concentrated under reduced pressure to obtain the crude residue. The residue obtained was purified by recrystallisation from methanol to afford 4.2 g (57.8% Yield) of 6-iodo-imidazo[1,2-a]pyridine-2-carboxylic acid ethyl ester. A mixture of imidazole (513 mg, 7.5 mmol), cuprous oxide (71 mg, 0.5 mmol), 6-iodo-imidazo[1,2-a]pyridine-2-carboxylic acid ethyl ester (1.6 g, 5.02 mmol), salox (137 mg, 1.0 mmol) and cesium carbonate (3.27 g, 10.05 mmol) in ACN (2 mL) in a seal tube were subjected to reaction in a microwave reactor (time: 15 min, temp: 85° C., power: zero, pressure: zero). The reaction mixture was filtered through celite and the filtrate collected was concentrated under reduced pressure. The residue was diluted with cold water, extracted with ethyl acetate, dried over sodium sulfate and concentrated under reduced pressure. The residue was purified by column chromatography (using neutral alumina and 0.2% MeOH in DCM as eluent) to afford 400 mg (31% Yield) of 6-pyrazol-1-yl-imidazo[1,2-a]pyridine-2-carboxylic acid ethyl ester. A mixture of 6-pyrazol-1-yl-imidazo[1,2-a]pyridine-2-carboxylic acid ethyl ester (250 mg, 0.97 mmol) in 8N aqueous HCl (3 mL) was stirred at 100° C. for 2 hrs. The reaction mixture was concentrated under reduced pressure to afford 130 mg (58.5% Yield) of 6-pyrazol-1-yl-imidazo[1,2-a]pyridine-2-carboxylic acid.

Example 196

Synthesis and Purification of 6-Pyrazol-1-yl-imidazo[1,2-a]pyridine-2-carboxylic acid {2-[4-(2-chloro-phenoxy)-piperidin-1-yl]-2-oxo-ethyl}-amide

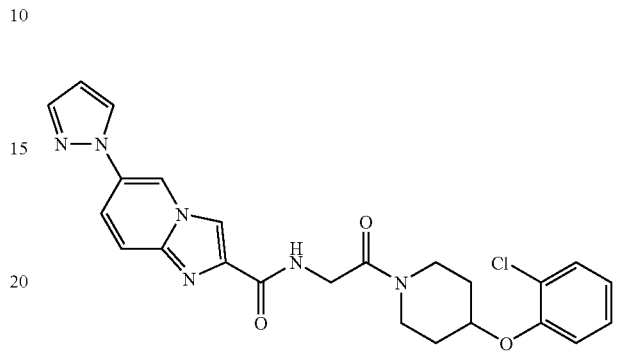

DIPEA (169 mg, 1.3 mmol) followed by HOBt (39 mg, 0.29 mmol) and EDCI (75 mg, 0.39 mmol) was added to a stirred solution of 6-pyrazol-1-yl-imidazo[1,2-a]pyridine-2-carboxylic acid (60 mg, 0.26 mmol) in DMF (1 mL). After 2 minutes of stirring, 2-amino-1-[4-(2-chloro-phenoxy)-piperidin-1-yl]-ethanone hydrochloride (80 mg, 0.26 mmol) (prepared according to Step 1 and 5 of the General Scheme) was added and the resulting mixture was stirred at room temperature overnight. Cold water was added and the reaction mixture was partitioned with ethyl acetate, the organic layer was dried over sodium sulfate and concentrated under reduced pressure. Purification by preparative HPLC afforded 45 mg (33% Yield) of 6-pyrazol-1-yl-imidazo[1,2-a]pyridine-2-carboxylic acid {2-[4-(2-chloro-phenoxy)-piperidin-1-yl]-2-oxo-ethyl}-amide. LC/MS [M+H]⁺: 479, 97.25%. ¹H NMR (300 MHz, DMSO-d₆): δ 9.2 (s, 1H), 8.5 (m, 2H), 8.4 (t, 1H), 8.0 (dd, 1H), 7.8 (m, 2H), 7.4 (dd, 1H), 7.53 (m, 2H), 7.0 (m, 1H), 6.6 (t, 1H), 4.8 (m, 1H), 4.0 (bs, 1H), 4.2 (d, 2H), 3.7 (m, 2H), 3.4 (m, 2H), 2.0 (m, 2H), 1.7 (m, 2H).

Example 197

Synthesis of 1-Pyridin-3-yl-1H-[1,2,3]triazole-4-carboxylic acid {2-[4-(3-cyano-phenoxy)-piperidin-1-yl]-2-oxo-ethyl}-amide

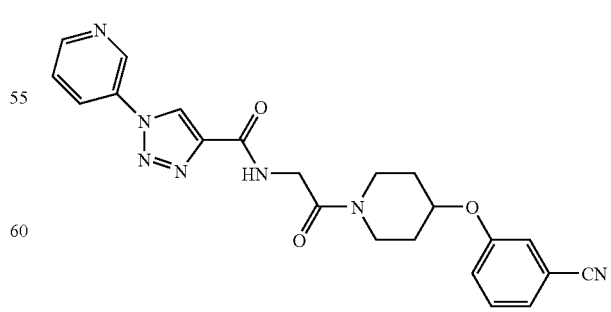

DIPEA (156.8 mg, 1.2 mmol) followed by HOBt (45 mg, 0.33 mmol) and EDCI (116 mg, 0.6 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (75 mg, 0.3 mmol) in DMF (3 mL). After 2 minutes of stirring, 3-(piperidin-4-yloxy)-benzonitrile hydrochloride (prepared by the method used for the synthesis of Intermediate 15) (72.4 mg, 0.3 mmol) was added and the resulting mixture was stirred at room temperature overnight. Cold water was added and formed precipitate was collected. Purification by preparative HPLC afforded 15 mg (11.5% Yield) of 1-pyridin-3-yl-1H-[1,2,3]triazole-4-carboxylic acid {2-[4-(3-cyano-phenoxy)-piperidin-1-yl]-2-oxo-ethyl}-amide. LC/MS [M+H]$^+$: 432.19, 99.3%. $^1$H NMR (300 MHz, DMSO-d$_6$): δ 9.5 (s, 1H), 9.22 (d, 1H), 8.8 (d, 1H), 8.58 (t, 1H), 8.44 (d, 1H), 7.7 (q, 1H), 7.58-7.44 (d, 2H), 7.44 (dd, 2H), 4.8 (m, 1H), 4.3 (d, 2H), 4.0 (bs, 1H), 3.8 (d, 1H), 2.5 (b, 2H), 2.1 (t, 2H), 1.7 (bd, 2H).

Example 198

Synthesis of 1-Pyridin-3-yl-1H-[1,2,3]triazole-4-carboxylic acid {2-[3-(3-fluoro-5-trifluoromethyl-phenoxy)-azetidin-1-yl]-2-oxo-ethyl}-amide

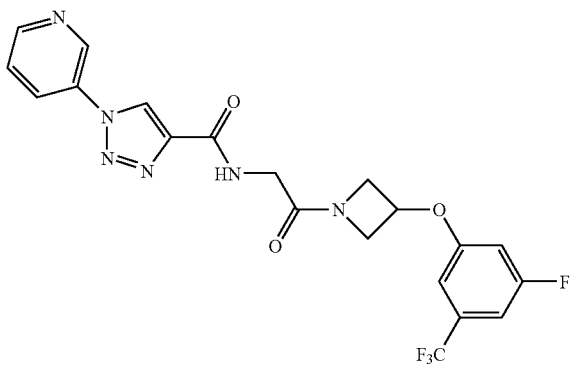

DIPEA (143 mg, 1.1 mmol) followed by HOBt (39 mg, 0.29 mmol) and EDCI (56 mg, 0.29 mmol) was added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (68.3 mg, 0.27 mmol) in DMF (2 mL). After 2 minutes of stirring, 3-(3-fluoro-5-trifluoromethyl-phenoxy)-azetidine hydrochloride (prepared by the method used for the synthesis of Intermediate 71) (75 mg, 0.27 mmol) was added and the resulting mixture was stirred at room temperature overnight. The reaction mixture was partitioned between cold water and ethyl acetate. The organic layer was, dried over sodium sulfate and concentrated under reduced pressure. Purification by preparative HPLC afforded 21 mg (16.4% Yield) of 1-pyridin-3-yl-1H-[1,2,3]triazole-4-carboxylic acid {2-[3-(3-fluoro-5-trifluoromethyl-phenoxy)-azetidin-1-yl]-2-oxo-ethyl}-amide. LC/MS [M+H]$^+$: 465, 93.03%. $^1$H NMR (300 MHz, DMSO-d$_6$): δ 9.5 (s, 1H), 9.2 (d, 1H), 8.7 (m, 2H), 8.4 (m, 1H), 8.3 (s, 1H), 7.65 (m, 1H), 7.3 (d, 1H), 7.1 (m, 2H), 5.2 (m, 1H), 4.7 (m, 1H), 4.4 (m, 1H), 4.2 (m, 1H), 3.8 (m, 3H).

Example 199

Synthesis of 1-Pyridin-3-yl-1H-[1,2,3]triazole-4-carboxylic acid {2-[4-(3-fluoro-5-trifluoromethyl-phenoxy)-piperidin-1-yl]-2-oxo-ethyl}-amide

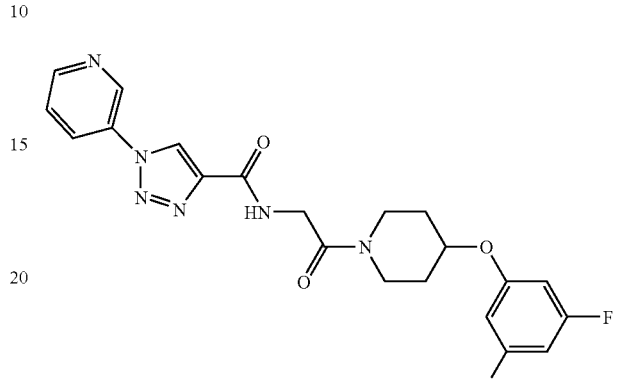

DIPEA (97 mg, 0.75 mmol) followed by HOBt (35 mg, 0.26 mmol) and EDCI (50 mg, 0.26 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (62 mg, 0.25 mmol) in DMF (3 mL). After 2 minutes of stirring, 4-(3-fluoro-5-trifluoromethyl-phenoxy)-piperidine hydrochloride (prepared by the method used for the synthesis of Intermediate 15) (75 mg, 0.25 mmol) was added and the resulting mixture was stirred at room temperature overnight. The reaction mixture was partitioned between cold water and ethyl acetate. The organic layer was dried over sodium sulfate and concentrated under reduced pressure. Purification by column chromatography (using silica gel 60-120 and 40% EtOAc in hexane as eluent) afforded 38.5 mg (32% Yield) of 1-pyridin-3-yl-1H-[1,2,3]triazole-4-carboxylic acid {2-[4-(3-fluoro-5-trifluoromethyl-phenoxy)-piperidin-1-yl]-2-oxo-ethyl}-amide. LC/MS [M+H]$^+$: 493, 98%. $^1$H NMR (300 MHz, DMSO-d$_6$): δ 9.43 (s, 1H), 9.2 (d, 1H), 8.75 (d, 1H), 8.5 (t, 1H), 7.7 (m, 1H), 7.26 (m, 3H), 4.85 (m, 1H), 4.3 (m, 2H), 3.9 (m, 1H), 3.7 (m, 1H), 3.4 (m, 1H), 3.3 (m, 1H), 2.0 (m, 2H), 1.6 (m, 2H).

Example 200

Synthesis of 1-Pyridin-3-yl-1H-[1,2,3]triazole-4-carboxylic acid {2-[3-(2-chloro-phenoxy)-pyrrolidin-1-yl]-2-oxo-ethyl}-amide

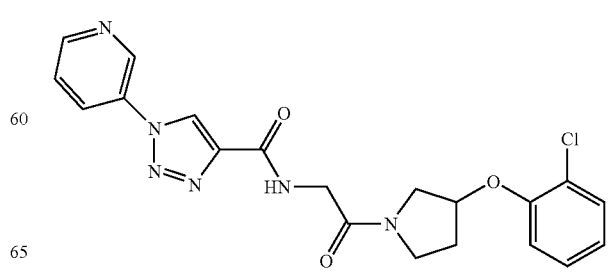

DIPEA (167 mg, 1.3 mmol) followed by HOBt (48 mg, 0.35 mmol) and EDCI (124 mg, 0.64 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (80 mg, 0.32 mmol) in DMF (2 mL). After 2 minutes of stirring, 3-(2-chloro-phenoxy)-pyrrolidine hydrochloride (prepared by the method used for the synthesis of Intermediate 72) (75.7 mg, 0.32 mmol) was added and the resulting mixture was stirred at room temperature overnight. The reaction mixture was partitioned between cold water and ethyl acetate. The organic layer was dried over sodium sulfate and concentrated under reduced pressure. Purification by recrystallisation from a mixture of DCM and hexane afforded 60 mg (43.4% Yield) of 1-pyridin-3-yl-1H-[1,2,3]triazole-4-carboxylic acid {2-[3-(2-chloro-phenoxy)-pyrrolidin-1-yl]-2-oxo-ethyl}-amide. LC/MS [M+H]⁺: 427. ¹H NMR (300 MHz, DMSO-d₆): δ 9.45 (s, 1H), 9.2 (d, 1H), 8.75 (d, 1H), 8.6 (q, 1H), 8.4 (m, 1H), 7.7 (q, 1H), 7.5-7.4 (m, 1H), 7.4-7.2 (m, 2H), 7.06-6.96 (m, 1H), 5.3-5.1 (d, 1H), 4.25-4.0 (m, 2H), 4.0-3.6 (m, 4H), 3.5-3.4 (m, 1H), 2.3-2.2 (m, 1H).

Example 201

Synthesis of 1-Pyridin-3-yl-1H-[1,2,3]triazole-4-carboxylic acid {2-[4-(4-fluoro-3-trifluoromethyl-phenoxy)-piperidin-1-yl]-2-oxo-ethyl}-amide

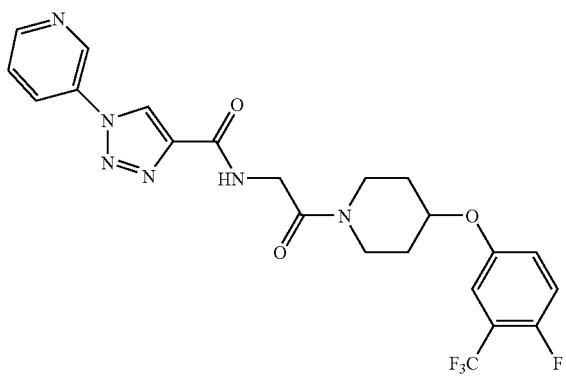

DIPEA (97 mg, 0.75 mmol) was added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (62 mg, 0.25 mmol) in DMF (2 mL) followed by HOBt (35 mg, 0.26 mmol) and EDCI (50 mg, 0.26 mmol). After 2 minutes of stirring, 4-(4-fluoro-3-trifluoromethyl-phenoxy)-piperidine hydrochloride (prepared by the method used for the synthesis of Intermediate 15) (75 mg, 0.25 mmol) was added and the resulting mixture was stirred at room temperature overnight. The reaction mixture was partitioned between cold water and ethyl acetate. The organic layer was dried over sodium sulfate and concentrated under reduced pressure. Purification by column chromatography (using silica gel 60-120 and 40% EtOAc in hexane as eluent) afforded 24 mg (20% Yield) of 1-pyridin-3-yl-1H-[1,2,3]triazole-4-carboxylic acid {2-[4-(4-fluoro-3-trifluoromethyl-phenoxy)-piperidin-1-yl]-2-oxo-ethyl}-amide. LC/MS [M+H]⁺: 493, 95.48%. ¹H NMR (300 MHz, DMSO-d₆): δ 9.43 (s, 1H), 9.2 (m, 1H), 8.75 (m, 1H), 8.5 (m, 1H), 8.4 (m, 1H), 7.7 (m, 1H), 7.4 (m, 3H), 4.75 (m, 1H), 4.3 (m, 2H), 3.9 (m, 1H), 3.7 (m, 1H), 3.5 (m, 2H), 2.0 (m, 2H), 1.6 (m, 2H).

Example 202

Synthesis of 1-Pyridin-3-yl-1H-[1,2,3]triazole-4-carboxylic acid {2-[3-(2-chloro-phenoxy)-azetidin-1-yl]-2-oxo-ethyl}-amide

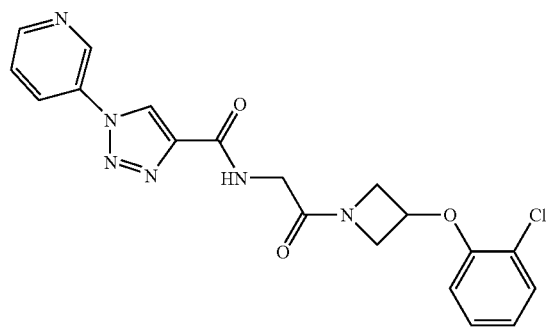

DIPEA (141 mg, 1.1 mmol) followed by HOBt (39 mg, 0.29 mmol) and EDCI (56 mg, 0.29 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (67.5 mg, 0.27 mmol) in DMF (3 mL). After 2 minutes of stirring, 3-(2-chloro-phenoxy)-azetidine hydrochloride (prepared by the method used for the synthesis of Intermediate 71) (60 mg, 0.27 mmol) was added and the resulting mixture was stirred at room temperature overnight. The reaction mixture was partitioned between cold water and ethyl acetate. The organic layer was dried over sodium sulfate and concentrated under reduced pressure. Purification by preparative HPLC afforded 33 mg (29.4% Yield) of 1-pyridin-3-yl-1H-[1,2,3]triazole-4-carboxylic acid {2-[3-(2-chloro-phenoxy)-azetidin-1-yl]-2-oxo-ethyl}-amide. LC/MS [M+H]⁺: 413, 98.7%. ¹H NMR (300 MHz, DMSO-d₆): δ 9.42 (s, 1H), 9.2 (d, 1H), 8.7 (m, 2H), 8.4 (m, 1H), 7.64 (m, 1H), 7.42 (m, 1H), 7.24 (m, 1H), 7.0 (t, 1H), 6.9 (d, 1H), 5.12 (m, 1H), 4.68 (m, 1H), 4.38 (m, 1H), 4.24 (m, 1H), 3.96 (m, 1H), 3.84 (m, 1H).

Example 203

Synthesis of 1-Pyridin-3-yl-1H-[1,2,3]triazole-4-carboxylic acid {2-[3-(5-cyano-2-methyl-phenoxy)-azetidin-1-yl]-2-oxo-ethyl}-amide

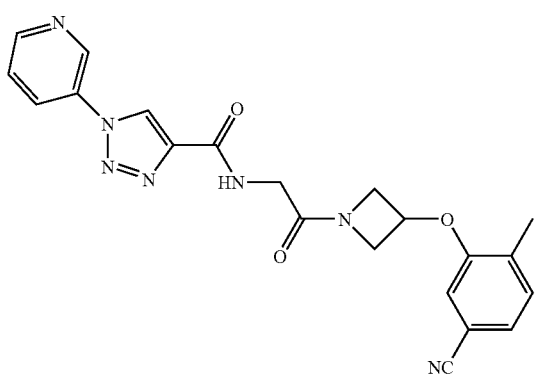

DIPEA (193.9 mg, 1.5 mmol) followed by HOBt (53 mg, 0.29 mmol) and EDCI (75 mg, 0.39 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (93 g, 0.37 mmol) in DMF (3 mL). After 2 minutes of stirring, 3-(azetidin-3-yloxy)-4-methyl-benzonitrile hydrochloride (prepared by the method used for the synthesis of Intermediate 71) (84 mg, 0.37 mmol) was added and the resulting mixture was stirred at room temperature overnight. The reaction mixture was partitioned between cold water and ethyl acetate. The organic layer was dried over sodium sulfate and concentrated under reduced pressure. Purification by preparative HPLC afforded 11 mg (7% Yield) of 1-pyridin-3-yl-1H-[1,2,3]triazole-4-carboxylic acid {2-[3-(5-cyano-2-methyl-phenoxy)-azetidin-1-yl]-2-oxo-ethyl}-amide. LC/MS [M+H]$^+$: 418, 96.08%. $^1$H NMR (300 MHz, DMSO-d$_6$): δ 9.42 (s, 1H), 9.2 (d, 1H), 8.7 (m, 2H), 8.38 (m, 1H), 7.62 (m, 1H), 7.4 (s, 1H), 7.16 (s, 1H), 5.1 (m, 1H), 4.7 (m, 1H), 4.4 (m, 1H), 4.2 (m, 1H), 4.0 (d, 2H), 3.8 (m, 1H).

Example 204

Synthesis of 1-Pyridin-3-yl-1H-[1,2,3]triazole-4-carboxylic acid {2-oxo-2-[4-(2-trifluoromethyl-phenoxy)-piperidin-1-yl]-ethyl}-amide

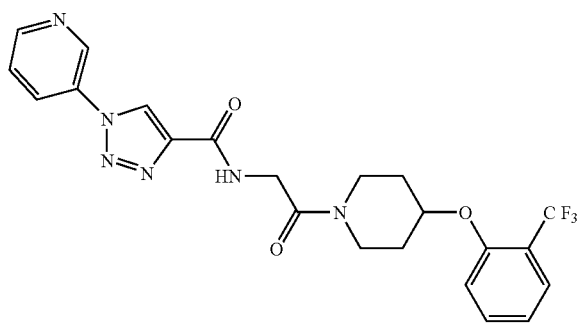

DIPEA (156.8 mg, 1.5 mmol) followed by HOBt (53 mg, 0.29 mmol) and EDCI (75 mg, 0.39 mmol) were added to a stirred solution of [(1-pyridin-3-yl-1H-[1,2,3]triazole-4-carbonyl)-amino]-acetic acid (prepared by the method used for the synthesis of Intermediate 64, starting from 3-aminopyridine, and subsequently, application of Step 3 of the General Scheme) (75 g, 0.3 mmol) in DMF (4 mL). After 2 minutes of stirring, 4-(2-trifluoromethyl-phenoxy)-piperidine trifluoroacetate (85 mg, 0.3 mmol) was added and the resulting mixture was stirred at room temperature overnight. Addition of cold water lead to the formation of a precipitate which was collected and purified by preparative HPLC to afford 24 mg (15.6% Yield) of 1-pyridin-3-yl-1H-[1,2,3]triazole-4-carboxylic acid {2-oxo-2-[4-(2-trifluoromethyl-phenoxy)-piperidin-1-yl]-ethyl}-amide. LC/MS [M+H]$^+$: 475, 99.07%. $^1$H NMR (300 MHz, DMSO-d$_6$): δ 9.45 (s, 1H), 9.2 (d, 1H), 8.75 (m, 1H), 8.5 (t, 1H), 8.4 (m, 1H), 7.7-7.6 (m, 3H), 7.4-7.35 (d, 1H), 7.1 (t, 1H), 5.0 (q, 1H), 4.25 (d, 2H), 3.7-3.5 (m, 4H), 2.0-1.8 (m, 2H), 1.8-1.5 (m, 2H).

Example 205

Synthesis of 5-Phenyl-1H-pyrazole-3-carboxylic acid {2-[3-(3-fluoro-5-trifluoromethyl-phenoxy)-azetidin-1-yl]-2-oxo-ethyl}-amide

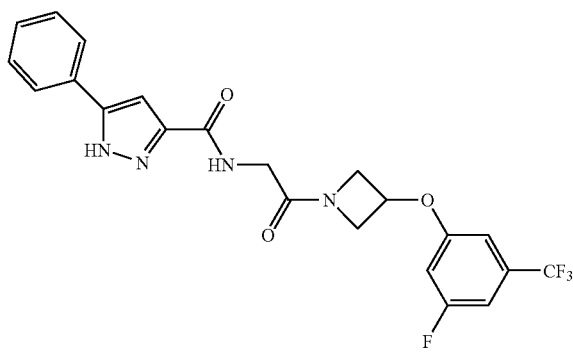

DIPEA (143 mg, 1.1 mmol) followed by HOBt (39 mg, 0.29 mmol) and EDCI (56 mg, 0.29 mmol) was added to a stirred solution of [(5-phenyl-1H-pyrazole-3-carbonyl)-amino]-acetic acid (68 mg, 0.27 mmol) in DMF (2 mL) After 2 minutes of stirring, 3-(3-fluoro-5-trifluoromethyl-phenoxy)-azetidine hydrochloride (prepared by the method used for the synthesis of Intermediate 71) (75 mg, 0.27 mmol) was added and the resulting mixture was stirred at room temperature overnight. The reaction mixture was partitioned between cold water and ethyl acetate. The organic layer was dried over sodium sulfate and concentrated under reduced pressure. Purification by preparative HPLC afforded 31 mg (24.4% Yield) of 5-phenyl-1H-pyrazole-3-carboxylic acid {2-[3-(3-fluoro-5-trifluoromethyl-phenoxy)-azetidin-1-yl]-2-oxo-ethyl}-amide. LC/MS [M+H]$^+$: 463, 81.67%. $^1$H NMR (300 MHz, DMSO-d$_6$): δ 13.75 (s, 1H), 7.8 (d, 2H), 7.42 (t, 2H), 7.26 (m, 2H), 7.1 (d, 1H), 7.04 (s, 1H), 5.2 (m, 1H), 4.7 (m, 1H), 4.4 (m, 1H), 4.2 (m, 2H), 3.7 (m, 2H).

Example 206

Synthesis of 5-Phenyl-1H-pyrazole-3-carboxylic acid {2-[4-(3-fluoro-5-trifluoromethyl-phenoxy)-piperidin-1-yl]-2-oxo-ethyl}-amide

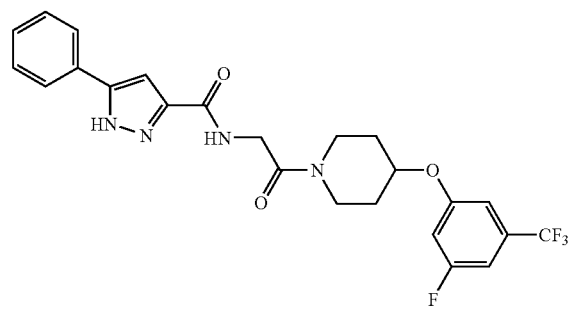

DIPEA (97 mg, 0.75 mmol) followed by HOBt (35 mg, 0.26 mmol) and EDCI (50 mg, 0.26 mmol) was added to a stirred solution of [(5-phenyl-1H-pyrazole-3-carbonyl)-amino]-acetic acid (62 mg, 0.25 mmol) in DMF (2 mL). After 2 minutes of stirring, 3-(3-fluoro-5-trifluoromethyl-phenoxy)-azetidine hydrochloride (prepared by the method used for the synthesis of Intermediate 15) (75 mg, 0.25 mmol) was added and the resulting mixture was stirred at room temperature overnight. The reaction mixture was partitioned between cold water and ethyl acetate. The organic layer was dried over sodium sulfate and concentrated under reduced pressure. Purification by column chromatography (using silica gel 60-120 and 40% EtOAc in hexane as eluent) afforded 54 mg (45% Yield) of 5-phenyl-1H-pyrazole-3-carboxylic acid {2-[4-(3-fluoro-5-trifluoromethyl-phenoxy)-piperidin-1-yl]-2-oxo-ethyl}-amide. LC/MS [M+H]$^+$: 491, 94%. $^1$H NMR (300 MHz, DMSO-d$_6$): δ 13.8 (s, 1H), 8.5 (b, 1H), 7.8 (d, 2H), 7.4 (m, 2H), 7.3 (m, 2H), 7.2 (m, 2H), 7.1 (m, 1H), 4.8 (m, 1H), 4.2 (m, 2H), 3.8 (m, 1H), 3.6 (m, 1H), 3.4 (m, 1H), 3.3 (m, 1H), 2.0 (m, 2H), 1.6 (m, 2H).

Example 207

Synthesis of 5-Phenyl-1H-pyrazole-3-carboxylic acid {2-[4-(4-fluoro-3-trifluoromethyl-phenoxy)-piperidin-1-yl]-2-oxo-ethyl}-amide

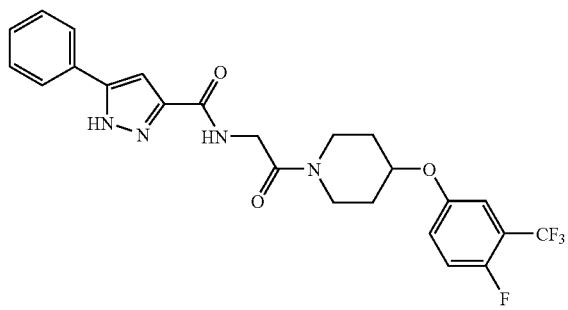

DIPEA (97 mg, 0.75 mmol) followed by HOBt (35 mg, 0.26 mmol) and EDCI (50 mg, 0.26 mmol) was added to a stirred solution of [(5-phenyl-1H-pyrazole-3-carbonyl)-amino]-acetic acid (62 mg, 0.25 mmol) in DMF (2 mL). After 2 minutes of stirring, 3-(3-fluoro-5-trifluoromethyl-phenoxy)-azetidine hydrochloride (prepared by the method used for the synthesis of Intermediate 15) (75 mg, 0.25 mmol) was added and the resulting mixture was stirred at room temperature overnight. The reaction mixture was partitioned between cold water and ethyl acetate. The organic layer was dried over sodium sulfate and concentrated under reduced pressure. Purification by column chromatography (using silica gel 60-120 and 40% EtOAc in hexane as eluent) afforded 55 mg (45% Yield) of 5-phenyl-1H-pyrazole-3-carboxylic acid {2-[4-(4-fluoro-3-trifluoromethyl-phenoxy)-piperidin-1-yl]-2-oxo-ethyl}-amide. LC/MS [M+H]$^+$: 491, 99%. $^1$H NMR (300 MHz, DMSO-d$_6$): δ 13.6 (m, 1H), 8.0 (m, 1H), 7.8 (m, 2H), 7.4 (m, 6H), 7.3 (m, 1H), 4.7 (m, 1H), 4.2 (m, 2H), 3.8 (m, 1H), 3.7 (m, 1H), 3.4 (m, 1H), 3.0 (m, 1H), 2.0 (m, 2H), 1.6 (m, 2H).

Example 208

Synthesis of 5-Phenyl-1H-pyrazole-3-carboxylic acid {2-[3-(2-chloro-phenoxy)-azetidin-1-yl]-2-oxo-ethyl}-amide

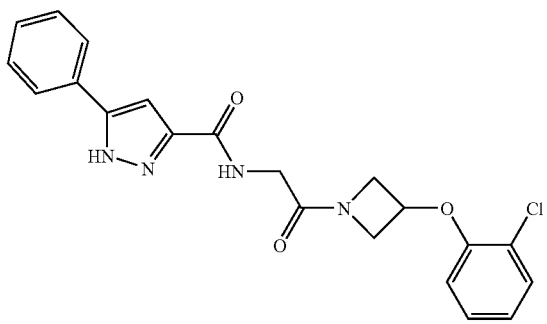

DIPEA (143 mg, 1.1 mmol) followed by HOBt (39 mg, 0.29 mmol) and EDCI (56 mg, 0.29 mmol) was added to a stirred solution of [(5-phenyl-1H-pyrazole-3-carbonyl)-amino]-acetic acid (67 g, 0.27 mmol) in DMF (2 mL). After 2 minutes of stirring, 3-(2-chloro-phenoxy)-azetidinehydrochloride (prepared by the method used for the synthesis of Intermediate 71) (60 mg, 0.27 mmol) was added and the resulting mixture was stirred at room temperature overnight. The reaction mixture was partitioned between cold water and ethyl acetate. The organic layer was dried over sodium sulfate and concentrated under reduced pressure. Purification by preparative HPLC afforded 48 mg (42.8% Yield) of 5-phenyl-1H-pyrazole-3-carboxylic acid {2-[3-(2-chloro-phenoxy)-azetidin-1-yl]-2-oxo-ethyl}-amide. LC/MS [M+H]$^+$: 411, 99.1%. $^1$H NMR (300 MHz, DMSO-d$_6$): δ 13.7 (s, 1H), 8.2 (t, 1H), 7.54 (m, 2H), 7.28 (m, 5H), 7.08 (d, 1H), 7.0 (t, 1H), 6.86 (d, 1H), 5.1 (m, 1H), 4.64 (m, 1H), 4.36 (m, 1H), 4.2 (m, 1H), 3.84 (m, 3H).

Example 209

Synthesis of 5-Phenyl-1H-pyrazole-3-carboxylic acid {2-[3-(5-cyano-2-methyl-phenoxy)-azetidin-1-yl]-2-oxo-ethyl}-amide

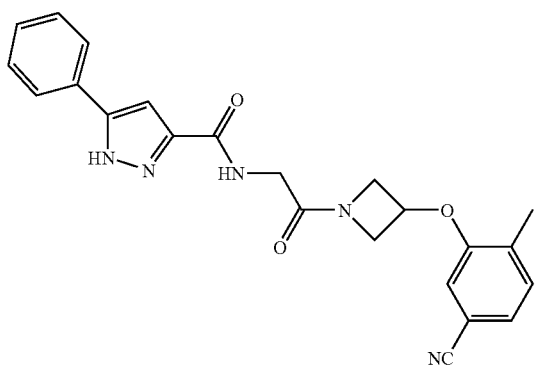

DIPEA (193.9 mg, 1.5 mmol) followed by HOBt (53 mg, 0.29 mmol) and EDCI (75 mg, 0.39 mmol) was added to a stirred solution of [(5-phenyl-1H-pyrazole-3-carbonyl)-amino]-acetic acid (92 g, 0.37 mmol) in DMF (3 mL) After 2 minutes of stirring, 3-(azetidin-3-yloxy)-4-methyl-benzonitrile hydrochloride (prepared by the method used for the synthesis of Intermediate 71) (84 mg, 0.37 mmol) was added and the resulting mixture was stirred at room temperature overnight. The reaction mixture was partitioned between cold water and ethyl acetate. The organic layer was dried over sodium sulfate and concentrated under reduced pressure. Purification by preparative HPLC afforded 35 mg (22.5% Yield) of 5-phenyl-1H-pyrazole-3-carboxylic acid {2-[3-(5-cyano-2-methyl-phenoxy)-azetidin-1-yl]-2-oxo-ethyl}-amide. LC/MS [M+H]$^+$: 416, 92.49%. $^1$H NMR (300 MHz, DMSO-d$_6$): δ 13.8 (s, 1H), 8.2 (t, 1H), 7.74 (t, 2H), 7.42 (m, 2H), 7.3 (m, 3H), 7.16 (s, 1H), 7.08 (s, 1H), 5.2 (m, 1H), 4.7 (m, 1H), 4.4 (m, 1H), 4.2 (m, 1H), 3.8 (m, 3H).

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A compound of the formula:

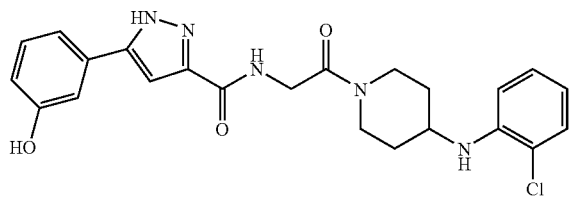

wherein
$R^1$ is aryl or heteroaryl;
$R^2$ is aryl or heteroaryl;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
m and n are, independently, 1 or 2;
X is —O—, —NR$^6$—, —S—, —S(O)— or —S(O)$_2$— where R$^6$ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, or enantiomer or diastereomer thereof;
with the proviso that said compound is not
4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

2. The compound of claim 1, wherein R1 is aryl that is substituted by one or more aryl groups.

3. The compound of claim 1, wherein R1 is heteroaryl and is substituted by one or more aryl or heteroaryl groups.

4. The compound of claim 1, wherein R1 is pyrazole, triazole, or isoxazole.

5. The compound of claim 1, wherein R2 is aryl.

6. The compound of claim 1, wherein the compound is selected from:
1-Cyclopentyl-1H-[1,2,3]triazole-4-carboxylic acid {2-[4-(5-chloro-pyridin-3-yloxy)-piperidin-1-yl]-2-oxo-ethyl}-amide;
1-Pyridin-3-yl-1H-[1,2,3]triazole-4-carboxylic acid {2-[4-(5-cyano-2-methyl-phenoxy)-piperidin-1-yl]-2-oxo-ethyl}-amide;
1-Morpholin-4-yl-1H-[1,2,3]triazole-4-carboxylic acid {2-oxo-2-[4-(3-trifluoromethyl-phenoxy)-piperidin-1-yl]-ethyl}-amide;
1-Morpholin-4-yl-1H-[1,2,3]triazole-4-carboxylic acid {2-[4-(2-chloro-5-fluoro-phenoxy)-piperidin-1-yl]-2-oxo-ethyl}-amide;
1-Pyridin-3-yl-1H-[1,2,3]triazole-4-carboxylic acid {2-[3-(2,5-difluoro-phenoxy)-pyrrolidin-1-yl]-2-oxo-ethyl}-amide;
1-Phenyl-1H-imidazole-4-carboxylic acid {2-[4-(2,5-difluoro-phenoxy)-piperidin-1-yl]-2-oxo-ethyl}-amide; and
1-Phenyl-1H-imidazole-4-carboxylic acid {2-[4-(2-chloro-phenoxy)-piperidin-1-yl]-2-oxo-ethyl}-amide, and pharmaceutically acceptable salts thereof.

7. The compound of claim 1, wherein the compound is selected from:
Biphenyl-4-carboxylic acid {2-oxo-2-[4-(2-trifluoromethyl-phenoxy)-piperidin-1-yl]-ethyl}-amide,
Biphenyl-4-carboxylic acid {2-[4-(2-bromo-phenoxy)-piperidin-1-yl]-2-oxo-ethyl}-amide,
Biphenyl-4-carboxylic acid {2-[4-(2-bromo-phenylamino)-piperidin-1-yl]-2-oxo-ethyl}-amide,
Biphenyl-4-carboxylic acid {2-[4-(2-chloro-phenylamino)-piperidin-1-yl]-2-oxo-ethyl}-amide,
Biphenyl-4-carboxylic acid {2-oxo-2-[4-(2-trifluoromethyl-phenylamino)-piperidin-1-yl]-ethyl}-amide,
Biphenyl-4-carboxylic acid (2-{4-[methyl-(2-trifluoromethyl-phenyl)-amino]-piperidin-1-yl}-2-oxo-ethyl)-amide,
Biphenyl-4-carboxylic acid (2-{4-[(2-chloro-phenyl)-methyl-amino]-piperidin-1-yl}-2-oxo-ethyl)-amide,
Biphenyl-4-carboxylic acid (2-{4-[(2-bromo-phenyl)-methyl-amino]-piperidin-1-yl}-2-oxo-ethyl)-amide,
5-Phenyl-isoxazole-3-carboxylic acid {2-[4-(2-bromo-phenoxy)-piperidin-1-yl]-2-oxo-ethyl}-amide, 5-Phenyl-isoxazole-3-carboxylic acid {2-[4-(2-bromo-phenylamino)-piperidin-1-yl]-2-oxo-ethyl}-amide,
5-Phenyl-isoxazole-3-carboxylic acid {2-[4-(2-chloro-phenylamino)-piperidin-1-yl]-2-oxo-ethyl}-amide,
5-Phenyl-isoxazole-3-carboxylic acid (2-{4-[(2-bromo-phenyl)-methyl-amino]-piperidin-1-yl}-2-oxo-ethyl)-amide,
5-Phenyl-isoxazole-3-carboxylic acid {2-oxo-2-[4-(2-trifluoromethyl-phenylamino)-piperidin-1-yl]-ethyl}-amide,
5-Phenyl-isoxazole-3-carboxylic acid (2-{-4-[methyl-(2-trifluoromethyl-phenyl)-amino]-piperidin-1-yl}-2-oxo-ethyl)-amide,
N-{2-oxo-2-[4-(2-trifluoromethyl-phenylamino)-piperidin-1-yl]-ethyl}-4-phenylamino-benzamide,
N-{2-[4-(2-Chloro-phenylamino)-piperidin-1-yl]-2-oxo-ethyl}-4-phenylamino-benzamide
N-{2-[4-(2-Bromo-phenylamino)-piperidin-1-yl]-2-oxo-ethyl}-4-phenylamino-benzamide
N-(2-{4-[Methyl-(2-trifluoromethyl-phenyl)-amino]-piperidin-1-yl}-2-oxo-ethyl)-4-phenylamino-benzamide,
N-{2-[4-(2-Bromo-phenoxy)-piperidin-1-yl]-2-oxo-ethyl}-4-phenylamino-benzamide
5-Phenyl-1H-pyrazole-3-carboxylic acid {2-[4-(2-bromo-phenylamino)-piperidin-1-yl]-2-oxo-ethyl}
5-Phenyl-1H-pyrazole-3-carboxylic acid {2-[4-(2-chloro-phenylamino)-piperidin-1-yl]-2-oxo-ethyl}
5-Phenyl-1H-pyrazole-3-carboxylic acid {2-[4-(2-bromo-phenoxy)-piperidin-1-yl]-2-oxo-ethyl}
5-Phenyl-1H-pyrazole-3-carboxylic acid {2-[4-(2-chloro-phenoxy)-piperidin-1-yl]-2-oxo-ethyl}
5-Phenyl-1H-pyrazole-3-carboxylic acid {2-[4-(2-chloro-5-fluoro-phenoxy)-piperidin-1-yl]-2-oxo-ethyl}
5-Phenyl-1H-pyrazole-3-carboxylic acid {2-oxo-2-[4-(2-trifluoromethyl-phenylsulfanyl)-piperidin-1-yl]-ethyl}-amide,
5-Phenyl-1H-pyrazole-3-carboxylic acid {2-[4-(2-chlorophenylsulfanyl)-piperidin-1-yl]-2-oxo-ethyl}-amide,
5-Phenyl-1H-pyrazole-3-carboxylic acid {2-[4-(2-nitro-phenoxy)-piperidin-1-yl]-2-oxo-ethyl}
5-Phenyl-1H-pyrazole-3-carboxylic acid {2-[4-(2-amino-phenoxy)-piperidin-1-yl]-2-oxo-ethyl}-amide,
5-Phenyl-1H-pyrazole-3-carboxylic acid {2-[4-(2,3-dimethyl-phenylamino)-piperidin-1-yl]-2-oxo-ethyl}-amide, and
5-Phenyl-1H-pyrazole-3-carboxylic acid {2-[4-(2,4-dimethyl-phenylamino)-piperidin-1-yl]-2-oxo-ethyl}-amide,
and pharmaceutically acceptable salts thereof.

8. The compound of claim 1, wherein the compound is selected from:
5-Phenyl-1H-pyrazole-3-carboxylic acid {2-[4-(2,5-dimethyl-phenylamino)-piperidin-1-yl]-2-oxo-ethyl}
5-Phenyl-1H-pyrazole-3-carboxylic acid {2-[4-(2-tert-butyl-phenylamino)-piperidin-1-yl]-2-oxo-ethyl}
5-Phenyl-1H-pyrazole-3-carboxylic acid {2-[4-(2,5-difluoro-phenoxy)-piperidin-1-yl]-2-oxo-ethyl}
5-Phenyl-1H-pyrazole-3-carboxylic acid {2-[4-(2-bromo-phenylsulfanyl)-piperidin-1-yl]-2-oxo-ethyl}
5-Phenyl-1H-pyrazole-3-carboxylic acid [2-oxo-2-(4-o-tolylamino-piperidin-1-yl)-ethyl]-amide,
5-(3-Hydroxy-phenyl)-1H-pyrazole-3-carboxylic acid {2-[4-(2-chloro-phenylamino)-piperidin-1-yl]-2-oxo-ethyl}-amide,
5-Phenyl-pyridine-2-carboxylic acid {2-oxo-2-[4-(2-chloro-phenoxy)-piperidin-1-yl]-ethyl}-amide,
5-Phenyl-pyridine-2-carboxylic acid {2-[4-(2-chloro-5-fluoro-phenoxy)-piperidin-1-yl]-2-oxo-ethyl}-amide,
5-(4-Hydroxy-phenyl)-1H-pyrazole-3-carboxylic acid {2-[4-(2-chloro-phenylamino)-piperidin-1-yl]-2-oxo-ethyl}-amide,
5-(2-Hydroxy-phenyl)-1-methyl-1H-pyrazole-3-carboxylic acid {2-[4-(2-chloro-phenylamino)-piperidin-1-yl]-2-oxo-ethyl}-amide,
Synthesis of 5-(2-Hydroxy-phenyl)-isoxazole-3-carboxylic acid {2-[4-(2-chloro-phenoxy)-piperidin-1-yl]-2-oxo-ethyl}-amide,
5-(2-Hydroxy-phenyl)-isoxazole-3-carboxylic acid {2-[4-(2-chloro-phenylamino)-piperidin-1-yl]-2-oxo-ethyl}-amide,
5-(2-Hydroxy-phenyl)-1H-pyrazole-3-carboxylic acid {2-[4-(2-chloro-phenylamino)-piperidin-1-yl]-2-oxo-ethyl}-amide,
5-(2-Hydroxy-phenyl)-1H-pyrazole-3-carboxylic acid {2-[4-(2-chloro-phenoxy)-piperidin-1-yl]-2-oxo-ethyl}-amide,
N-{2-[4-(2-Chloro-phenoxy)-piperidin-1-yl]-2-oxo-ethyl}-6-phenylamino-nicotinamide,
N-{2-[4-(2-Chloro-phenylamino)-piperidin-1-yl]-2-oxo-ethyl}-6-phenylamino-nicotinamide,
5-Phenylamino-pyridine-2-carboxylic acid {2-[4-(2-chloro-phenylamino)-piperidin-1-yl]-2-oxo-ethyl}-amide,
5-Phenylamino-pyridine-2-carboxylic acid {2-[4-(2-chloro-phenylamino)-piperidin-1-yl]-2-oxo-ethyl}-amide,
5-Phenyl-1H-pyrazole-3-carboxylic acid {2-[4-(5-bromo-2-methoxy-phenylamino)-piperidin-1-yl]-2-oxo-ethyl}-amide,
5-Phenyl-1H-pyrazole-3-carboxylic acid {2-oxo-2-[4-(3-trifluoromethyl-phenoxy)-piperidin-1-yl]-ethyl}-amide,
5-Phenyl-1H-pyrazole-3-carboxylic acid {2-[4-(2-cyano-phenoxy)-piperidin-1-yl]-2-oxo-ethyl}-amide,
5-(2-Fluoro-phenyl)-1H-pyrazole-3-carboxylic acid {2-[4-(2-chloro-phenylamino)-piperidin-1-yl]-2-oxo-ethyl}-amide,
5-Phenyl-1H-pyrazole-3-carboxylic acid {2-[4-(2,4-difluoro-phenylamino)-piperidin-1-yl]-2-oxo-ethyl}-amide,
5-Phenyl-1H-pyrazole-3-carboxylic acid {2-[4-(5-fluoro-2-trifluoromethyl-phenylamino)-piperidin-1-yl]-2-oxo-ethyl}-amide,
5-Phenyl-1H-pyrazole-3-carboxylic acid {2-[4-(4-fluoro-2-trifluoromethyl-phenylamino)-piperidin-1-yl]-2-oxo-ethyl}-amide,
5-Phenyl-1H-pyrazole-3-carboxylic acid {2-[4-(2-acetyl-phenoxy)-piperidin-1-yl]-2-oxo-ethyl}-amide,
5-Phenyl-1H-pyrazole-3-carboxylic acid {2-[4-(5-cyano-2-methyl-phenylamino)-piperidin-1-yl]-2-oxo-ethyl}-amide,
5-Phenyl-1H-pyrazole-3-carboxylic acid {2-oxo-2-[4-(2-trifluoromethyl-benzenesulfinyl)-piperidin-1-yl]-ethyl}-amide,
5-Phenyl-1H-pyrazole-3-carboxylic acid {2-oxo-2-[4-(pyridin-4-yloxy)-piperidin-1-yl]-ethyl}-amide, and
5-Phenyl-1H-pyrazole-3-carboxylic acid {2-[4-(5-chloro-pyridin-3-yloxy)-piperidin-1-yl]-2-oxo-ethyl}-amide,
and pharmaceutically acceptable salts thereof.

9. The compound of claim 1, wherein the compound is selected from:
5-Phenyl-1H-pyrazole-3-carboxylic acid {2-[4-(2-hydroxy-phenoxy)-piperidin-1-yl]-2-oxo-ethyl}-amide, 5-Phenyl-1H-pyrazole-3-carboxylic acid {2-oxo-2-[4-(2-trifluoromethyl-benzenesulfonyl)-piperidin-1-yl]-ethyl}-amide,
5-Phenyl-1H-pyrazole-3-carboxylic acid {2-[4-(6-chloro-pyridin-2-yloxy)-piperidin-1-yl]-2-oxo-ethyl}-amide,
4-Methyl-3-(1-{2-[(5-phenyl-1H-pyrazole-3-carbonyl)-amino]-acetyl}-piperidin-4-yloxy)-benzoic acid methyl ester,
5-Phenyl-1H-pyrazole-3-carboxylic acid {2-[4-(2-fluoro-5-trifluoromethyl-phenoxy)-piperidin-1-yl]-2-oxo-ethyl}-amide,
5-(2-Fluoro-phenyl)-1H-pyrazole-3-carboxylic acid {2-[4-(2-chloro-phenoxy)-piperidin-1-yl]-2-oxo-ethyl}-amide,
5-(2-Fluoro-phenyl)-1H-pyrazole-3-carboxylic acid {2-oxo-2-[4-(3-trifluoromethyl-phenoxy)-piperidin-1-yl]-ethyl}-amide,
5-(4-Trifluoromethyl-phenyl)-1H-pyrazole-3-carboxylic acid {2-[4-(2-chloro-phenoxy)-piperidin-1-yl]-2-oxo-ethyl}-amide,
5-(3-Fluoro-phenyl)-1H-pyrazole-3-carboxylic acid {2-oxo-2-[4-(3-trifluoromethyl-phenoxy)-piperidin-1-yl]-ethyl}-amide,
5-(3-Fluoro-phenyl)-1H-pyrazole-3-carboxylic acid {2-[4-(2-chloro-phenylamino)-piperidin-1-yl]-2-oxo-ethyl}-amide,
5-(2-Trifluoromethyl-phenyl)-1H-pyrazole-3-carboxylic acid {2-oxo-2-[4-(3-trifluoromethyl-phenoxy)-piperidin-1-yl]-ethyl}-amide,
5-(4-Hydroxy-phenyl)-1H-pyrazole-3-carboxylic acid {2-oxo-2-[4-(3-trifluoromethyl-phenoxy)-piperidin-1-yl]-ethyl}-amide,
5-(3-Hydroxy-phenyl)-1H-pyrazole-3-carboxylic acid {2-oxo-2-[4-(3-trifluoromethyl-phenoxy)-piperidin-1-yl]-ethyl}-amide,
5-(4-Fluoro-phenyl)-1H-pyrazole-3-carboxylic acid {2-oxo-2-[4-(3-trifluoromethyl-phenoxy)-piperidin-1-yl]-ethyl}-amide,
5-(4-Fluoro-phenyl)-1H-pyrazole-3-carboxylic acid {2-[4-(2-chloro-pyridin-3-yloxy)-piperidin-1-yl]-2-oxo-ethyl}-amide,
5-(4-Fluoro-phenyl)-1H-pyrazole-3-carboxylic acid {2-[4-(5-chloro-pyridin-3-yloxy)-piperidin-1-yl]-2-oxo-ethyl}-amide,
5-Phenyl-1H-pyrazole-3-carboxylic acid {2-[4-(3-chloro-phenoxy)-piperidin-1-yl]-2-oxo-ethyl}-amide,
3-(1-{2-[(5-Phenyl-1H-pyrazole-3-carbonyl)-amino]-acetyl}-piperidin-4-yloxy)-benzoic acid,
5-(3-Fluoro-phenyl)-1H-pyrazole-3-carboxylic acid {2-[4-(5-chloro-pyridin-3-yloxy)-piperidin-1-yl]-2-oxo-ethyl}-amide,
5-Phenyl-1H-pyrazole-3-carboxylic acid [2-oxo-2-(4-m-tolyloxy-piperidin-1-yl)-ethyl]-amide,
5-Phenyl-1H-pyrazole-3-carboxylic acid {2-[4-(2-methyl-pyridin-3-yloxy)-piperidin-1-yl]-2-oxo-ethyl}-amide,
5-Pyridin-2-yl-1H-pyrazole-3-carboxylic acid {2-[4-(2-chloro-phenoxy)-piperidin-1-yl]-2-oxo-ethyl}-amide,
3-(5-{2-oxo-2-[4-(3-trifluoromethyl-phenoxy)-piperidin-1-yl]-ethylcarbamoyl}-1H-pyrazol-3-yl)-benzoic acid,
5-Pyridin-3-yl-1H-pyrazole-3-carboxylic acid {2-oxo-2-[4-(3-trifluoromethyl-phenoxy)-piperidin-1-yl]-ethyl}-amide,
5-Pyridin-3-yl-1H-pyrazole-3-carboxylic acid {2-[4-(2-chloro-phenoxy)-piperidin-1-yl]-2-oxo-ethyl}-amide,
5-Phenyl-1H-pyrazole-3-carboxylic acid {2-[4-(4-methyl-pyridin-3-yloxy)-piperidin-1-yl]-2-oxo-ethyl}-amide,
5-Phenyl-1H-pyrazole-3-carboxylic acid {2-oxo-2-[4-(5-trifluoromethyl-pyridin-3-yloxy)-piperidin-1-yl]-ethyl}-amide,
5-(5-Chloro-thiophen-2-yl)-1H-pyrazole-3-carboxylic acid {2-oxo-2-[4-(3-trifluoromethyl-phenoxy)-piperidin-1-yl]-ethyl}-amide,
5-(5-Chloro-thiophen-2-yl)-1H-pyrazole-3-carboxylic acid {2-[4-(2,5-difluoro-phenoxy)-piperidin-1-yl]-2-oxo-ethyl}-amide, and
5-(2-Hydroxy-phenyl)-1H-pyrazole-3-carboxylic acid {2-oxo-2-[4-(3-trifluoromethyl-phenoxy)-piperidin-1-yl]-ethyl}-amide,
and pharmaceutically acceptable salts thereof.

10. The compound of claim 1, wherein the compound is selected from:

5-Phenyl-1H-pyrazole-3-carboxylic acid {2-[4-(2-methanesulfonyl-phenoxy)-piperidin-1-yl]-2-oxo-ethyl}-amide,
5-(2-Fluoro-phenyl)-isoxazole-3-carboxylic acid {2-[4-(2-chloro-phenylamino)-piperidin-1-yl]-2-oxo-ethyl}-amide,
5-Phenyl-isoxazole-3-carboxylic acid {2-oxo-2-[4-(3-trifluoromethyl-phenoxy)-piperidin-1-yl]-ethyl}-amide,
5-(2-Fluoro-phenyl)-isoxazole-3-carboxylic acid {2-oxo-2-[4-(3-trifluoromethyl-phenoxy)-piperidin-1-yl]-ethyl}-amide,
5-(2-Hydroxy-phenyl)-isoxazole-3-carboxylic acid {2-oxo-2-[4-(3-trifluoromethyl-phenoxy)-piperidin-1-yl]-ethyl}-amide,
5-(3-Hydroxy-phenyl)-isoxazole-3-carboxylic acid {2-oxo-2-[4-(3-trifluoromethyl-phenoxy)-piperidin-1-yl]-ethyl}-amide,
5-(4-Hydroxy-phenyl)-isoxazole-3-carboxylic acid {2-oxo-2-[4-(3-trifluoromethyl-phenoxy)-piperidin-1-yl]-ethyl}-amide,
5-(3-Fluoro-phenyl)-isoxazole-3-carboxylic acid {2-oxo-2-[4-(3-trifluoromethyl-phenoxy)-piperidin-1-yl]-ethyl}-amide,
5-(4-Fluoro-phenyl)-isoxazole-3-carboxylic acid {2-oxo-2-[4-(3-trifluoromethyl-phenoxy)-piperidin-1-yl]-ethyl}-amide,
5-(4-Fluoro-phenyl)-isoxazole-3-carboxylic acid {2-[4-(5-chloro-pyridin-3-yloxy)-piperidin-1-yl]-2-oxo-ethyl}-amide,
5-(4-Fluoro-phenyl)-isoxazole-3-carboxylic acid {2-[4-(2-chloro-pyridin-3-yloxy)-piperidin-1-yl]-2-oxo-ethyl}-amide,
5-(3-Fluoro-phenyl)-isoxazole-3-carboxylic acid {2-[4-(5-chloro-pyridin-3-yloxy)-piperidin-1-yl]-2-oxo-ethyl}-amide,
1-Phenyl-1H-pyrazole-4-carboxylic acid {2-[4-(2-chloro-phenoxy)-piperidin-1-yl]-2-oxo-ethyl}-amide,
2-[(Biphenyl-4-ylmethyl)-amino]-1-[4-(2-chloro-phenoxy)-piperidin-1-yl]-ethanone,
N-{2-[4-(2-Chloro-phenoxy)-piperidin-1-yl]-2-oxo-ethyl}-4-[1,3,4]oxadiazol-2-yl-benzamide,
4-Phenyl-pyrazole-1-carboxylic acid {2-[4-(2-chloro-phenoxy)-piperidin-1-yl]-2-oxo-ethyl}-amide,
1-Phenyl-1H-[1,2,3]triazole-4-carboxylic acid {2-[4-(2-chloro-phenoxy)-piperidin-1-yl]-2-oxo-ethyl}-amide,
1-Phenyl-1H-[1,2,3]triazole-4-carboxylic acid {2-[4-(2-chloro-phenoxy)-piperidin-1-yl]-2-oxo-ethyl}-amide, 1-(3-Fluoro-phenyl)-1H-[1,2,3]triazole-4-carboxylic acid {2-oxo-2-[4-(3-trifluoromethyl-phenoxy)-piperidin-1-yl]-ethyl}-amide,
1-(3-Fluoro-phenyl)-1H-[1,2,3]triazole-4-carboxylic acid {2-[4-(2-chloro-5-fluoro-phenoxy)-piperidin-1-yl]-2-oxo-ethyl}-amide
1-m-Tolyl-1H-[1,2,3]triazole-4-carboxylic acid {2-oxo-2-[4-(3-trifluoromethyl-phenoxy)-piperidin-1-yl]-ethyl}-amide,
1-m-Tolyl-1H-[1,2,3]triazole-4-carboxylic acid {2-[4-(2-chloro-5-fluoro-phenoxy)-piperidin-1-yl]-2-oxo-ethyl}-amide,
1-(2-Cyano-phenyl)-1H-[1,2,3]triazole-4-carboxylic acid {2-oxo-2-[4-(3-trifluoromethyl-phenoxy)-piperidin-1-yl]-ethyl}-amide,
1-(2-Cyano-phenyl)-1H-[1,2,3]triazole-4-carboxylic acid {2-oxo-2-[4-(3-trifluoromethyl-phenoxy)-piperidin-1-yl]-ethyl}-amide,
1-o-Tolyl-1H-[1,2,3]triazole-4-carboxylic acid {2-oxo-2-[4-(3-trifluoromethyl-phenoxy)-piperidin-1-yl]-ethyl}-amide,
1-Pyridin-3-yl-1H-[1,2,3]triazole-4-carboxylic acid {2-[4-(2-chloro-phenoxy)-piperidin-1-yl]-2-oxo-ethyl}-amide,
1-Cyclopentyl-1H-[1,2,3]triazole-4-carboxylic acid {2-[4-(5-chloro-pyridin-3-yloxy)-piperidin-1-yl]-2-oxo-ethyl}-amide,
1-(5-Fluoro-pyridin-3-yl)-1H-[1,2,3]triazole-4-carboxylic acid {2-[4-(2-chloro-phenoxy)-piperidin-1-yl]-2-oxo-ethyl}-amide,
N-{2-[4-(2-Chloro-phenoxy)-piperidin-1-yl]-2-oxo-ethyl}-4-(5-methyl-[1,3,4]oxadiazol-2-yl)-benzamide, and
3'-Dimethylamino-biphenyl-4-carboxylic acid {2-[4-(2-chloro-phenoxy)-piperidin-1-yl]-2-oxo-ethyl}-amide,
and pharmaceutically acceptable salts thereof.

11. The compound of claim 1, wherein the compound is selected from:
N-{2-Oxo-2-[4-(3-trifluoromethyl-phenoxy)-piperidin-1-yl]-ethyl}-4-(pyrrolidine-1-carbonyl)-benzamide,
9H-Carbazole-3-carboxylic acid {2-oxo-2-[4-(3-trifluoromethyl-phenoxy)-piperidin-1-yl]-ethyl}-amide,
1-Phenyl-1H-imidazole-4-carboxylic acid {2-oxo-2-[4-(3-trifluoromethyl-phenoxy)-piperidin-1-yl]-ethyl}-amide,
1-Phenyl-1H-imidazole-4-carboxylic acid {2-[4-(2-chloro-5-fluoro-phenoxy)-piperidin-1-yl]-2-oxo-ethyl}-amide,
5-Phenyl-1H-pyrazole-3-carboxylic acid {2-[4-(2-formyl-phenoxy)-piperidin-1-yl]-2-oxo-ethyl}-amide,
2-(1-{2-[(5-Phenyl-1H-pyrazole-3-carbonyl)-amino]-acetyl}-piperidin-4-yloxy)-benzoic acid,
5-Phenyl-1H-pyrazole-3-carboxylic acid {2-[4-(2-hydroxymethyl-phenoxy)-piperidin-1-yl]-2-oxo-ethyl}-amide,
5-Phenyl-1H-pyrazole-3-carboxylic acid {2-oxo-2-[4-(3,4,5-trifluoro-phenoxy)-piperidin-1-yl]-ethyl}-amide,
5-Phenyl-1H-pyrazole-3-carboxylic acid (2-{4-[2-(hydroxyimino-methyl)-phenoxy]-piperidin-1-yl}-2-oxo-ethyl)-amide,
5-Phenyl-1H-pyrazole-3-carboxylic acid {2-oxo-2-[4-(2-trifluoromethyl-phenoxy)-piperidin-1-yl]-ethyl}-amide,
5-Phenyl-1H-pyrazole-3-carboxylic acid {2-[4-(3-cyano-phenoxy)-piperidin-1-yl]-2-oxo-ethyl}-amide,
5-Phenyl-1H-pyrazole-3-carboxylic acid (2-{4-[2-(methoxyimino-methyl)-phenoxy]-piperidin-1-yl}-2-oxo-ethyl)-amide,
5-Phenyl-1H-pyrazole-3-carboxylic acid {2-[4-(2-methylcarbamoyl-phenoxy)-piperidin-1-yl]-2-oxo-ethyl}-amide,
5-Phenyl-1H-pyrazole-3-carboxylic acid {2-[4-(2-carbamoyl-phenoxy)-piperidin-1-yl]-2-oxo-ethyl}-amide,
5-(2-Trifluoromethyl-phenyl)-1H-pyrazole-3-carboxylic acid {2-[4-(2-chloro-phenylamino)-piperidin-1-yl]-2-oxo-ethyl}-amide,
5-Phenyl-1H-pyrazole-3-carboxylic acid {2-[4-(3-cyano-phenylamino)-piperidin-1-yl]-2-oxo-ethyl}-amide,
5-Phenyl-1H-pyrazole-3-carboxylic acid {2-[4-(adamantan-2-ylamino)-piperidin-1-yl]-2-oxo-ethyl}-amide,
5-(2-Methoxy-phenyl)-1H-pyrazole-3-carboxylic acid {2-[4-(2-chloro-phenylamino)-piperidin-1-yl]-2-oxo-ethyl}-amide,
1-Pyrrolidin-3-yl-1H-[1,2,3]triazole-4-carboxylic acid {2-oxo-2-[4-(3-trifluoromethyl-phenoxy)-piperidin-1-yl]-ethyl}-amide,
1-(1-Methyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide,
1-(3,5-Difluoro-phenyl)-1H-[1,2,3]triazole-4-carboxylic acid {2-[4-(2-chloro-phenoxy)-piperidin-1-yl]-2-oxo-ethyl}-amide,
1-(3,5-Difluoro-phenyl)-1H-[1,2,3]triazole-4-carboxylic acid {2-[4-(5-chloro-pyridin-3-yloxy)-piperidin-1-yl]-2-oxo-ethyl}-amide,
1-Piperidin-4-yl-1H-[1,2,3]triazole-4-carboxylic acid {2-oxo-2-[4-(3-trifluoromethyl-phenoxy)-piperidin-1-yl]-ethyl}-amide hydrochloride,
1-(1-Methyl-piperidin-4-yl)-1H-[1,2,3]triazole-4-carboxylic acid {2-oxo-2-[4-(3-trifluoromethyl-phenoxy)-piperidin-1-yl]-ethyl}-amide,
1-Pyridin-3-yl-1H-[1,2,3]triazole-4-carboxylic acid {2-[4-(2,5-difluoro-phenoxy)-piperidin-1-yl]-2-oxo-ethyl}-amide,
1-Pyridin-3-yl-1H-[1,2,3]triazole-4-carboxylic acid {2-[4-(5-cyano-2-methyl-phenoxy)-piperidin-1-yl]-2-oxo-ethyl}-amide,
5-Phenyl-1H-pyrazole-3-carboxylic acid {2-oxo-2-[3-(3-trifluoromethyl-phenoxy)-pyrrolidin-1-yl]-ethyl}-amide,
4-(2-Oxo-pyrrolidin-1-yl)-N-{2-oxo-2-[4-(3-trifluoromethyl-phenoxy)-piperidin-1-yl]-ethyl}-benzamide,
1-Cyclopropyl-1H-[1,2,3]triazole-4-carboxylic acid {2-oxo-2-[4-(3-trifluoromethyl-phenoxy)-piperidin-1-yl]-ethyl}-amide, and
1-Morpholin-4-yl-1H-[1,2,3]triazole-4-carboxylic acid {2-oxo-2-[4-(3-trifluoromethyl-phenoxy)-piperidin-1-yl]-ethyl}-amide,
and pharmaceutically acceptable salts thereof.

12. The compound of claim 1, wherein the compound is selected from:
1-Phenyl-1H-[1,2,3]triazole-4-carboxylic acid {2-[4-(3-cyano-phenoxy)-piperidin-1-yl]-2-oxo-ethyl}-amide,
1-Pyridin-3-yl-1H-[1,2,3]triazole-4-carboxylic acid {2-[3-(2,5-difluoro-phenoxy)-pyrrolidin-1-yl]-2-oxo-ethyl}-amide,
5-Phenyl-1H-pyrazole-3-carboxylic acid {2-oxo-2-[3-(3-trifluoromethyl-phenoxy)-azetidin-1-yl]-ethyl}-amide,
5-Pyridin-3-yl-1H-pyrazole-3-carboxylic acid {2-oxo-2-[3-(3-trifluoromethyl-phenoxy)-azetidin-1-yl]-ethyl}-amide, 5-Phenyl-1H-pyrazole-3-carboxylic acid {2-[3-(2,5-difluoro-phenoxy)-pyrrolidin-1-yl]-2-oxo-ethyl}-amide,
1-Phenyl-1H-imidazole-4-carboxylic acid {2-[4-(2,5-difluoro-phenoxy)-piperidin-1-yl]-2-oxo-ethyl}-amide,
1-Phenyl-1H-imidazole-4-carboxylic acid {2-[4-(2-chloro-phenoxy)-piperidin-1-yl]-2-oxo-ethyl}-amide,
1-Phenyl-1H-imidazole-4-carboxylic acid {2-[4-(5-cyano-2-methyl-phenoxy)-piperidin-1-yl]-2-oxo-ethyl}-amide,
1-Phenyl-1H-imidazole-4-carboxylic acid {2-[3-(3-fluoro-5-trifluoromethyl-phenoxy)-azetidin-1-yl]-2-oxo-ethyl}-amide,
1-Phenyl-1H-imidazole-4-carboxylic acid {2-[4-(3-fluoro-5-trifluoromethyl-phenoxy)-piperidin-1-yl]-2-oxo-ethyl}-amide,
1-Phenyl-1H-imidazole-4-carboxylic acid {2-[4-(4-fluoro-3-trifluoromethyl-phenoxy)-piperidin-1-yl]-2-oxo-ethyl}-amide,
1-Phenyl-1H-imidazole-4-carboxylic acid {2-[3-(2-chloro-phenoxy)-azetidin-1-yl]-2-oxo-ethyl}-amide,
1-Phenyl-1H-imidazole-4-carboxylic acid {2-[3-(5-cyano-2-methyl-phenoxy)-azetidin-1-yl]-2-oxo-ethyl}-amide,
1-Phenyl-1H-imidazole-4-carboxylic acid {2-[3-(2-chloro-phenoxy)-pyrrolidin-1-yl]-2-oxo-ethyl}-amide,
5-Phenyl-isoxazole-3-carboxylic acid {2-[3-(2,5-difluoro-phenoxy)-pyrrolidin-1-yl]-2-oxo-ethyl}-amide,
2-Phenyl-4H-thieno[3,2-b]pyrrole-5-carboxylic acid {2-[4-(2-chloro-5-fluoro-phenoxy)-piperidin-1-yl]-2-oxo-ethyl}-amide,
6-Pyrazol-1-yl-imidazo[1,2-a]pyridine-2-carboxylic acid {2-[4-(2-chloro-phenoxy)-piperidin-1-yl]-2-oxo-ethyl}-amide,
1-Pyridin-3-yl-1H-[1,2,3]triazole-4-carboxylic acid {2-[4-(3-cyano-phenoxy)-piperidin-1-yl]-2-oxo-ethyl}-amide,
1-Pyridin-3-yl-1H-[1,2,3]triazole-4-carboxylic acid {2-[3-(3-fluoro-5-trifluoromethyl-phenoxy)-azetidin-1-yl]-2-oxo-ethyl}-amide,
1-Pyridin-3-yl-1H-[1,2,3]triazole-4-carboxylic acid {2-[4-(3-fluoro-5-trifluoromethyl-phenoxy)-piperidin-1-yl]-2-oxo-ethyl}-amide,
1-Pyridin-3-yl-1H-[1,2,3]triazole-4-carboxylic acid {2-[3-(2-chloro-phenoxy)-pyrrolidin-1-yl]-2-oxo-ethyl}-amide,
1-Pyridin-3-yl-1H-[1,2,3]triazole-4-carboxylic acid {2-[4-(4-fluoro-3-trifluoromethyl-phenoxy)-piperidin-1-yl]-2-oxo-ethyl}-amide,
1-Pyridin-3-yl-1H-[1,2,3]triazole-4-carboxylic acid {2-[3-(2-chloro-phenoxy)-azetidin-1-yl]-2-oxo-ethyl}-amide,
1-Pyridin-3-yl-1H-[1,2,3]triazole-4-carboxylic acid {2-[3-(5-cyano-2-methyl-phenoxy)-azetidin-1-yl]-2-oxo-ethyl}-amide,
1-Pyridin-3-yl-1H-[1,2,3]triazole-4-carboxylic acid {2-oxo-2-[4-(2-trifluoromethyl-phenoxy)-piperidin-1-yl]-ethyl}-amide,
5-Phenyl-1H-pyrazole-3-carboxylic acid {2-[3-(3-fluoro-5-trifluoromethyl-phenoxy)-azetidin-1-yl]-2-oxo-ethyl}-amide,
5-Phenyl-1H-pyrazole-3-carboxylic acid {2-[4-(3-fluoro-5-trifluoromethyl-phenoxy)-piperidin-1-yl]-2-oxo-ethyl}-amide,
5-Phenyl-1H-pyrazole-3-carboxylic acid {2-[4-(4-fluoro-3-trifluoromethyl-phenoxy)-piperidin-1-yl]-2-oxo-ethyl}-amide,
5-Phenyl-1H-pyrazole-3-carboxylic acid {2-[3-(2-chloro-phenoxy)-azetidin-1-yl]-2-oxo-ethyl}-amide, and
5-Phenyl-1H-pyrazole-3-carboxylic acid {2-[3-(5-cyano-2-methyl-phenoxy)-azetidin-1-yl]-2-oxo-ethyl}-amide,
and pharmaceutically acceptable salts thereof.

13. A compound of the formula:

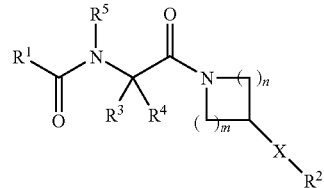

wherein
$R^1$ is heteroaryl;
$R^2$ is aryl or heteroaryl;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
m and n are, independently, 1 or 2;
X is —O—, —$NR^6$—, —S—, —S(O)— or —$S(O)_2$— where $R^6$ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts or enantiomer or diastereomer thereof.

14. A compound of the formula:

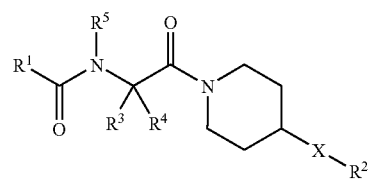

wherein
$R^1$ is aryl or heteroaryl;
$R^2$ is aryl or heteroaryl;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
X is —O—, —$NR^6$—, —S—, —S(O)— or —$S(O)_2$— where $R^6$ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

and pharmaceutically acceptable salts thereof;

with the proviso that said compound is not

4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide, N-[2-[4-[[4-amino-5-(2,6-difluorobenzoyl)-2-thiazolyl]amino]-1-piperidinyl]-2-oxoethyl]-M-methyl-benzamide, 4-amino-N-[2-[4-[[4-amino-5-(2,6-difluorobenzoyl)-2-thiazolyl]amino]-1-piperidinyl]-2-oxoethyl]-benzamide, or a pharmaceutically acceptable salt thereof.

15. A compound of the formula:

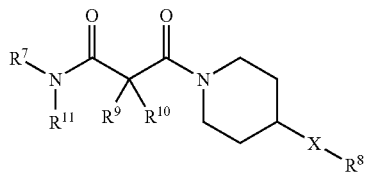

wherein
$R^7$ is aryl or heteroaryl;
$R^8$ is aryl or heteroaryl;
$R^9$ and $R^{10}$ are each independently hydrogen, halogen or alkyl; or
$R^9$ and $R^{10}$, together with the carbon atom to which they are attached, form a cycloalkyl group;
$R^{11}$ is hydrogen or alkyl;
X is —O—, —NR$^{12}$—, —S—, —S(O)— or —S(O)$_2$— where $R^{12}$ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof.

16. The compound of claim 1, wherein the compound is selected from:

N-Biphenyl-4-yl-3-[4-(2-bromo-phenoxy)-piperidin-1-yl]-3-oxo-propionamide,
N-Biphenyl-4-yl-3-[4-(2-chloro-5-fluoro-phenoxy)-piperidin-1-yl]-3-oxo-propionamide,
N-Biphenyl-4-yl-3-[4-(2-bromo-phenylamino)-piperidin-1-yl]-3-oxo-propionamide,
N-Biphenyl-4-yl-3-[4-(2-bromo-phenylsulfanyl)-piperidin-1-yl]-3-oxo-propionamide,
N-Biphenyl-4-yl-3-oxo-3-(4-o-tolylamino-piperidin-1-yl)-propionamide,
N-Biphenyl-4-yl-3-[4-(2-nitro-phenoxy)-piperidin-1-yl]-3-oxo-propionamide,
3-[4-(2-Amino-phenoxy)-piperidin-1-yl]-N-biphenyl-4-yl-3-oxo-propionamide,
N-Biphenyl-4-yl-3-[4-(2,3-dimethyl-phenylamino)-piperidin-1-yl]-3-oxo-propionamide,
N-Biphenyl-4-yl-3-[4-(2,4-dimethyl-phenylamino)-piperidin-1-yl]-3-oxo-propionamide,
N-Biphenyl-4-yl-3-[4-(2,5-dimethyl-phenylamino)-piperidin-1-yl]-3-oxo-propionamide,
N-Biphenyl-4-yl-3-[4-(2-tert-butyl-phenylamino)-piperidin-1-yl]-3-oxo-propionamide,
N-Biphenyl-4-yl-3-[4-(2,5-difluoro-phenoxy)-piperidin-1-yl]-3-oxo-propionamide,
Synthesis of 3-[4-(2-Chloro-5-fluoro-phenoxy)-piperidin-1-yl]-3-oxo-N-(6-phenyl-pyridin-3-yl)-propionamide,
3-[4-(2-Chloro-5-fluoro-phenoxy)-piperidin-1-yl]-3-oxo-N-(5-phenyl-pyridin-2-yl)-propionamide,
3-[4-(2-Chloro-phenoxy)-piperidin-1-yl]-3-oxo-N-(6-phenyl-pyridin-3-yl)-propionamide,
3-[4-(2-Chloro-phenylamino)-piperidin-1-yl]-3-oxo-N-(6-phenyl-pyridin-3-yl)-propionamide,
3-[4-(2-Bromo-phenylamino)-piperidin-1-yl]-3-oxo-N-(6-phenyl-pyridin-3-yl)-propionamide,
3-Oxo-N-(6-phenyl-pyridin-3-yl)-3-[4-(2-trifluoromethyl-phenylamino)-piperidin-1-yl]-propionamide,
3-[4-(2-Chloro-phenylsulfanyl)-piperidin-1-yl]-3-oxo-N-(6-phenyl-pyridin-3-yl)-propionamide,
3-[4-(2-Bromo-phenylsulfanyl)-piperidin-1-yl]-3-oxo-N-(6-phenyl-pyridin-3-yl)-propionamide,
3-Oxo-N-(6-phenyl-pyridin-3-yl)-3-[4-(2-trifluoromethyl-phenylsulfanyl)-piperidin-1-yl]-propionamide,
3-Oxo-N-(6-phenyl-pyridin-3-yl)-3-[4-(2-trifluoromethyl-phenoxy)-piperidin-1-yl]-propionamide,
3-Oxo-N-(6-phenyl-pyridin-3-yl)-3-(4-o-tolylamino-piperidin-1-yl)-propionamide,
3-[4-(2-Chloro-phenoxy)-piperidin-1-yl]-3-oxo-N-(3-phenyl-[1,2,4]thiadiazol-5-yl)-propionamide,
3-[4-(2-Chloro-phenoxy)-piperidin-1-yl]-N-(4-[1,2,4]oxadiazol-3-yl-phenyl)-3-oxo-propionamide,
3-[4-(2-Chloro-phenoxy)-piperidin-1-yl]-3-oxo-N-(5-phenyl-thiazol-2-yl)-propionamide,
3-[4-(2-Chloro-phenylamino)-piperidin-1-yl]-3-oxo-N-(5-phenyl-thiazol-2-yl)-propionamide,
1-[4-(2-Chloro-phenoxy)-piperidine-1-carbonyl]-cyclopropane carboxylic acid biphenyl-4-ylamide,
N-Biphenyl-4-yl-3-oxo-3-[4-(3,4,5-trifluoro-phenoxy)-piperidin-1-yl]-propionamide, and
N-Biphenyl-4-yl-3-[4-(3-cyano-phenoxy)-piperidin-1-yl]-3-oxo-propionamide, and pharmaceutically acceptable salts thereof.

17. A pharmaceutical composition comprising a compound of claim 1 and a pharmaceutically acceptable carrier.

18. The compound of claim 1, wherein the compound is:

Biphenyl-4-carboxylic acid (2-{4-[methyl-(2-trifluoromethyl-phenyl)-amino ]-piperidin-1-yl}-2-oxo-ethyl)-amide or a pharmaceutically acceptable salt thereof.

19. The compound of claim 1, wherein the compound is:

5-Phenyl-isoxazole-3-carboxylic acid {2-[4-(2-chloro-phenylamino)-piperidin-1-yl]-2-oxo-ethyl}-amide or a pharmaceutically acceptable salt thereof.

20. The compound of claim 1, wherein the compound is:
5-Phenyl-1H-pyrazole-3-carboxylic acid {2-oxo-2-[4-(3-trifluoromethyl-phenoxy)-piperidin-1-yl]-ethyl}-amide or a pharmaceutically acceptable salt thereof 21. The compound of claim 1, wherein the compound is:
1-Pyridin-3-yl-1H-[1,2,3]triazole-4-carboxylic acid {2-[4-(5-cyano-2-methyl-phenoxy)-piperidin-1-yl]-2-oxo-ethyl}-amide or a pharmaceutically acceptable salt thereof.

22. The compound of claim 1, wherein the compound is:
1-Phenyl-1H-imidazole-4-carboxylic acid {2-[4-(2,5-difluoro-phenoxy)-piperidin-1-yl]-2-oxo-ethyl}-amide or a pharmaceutically acceptable salt thereof.

\* \* \* \* \*